(12) United States Patent
Wargent et al.

(10) Patent No.: US 11,147,221 B2
(45) Date of Patent: Oct. 19, 2021

(54) METHODS OF SEED TREATMENT AND RESULTING PRODUCTS

(71) Applicant: Biolumic Limited, Palmerston North (NZ)

(72) Inventors: Jason John Wargent, Palmerston North (NZ); Luke James Cooney, Palmerston North (NZ)

(73) Assignee: BIOLUMIC LIMITED, Palmerston North (NZ)

( * ) Notice: Subject to any disclaimer, the term of this patent is extended or adjusted under 35 U.S.C. 154(b) by 144 days.

(21) Appl. No.: 16/326,871

(22) PCT Filed: Aug. 21, 2017

(86) PCT No.: PCT/IB2017/001152
§ 371 (c)(1),
(2) Date: Feb. 20, 2019

(87) PCT Pub. No.: WO2018/037281
PCT Pub. Date: Mar. 1, 2018

(65) Prior Publication Data
US 2019/0183034 A1 Jun. 20, 2019

Related U.S. Application Data

(60) Provisional application No. 62/377,909, filed on Aug. 22, 2016.

(51) Int. Cl.
*A01H 3/02* (2006.01)
*A01G 7/04* (2006.01)
(Continued)

(52) U.S. Cl.
CPC .............. *A01H 3/02* (2013.01); *A01C 1/00* (2013.01); *A01C 1/02* (2013.01); *A01C 21/00* (2013.01);
(Continued)

(58) Field of Classification Search
CPC ... A01H 3/02; A01H 1/06; A01C 1/00; A01G 7/045; A01G 7/04
See application file for complete search history.

(56) References Cited

U.S. PATENT DOCUMENTS 4,943,674 A 7/1990 Houck et al.
4,987,071 A 1/1991 Cech et al.
(Continued)

FOREIGN PATENT DOCUMENTS

CN 1447646 A 10/2003
CN 101909425 A 12/2010
(Continued)

OTHER PUBLICATIONS

Aldemita et al., Agrobacterium tumefaciens-mediated transformation of japonica and indica rice varieties. Planta 199: 612-617 (1996).
(Continued)

*Primary Examiner* — Kent L Bell
(74) *Attorney, Agent, or Firm* — Wilson Sonsini Goodrich & Rosati

(57) ABSTRACT

Provided herein are methods, compositions, and devices relating to administration of UV-B to a seed.

19 Claims, 55 Drawing Sheets

(51) Int. Cl.
*A01C 1/02* (2006.01)
*A01C 1/00* (2006.01)
*A01C 21/00* (2006.01)
*A01D 91/00* (2006.01)
*B65B 1/00* (2006.01)

(52) U.S. Cl.
CPC ............. *A01D 91/00* (2013.01); *A01G 7/045* (2013.01); *B65B 1/00* (2013.01)

(56) References Cited

U.S. PATENT DOCUMENTS

| | | |
|---|---|---|
| 5,159,135 A | 10/1992 | Umbeck |
| 5,231,020 A | 7/1993 | Jorgensen et al. |
| 5,268,526 A | 12/1993 | Hershey et al. |
| 5,510,471 A | 4/1996 | Lebrun et al. |
| 5,538,880 A | 7/1996 | Lundquist et al. |
| 5,545,508 A | 8/1996 | Marchesano et al. |
| 5,571,706 A | 11/1996 | Baker et al. |
| 5,583,021 A | 12/1996 | Dougherty et al. |
| 5,589,615 A | 12/1996 | De Clercq et al. |
| 5,597,945 A | 1/1997 | Jaynes et al. |
| 5,610,042 A | 3/1997 | Chang et al. |
| 5,677,175 A | 10/1997 | Hodges et al. |
| 5,736,369 A | 4/1998 | Bowen et al. |
| 5,744,693 A | 4/1998 | Meyerowitz et al. |
| 5,750,341 A | 5/1998 | MacEvicz |
| 5,750,386 A | 5/1998 | Conkling et al. |
| 5,750,871 A | 5/1998 | Moloney et al. |
| 5,773,269 A | 6/1998 | Somers et al. |
| 5,773,697 A | 6/1998 | Tomes et al. |
| 5,780,708 A | 7/1998 | Lundquist et al. |
| 5,783,393 A | 7/1998 | Kellogg et al. |
| 5,792,929 A | 8/1998 | Mariani et al. |
| 6,306,597 B1 | 10/2001 | Macevicz |
| 6,875,857 B2 | 4/2005 | Simms |
| 7,115,400 B1 | 10/2006 | Adessi et al. |
| 7,211,390 B2 | 5/2007 | Rothberg et al. |
| 7,232,656 B2 | 6/2007 | Balasubramanian et al. |
| 7,244,559 B2 | 7/2007 | Rothberg et al. |
| 7,264,929 B2 | 9/2007 | Rothberg et al. |
| 7,323,305 B2 | 1/2008 | Leamon et al. |
| 7,348,475 B2 | 3/2008 | Shin et al. |
| 7,774,979 B2 | 8/2010 | Hurst |
| 7,948,015 B2 | 5/2011 | Rothberg et al. |
| 8,001,722 B2 | 8/2011 | Wilson et al. |
| 8,845,149 B2 | 9/2014 | Cheng et al. |
| 8,898,818 B1 | 12/2014 | Whitcomb |
| 1,072,187 A1 | 7/2020 | Wargent et al. |
| 2006/0016125 A1 | 1/2006 | Krauss et al. |
| 2008/0120736 A1 | 5/2008 | Hurst |
| 2008/0160580 A1 | 7/2008 | Adessi et al. |
| 2008/0286795 A1 | 11/2008 | Kawashima et al. |
| 2008/0298052 A1 | 12/2008 | Hurst et al. |
| 2009/0272029 A1 | 11/2009 | Aiking et al. |
| 2010/0193707 A1 | 8/2010 | Yamada et al. |
| 2011/0163246 A1 | 7/2011 | Ishiwata et al. |
| 2012/0054061 A1 | 3/2012 | Fok et al. |
| 2013/0008085 A1 | 1/2013 | Aikala et al. |
| 2013/0294065 A1 | 11/2013 | Wells |
| 2014/0204567 A1 | 7/2014 | Cheng et al. |
| 2014/0273235 A1 | 9/2014 | Voytas et al. |
| 2015/0167053 A1 | 6/2015 | Mertz, Jr. et al. |
| 2016/0073599 A1* | 3/2016 | Wargent .................. A01C 1/00 800/276 |
| 2016/0184237 A1 | 6/2016 | Lowe et al. |
| 2016/0345512 A1 | 12/2016 | Wargent |
| 2017/0000041 A1 | 1/2017 | Wargent |

FOREIGN PATENT DOCUMENTS

| | | |
|---|---|---|
| CN | 102149272 A | 8/2011 |
| CN | 103194453 A | 7/2013 |
| CN | 103209582 A | 7/2013 |
| CN | 103415199 A | 11/2013 |
| CN | 103476243 A | 12/2013 |
| CN | 103999748 A | 8/2014 |
| DE | 19900616 A1 | 7/2000 |
| EP | 1300066 A1 | 4/2003 |
| EP | 2172097 A1 | 4/2010 |
| JP | 2001028947 A | 2/2001 |
| JP | 2003339236 A | 12/2003 |
| JP | 2004166638 A | 6/2004 |
| JP | 2005328734 A | 12/2005 |
| JP | 2006158262 A | 6/2006 |
| JP | 2010094109 A | 4/2010 |
| JP | 2013051939 A | 3/2013 |
| JP | 2013153691 A | 8/2013 |
| NZ | 702063 A | 11/2016 |
| TW | M458082 U | 8/2013 |
| WO | WO-0051414 A1 | 9/2000 |
| WO | WO-2012040838 A1 | 4/2012 |
| WO | WO-2012085336 A1 | 6/2012 |
| WO | WO-2015119510 A1 | 8/2015 |
| WO | WO-2015137825 A1 | 9/2015 |
| WO | WO-2016043605 A1 | 3/2016 |
| WO | WO-2016054268 A1 | 4/2016 |
| WO | WO-2018037281 A1 | 3/2018 |
| WO | WO-2019002946 A1 | 1/2019 |
| WO | WO-2019038594 A2 | 2/2019 |

OTHER PUBLICATIONS

Altschul et al. Basic local alignment search tool. J Mol Biol 215(3):403-410 (1990).

Altschul, et al. Gapped BLAST and PSI-BLAST: a new generation of protein database search programs. Nucleic Acids Res 25:3389-3402 (1977).

An et al., Organ-Specific and Developmental Regulation of the Nopaline Synthase Promoter in Transgenic Tobacco Plants. Plant Physiol 88: 547-552 (1988).

Baerson et al., Developmental regulation of an acyl carrier protein gene promoter in vegetative and reproductive tissues. Plant Molecular Bio 22: 255-267 (1993).

Baerson et al., Identification of domains in an *Arabidopsis* acyl carrier protein gene promoter required for maximal organ-specific expression. Plant Mol Bio 1947-1959 (1994).

Baumann et al., The DNA Binding Site of the Dof Protein NtBBF1 is Essential for Tissue-Specific and Auxin-Regulated Expression of the rolB Oncogene in Plants. The Plant Cell 11: 323-333 (1999).

Bevan, Binary Agrobacterium vectors for plant transformation. Nucleic Acids Res 12(22): 8711-8721 (1984).

Bird et al., The tomato polygalacturonase gene and ripening-specific expression in transgenic plants. Plant Molecular Biology 11: 651-662 (1988).

Cho, et al. Targeted genome engineering in human cells with the Cas9 RNA-guided endonuclease. Nat Biotechnol. Mar. 2013;31(3):230-2. doi: 10.1038/nbt2507. Epub Jan. 29, 2013.

Christou et al., Production of Transgenic Rice (*Oryza sativa* L.) Plants from Agronomically Important Indica and Japonica Varieties via Electric Discharge Particle Acceleration of Exogenous DNA into Immature Zygotic Embryos. Bio/Technology 9: 957-962 (1991).

Cong et al. Multiplex genome engineering using CRISPR/Cas systems. Science 339(6121):819-23 (2013).

DiCarlo, et al. Genome engineering in *Saccharomyces cerevisiae* using CRISPR-Cas systems. Nucleic Acids Res. Apr. 2013;41(7):4336-43. doi: 10.1093/nar/gkt135. Epub Mar. 4, 2013.

Dong et al., Agrobacterium-mediated transformation of *Javanica* rice. Molecular Breeding 2: 267-276 (1996).

Fromm et al., An Octopine Synthase Enhancer Element Directs Tissue-Specific Expression and Binds ASF-1, a Factor from Tobacco Nuclear Extracts. The Plant Cell 1: 977-984 (1989).

Fromm et al., Inheritance and Expression of Chimeric Genes in the Progeny of Transgenic Maize Plants. Bio/Tech 8: 833-839 (1990).

Gordon-Kamm et al., Transformation of Maize Cells and Regeneration of Fertile Transgenic Plants. Plant Cell, 2.7 (Jul. 1990): 603-618.

Gudmundsson, et al. Genome-wide association and replication studies identify four variants associated with prostate cancer susceptibility. Nat Genet. Oct. 2009;41(10):1122-6. doi: 10.1038/ng. 448. Epub Sep. 20, 2009.

(56) References Cited

OTHER PUBLICATIONS

Guevara-Garcia et al., A 42 bp fragment of the pmas1' promoter containing an ocs-like element confers a developmental, wound and chemically inducible expression pattern. Plant Mol Bio 38: 743-753 (1998).
Henikoff et al. Amino acid substitution matrices from protein blocks. PNAS USA 89(22):10915-10919 (1992).
Herrera-Estrella, et al. Expression of chimaeric genes transferred into plant cells using a Ti-plasmid-denved vector. Nature. 1983; 303:209-213.
Hiei et al., Efficient transformation of rice (*Oryza sativa* L.) mediated by Agrobacterium and sequence analysis of the boundaries of the T-DNA. Plant J. 6(2): 271-282 (1994).
Hwang, et al. Efficient genome editing in zebrafish using a CRISPR-Cas system. Nat Biotechnol. Mar. 2013;31(3):227-9. doi: 10.1038/nbt.2501. Epub Jan. 29, 2013.
"Irradiance" Wikipedia (1999).
Ishida et al., High efficiency transformation of maize (*Zea mays* L.) mediated by Agrobacterium tumefaciens. Nat Biotechnol. 14(6): 745-750 (1996).
Jiang, et al. RNA-guided editing of bacterial genomes using CRISPR-Cas systems. Nat Biotechnol. Mar. 2013;31(3):233-9. doi: 10.1038/nbt.2508. Epub Jan. 29, 2013.
Jinek et al.: Creating Heritable Mutations in *Drosophila* with CRISPR-Cas9; Science, 337:816-821 (2012).
"Kaempferol" Wikipedia (2011).
Kaiser et al., Cis-acting elements of the CHS1 gene from white mustard controlling promoter activity and spatial patterns of expression. Plant Mol Bio 28: 231-243 (1995).
Klee et al., Vectors for Transformation of Higher Plants. Bio/Technology 3: 637-642 (1985).
Kreft et al., Rutin in buckwheat herbs grown at different UV-B radiation levels: comparison of two UV spectrophotometric and an HPLC method. Journal of Experimental Botany. 53(375):1801-1804 (2002).
Makarova et al. Evolution and classification of the CRISPR-Cas systems. Nat Rev Microbiol 9:467-477 (2011).
Mali et al. RNA-guided human genome engineering via Cas9. Science 339(6121):823-826 (2013).
Odell et al., Identification of DNA sequences required for activity of the cauliflower mosaic virus 35S promoter. Nature 313(6005): 810-812 (1985).
Ohl et al., Functional Properties of Phenylalanine Ammonia-Lyase Promoter from *Arabidopsis*. The Plant Cell 2: 837-848 (1990).
Out, et al. Deep sequencing to reveal new variants in pooled DNA samples. Hum Mutat. Dec. 2009; 30(12): 1703-12. doi: 10.1002/humu.21122.
PCT/IB19/01422 International Search Report and Written Opinion dated Jul. 24, 2020.
PCT/IB2018/000839 International Preliminary Report on Patentability dated Dec. 31, 2019.
Ringli et al., Specific interaction of the tomato bZIP transcription factor VSF-1 with a non-palindromic DNA sequence that controls vascular gene expression. Plant Molecular Bio 37: 977-988 (1998).
Shi et al., Gibberellin and abscisic acid regulate GAST1 expression at the level of transcription. Plant Mol Bio 38: 1053-1060 (1998).
Shimamoto et al., Fertile transgenic rice plants regenerated from transformed protoplasts. Nature 338: 274-276 (1989).
Tohge et al., Transcriptional and metabolic programs following exposure of plants to UV-B irradiation. Plant Signaling & Behavior 6(12): 1987-1992 (2011).
Turner, et al. Massively parallel exon capture and library-free resequencing across 16 genomes. Nat Methods. May 2009; 6(5): 315-6. doi: 10.1038/nmeth.f.248. Epub Apr. 6, 2009.
U.S. Appl. No. 14/857,486 Final Office Action dated Jan. 13, 2020.
U.S. Appl. No. 15/117,157 Final Office Action dated Sep. 17, 2019.
Van der Kop et al., Selection of *Arabidopsis* mutants overexpressing genes driven by the promoter of an auxin-inducible glutathione S-transferase gene. Plant Mol Bio 39: 979-990 (1999).

Vasil et al., Herbicide Resistant Fertile Transgenic Wheat Plants Obtained by Microprojectile Bombardment of Regenerable Embryogenic Callus. Bio/Technology 10: 667-674 (1992).
Vasil et al., Regeneration of Plants from Embryogenic Suspension Culture Protoplasts of Wheat (*Triticum aestivum* L.) Bio/Technology 8: 429-434 (1990).
Voytas, Plant Genome Engineering with Sequence-Specific Nucleases. Annu. Rev. Plant Biol. 64: 327-350 (2013).
Wan et al., Generation of Large Numbers of Independently Transformed Fertile Barley Plants. Plant Physiol. 104(1): 37-48 (1994).
Weeks et al., Rapid Production of Multiple Independent Lines of Fertile Transgenic Wheat (*Triticum aestivum*). Plant Physiol. 102(4): 1077-1084 (1993).
Willmott et al., DNase1 footprints suggest the involvement of at least three types of transcription factors in the regulation of alpha-Amy2/A by gibberellin. Plant Mol Bio 38: 817-825 (1998).
Australia Patent Application No. 2015214665 Examination Report dated Apr. 10, 2019.
Behn, H. et al. Development-dependent UV-B Responses in Red Oak Leaf Lettuce (*Lactuca sativa* L.): Physiological Mechanisms and Significance for Hardening, European Journal of Horticultural Science vol. 76, No. 2, pp. 33-40 (2011).
Besteriro et al. *Arabidopsis* MAP kinase phosphatase 1 and its target MAP kinases 3 and 6 antagonistically determine UV-B stress tolerance, independent of the UVR8 photoreceptor pathway. Plant Journal 58:727-737 (2011).
Chen et al. Shoot-to-Root Mobile Transcription Factor HY5 Coordinates Plant Carbon and Nitrogen Acquisition. Curr Biol 26(5):640-646 (Mar. 2016).
Chinese Patent Application No. 201580015856.9 Office Action dated Apr. 17, 2019.
Chinese Patent Application No. 2015800262327 Office Action dated Apr. 10, 2019.
Cluis e tal. The *Arabidopsis* transcription factor HY5 integrates light and hormone signaling pathways. Plant J 38(2):332-347 (2004).
Davey, M.P. et al. The UV-B photoreceptor UVR8 promotes photosynthetic efficiency in *Arabidopsis thaliana* exposed to elevated levels of UV-B, Photosynthesis Research, 2012, vol. 114, pp. 121-131.
Ebisawa et al. Supplementary ultraviolet radiation B together with blue light at night increased quercetin content and flavonol synthase gene expression in leaf lettuce (*Lactuca sativa* L.). Environmental Control in Biology 46(1):1-11 (2008).
European Application No. 15761440.5 Extended European Search Report dated Sep. 19, 2017.
European Application No. 15841342 Search Report and Opinion dated Feb. 13, 2018.
European Patent Application No. 15761440.5 Office Action dated Nov. 2, 2018.
European Patent Application No. 15761440.5 Summons to Attend Oral Proceedings Pursuant to Rule 115(1) EPC dated Jun. 4, 2019.
European Patent Application No. 15841342.7 Office Action dated May 28, 2019.
European Patent Application No. EP15746659.0 Extended European Search Report dated Oct. 11, 2017.
Favory et al. Interaction of COP1 and UVR8 regulates UV-B-induced photomorphogenesis and stress acclimation in *Arabidopsis*, Embo Journal, 28(5); 591-601 (2009).
Folta et al. Light as a Growth Regulator: Controlling Plant Biology with Narrow-bandwidth Solid-state Lighting Systems. Hortscience 43:1957-1964 (2008).
Gangappa et al. The Multifaceted Roles of HY5 in Plant Growth and Development. Mol Plant 9(10):1353-1365 (Oct. 2016).
Heil et al. Induced systemic resistance (ISR) against pathogens—a promising field for ecological research, Perspectives in Plant Ecology, Evolution and Systematics, vol. 4, 2001, pp. 65-79.
Huche-Thelier et al. Light signaling and plant responses to blue and UV radiations—Perspectives for applications in horticulture. Environmental and Experimental Botany, Elsevier, Amsterdam, NL 121:22-38 (2015).

(56) References Cited

OTHER PUBLICATIONS

Iarc Monographs on the Evaluation of Carcinogenic Risks to Humans. vol. 55—Solar and ultraviolet radiation; Chapter 1; Exposure data (1992) (International Agency for Research on Cancer—World Health Organization).
Ibdah et al. Spectral dependence of flavonol and betacyanin accumulation in Mesembryanthemum crystallinum under enhanced ultraviolet radiation, Plant, Cell and Environment 25: 1145-1154 (2002).
International Application No. PCT/IB2017/001152 International Search Report and Written Opinion dated Nov. 8, 2017.
International Application No. PCT/IB2018/000839 International Search Report and Written Opinion dated Oct. 18, 2018.
International Application No. PCT/IB2018/001056 International Search Report and Written Opinion dated Apr. 3, 2019.
International Application No. PCT/NZ2015/000008 International Preliminary Report on Patentability dated Apr. 19, 2016.
International Application No. PCT/NZ2015/000008 Written Opinion dated Jan. 14, 2016.
International Application No. PCT/NZ2015/000014 International Preliminary Report on Patentability dated Nov. 16, 2015.
International Application No. PCT/NZ2015/000014 Written Opinion dated Jun. 3, 2015.
International Application No. PCT/NZ2015/050153 International Search Report dated Nov. 23, 2015.
International Application No. PCT/NZ2015/050153 Written Opinion dated Feb. 18, 2016.
Jansen. Low threshold levels of ultraviolet-B in a background of photosynthetically active radiation trigger rapid degradation of the D2 protein of photosystem-II. The Plant Journal 9(5):693-699 (1996).
Japanese Application No. 2016-556020 Office Action dated Dec. 30, 2018.
Japanese Patent Application No. 2016-556020 Decision of Rejection dated Jul. 22, 2019.
Japanese Patent Application No. 2017-514617 Office Action dated Aug. 6, 2019.
Jenkins, G.I. Signal Transduction in Responses to UV-B Radiation, Annual Review of Plant Biology, vol. 60, 2009, pp. 407-431.
Kakani, VG et al. Field crop responses to ultraviolet-B radiation: a review. Agricultural and Forest Meteorology, 120(1-4):191-218 (Dec. 24, 2003).
Kubasek, W.L. et al. Regulation of flavonoid biosynthetic genes in germinating *Arabidopsis* seedlings, The Plant Cell, 1992, vol. 4, pp. 1229-1236.
Lee et al. Analysis of transcription factor HY5 genomic binding sites revealed its hierarchical role in light regulation of development. Plant Cell 19(3):731-749 (2007).
Li, X. et al. Effect of UV-B irradiation on seed germination and seedling growth of *Arabidopsis*', Chinese Bulletin of Botany, 2013, vol. 48, pp. 52-58.
Liu, Bing et al. Effects of enhanced UV-B radiation on seed growth characteristics and yield components in soybean. Field Crops Research, 154:158-163 (2013).
Lydon et al. UV-B Radiation Effects on Photosynthesis. Growth and Cannabinoid Production of Two Cannabis sativa Chemotypes. Photochemistry and Photobiology 46(2):201-206 (1987).
Marzocca, A. et al. Tratamiento de semillas de 'Kok-saghyz' con rayos ultravioletas', Revista de Investigaciones Agrícolas, 1957, vol. XI, pp. 227-245.
Mexico Patent Application No. MX/a/2016/010361 Examination Report dated May 24, 2019.
Mishra, A. et al. Effect of UVB radiation on seed germination, seedling growth, photosynthetic pigments and biochemical responses of *Postum sativum* (L.). Photosynthetic Pigments and Biochemical Responses of *Pistum sativum* (L.) Zenith International Journal of Multidisciplinary Research, vol. 5(1), pp. 124-129, Jan. 2015.
Musil et al. Ultraviolet-B Irradiation of Seeds Affects Photochemical and Reproductive Performance of the Arid-Environment Ephemeral Dimorphotheca Pluvialis. Environmental and Experimental Botany 34(4):371-378 (1994).

Ozbolt, L. et al. Distribution of selenium and phenolics in buckwheat plants grown from seeds soaked in Se solution and under different levels of UV-B radiation. Food Chemistry 110(3):691-696 (Oct. 1, 2008).
Peykarestan et al., Uv irradiation effects on seed germination and growth, protein content, peroxidase and protease activity in redbean. International Research Journal of Applied and Basic Sciences. 3(1):92-102 (2012).
Qaderi et al. Morphological and physiological responses of canola (*Brassica napus*) siliquas and seeds to UVB and CO2 under controlledenvironment conditions. Environmental and Experimental Botany 60:428-437 (2007).
Rizzini, L. et al. Perception of UV-B by the *Arabidopsis* UVR8 Protein, Science vol. 332, No. 6025; pp. 103-106 (2011).
Rozema, J. et al. UV-B as an environmental factor in plant life: stress and regulation, Trends in Ecology & Evolution, vol. 12, 1997, pp. 22-28.
Setlow. The Wavelengths in Sunlight Effective in Producing Skin Cancer: A Theoretical Analysis. PNAS 71:3363-3366. (1974).
Shaukat, S.S., et al. Effect of Supplemental UV-B Radiation on Germination, Seedling Growth, and Biochemical Responses of Sunflower (*Helianthus annuus* L.). Fuuast Journal of Biology vol. 1, No. 1, pp. 27-33 (2011).
Siddiqui, S. et al. Effect of UV-B radiation on seed germination, plant height, foliage and seed yield of soybean (*Glicine max* L. Merrill), Progressive Agriculture, 2005, vol. 7, pp. 42-45.
Sosa-Flores, V. P. et al. Study of morphological and histological changes in melon plants grown from seeds irradiated with UV-B, Journal of Applied Horticulture, Oct.-Dec. 2104, vol. 16, pp. 199-204.
Tegelberg et al., Red : far-red light ratio and UV-B radiation: their effects on leaf phenolics and growth of silver birch seedlings. Plant, Cell & Environment. 27(8):1005-1013 (2004).
Tepfer et al. Survival of Plant Seeds, Their UV Screens, and nptll DNA for 18 Months Outside the International Space Station. Astrobiology 12:517-528 (2012).
U.S. Appl. No. 14/857,486 Advisory Office Action dated Jul. 27, 2018.
U.S. Appl. No. 14/857,486 Non-Final Office Action dated Jun. 16, 2017.
U.S. Appl. No. 14/857,486 Office Action dated May 16, 2019.
U.S. Appl. No. 15/117,157 Office Action dated Apr. 3, 2019.
U.S. Appl. No. 15/125,698 Office Action dated Apr. 25, 2019.
U.S. Appl. No. 14/857,486 Non-Final Office Action dated Apr. 18, 2018.
Vallad et al. Systemic Acquired Resistance and Induced Systemic Resistance in Conventional Agriculture, Crop Science, vol. 44, Nov.-Dec. 2004.
Vyn, T.J. et al. Potassium fertilization effects on isoflavone concentrations in soybean [*Glycine max* (L.) Merr.], Journal of Agricultural and Food Chemistry, 2002, vol. 50, pp. 3501-3506.
Wargent, J.J. et al. Increased exposure to UV-B radiation during early development leads to enhanced photoprotection and improved long-term performance in *Lactuca sativa*, Plant, Cell & Environment, 2011, vol. 34, pp. 1401-1413.
Wu, M. et al. Computational Evidence for the Role of *Arabidopsis thaliana* UVR8 as UV-B Photoreceptor and Identification of Its Chromophore Amino Acids, Journal of Chemical Information and Modeling, 2011, vol. 51, pp. 1287-1295.
Zoratti et al. Light-controlled flavonoid biosynthesis in fruits. Frontiers in Plant Science 5(534):16 pgs (2014).
Gaska et al., Post-Harvest Produce Preservation using Deep UV LED Technology. Biotech, Biomaterials and Biomedical. TechConnect Briefs: 9-12 (2016).
Pang et al., UV-B-Inducible and Temperature-Sensitive Photoreactivation of Cyclobutane and Pyrimidine Dimers in *Arabidopsis thaliana*. Plant Physiology 536-543 (1991).
PCT/IB2018/001056 International Preliminary Report on Patentability dated Feb. 25, 2020.
Poulson et al., Enhanced tolerance of photosynthesis to high-light and drought stress in Pseudotsuga menziesii seedlings grown in ultraviolet-B radiation. Tree Physiology 22(12): 829-838 (2002).

(56) References Cited

OTHER PUBLICATIONS

U.S. Appl. No. 16/727,752 Non-Final office Action dated Mar. 30, 2021.
Yang et al., Ultraviolet-B irradiation-induced freezing tolerance in relation to antioxidant system in winter wheat (*Triticum aestivum* L.) leaves. Environmental and Experimental Botany 60(3): 300-307 (2007).

* cited by examiner

METHODS OF SEED TREATMENT AND RESULTING PRODUCTS

CROSS-REFERENCE

This application is a national stage entry of International Application No. PCT/IB2017/001152, filed Aug. 21, 2017, which claims the benefit of U.S. Provisional Application No. 62/377,909 filed on Aug. 22, 2016, which is incorporated herein by reference in its entirety.

BACKGROUND

There is an important societal and commercial impetus to find ways of improving yield and quality of crops, primarily for human consumption in a safe and sustainable manner. There is an aim to move away from chemical agents or pesticides. The method of treating a seed for sowing with UV-B irradiation is described as an effective method in improving plant performance.

BRIEF DESCRIPTION OF THE DRAWINGS

A better understanding of the features and advantages of the present disclosure will be obtained by reference to the following detailed description that sets forth illustrative embodiments, in which the principles of the present disclosure are utilized, and the accompanying drawings.

DETAILED DESCRIPTION

The present technology relates to treating a seed for sowing with UV-B irradiation. Described herein are methods, compositions, and devices for administering UV-B irradiation to seeds for sowing. These methods, compositions, and devices allow for improvement in yield and quality of crops, in some instances through concurrent increase in both hardiness and growth of plants germinating from treated seeds.

Through practice of the methods herein, seeds are treated with at least one UV-B dose so as to trigger both increased hardiness, manifest in increased tolerance to biotic or abiotic stress, and increased growth in the absence of such stress, such that overall yield is increased both in the presence and in the absence of abiotic stress relative to plants grown from comparable untreated seeds.

Methods and Compositions for Administering UV-B

Provided herein are methods and devices for improving plant performance and hardiness of a plant material. In some instances, methods and devices comprise administering UV-B irradiation to a plant material. The plant material may include a seed for sowing, a seedling, or a plant. Various conditions for UV-B administration are contemplated herein.

Figure 1:
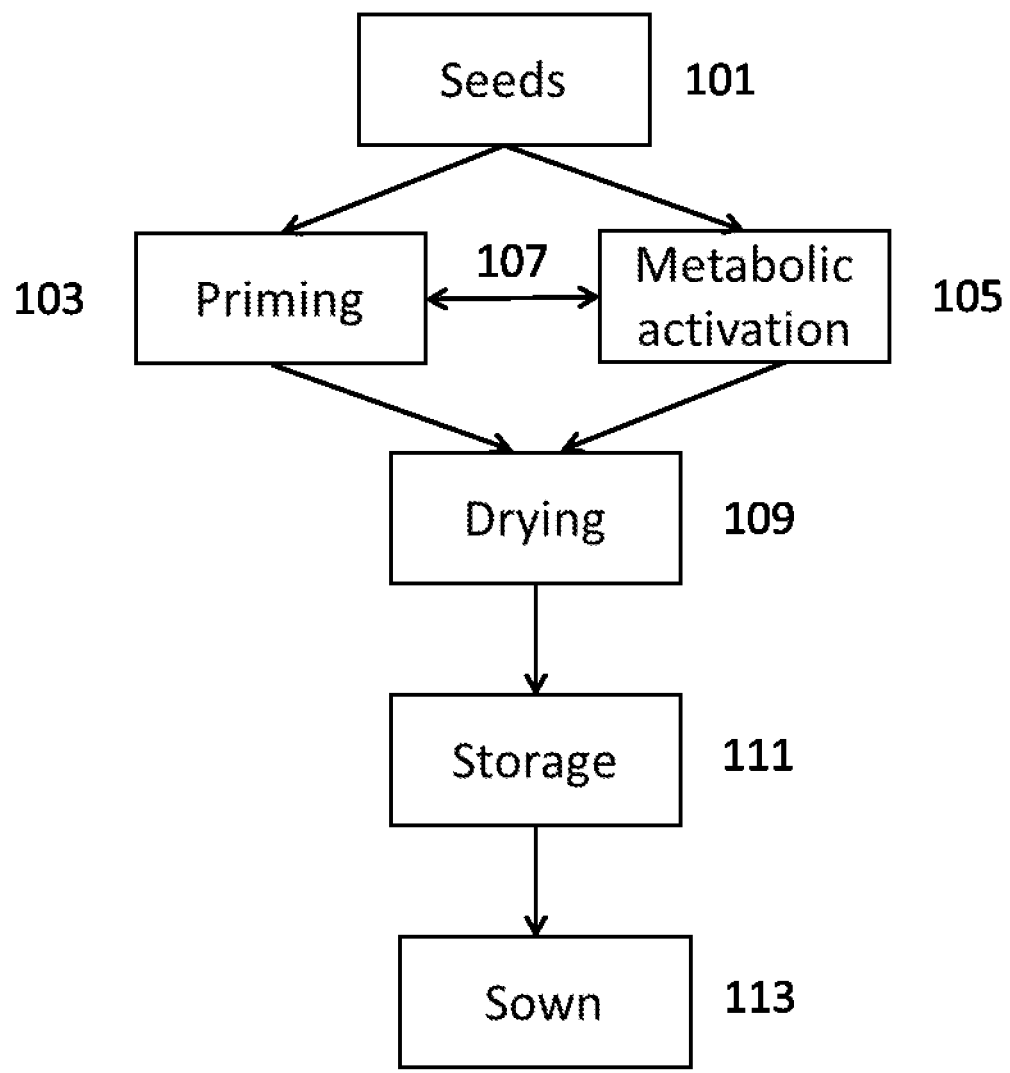
FIG. 1 depicts a schema for UV-B administration.

An exemplary process for administering UV-B is depicted in FIG. 1. Seeds 101 are subject to priming 103 and metabolic activation 105. In some instances, priming 103 and metabolic activation 105 occur simultaneously 107. In some instances, priming 103 occurs prior to metabolic activation 105. Metabolic activation 105 may occur by administration of light enriched for UV-B. Various doses and irradiance of UV-B may be administered to the seeds 101. In some instances, duration of at least one of priming and administration of UV-B varies. Following priming 103 and metabolic activation 105, the seeds 101 are subject to drying 109 and storage 111. In some instances, drying 109 comprises reducing internal moisture of the seeds. In some instances, storage 111 comprises bagging the seeds 101. In some instances, the seeds 101 are bagged for sale. In some instances the bagged seeds are stored for at least 1, 2, 3, 4 or more than 4 weeks, or at least 1, 2, 3, 4, 5, 6, or more than 6 months, or at least 1 year. The seeds 101 are then sown 113, for example in a field.

Often UV-B radiation is administered in a UV-B waveband in a range of about 280 nm to about 320 nm. In some cases, UV-B is administered at 280 nm (±5 nm), 286 nm (±5 nm), 294 nm (±5 nm), or about 317 nm. The UV-B can be about 280 nm, about 281 nm, about 282 nm, about 283 nm, about 284 nm, about 285 nm, about 286 nm, about 287 nm, about 288 nm, about 289 nm, about 290 nm, about 291 nm, about 292 nm, about 293 nm, about 294 nm, about 295 nm, about 296 nm, about 297 nm, about 298 nm, about 299 nm, about 300 nm, about 301 nm, about 302 nm, about 303 nm, about 304 nm, about 305 nm, about 306 nm, about 307 nm, about 308 nm, about 309 nm, about 310 nm, about 311 nm, about 312 nm, about 313 nm, about 314 nm, about 315 nm, about 316 nm, about 317 nm, about 318 nm, about 319 nm, or about 320 nm.

A number of UV-B administration durations are consistent with the disclosure herein. For example, a length of time of UV-B irradiation is up to 72 hours, up to 60 hours, up to 48 hours, up to 36 hours, up to 24 hours, up to 23, hours, up to 22 hours, up to 21 hours, up to 20 hours, up to 19 hours, up to 18 hours, up to 17 hours, up to 16 hours, up to 15 hours, up to 14 hours, up to 13 hours, up to 12 hours, up to 11 hours, up to 10 hours, up to 9 hours, up to 8 hours, up to 7 hours, up to 6 hours, up to 5 hours, up to 4 hours, up to 3 hours, up to 2 hours, up to 1 hour, or less than one hour. In some cases, UV-B irradiation for about 40 minutes or exactly 40 minutes is used. In some instances, UV-B treatment is 9 hours. Often UV-B treatment is about 1 hour, 2 hours, 3 hours, 4 hours, 5 hours, 6 hours, 7 hours, 8 hours, 9 hours, 10 hours, 12 hours, 14 hours, 16 hours, 18 hours, 20 hours, 24 hours, 30 hours, 32 hours, 50 hours, 72 hours, or more than 72 hours. Some treatments are for less than about or at least 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, 30 minutes, 31 minutes, 32 minutes, 33 minutes, 34 minutes, 35 minutes, 36 minutes, 37 minutes, 38 minutes, 39 minutes, 40 minutes, 41 minutes, 42 minutes, 43 minutes, 44 minutes, 45 minutes, 46 minutes, 47 minutes, 48 minutes, 49 minutes, 50 minutes, 51 minutes, 52 minutes, 53 minutes, 54 minutes, 55 minutes, 56 minutes, 57 minutes, 58 minutes, 59 minutes, 60 minutes, or more than 60 minutes. In some instances, UV-B administration duration is in a range of about 0 hours to about 60 hours or about 5 hours to about 30 hours. In some instances, UV-B administration duration is about 18 hours. In some instances, UV-B administration duration is about 20 hours. In some instances, UV-B administration duration is about 21 hours. In some instances, UV-B administration duration is about 24 hours. In some instances, UV-B administration duration is about 27 hours. In some instances, UV-B administration duration is about 28 hours.

UV-B administration may be accomplished in a single dose. In some embodiments, the UV-B administration is a single or multitude time point treatment. In cases of multitude time point treatment, UV-B administration may be separated by any appropriate interval. In some instances, UV-B administration is separated by intervals of less than, about, exactly or at least 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, 30 minutes, 31 minutes, 32 minutes, 33 minutes, 34 minutes, 35 minutes, 36 minutes, 37 minutes, 38 minutes, 39 minutes, 40 minutes, 41 minutes, 42 minutes, 43 minutes, 44 minutes, 45 minutes, 46 minutes, 47 minutes, 48 minutes, 49 minutes, 50 minutes, 51 minutes, 52 minutes, 53 minutes, 54 minutes, 55 minutes, 56 minutes, 57 minutes, 58 minutes, 59 minutes, or 60 minutes. In some instances, UV-B administration is separated by intervals of or less than, about, exactly or at least 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 49 hours, 50 hours, 51 hours, 52 hours, 53 hours, 54 hours, 55 hours, 56 hours, 57 hours, 58 hours, 59 hours, 60 hours, or more than 60 hours.

Administration of UV-B may result in metabolic activation. In some instances, UV-B induced metabolic activation is in a seed for sowing. In some instances, UV-B induced metabolic activation results in increased germination in a plurality of seeds. In some instances, UV-B induced metabolic activation results in at least one of improved plant performance and improved hardiness in the seed for sowing and resultant seedlings or crops. Other methods for inducing metabolic activation are contemplated herein. In some instances, metabolic activation is induced using exogenous administration of light, hormones, chemicals, steroids, or vitamins. Exemplary hormones for inducing metabolic activation include, but are not limited to, auxins, cytokinins, abscisic acids, and gibberellins.

UV-B may be administered alone or in combination with light of another wavelength. In some instances, UV-B is co-administered with visible light. In some instances, the visible light comprises or is exclusively at least one of blue and red light. In some cases, visible light is administered at about or up to 500 umol $m^{-2}$ $s^{-1}$. In some instances, visible light is administered at about or up to 400 umol $m^{-2}$ $s^{-1}$, about or up to 300 umol $m^{-2}$ $s^{-1}$, about or up to 200 umol $m^{-2}$ $s^{-1}$, about or up to 100 umol $m^{-2}$ $s^{-1}$, about or up to 50 umol $m^{-2}$ $s^{-1}$, or about or less than 50 umol $m^{-2}$ $s^{-1}$. Often visible light is administered at about 50 umol $m^{-2}$ $s^{-1}$. In some cases, about 20 umol $m^{-2}$ $s^{-1}$ of visible light is administered. Often the visible light can have a photon number in a range of 10 $m^{-2}$ $s^{-1}$-550 $m^{-2}$ $s^{-1}$, 20 $m^{-2}$ $s^{-1}$-500 $m^{-2}$ $s^{-1}$, 40 $m^{-2}$ $s^{-1}$, 450 $m^{-2}$ $s^{-1}$, 45 $m^{-2}$ $s^{-1}$-400 $m^{-2}$ $s^{-1}$, 50 $m^{-2}$ $s^{-1}$-350 $m^{-2}$ $s^{-1}$, 100 $m^{-2}$ $s^{-1}$-300 $m^{-2}$ $s^{-1}$, or 100 $m^{-2}$ $s^{-1}$-200 umol $m^{-2}$ $s^{-1}$.

UV-B may be co-administered with UV-A treatment, alone or in combination with visible light administration.

Duration of light administration such as visible light and UV-A may vary. In some instances, duration of light administration is up to 72 hours, up to 60 hours, up to 48 hours, up to 36 hours, up to 24 hours, up to 23, hours, up to 22 hours, up to 21 hours, up to 20 hours, up to 19 hours, up to 18 hours, up to 17 hours, up to 16 hours, up to 15 hours, up to 14 hours, up to 13 hours, up to 12 hours, up to 11 hours, up to 10 hours, up to 9 hours, up to 8 hours, up to 7 hours, up to 6 hours, up to 5 hours, up to 4 hours, up to 3 hours, up to 2 hours, up to 1 hour, or less than one hour. In some cases, duration of light administration for about 40 minutes or exactly 40 minutes is used. In some instances, duration of light administration is 9 hours. In some instances, duration of light administration is about 1 hour, 2 hours, 3 hours, 4 hours, 5 hours, 6 hours, 7 hours, 8 hours, 9 hours, 10 hours, 12 hours, 14 hours, 16 hours, 18 hours, 20 hours, 24 hours, 30 hours, 32 hours, 50 hours, 72 hours, or more than 72 hours. Some treatments are for less than about or at least 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, 30 minutes, 31 minutes, 32 minutes, 33 minutes, 34 minutes, 35 minutes, 36 minutes, 37 minutes, 38 minutes, 39 minutes, 40 minutes, 41 minutes, 42 minutes, 43 minutes, 44 minutes, 45 minutes, 46 minutes, 47 minutes, 48 minutes, 49 minutes, 50 minutes, 51 minutes, 52 minutes, 53 minutes, 54 minutes, 55 minutes, 56 minutes, 57 minutes, 58 minutes, 59 minutes, 60 minutes, or more than 60 minutes. In some instances, duration of light administration is in a range of about 0 hours to about 60 hours or about 5 hours to about 30 hours. In some instances, duration of light administration is about 18 hours. In some instances, duration of light administration is about 20 hours. In some instances, duration of light administration is about 21 hours. In some instances, duration of light administration is about 24 hours. In some instances, duration of light administration is about 27 hours. In some instances, duration of light administration is about 28 hours.

In some instances, when UV-B is co-administered with light of another wavelength, UV-B is enriched as compared to the light of another wavelength. In some instances, UV-B is enriched at least or about 15%, 20%, 25%, 30%, 35%, 40%, 45%, 50%, 60%, 70%, 80%, 90%, 100%, 125%, 150%, 175%, 200%, 225%, 250%, 275%, 300%, or more than 300% more than the light of another wavelength. In some instances, UV-B is supplemented. In some instances, UV-B is the predominant wavelength during light administration. In some instances, UV-B comprises at least or about 15%, 20%, 25%, 30%, 35%, 40%, 45%, 50%, 60%, 70%, 80%, 90%, 100% of light for light administration.

Provided herein are methods and devices relating to UV-B administration, wherein UV-B is administered following a seed priming process or during a seed priming process. In some instances, UV-B is administered during such as concurrently with the seed priming process. In some instances, the seed priming process comprises methods for improving subsequent seed germination. In some instances, priming is at least one of hydropriming, osmopriming, redox priming, chemical priming, and hormonal priming. In some instances, priming comprises methods for affecting the osmotic potential or water potential of a seed environment. In some instances, methods affecting osmotic potential or water potential comprise a priming medium. In some instances, the priming medium is water. In some instances, the water is distilled water. In some instances, priming comprises a chemical that affects osmotic potential. For example, polyethylene glycol is used as a priming medium. Non-limiting examples of priming media include, but are not limited to, glycerol, mannitol, saline, and water. In some instances, the seed priming process includes treatment with an osmoticum, which helps to manage the seed hydration process.

In some instances, seeds are primed while being fully submerged. Seeds are often primed or stratified in seed trays with a water level that is maintained at about 1-2 mm above fully submerged seeds. In some cases, any floating seeds are tapped down until fully submerged.

Priming duration may vary. In some instances, priming duration is at least or about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 49 hours, 50 hours, 51 hours, 52 hours, 53 hours, 54 hours, 55 hours, 56 hours, 57 hours, 58 hours, 59 hours, 60 hours, or more than 60 hours. In some instances, priming duration is in a range of about 8 hours to about 44 hours. In some instances, priming duration is about 8 hours. In some instances, priming duration is about 18 hours. In some instances, priming duration is about 19.5 hours. In some instances, priming duration is about 20 hours. In some instances, priming duration is about 24 hours. In some instances, priming duration is about 27 hours. In some instances, priming duration is about 44 hours.

In some cases, the seeds are primed in at least one of the dark, light, and visible light.

Often the seeds are primed in a plant growth chamber at a desirable temperature. In some cases, the seeds are primed at about 25° C. In some instances, the seeds are primed at about 22° C. In some instances, the seeds are primed at about 10° C. The seeds may be primed at least at or about 10° C., 12° C., 15° C., 18° C., 20° C., 22° C., 25° C., 27° C., 30° C., 35° C., 40° C., 50° C., or more than 50° C. The seeds may be primed at most 10° C., 12° C., 15° C., 18° C., 20° C., 22° C., 25° C., 27° C., 30° C., 35° C., 40° C., or 50° C. The seeds may be primed at a temperature range of about 10° C.-50° C., 15° C.-30° C., 18° C.-25° C., or 20° C.-30° C.

The seeds may be primed at a suitable relative humidity. In some instances, the seeds are primed at a relative humidity of about 95%. The seeds may be primed at a relative humidity of at least or about 10%, 20%, 30%, 40%, 50%, 60%, 70%, 80%, 90%, 95%, 99%, or greater. Alternately, the seeds may be primed at a relative humidity of at most 10%, 20%, 30%, 40%, 50%, 60%, 70%, 80%, 90%, 95%, 99%, or 100%. The seeds may be primed at a relative humidity ranged from about 10%-100%, 15%-90%, 20%-80%, 30%-70%, 40%-60, 45%-75%, 50%-60%, 70%-90%, 85%-95%, or 95%-99%.

In some cases, the UV-B irradiation is administered following an initial water hydration process, which the different levels of hydration or priming medium may be fine-tuned during treatment regimes. Often the seeds are washed under cold water in order to remove the red fungicide coating and prepare the seeds for priming or otherwise stratified prior to treatment.

Provided herein are methods and devices related to UV-B administration, wherein a plant material is arranged during UV-B administration to increase UV-B irradiation efficacy. In some instances, the plant material comprises seeds. In some instances, the seeds are arranged in which the embryo is positioned to increase UV-B irradiation efficacy. In some cases, the seeds are arranged with the embryo-side up in order to increase UV-B irradiation efficacy. In some instances, seeds are positioned on a moist surface during UV-B administration. For example, the most surface is a moist filter paper. In some instances, seeds are submerged in medium during UV-B administration.

In some instances, seeds are arranged in trays during UV-B irradiation. The seeds may be split across many trays in order to reduce pseudo-replication. In some cases, the seeds are arranged on trays in order to maximize or increase the efficacy of UV-B irradiation.

Consistent therewith, trays are disclosed having grooves such that a population of seeds distributed in the tray are oriented so as to maximize the efficacy of UV-B irradiation. In some cases, the tray grooves direct the seeds such that, for example, upon gentle administration of agitation to the tray, the seeds fall into an orientation such that they are positioned to maximize or increase UV-B administration efficacy. In various embodiments, trays are variously configured to accommodate seeds from a diversity of plant crops, such as maize, lettuce, rice, sorghum, cotton, alfalfa, wheat, or any other crop or ornamental seed plant disclosed herein.

Following priming or at any time during treatment, the seeds may be stored. In some cases, the seeds are stored in a container at about or exactly 4° C. In some cases, seeds are subsequently stored for over 1 hour, 2 hours, 3 hours, 4 hours, 5 hours, 6 hours, 7 hours, 8 hours, 9 hours, 10 hours, 12 hours, 15 hours, 20 hours, 24 hours, or more than 24 hours. The seeds may be kept in a refrigerator for over 24 hours. The seeds are variously kept at a temperature in a range of about 15° C.-40° C., 18° C.-25° C., 20° C.-22° C., or 24° C.-28° C., or various permutations thereof. The seeds may be kept at room temperature. The seeds may be kept at room temperature or a temperature mentioned above for over 1 hour, 2 hours, 3 hours, 4 hours, 5 hours, 6 hours, 7 hours, 8 hours, 9 hours, 10 hours, 12 hours, 15 hours, 20 hours, 24 hours, or more than 24 hours. The seeds may be kept in a refrigerator for over 24 hours. The seeds may be kept at room temperature or a temperature mentioned above for over 24 hours. The seeds may be kept at a relative humidity in a range of about 30%-100%, 40%-95%, 50%-90%, 60%-85%, 65%-'75%, 70%-80%, or 45%-55%. In some instances, the seeds are stored in a bag. In some instances, the seeds are stored in a bag prior to being sown. The seeds may be stored in a bag for any suitable time prior to being sown. In various embodiments the seeds are stored for at least 1 hour, 10 hours, 24 hours, 1 day, 2 days, 3 days, 4 days, 5 days, 6 days, 7 days, 2 weeks, 3 weeks, 1 month, 2 months, 3 months, 4 months, 5 months, 6 months, 7 months, 8 months, 9 months, 10 months, 11 months, 1 year, 2 year, or more than 2 years.

Provided herein are methods and devices relating to administration of UV-B, wherein light is administered using a light source. The light source may administer light of various wavelengths. For example, the light source is configured to emit one or more wavelengths of light in a range of about 300 nm and about 800 nm. In some instances, the light source emits one or more wavelengths in a range of about 280 nm to about 320 nm. In some instances, one or more light sources are used to emit the one or more wavelengths of light. The light source may be selected from the group consisting of a light emitting diode (LED), a laser, an incandescent light bulb, and a gas discharge bulb.

In some instances, the light source is a LED. Often LED lights are configured to administer a peak irradiance wavelength of light, for instance at about 280 nm, a range within 10 nm, 9 nm, 8 nm, 7 nm, 6 nm, 5 nm, 4 nm, 3 nm, 2 nm, or 1 nm of 280 nm, or exactly 280 nm, at about 286 nm, a range within 10 nm, 9 nm, 8 nm, 7 nm, 6 nm, 5 nm, 4 nm, 3 nm, 2 nm, or 1 nm of 286 nm, or exactly 286 nm. Alternately, LED lights are configured to administer light at a standard white light spectrum which is supplemented by light in the UV-B range, for example at about 280 nm, a range within 10 nm, 9 nm, 8 nm, 7 nm, 6 nm, 5 nm, 4 nm, 3 nm, 2 nm, or 1 nm of 280 nm, or exactly 280 nm, at about 286 nm, a range within 10 nm, 9 nm, 8 nm, 7 nm, 6 nm, 5 nm, 4 nm, 3 nm, 2 nm, or 1 nm of 286 nm, or exactly 286 nm.

LEDs as used herein may be appropriately configured for UV-B administration. In some instances, LED panels are configured at a height of about 80 mm. A LED panel may be arranged above a row of seeds at about 20 mm, 40 mm, 60 mm, 80 mm, 100 mm, 120 mm, 150 mm, or 200 mm height. The LED panel may be arranged at a range of about 20 mm-200 mm, 40 mm-150 mm, 60 mm-120 mm, or 80 mm-100 mm. Often the distance between UV panels is about 10 mm. In some cases, the distance between UV panels is about 1 mm, 2 mm, 3 mm, 4 mm, 5 mm, 6 mm, 7 mm, 8 mm, 9 mm, 10 mm, 12 mm, 15 mm, or 20 mm. Alternately, the distance between UV panels is in a range of about 1 mm-20 mm, 2 mm-15 mm, 3 mm-10 mm, or 4 mm-9 mm. Often the minimum distance between UV and control panels is about 400 mm. In some instances, the minimum distance between the UV and central panels is about 50 mm, 100 mm, 150 mm, 200 mm, 250 mm, 300 mm, 350 mm, 400 mm, 450 mm, 500 mm, 600 mm, 700 mm, or 800 mm. Alternately, the distance between the UV and central panels is in a range about 50 mm-800 mm, 100 mm-700 mm, 150 mm-600 mm, 200 mm-500 mm, or 250 mm-400 mm.

In some cases, the seed trays are placed directly below LED panels at a height of about 8 cm or within a range of 7 cm, 6 cm, 5 cm, 4 cm, 3 cm, 2 cm, and 1 cm and at about or at least 20 cm between each treatment in order to prevent direct irradiance from adjacent treatments and covered before start of the treatment. In some cases, a distance between each treatment is in a range of about 20 cm-200 cm, 30 cm-100 cm, or 40 cm-90 cm. Often evaporated water is replaced, and the lid is removed prior to light treatment. Various LED configurations are consistent with the disclosure herein, and as is known to one of skill in the art, light intensity and distance from seeds can be varied in concert such that the total, mean or average dosage of UV-B light remains constant.

Following light treatment, the seeds are often dried using a paper towel to remove excess water and then air dried for 72 hours. The seeds may be dried with a paper towel then left to air dry for less than, about, exactly, or at least 12 hours, 24 hours, 36 hours, 48 hours, 60 hours, 72 hours, 84 hours, 96 hours, or more hours. In some cases, the seeds are subsequently stored and covered.

In some instances, seeds are dried after priming and concurrent administration of UV-B. In some instances, the seeds are dried to reduce an internal moisture of the seed. In some instances, the seeds are dried using air, reducing humidity, adjusting a temperature, or using a desiccant such as silica gel. In some instances, the seeds are dried to a determined internal moisture. For example, the seeds are dried to at most or about 2%, 3%, 4%, 5%, 6%, 7%, 8%, 9%, 10%, 12%, 15%, 18%, 20%, 25%, 30%, 35%, 40%, 45%, 50%, 55%, 60%, 65%, 70%, or more than 70% internal moisture. Drying the seed may occur any time following priming and concurrent administration of UV-B to the seeds. In some instances, the seeds are dried prior to being sown. In some instances, the seeds are dried prior to being germinated. The seeds may be dried for at least or about 5 minutes, 10 minutes, 20 minutes, 30 minutes, 45 minutes, 1 hour, 2 hours, 3 hours, 4 hours, 5 hours, 6, hours, 7 hours, 8 hours, 9, hours, 10 hours, 12 hours, 24 hours, 36 hours, 48 hours, 60 hours, 72 hours, 84 hours, 96 hours, or more than 96 hours prior to being sown or germinated.

Following drying of a seed or reducing internal moisture of the seed, the seed may be stored. In some instances, the seed is stored and bagged. In some instances, the seed is bagged for sale. The seed may be stored and bagged for any suitable period of time. For example, the seeds are stored and bagged for at least 1 hour, 10 hours, 24 hours, 1 day, 2 days, 3 days, 4 days, 5 days, 6 days, 7 days, 2 weeks, 3 weeks, 1 month, 2 months, 3 months, 4 months, 5 months, 6 months, 7 months, 8 months, 9 months, 10 months, 11 months, 1 year, 2 year, or more than 2 years.

UV-B treatment may be initiated at different time-points or durations. For instance, UV-B treatment is variously applied to at least one of prior to seed hydration, prior to seed germination, during initial germination (e.g. following moisture application for seed germination), and during a priming treatment. In some instances, UV-B is administered during seed priming.

In some embodiments, the germination temperature may vary.

Various dosages of UV-B are contemplated herein. In some instances, the dosage is in the range of about 0.01 kJ m$^{-2}$ to about 368 kJ m$^{-2}$. In some instances, the dosage is about 0.01 kJ m$^{-2}$-368 kJ m$^{-2}$, 0.1 kJ m$^{-2}$-300 kJ m$^{-2}$, 1 kJ m$^{-2}$-250 kJ m$^{-2}$, 10 kJ m$^{-2}$-200 kJ m$^{-2}$, 100 kJ m$^{-2}$-150 kJ m$^{-2}$, 200 kJ m$^{-2}$-300 kJ m$^{-2}$, 250 kJ m$^{-2}$-350 kJ m$^{-2}$, or 300 kJ m$^{-2}$-368 kJ m$^{-2}$. In some instances, the dosage is in the range of about 0.1 to about 12 kJ m$^{-2}$. In some instances, the dosage is about 13 kJ m$^{-2}$. The light treatment may be at a dose of about 13 kJ m$^{-2}$, exactly 13 kJ m$^{-2}$, or at least 13 kJ m$^{-2}$. In some instances, the dosage is about 37 kJ m$^{-2}$. In some instances, the dosage is about 69 kJ m$^{-2}$. In some instances, the dosage is about 78 kJ m$^{-2}$. In some instances, the dosage is about 98 kJ m$^{-2}$. In some instances, the dosage is about 100 kJ m$^{-2}$. The light treatment may be at a dose of about 100 kJ m$^{-2}$, exactly 100 kJ m$^{-2}$, or more than 100 kJ m$^{-2}$. In some instances, the dosage is about 125 kJ m$^{-2}$. In some instances, the dosage is about 204 kJ m$^{-2}$. The light treatment may be at a dose range of about 13 kJ m$^{-2}$ to 100 kJ m$^{-2}$. The UV-B can be at a dose in a range of about 1 kJ m$^{-2}$-1000 kJ m$^{-2}$, 10 kJ m$^{-2}$-800 kJ m$^{-2}$, 20 kJ m$^{-2}$-600 kJ m$^{-2}$, 30 kJ m$^{-2}$-400 kJ m$^{-2}$, 50 kJ m$^{-2}$-200 kJ m$^{-2}$, 100 kJ m$^{-2}$-150 kJ m$^{-2}$, 30 kJ m$^{-2}$-60 kJ m$^{-2}$, or 150 kJ m$^{-2}$-250 kJ m$^{-2}$. In some instances, the UV-B is in a range of 0 kJ m$^{-2}$-20 kJ m$^{-2}$, 20 kJ m$^{-2}$-40 kJ m$^{-2}$, 40 kJ m$^{-2}$-60 kJ m$^{-2}$, 60 kJ m$^{-2}$-80 kJ m$^{-2}$, or 80 kJ m$^{-2}$-100 kJ m$^{-2}$.

Various irradiances of UV-B may be used. In some cases, the irradiance is in a range of about $4\times10^{-5}$ W cm$^{-2}$ s$^{-1}$ to about $1.3 \times 10^{-4}$ W cm$^{-2}$ s$^{-1}$. The irradiance range can be at about $4 \times 10^{-5}$ W cm$^{-2}$ s$^{-1}$, exactly $4 \times 10^{-5}$ W cm$^{-2}$ s$^{-1}$, or at least $4 \times 10^{-5}$ W cm$^{-2}$ s$^{-1}$. In some cases, the irradiance is in a range of about $1.3 \times 10^{-4}$ W cm$^{-2}$ s$^{-1}$ exactly $1.3 \times 10^{-4}$ W cm$^{-2}$ s$^{-1}$ or more than $1.3 \times 10^{-4}$ W cm$^{-2}$ s$^{-1}$. The irradiance range can be about $4 \times 10^{-5}$ W cm$^{-2}$ s$^{-1}$-$6 \times 10^{-5}$ W cm$^{-2}$ s$^{-1}$, $6 \times 10^{-5}$ W cm$^{-2}$ s$^{-1}$-$8 \times 10^{-5}$ W cm$^{-2}$ s$^{-1}$, $8 \times 10^{-5}$ W cm$^{-2}$ s$^{-1}$-$1 \times 10^{-4}$ W or $1 \times 10^{-4}$ W cm$^{-2}$ s$^{-1}$-$1.5 \times 10^{-5}$ W cm$^{-2}$ s$^{-1}$. Dosage may change in relation to treatment protocols such as hydration protocols.

In some cases, UV half bandwidth size varies.

In some cases, UV-B is administered to a plant prior to seed harvest from the plant to be subsequently used for sowing. The effective dosage for a growing plant may differ to that of a harvested seed due to differences in physiology. Alternately, the UV-B treatment is applied to a plant prior to seed harvest from the plant for subsequent plant breeding applications as opposed to plant/crop performance.

Various treatment conditions and combinations of treatments described previously may be used. The treatment conditions may comprise, but are not limited to, priming method, temperature, UV-B dosage, UV-B irradiance, and plant material position during UV-B administration. In some instances, treatment conditions may comprise 1 condition, 2 conditions, 3 conditions, 4 conditions, more than 4 conditions, and permutations and combinations thereof. In some instances, a priming method varies. For example, seeds are primed in water or in polyethylene glycol. In some instances, a temperature of a growth chamber varies. In some instances, the temperature of the growth chamber is at least or about 10° C., 12° C., 14° C., 16° C., 18° C., 20° C., 22° C., 24° C., 26° C., 28° C., or 30° C. UV-B may be administered in a growth chamber of about 22° C. or about 10° C. In some instances, a dosage of UV-B varies. In some instances, the dosage is in a range of about 30 kJ m$^{-2}$ to about 250 kJ m$^{-2}$. In some instances, UV-B irradiance varies. For example, irradiance is administered in a range of about 40 uW cm$^{-2}$ to about 200 uW cm$^{-2}$. In some instances, irradiance is administered in a range of about 1.5 umol m$^{-1}$ s$^{-1}$ to about 8 umol m$^{-1}$ s$^{-1}$. In some instances, irradiance is administered at least or about 1.5 umol m$^{-1}$ s$^{-1}$, 2 umol m$^{-1}$ s$^{-1}$, 2.5 umol m$^{-1}$ s$^{-1}$, 3 umol m$^{-1}$ s$^{-1}$, 3.5 umol m$^{-1}$ s$^{-1}$, 4 umol m$^{-1}$ s$^{-1}$, 4.5 umol m$^{-1}$ s$^{-1}$, 5 umol m$^{-1}$ s$^{-1}$, 5.5 umol m$^{-1}$ s$^{-1}$, 6 umol m$^{-1}$ s$^{-1}$, 6.5 umol m$^{-1}$ s$^{-1}$, 7 umol m$^{-1}$ s$^{-1}$, 7.5 umol m$^{-1}$ s$^{-1}$, 8 umol m$^{-1}$ s$^{-1}$, 8.5 umol m$^{-1}$ s$^{-1}$, 9 umol m$^{-1}$ s$^{-1}$, 9.5 umol m$^{-1}$ s$^{-1}$, 10 umol m$^{-1}$ s$^{-1}$, or more than 10 umol m$^{-1}$ s$^{-1}$. In some instances, a duration of UV-B administration varies. Duration of UV-B administration may include at least or about 1 hour, 2 hours, 3 hours 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, or more than 30 hours. In some instances, UV-B duration is about 8 hours, about 18 hours, about 20 hours, about 21 hours, about 24 hours, about 27 hours or about 28 hours. A position of a seed during UV-B administration may vary. In some instances, seeds are placed on a moist surface during UV-B administration. In some instances, seeds are submerged in priming medium during UV-B administration.

In one embodiment, treatment conditions comprise priming seeds in distilled water and submerging seeds in the priming medium during administration of UV-B for a duration in a range of about 8 hours to about 44 hours in a growth chamber of about 22° C. In one embodiment, treatment conditions comprise priming seeds in distilled water and administering UV-B for a duration in a range of about 8 hours to about 44 hours in a growth chamber of about 10° C. while seeds are placed on top of a moist filter paper. In one embodiment, treatment conditions comprise priming seeds in distilled water and submerging seeds in the priming medium during administration of UV-B for a duration in a range of about 8 hours to about 44 hours in a growth chamber of about 10° C. In one embodiment, treatment conditions comprise priming seeds in polyethylene glycol and submerging seeds in the priming medium during administration of UV-B for a duration in a range of about 8 hours to about 44 hours in a growth chamber of about 22° C. In one embodiment, treatment conditions comprise priming seeds in polyethylene glycol and submerging seeds in the priming medium during administration of UV-B for a duration in a range of about 8 hours to about 44 hours and using an irradiance in a range of about 40 uW cm$^{-2}$ to about 200 uW cm$^{-2}$ in a growth chamber of about 10° C. In one embodiment, treatment conditions comprise priming seeds in polyethylene glycol and submerging seeds in the priming medium during administration of UV-B for a duration in a range of about 8 hours to about 44 hours in a growth chamber of about 10° C.

Any one of the methods described herein may be performed in a suitable environment. Methods described herein include, but are not limited to, priming a plant material and administering UV-B. For example, any one of the methods may occur indoors, for example, a greenhouse. In some instances, UV-B is administered indoors. In some instances, UV-B is administered outdoors. In some instances, UV-B is administered outdoors in a field. In some instances, plant material is primed indoors followed by transplantation outdoors for subsequent growth.

Plant performance in plant material treated using methods as described herein may result in improved plant performance as compared to the counterpart plant material that has not been treated. In some instances, hardiness of the plant material is improved using methods as described herein. In some instances, the plant material is a seed. In some instances, following UV-B treatment of seeds as described herein, resultant seedlings or plants demonstrate improved plant performance.

In some instances, plant performance is improved in a resultant seedling from seeds irradiated using UV-B. In some instances, plant performance in resultant seedlings comprising at least one of flavonoid levels, anthocyanin levels, size, dry weight, nitrogen index, shoot dry weight, shoot fresh weight, shoot length, radical length, pigment production, leaf size, hypocotyl length, chlorophyll level, leaf area, and root dry weight is improved in seedlings from seeds irradiated with UV-B as described herein. In some instances, improved plant performance in seedlings is an elevated level of at least one of flavonoid levels and anthocyanin levels. Plant performance may be measured in seedlings from seeds irradiated with UV-B as described herein prior to sowing.

In some instances, hardiness is improved in resultant seedlings from seeds irradiated using UV-B. The seedlings may comprise improved resilience following at least one of heat, flood, drought, frost, unusual climate events, salinity stress, and high visible light stress. In some instances, improved resilience in seedlings from UV-B irradiated seeds comprises ability to germinate despite exposure to stress. In some instances, the seedlings are inspected following at least one of heat, flood, drought, frost, unusual climate events, salinity stress, and high visible light stress.

At least one of plant performance and hardiness in resultant seedlings from a UV-B irradiated seed may be increased by a significant percentage when compared to a counterpart seedling from a seed that has not been irradiated with a UV-B regimen disclosed herein. At least one of plant performance and hardiness may be increased by about 5%-100%, 10%-90%, 20%-80%, 30%-70%, 40%-60%, 50%-95%, 65%-85%, or 75%-95%. At least one of plant performance and hardiness may be increased by at least about 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, 99%, or 100%. At least one of plant performance and hardiness may be increased by at least 5%. At least one of plant performance and hardiness may be increased by at least 10%. Plant performance or hardiness may be increased by at least 30%. At least one of plant performance and hardiness may be increased by at least 50%.

Plant performance may be improved in resultant plants or crops from seeds irradiated using UV-B. Following UV-B treatment of seeds, seedlings may be planted and plant performance may be measured in a resultant plant or crop. In some instances, plant performance is measured as improvements in at least one of flavonoid levels, anthocyanin levels, size, dry weight, nitrogen index, shoot dry weight, shoot fresh weight, shoot length, radical length, pigment production, leaf size, hypocotyl length, chlorophyll level, leaf area, and root dry weight. In some cases, plant performance in the resultant plants or crops is measured as improved quality comprising at least one of a longer shelf-life, a resistance to bruising or post-harvesting handling, an increased nutrient value, an improved taste, an improved shape, an improved color, an improved size, and an improved texture. Plant performance may be measured in the resultant plants or crops from seeds irradiated with UV-B as described herein during or following sowing.

In some instances, hardiness is improved in a resultant plant or crop from seeds irradiated using UV-B. The plant or crop may comprise improved resilience following at least one of heat, flood, drought, frost, unusual climate events, salinity stress, and high visible light stress. In some instances, improved resilience comprises unaffected or improved growth and survival despite exposure to stress. In some instances, improved resilience comprises improved growth and survival despite exposure to stress as compared to plants or crops from non-UV-B irradiated seeds. In some instances, improved resilience comprises ability to bear fruit despite exposure to stress. In some instances, improved resilience comprises improved ability to bear fruit despite exposure to stress as compared to plants or crops from non-UV-B irradiated seeds. In some instances, the resultant plants or crops is inspected following at least one of heat, flood, drought, frost, unusual climate events, salinity stress, and high visible light stress.

At least one of plant performance and hardiness in resultant plants or crops from a UV-B irradiated seed may be increased by a significant percentage when compared to counterpart plants or crops from a seed that has not been irradiated with a UV-B regimen disclosed herein. At least one of plant performance and hardiness may be increased by about 5%-100%, 10%-90%, 20%-80%, 30%-70%, 40%-60%, 50%-95%, 65%-85%, or 75%-95%. At least one of plant performance and hardiness may be increased by at least about 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, 99%, or 100%. At least one of plant performance and hardiness may be increased by at least 5%. At least one of plant performance and hardiness may be increased by at least 10%. At least one of plant performance and hardiness may be increased by at least 30%. At least one of plant performance and hardiness may be increased by at least 50%.

In some embodiments, a crop planted from a seed that is UV-B irradiated is exposed to stress. In some instances, the stress is a result of heat, flood, drought, frost, unusual climate events, salinity stress, or high visible light stress.

Prior to exposure to stress, a seed that is UV-B irradiated may be prepared prior to UV-B irradiation. In some instances, seeds for sowing are washed in cold water. In some instances, seeds are primed in a growth chamber. For example, the growth chamber is at about 25° C. and 95% humidity. In some instances, a temperature of the growth chamber is at least or about 10° C., 12° C., 14° C., 16° C., 18° C., 20° C., 22° C., 24° C., 26° C., 28° C., or 30° C. In some instances, seeds are primed in a priming medium for a suitable amount of time. The priming medium may be water or polyethylene glycol. In some instances, priming occurs for about 16 hours. Priming may be for about 1 hour, 2 hours, 3 hours, 4 hours, 5 hours, 6 hours, 7 hours, 8 hours, 9 hours, 10 hours, 12 hours, 14 hours, 16 hours, 18 hours, 20 hours, or 24 hours. Following priming or during priming, the seeds are irradiated using UV-B and co-administered visible light, and in other instances, UV-B is administered alone. Often the UV-B waveband is administered in the UV-B waveband at about 280 nm to about 320 nm. In some cases, UV-B is administered at 280 nm (±5 nm). The UV-B can be about 280 nm, 281 nm, 282 nm, 283 nm, 284 nm, 285 nm, 286 nm, 287 nm, 288 nm, 289 nm, 290 nm, 291 nm, 292 nm, 293 nm, 294 nm, 295 nm, 296 nm, 297 nm, 298 nm, 299 nm, 300 nm, 301 nm, 302 nm, 303 nm, 304 nm, 305 nm, 306 nm, 307 nm, 308 nm, 309 nm, 310 nm, 311 nm, 312 nm, 313 nm, 314 nm, 315 nm, 316 nm, 317 nm, 318 nm, 319 nm, or 320 nm. A dosage of UV-B administration may vary. In some cases, the UV-B dose is administered at about 13 kJ $m^{-2}$ for 9 hours. In some instances, UV-B is administered at about 100 kJ $m^{-2}$ for 21 hours. In some cases, the UV-B dose is in a range of about 0 kJ $m^{-2}$-100 kJ $m^{-2}$, 10 kJ $m^{-2}$-90 kJ $m^{-2}$, 20 kJ $m^{-2}$-80 kJ $m^{-2}$, 30 kJ $m^{-2}$-70 kJ $m^{-2}$, and 40 kJ $m^{-2}$-50 kJ $m^{-2}$. Often the visible light can have a photon number in a range of about 10 umol $m^{-2}$ $s^{-1}$-550 umol $m^{-2}$ $s^{-1}$, 20 umol $m^{-2}$ $s^{-1}$-500 umol $m^{-2}$ $s^{-1}$, 40 umol $m^{-2}$ $s^{-1}$-450 umol $m^{-2}$ $s^{-1}$, 45 umol $m^{-2}$ $s^{-1}$-400 umol $m^{-2}$ $s^{-1}$, 50 umol $m^{-2}$ $s^{-1}$-350 umol $m^{-2}$ $s^{-1}$, 100 umol $m^{-2}$ $s^{-1}$-300 umol $m^{-2}$ $s^{-1}$, or 100 umol $m^{-2}$ $s^{-1}$-200 umol $m^{-2}$ $s^{-1}$. UV-B treatment can be a single time or multiple times. Following UV-B treatment, seeds are often dried for 72 hours. The seeds can be dried up to 72 hours, up to 60 hours, up to 48 hours, up to 36 hours, up to 24 hours, up to 12 hours, and up to 6 hours. In some cases, after a suitable time, seedlings are planted. In some instances, seedlings are planted after 1 day, 2 days, 3 days, 4 days, 5 days, 6 days, 1 week, 2 weeks, 3 weeks, 4 weeks, 1 month, 2 months, 3 months, 4 months, 5 months, 6 months, 7 months, 8 months, or more than 8 months. In some instances, seedlings are planted after 4 weeks. Following planting, resultant crops may be exposed to stress such as heat.

In some instances, following stress, plant performance is measured comprising at least one of flavonoid level, anthocyanin level, leaf size, leaf surface area, dry weight, nitrogen content, shoot dry weight, shoot fresh weight, root dry weight, vegetable development, yield of fruiting parts, weight of fruiting parts, hardiness, or seed germination rate. In some cases, plant performance is measured as improved quality comprising at least one of a longer shelf-life, a resistance to bruising or post-harvesting handling, an increased nutrient value, and an improved taste, shape, color, size, and texture. Often following heat stress, plants grown from UV-B irradiated seeds show an increase in plant performance compared to plants grown from non-UV-B irradiated seeds. In an alternate embodiment, the plant is exposed to flood, drought, frost, unusual climate events, salinity stress, and high visible light stress.

Alternately, a plant is exposed to infection. Infection may be caused by organisms including, but not limited to, fungi, oomycetes, bacteria, viruses, viroids, virus-like organisms, phytoplasmas, protozoa, nematodes and parasitic plants. In some cases, following UV-B treatment of seeds as described in the methods herein, plant performance is unaffected or improved despite infections caused by such organisms. In some cases, following UV-B treatment of seeds as described in the methods herein, plant performance is improved despite infections caused by such organisms as compared to non-UV-B irradiated seeds. In some cases, plant performance is inspected for infections caused by such organisms. Often plant performance is inspected for at least one of leaf disease, ear rot disease, stalk rot disease, and seeding and root disease.

In some instances, plant performance is measured by at least one of a reduction in fertilizer, herbicide, insecticide, and pesticide use without affecting crop yield. Reduction to fertilizer, herbicide, insecticide, or pesticide use may be determined by comparison to the industry use for a crop over ten years, to the state-wide average, or the national average. The reduction of fertilizer, use may be at least 5%. In some cases, the reduction of fertilizer is in the range of about 5%-100%, 10%-90%, 20%-80%, 30%-70%, 40%-60%, 50%-95%, 65%-85%, or 75%-95%. In some instances, the reduction of herbicide use is at least 5%. In some cases, the reduction of herbicide is in the range of about 5%-100%, 10%-90%, 20%-80%, 30%-70%, 40%-60%, 50%-95%, 65%-85%, or 75%-95%. In some instances, the reduction of insecticide use is at least 5%. In some cases, the reduction of insecticide is in the range of about 5%-100%, 10%-90%, 20%-80%, 30%-70%, 40%-60%, 50%-95%, 65%-85%, or 75%-95%. In some instances, the reduction of pesticide use is at least 5%. In some cases, the reduction of pesticide is in the range of about 5%-100%, 10%-90%, 20%-80%, 30%-70%, 40%-60%, 50%-95%, 65%-85%, or 75%-95%.

In one embodiment, a plant grown from a UV-B irradiated seed requires less pesticide compared to a plant grown from a non-UV-B irradiated seed. Prior to UV-B irradiation, the seed may be prepared. In some instances, seeds for sowing are washed in cold water. In some instances, seeds are primed in a growth chamber. For example, the growth chamber is at about 25° C. and 95% humidity. In some instances, a temperature of the growth chamber is at least or about 10° C., 12° C., 14° C., 16° C., 18° C., 20° C., 22° C., 24° C., 26° C., 28° C., or 30° C. In some instances, seeds are primed in a priming medium for a suitable amount of time. The priming medium may be water or polyethylene glycol. In some instances, priming occurs for about 16 hours. Priming may be for about 1 hour, 2 hours, 3 hours, 4 hours, 5 hours, 6 hours, 7 hours, 8 hours, 9 hours, 10 hours, 12 hours, 14 hours, 16 hours, 18 hours, 20 hours, or 24 hours. Following priming or during priming, the seeds are irradiated using UV-B and co-administered visible light, and in other instances, UV-B is administered alone. Often the UV-B waveband is administered in the UV-B waveband at about 280 nm to about 320 nm. In some cases, UV-B is administered at 280 nm (±5 nm). The UV-B can be about 280 nm, 281 nm, 282 nm, 283 nm, 284 nm, 285 nm, 286 nm, 287 nm, 288 nm, 289 nm, 290 nm, 291 nm, 292 nm, 293 nm, 294 nm, 295 nm, 296 nm, 297 nm, 298 nm, 299 nm, 300 nm, 301 nm, 302 nm, 303 nm, 304 nm, 305 nm, 306 nm, 307 nm, 308 nm, 309 nm, 310 nm, 311 nm, 312 nm, 313 nm, 314 nm, 315 nm, 316 nm, 317 nm, 318 nm, 319 nm, or 320 nm. A dosage of UV-B administration may vary. In some cases, the UV-B dose is administered at about 13 kJ m$^{-2}$ for 9 hours. In some instances, UV-B is administered at about 100 kJ m$^{-2}$ for 21 hours. In some cases, the UV-B dose is in a range of about 0.1 kJ m$^{-2}$-100 kJ m$^{-2}$, 10 kJ m$^{-2}$-90 kJ m$^{-2}$, 20 kJ m$^{-2}$-80 kJ m$^{-2}$, 30 kJ m$^{-2}$-70 kJ m$^{-2}$, and 40 kJ m$^{-2}$-50 kJ m$^{-2}$. Often the visible light can have a photon number in a range of about 10 umol m$^{-2}$ s$^{-1}$-550 umol m$^{-2}$ s$^{-1}$, 20 umol m$^{-2}$ s$^{-1}$-500 umol m$^{-2}$ s$^{-1}$, 40 umol m$^{-2}$ s$^{-1}$-450 umol m$^{-2}$ s$^{-1}$, 45 umol m$^{-2}$ s$^{-1}$-400 umol m$^{-2}$ s$^{-1}$, 50 umol m$^{-2}$ s$^{-1}$-350 umol m$^{-2}$ s$^{-1}$, 100 umol m$^{-2}$ s$^{-1}$-300 umol m$^{-2}$ s$^{-1}$, or 100 umol m$^{-2}$ s$^{-1}$- 200 umol m$^{-2}$ s$^{-1}$. UV-B treatment can be a single time or multiple times. Following UV-B treatment, seeds are often dried for 72 hours. The seeds can be dried up to 72 hours, up to 60 hours, up to 48 hours, up to 36 hours, up to 24 hours, up to 12 hours, and up to 6 hours. In some instances, the seeds are dried to reduce internal moisture of the seed. In some instances, seeds are stored. In some instances seeds are stored and bagged. The seeds may be stored and bagged for any suitable time. Following storage, in some cases, seeds are planted. In some instances, seeds are planted after 1 day, 2 days, 3 days, 4 days, 5 days, 6 days, 1 week, 2 weeks, 3 weeks, 4 weeks, 1 month, 2 months, 3 months, 4 months, 5 months, 6 months, 7 months, 8 months, or more than 8 months. In some instances, seeds are planted after 4 weeks. Following planting, resultant crops may require less fertilizer. In some instances, a reduction in fertilizer is at least or about 5%, 10%, 15%, 20%, 25%, 30%, 35%, 40%, 45%, 50%, or more than 50%.

Plant performance may be measured in resultant crops requiring less fertilizer. In some instances, plant performance is measured when the crops are sowed or at one or multiple times before the crops are sowed. Plant performance, includes but is not limited to, flavonoid level, anthocyanin level, leaf size, leaf surface area, dry weight, nitrogen content, shoot dry weight, shoot fresh weight, root dry weight, vegetable development, yield of fruiting parts, weight of fruiting parts, hardiness, or seed germination rate. In some cases, plant performance is measured as improved quality comprising at least one of a longer shelf-life, a resistance to bruising or post-harvesting handling, an increased nutrient value, and an improved taste, shape, color, size, and texture. Often plants grown from UV-B irradiated seeds require less fertilizer without any concomitant decrease in plant performance compared to plants grown from non-UV-B irradiated seeds. In an alternate embodiment, plants grown from UV-B irradiated seeds require less of at least one of less herbicide, fungicide, and insecticide. In some instances, the resultant plant is grown with a reduction in at least one of herbicide, insecticide, and pesticide, enabling organic crops for animal or human consumption.

Plant performance is measured in a number of ways in various embodiments described herein. For example, performance is measured as yield, nutritional value, flavonoid production, anthocyanin production, resistance to an insect challenge, resistance to a bacterial or fungal challenge, resistance to an abiotic stress such as drought, heat, cold, or nutrient stress. Alternately, or in combination, plant performance is identified as reduction in herbicide, pesticide, insecticide, or fertilizer application. Increased plant performance in some instances can result in harvesting a crop sooner. Alternate definitions of plant performance are consistent with the disclosure herein. Notably, upon treatment of seeds with UV-B supplementation as disclosed herein, the resultant plants often demonstrate both and increased hardiness and an increased growth in the absence of environmental stress. That is, plants grown from treated seeds, such as seeds treated with 280 nm UV-B supplementation, exhibit an increased resistance to biotic stress, such as bacterial, insect or fungal pathogen stress, an increased resistance to abiotic stress such as heat, cold, drought, salinity, light, nutrients or wind, and, surprisingly, an increased growth rate in the absence of such stresses relative to plants grown from untreated seeds. As a consequence, plants grown from treated seeds demonstrate an increased in yield relative to plants grown from untreated seeds both in the presence and in the absence of stress. Alternately or in combination, plants grown from treated seeds attain comparable or improved yield relative to plants grown from untreated seeds despite decreased fertilizer administration, decreased watering, decreased herbicide administration, or decreased soil quality, for example, relative to that of plants grown from untreated seeds.

Accordingly, UV-B supplementation enables methods of growing crops such that pesticide use, herbicide use, fertilizer administration, or water administration is reduced relative to plants grown from untreated seeds without any concomitant decrease in yield. In some cases, UV-B supplementation enables a substantial decrease in overall environmental impact without decrease in crop yield.

Untreated seeds may be used to determine improvements in at least one of hardiness and plant performance as compared to seeds administered UV-B according to methods described herein. In some instances, untreated seeds are seeds that are not administered UV-B according to methods described herein. In some instances, untreated seeds are treated similarly but are not administered UV-B. In some instances, untreated seeds comprise seeds that vary by at least 1, 2, 3, 4, 5, or more than 5 treatment conditions described herein.

Improvements in at least one of hardiness and plant performance may be determined from resultant seedlings or crops of seeds administered UV-B using methods described herein. For example, seedlings from UV-B irradiated seeds are compared to seedlings from seeds that are not irradiated using UV-B by methods described herein. In some instances, improvements in the resultant crops are compared to a crop grown under similar conditions but from seeds that are not administered UV-B using methods described herein. Similar conditions may be similar environment or similar growing conditions. Environmental factors include, but are not limited to, sun exposure, temperature, soil composition, soil moisture, wind, humidity, and soil pH. Growing conditions, include but are not limited to, amount of watering, amount of pesticide, amount of herbicide, amount of insecticide, duration of priming, duration of germination, and timing of sowing. In some instances, the resultant crops are compared to crops grown at a same time. For example, the crops grown at the same time are grown on an adjacent or nearby field. In some instances, the resultant crops are compared to crops from a previous growing season. In some instances, a yield of the resultant crops is compared to a comparable crop. Yield may comprise improvements in at least one of plant performance and hardiness. In some instances, yield from a comparable crop is referred to standard yield. In some instances, the comparable crop is a crop that is grown at a same time or subject to similar growing conditions.

In some instances, seedlings are irradiated with a UV-B regimen as described herein. Plant performance in the seedlings may result in improved plant performance as compared to the counterpart seedlings that have not been treated. In some instances, hardiness of the seedlings is improved using methods as described herein.

In some instances, plant performance is improved in seedlings irradiated using UV-B. In some instances, plant performance in the seedlings comprises at least one of flavonoid levels, anthocyanin levels, size, dry weight, nitrogen index, shoot dry weight, shoot fresh weight, shoot length, radical length, pigment production, leaf size, hypocotyl length, chlorophyll level, leaf area, and root dry weight is improved in the seedlings irradiated with UV-B as described herein. In some instances, plant performance in the seedlings is an elevated level of at least one of flavonoid levels and anthocyanin levels. Plant performance may be measured in the seedlings irradiated with UV-B as described herein prior to sowing.

In some instances, hardiness is improved in seedlings irradiated using UV-B. The seedlings may comprise improved resilience following at least one of heat, flood, drought, frost, unusual climate events, salinity stress, and high visible light stress. In some instances, the seedlings are inspected following at least one of heat, flood, drought, frost, unusual climate events, salinity stress, and high visible light stress.

At least one of plant performance and hardiness in seedlings irradiated with UV-B may be increased by a significant percentage when compared to counterpart seedlings that have not been irradiated with a UV-B regimen disclosed herein. At least one of plant performance and hardiness may be increased by about 5%-100%, 10%-90%, 20%-80%, 30%-70%, 40%-60%, 50%-95%, 65%-85%, or 75%-95%. At least one of plant performance and hardiness may be increased by at least about 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, 99%, or 100%. At least one of plant performance and hardiness may be increased by at least 5%. At least one of plant performance and hardiness may be increased by at least 10%. At least one of plant performance and hardiness may be increased by at least 30%. At least one of plant performance and hardiness may be increased by at least 50%.

In some instances, plant performance is improved in resultant plants or crops from seedlings irradiated using UV-B. In some instances, plant performance in the resultant plants or crops comprises at least one of flavonoid levels, anthocyanin levels, size, dry weight, nitrogen index, shoot dry weight, shoot fresh weight, shoot length, radical length, pigment production, leaf size, hypocotyl length, chlorophyll level, leaf area, and root dry weight is improved in plants or crops from seedlings irradiated with UV-B as described herein. In some cases, plant performance in the resultant plants or crops is measured as improved quality comprising at least one of a longer shelf-life, a resistance to bruising or post-harvesting handling, an increased nutrient value, an improved taste, an improved shape, an improved color, an improved size, and an improved texture. Plant performance may be measured in the resultant plants or crops from seedlings irradiated with UV-B as described herein during or following sowing. In some instances, the resultant plants or crops are inspected following at least one of heat, flood, drought, frost, unusual climate events, salinity stress, and high visible light stress.

In some instances, hardiness is improved in a resultant plant or crop from seedlings irradiated using UV-B. The plant or crop may comprise improved resilience following at least one of heat, flood, drought, frost, unusual climate events, salinity stress, and high visible light stress.

At least one of plant performance and hardiness in resultant plants or crops from a UV-B irradiated seedling may be increased by a significant percentage when compared to counterpart plants or crops from seedlings that have not been irradiated with a UV-B regimen disclosed herein. At least one of plant performance and hardiness may be increased by about 5%-100%, 10%-90%, 20%-80%, 30%-70%, 40%-60%, 50%-95%, 65%-85%, or 75%-95%. At least one of plant performance and hardiness may be increased by at least 5%, 10%, 15%, 20%, 25%, 30%, 35%, 40%, 45%, 50%, 55%, 60%, 65%, 70%, 75%, 80%, 85%, 90%, 95%, 99%, or 100%. At least one of plant performance and hardiness may be increased by at least 5%. At least one of plant performance and hardiness may be increased by at least 10%. At least one of plant performance and hardiness may be increased by at least 30%. At least one of plant performance and hardiness may be increased by at least 50%.

Provided herein, in certain embodiments, are methods for treating plants or crops with UV-B. In some instances, methods as described herein result in improved plant performance in plants or crops as compared to the counterpart plants or crops that have not been treated. Plant performance includes, but is not limited to, flavonoid level, anthocyanin level, leaf size, leaf surface area, dry weight, nitrogen content, shoot dry weight, shoot fresh weight, root dry weight, vegetable development, yield of fruiting parts, weight of fruiting parts, hardiness, seed germination rate, longer shelf-life, a resistance to bruising or post-harvesting handling, an increased nutrient value, an improved taste, an improved shape, an improved color, an improved size, and an improved texture. Improvement in plant performance may be increased by about 5%-100%, 10%-90%, 20%-80%, 30%-70%, 40%-60%, 50%-95%, 65%-85%, or 75%-95%. In some instances, plant performance is increased by at least 5%, 10%, 15%, 20%, 25%, 30%, 35%, 40%, 45%, 50%, 55%, 60%, 65%, 70%, 75%, 80%, 85%, 90%, 95%, 99%, or 100%. In some instances, plant performance is increased by at least 5%. In some instances, plant performance is be increased by at least 10%. In some instances, plant performance is increased by at least 30%. In some instances, plant performance is increased by at least 50%. Alternately, or in combination, there is an improvement in hardiness or resilience to stress. In some instances, UV-B irradiation of plants or crops results in improved hardiness or resilience following at least one of heat, flood, drought, frost, unusual climate events, salinity stress, and high visible light stress. Improvement in hardiness may be increased by about 5%-100%, 10%-90%, 20%-80%, 30%-70%, 40%-60%, 50%-95%, 65%-85%, or 75%-95%. In some instances, hardiness is increased by at least 5%, 10%, 15%, 20%, 25%, 30%, 35%, 40%, 45%, 50%, 55%, 60%, 65%, 70%, 75%, 80%, 85%, 90%, 95%, 99%, or 100%. In some instances, hardiness is increased by at least 5%. In some instances, hardiness is increased by at least 10%. In some instances, hardiness is increased by at least 30%. In some instances, hardiness is increased by at least 50%.

Devices for Administering UV-B

Provided herein, in certain embodiments, are devices and systems for administering UV-B to a plant material. In some instances, the plant material is a seed. In some instances, the devices are configured to provide a UV-B administration regimen to the seed.

Figure 35:
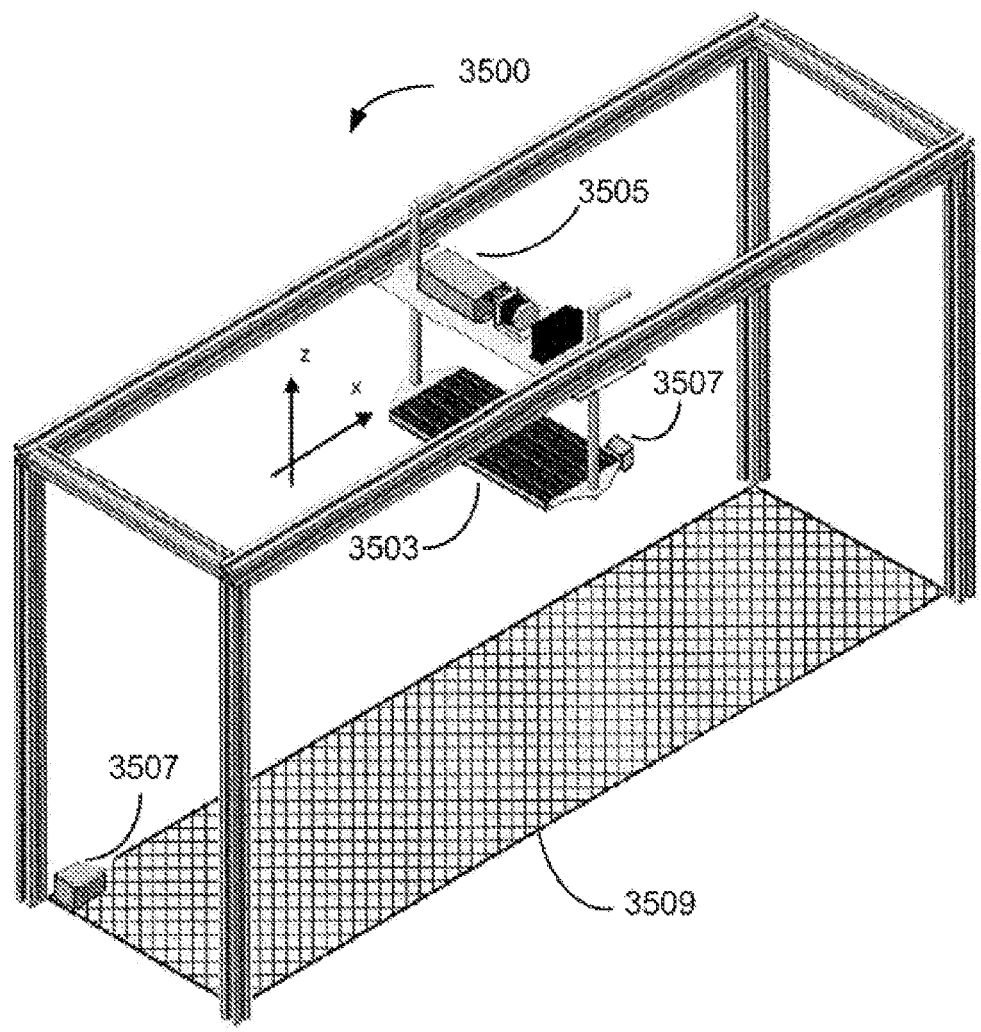
FIG. 35 depicts an exemplary device for administering UV-B.

An exemplary device is seen in FIG. 35. The device 3500 comprises a light source 3503 for administering light to a target area 3509. In some instances, the light source administers light enriched for UV-B. In some instances, the lighting source administers only UV-B. In some instances, the light source administers UV-B in combination with other light. The lighting source may remain stationary or may move in any one of X, Y, or Z direction. The device further comprises a processor 3505 for providing information to the light source 3503 or to a lighting controller. The device further comprises sensors 3507. The sensors 3507 are configured to detect at least one of directionality of a light source, position of a light source, humidity, pressure, temperature, dosage, intensity, or irradiance during UV-B administration.

Devices and systems for administering light may comprise at least one light source. In some instances, the at least one light source administer light of various wavelengths. For example, the at least one light source are configured to administer UV-B and light of another wavelength including, but not limited to, visible light and UV-A. In some instances, the at least one light source administer UV-B alone. The at least one light source may be selected from the group consisting of a light emitting diode (LED), a laser, an incandescent light bulb, a gas discharge bulb, and combinations thereof. In some instances, the at least one light source comprises one or more LEDs.

Devices and systems as described herein may comprise at least one light source that moves positions during UV-B administration. For example, the at least one light source may provide UV-B by moving above a plant material. In some instances, the plant material is a seed. In some instances, the at least one light source changes directionality during UV-B administration. In some instances, the at least one light source changes direction along the X-axis, Y-axis, or Z-axis during UV-B administration. In some instances, a height of the at least one light source is adjustable. A height of the at least one light source may be at about 20 mm, 40 mm, 60 mm, 80 mm, 100 mm, 120 mm, 150 mm, or 200 mm above the seeds. In some instances, the height is in a range of about 20 mm-200 mm, 40 mm-150 mm, 60 mm-120 mm, or 80 mm-100 mm above the seeds. In some instances, the directionality or position of the at least one light emitter is adjusted depending on the type of seed or treatment regimen.

Alternatively or in combination, devices and systems comprise at least one light source that remains stationary during UV-B administration. In such a system, a conveyor comprising plant material such as seeds travels under the at least one source. In some instances, the conveyor travels at a determined rate or for a determined duration. In some instances, a height between the conveyor and the at least one light source is about 20 mm, 40 mm, 60 mm, 80 mm, 100 mm, 120 mm, 150 mm, or 200 mm. In some instances, the height is in a range of about 20 mm-200 mm, 40 mm-150 mm, 60 mm-120 mm, or 80 mm-100 mm.

In some instances, devices and systems described herein administer light of a determined wavelength. In some instances, the devices and systems provide UV-B in a range of about 280 nm to about 320 nm. In some instances, the devices and systems provide UV-B in a range of about 280 nm to about 290 nm. In some instances, the devices and systems provide UV-B at wavelength of about 280 nm, about 281 nm, about 282 nm, about 283 nm, about 284 nm, about 285 nm, about 286 nm, about 287 nm, about 288 nm, about 289 nm, about 290 nm, about 291 nm, about 292 nm, about 293 nm, about 294 nm, about 295 nm, about 296 nm, about 297 nm, about 298 nm, about 299 nm, about 300 nm, about 301 nm, about 302 nm, about 303 nm, about 304 nm, about 305 nm, about 306 nm, about 307 nm, about 308 nm, about 309 nm, about 310 nm, about 311 nm, about 312 nm, about 313 nm, about 314 nm, about 315 nm, about 316 nm, about 317 nm, about 318 nm, about 319 nm, or about 320 nm. In some instances, the devices and systems provide visible light. In some instances, the devices and systems provide UV-A.

Devices and systems as described herein may provide light of a determined dosage. For example, the devices and systems provide UV-B in a dosage in a range of about 0.1 kJ $m^{-2}$-100 kJ $m^{-2}$, 10 kJ $m^{-2}$-90 kJ $m^{-2}$, 20 kJ $m^{-2}$-80 kJ $m^{-2}$, 30 kJ $m^{-2}$-70 kJ $m^{-2}$, and 40 kJ $m^{-2}$-50 kJ $m^{-2}$. In some instances, the devices and systems provide visible light having a photon number in a range of about 10 umol $m^{-2}$ $s^{-1}$-550 umol $m^{-2}$ $s^{-1}$, 20 umol $m^{-2}$ $s^{-1}$-500 umol $m^{-2}$ $s^{-1}$, 40 umol $m^{-2}$ $s^{-1}$-450 umol $m^{-2}$ $s^{-1}$, 45 umol $m^{-2}$ $s^{-1}$-400 umol $m^{-2}$ $s^{-1}$, 50 umol $m^{-2}$ $s^{-1}$-350 umol $m^{-2}$ $s^{-1}$, 100 umol $m^{-2}$ $s^{-1}$-300 umol $m^{-2}$ $s^{-1}$, or 100 umol $m^{-2}$ $s^{-1}$-200 umol $m^{-2}$ $s^{-1}$.

In some instances, devices and systems control UV-B irradiance. For example, the devices and systems administer UV-B irradiance in range of about 40 uW $cm^{-2}$ to about 200 uW $cm^{-2}$. In some instances, the devices and systems administer UV-B irradiance at least or about 1.5 umol $m^{-1}$ $s^{-1}$, 2 umol $m^{-1}$ $s^{-1}$, 2.5 umol $m^{-1}$ $s^{-1}$, 3 umol $m^{-1}$ $s^{-1}$, 3.5 umol $m^{-1}$ $s^{-1}$, 4 umol $m^{-1}$ $s^{-1}$, 4.5 umol $m^{-1}$ $s^{-1}$, 5 umol $m^{-1}$ $s^{-1}$, 5.5 umol $m^{-1}$ $s^{-1}$, 6 umol $m^{-1}$ $s^{-1}$, 6.5 umol $m^{-1}$ $s^{-1}$, 7 umol $m^{-1}$ $s^{-1}$, 7.5 umol $m^{-1}$ $s^{-1}$, 8 umol $m^{-1}$ $s^{-1}$, 8.5 umol $m^{-1}$ $s^{-1}$, 9 umol $m^{-1}$ $s^{-1}$, 9.5 umol $m^{-1}$ $s^{-1}$, 10 umol $m^{-1}$ $s^{-1}$, or more than 10 umol $m^{-1}$ $s^{-1}$.

Devices and systems as described herein may be configured to provide light for a specified duration. Duration of UV-B administration may include at least or about 1 hour, 2 hours, 3 hours 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, or more than 30 hours In some instances, devices and systems are configured to prime and concurrently administer UV-B to a plant material. For example, the devices and systems comprise a surface for priming and concurrently administering UV-B to the plant material. In some instances, the surface for priming and concurrently administering UV-B to the plant material is positioned a distance from at least one light source. In some instances, the is at least or about 20 mm, 40 mm, 60 mm, 80 mm, 100 mm, 120 mm, 150 mm, or 200 mm above the surface. In some instances, the distance between the surface and the at least one source is adjustable. In some instances, the distance is adjustable depending on the amount of priming medium. In some instances, other features of the treatment regimen including, but not limited to, directionality of the at least one light source, position of the at least one light source, humidity, pressure, temperature, dosage, intensity, and irradiance are adjusted based on the priming medium.

In some instances, devices and systems for administering light comprise a lighting controller. The lighting controller may be configured to administer light at a determined regimen. For example, the light controller controls wavelength of light emitted, dosage of light, duration of light administration, intensity of light, irradiance of light, and directionality of light emitted. In some instances, the light controller is configured to provide UV-B at a specified dosage, duration, intensity, irradiance, and directionality. In some instances, the light controller adjusts for UV-B dosage, duration, intensity, or irradiance during a treatment regimen.

In some instances, devices and systems comprise a computer processor or use of the same. In some instances, the computer processor provides information to the lighting controller. In some instances, the computer processor comprises a computer program. In some instances, the computer program includes a sequence of instructions, executable in the digital processing device's CPU, written to provide a UV-B regimen to a seed. In some instances, computer readable instructions are implemented as program modules, such as functions, features, Application Programming Interfaces (APIs), data structures, and the like, for administering UV-B to the seed.

Figure 36:
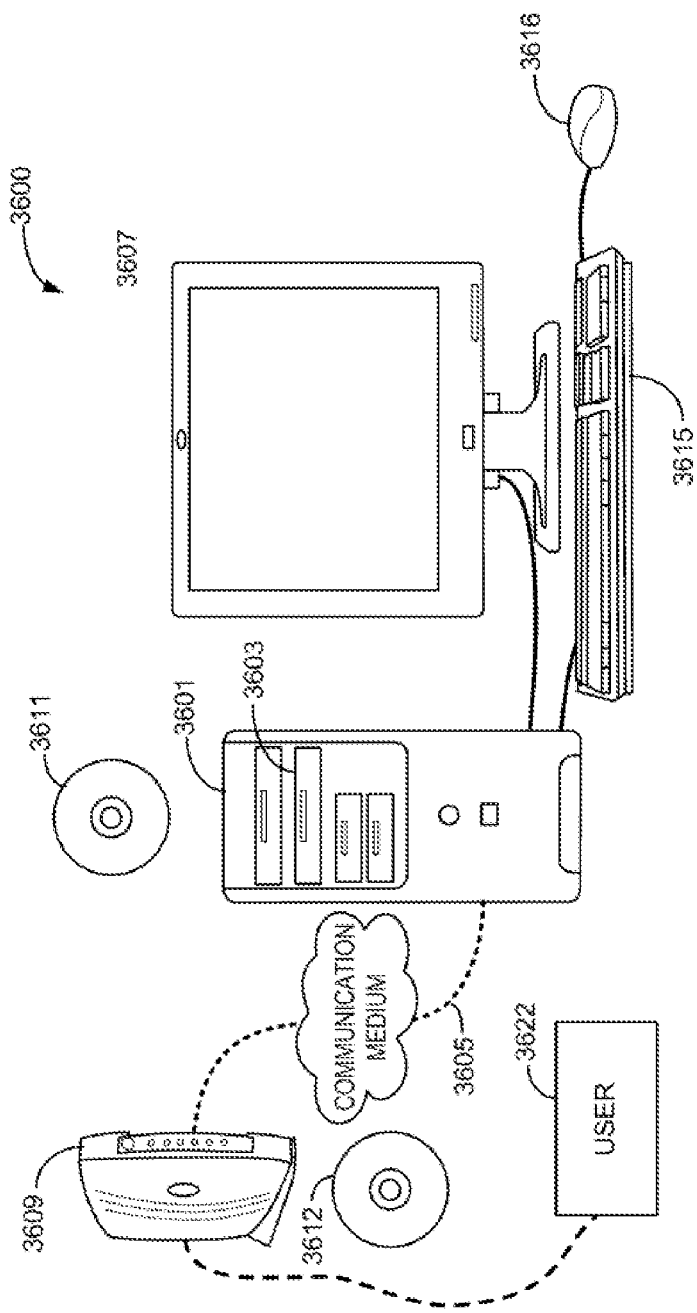
FIG. 36 depicts a computer system consistent with the disclosure herein.

An exemplary computer system is seen in FIG. 36. The computer system 3600 may be understood as a logical apparatus that can read instructions from media 3611 and/or a network port 3605, which can optionally be connected to server 3609 having fixed media 3612. The system, can include a CPU 3601, disk drives 3603, optional input devices such as keyboard 3615 and/or mouse 3616 and optional monitor 3607. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a user 3622 as illustrated in FIG. 36.

Devices and systems as described herein may further comprise a sensor. In some instances, the sensor detects directionality of a light source, position of a light source, humidity, pressure, temperature, dosage, intensity, or irradiance during UV-B administration. In some instances, the sensor provides information to a lighting controller such that the directionality of a light source, position of a light source, humidity, pressure, temperature, dosage, intensity, or irradiance can be adjusted.

Turning to the figures, one observes the following:

FIG. 1 depicts a schema for UV-B administration.

Figure 2:
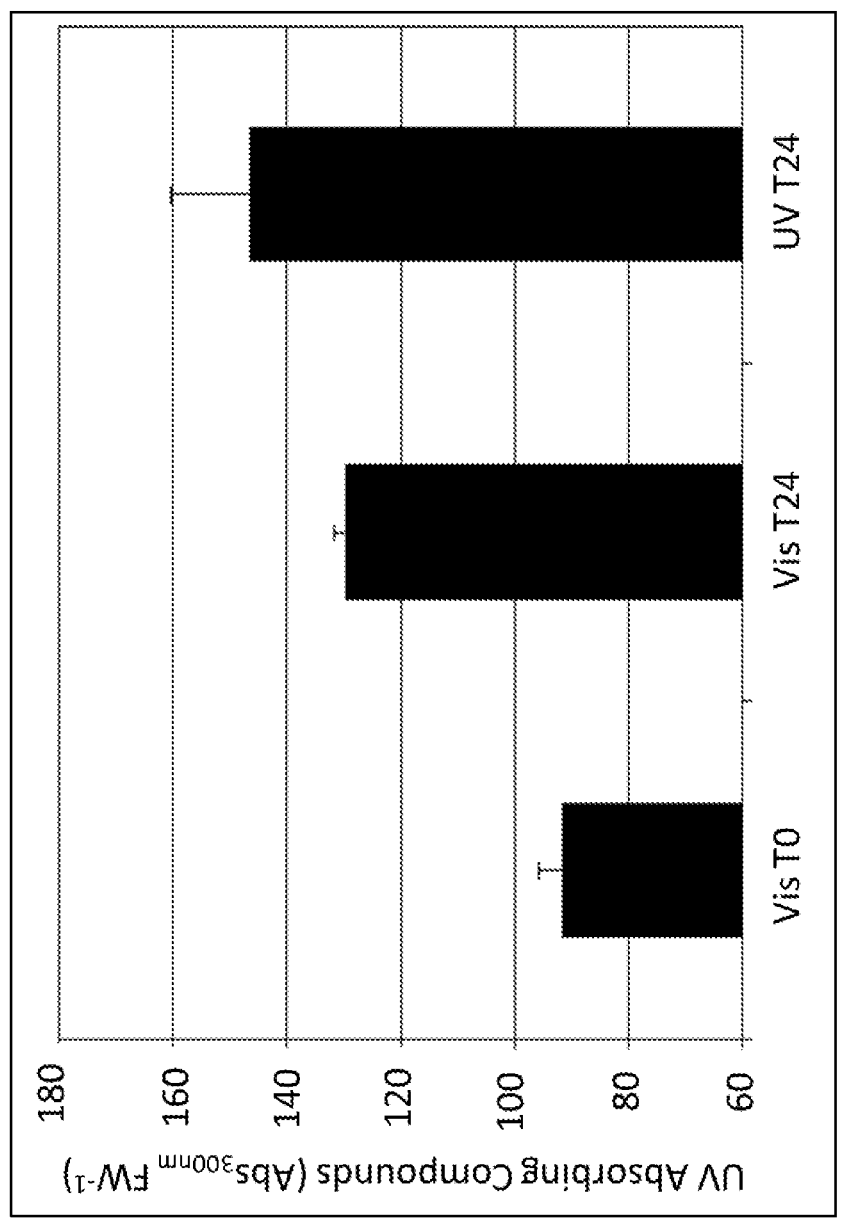
FIG. 2 depicts an analysis of flavonoid levels in seeds following UV-B treatment.

FIG. 2 depicts flavonoid levels following light administration. UV-B absorbing compounds is measured at an absorbance of 300 nm in seeds that are administered visible light only ("Vis") or administered UV-B at 286 nm ("UV"). Visible light or UV-B treatment is applied after 0 hours of water imbibing ("T0") or 24 hours after water imbibing ("T24"). The x-axis shows the different seed treatment conditions: visible light following 0 hours of water imbibing ("Vis T0"), visible light following 24 hours of water imbibing ("Vis T24"), and UV-B administration following 24 hours of water imbibing ("UV T24"). The y-axis shows UV Absorbing Compounds ($Abs_{300nm}$ $FW^{-1}$) and has a scale from 60 to 180. Flavonoids are 18% higher in UV T24 seeds as compared to Vis T24 seeds. Flavonoids are 60% higher in UV T24 seeds as compared Vis T0 seeds. This figure shows increase in flavonoid levels following UV-B administration.

Figure 3A:
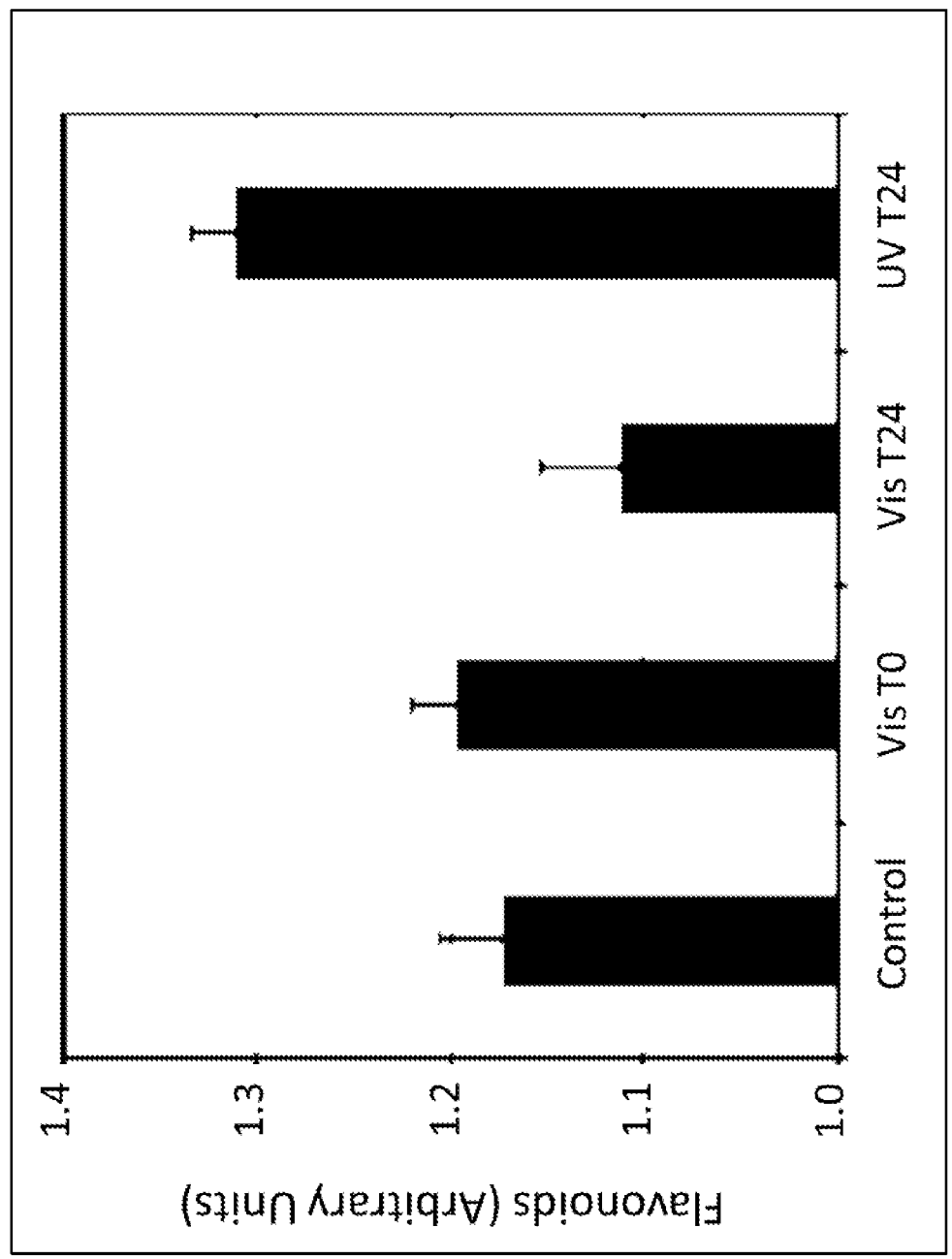
FIG. 3A illustrates an analysis of flavonoid levels in Ezmina lettuce plant leaves 20 days after UV-B administration.

FIG. 3A depicts flavonoid levels in leaves of Ezmina lettuce plants following light administration. Flavonoid levels are measured from leaves of 11-14 plants per treatment condition 20 days after seed treatment. Seeds are maintained under dark foil wrapped conditions ("Control"), administered visible light only ("Vis"), or administered UV-B treatment at 286 nm ("UV"). Visible light or UV-B treatment is applied after 0 hours of water imbibing ("T0") or 24 hours after water imbibing ("T24"). The x-axis shows the different treatment conditions: dark ("Control"), visible light following 0 hours of water imbibing ("Vis T0"), visible light following 24 hours of water imbibing ("Vis T24"), and UV-B administration following 24 hours of water imbibing ("UV T24"). The y-axis shows flavonoids (arbitrary units) and has a scale of 1.0 to 1.4. Flavonoid levels in leaves from UV T24 seeds are significantly higher as compared to leaves from Vis T0 seeds and leaves from Vis T24 seeds. This figure shows increase in flavonoid levels of resulting plant material from seeds administered UV-B.

Figure 3B:
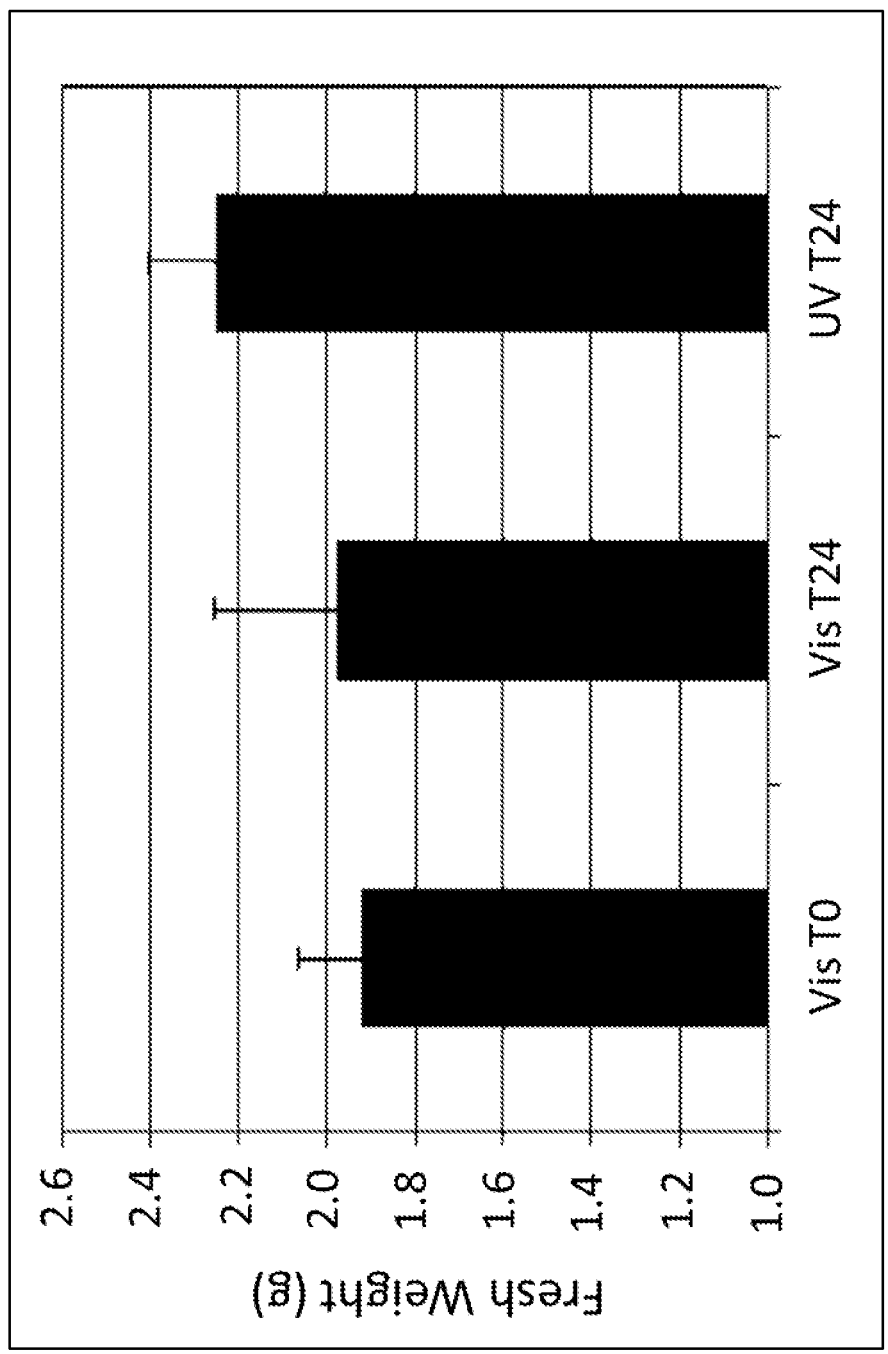
FIG. 3B depicts an analysis of plant productivity (measured by fresh shoot weight) following UV-B administration.

FIG. 3B depicts effects of light administration on fresh weight. Shoot fresh weight is measured in Legacy lettuce plants 30 days after seed treatment. Seeds are administered visible light only ("Vis") or administered UV-B at 286 nm ("UV"). Visible light or UV-B treatment is applied after 0 hours of water imbibing ("T0") or 24 hours after water imbibing ("T24"). The x-axis shows the different seed treatment conditions: visible light following 0 hours of water imbibing ("Vis T0"), visible light following 24 hours of water imbibing ("Vis T24"), and UV-B administration following 24 hours of water imbibing ("UV T24"). The y-axis shows fresh weight in grams (g) and has a scale of 1.0 to 2.6. Fresh weight in plants of UV T24 seeds is increased 17% as compared to plants of Vis T0 seeds. This figure shows the increase in plant performance such as crop yield following UV-B administration.

Figure 4A:
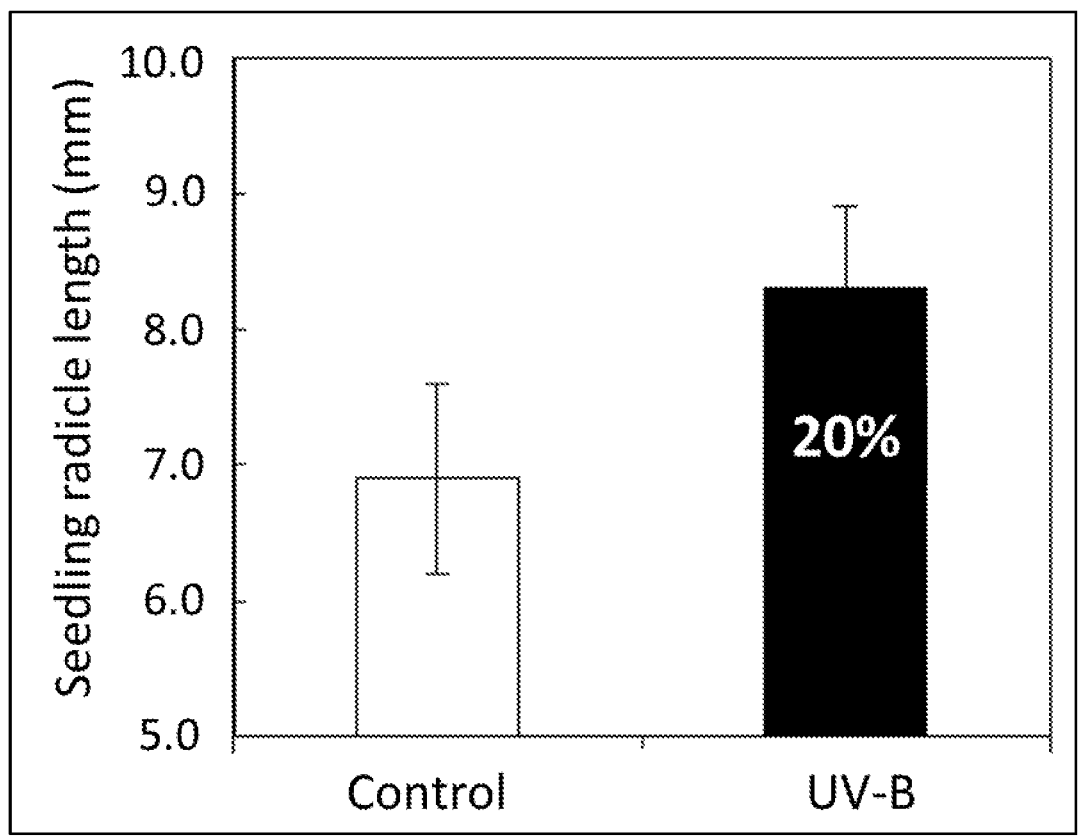
FIGS. 4A-4B depict graphs of increased growth of kale seedlings subject to drought stress.
Figure 4B:
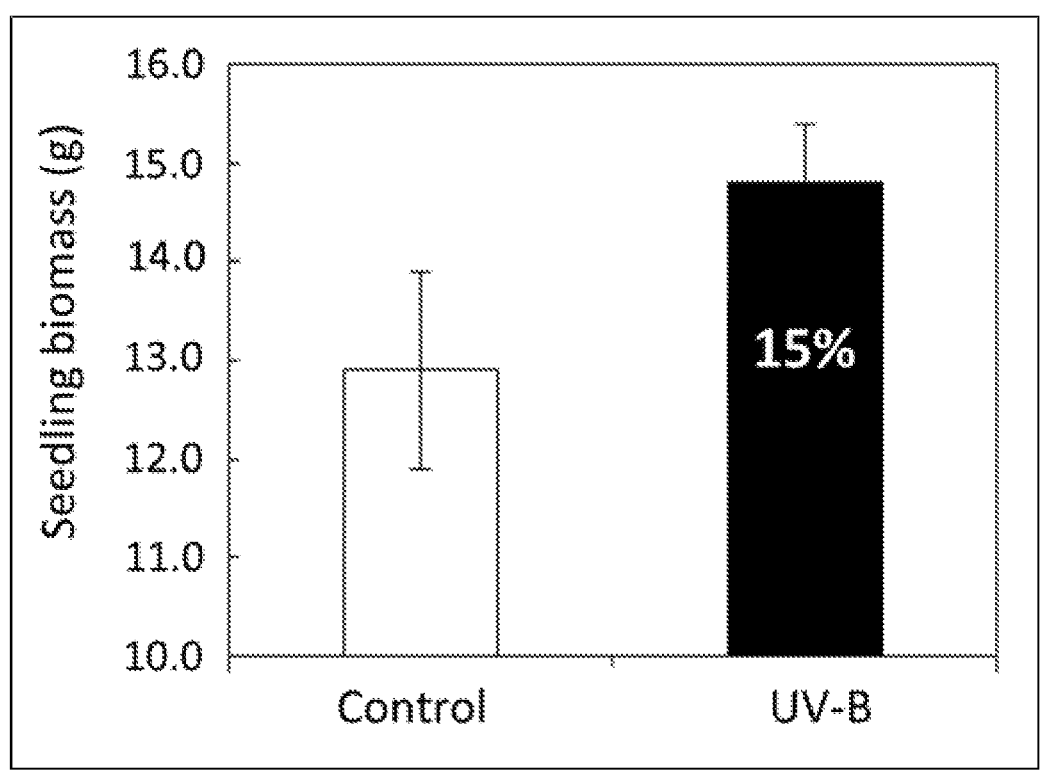

FIGS. 4A-4B depict effects of UV-B administration on growth of kale seedlings subject to drought stress. Kale (Brassica oleracea var. Regal) seeds are primed and administered UV-B. Following UV-B administration, seeds are subject to drought stress during germination. "Control" and "UV-B" seeds are germinated in water or PEG8000. After 72 hours of stress, seedling weight and radicle length are quantified. The x-axis of FIGS. 4A-4B shows the following seed treatment condition: "Control" and "UV-B." Referring to FIG. 4A, UV-B administration results in a 20% increase in seedling radicle length as compared to control. The y-axis of FIG. 4A shows seedling radicle length (mm) and has a scale of 5.0 to 10.0. Referring to FIG. 4B, UV-B administrations results in a 15% increase in seedling biomass as compared to control. The y-axis of FIG. 4B shows seedling biomass (g) and has a scale from 10.0 to 16.0. These figures show an increase in seedling growth as a result of UV-B administration.

Figure 5A:
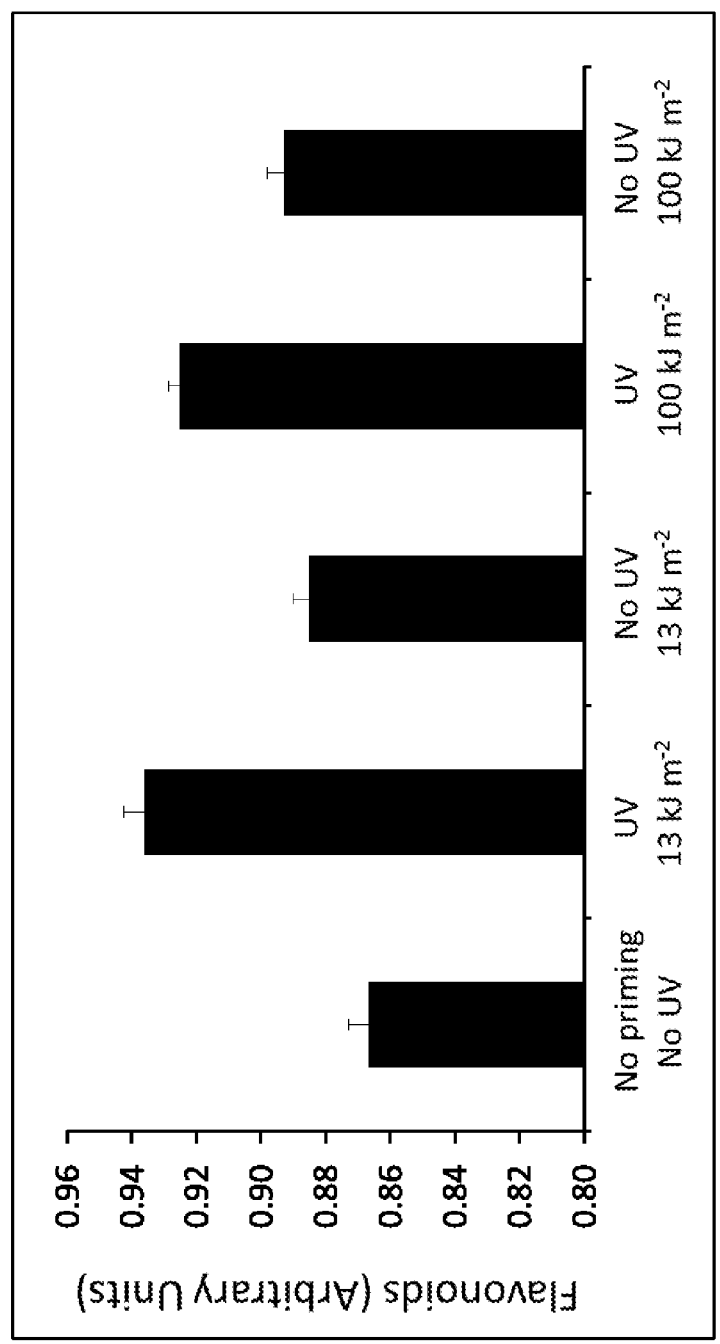
FIGS. 5A-5H depict an analysis of flavonoid levels in maize seeds after administration of UV-B of 13 kJ $m^{-2}$ dosage and 100 kJ $m^{-2}$ dosage.
Figure 5B:
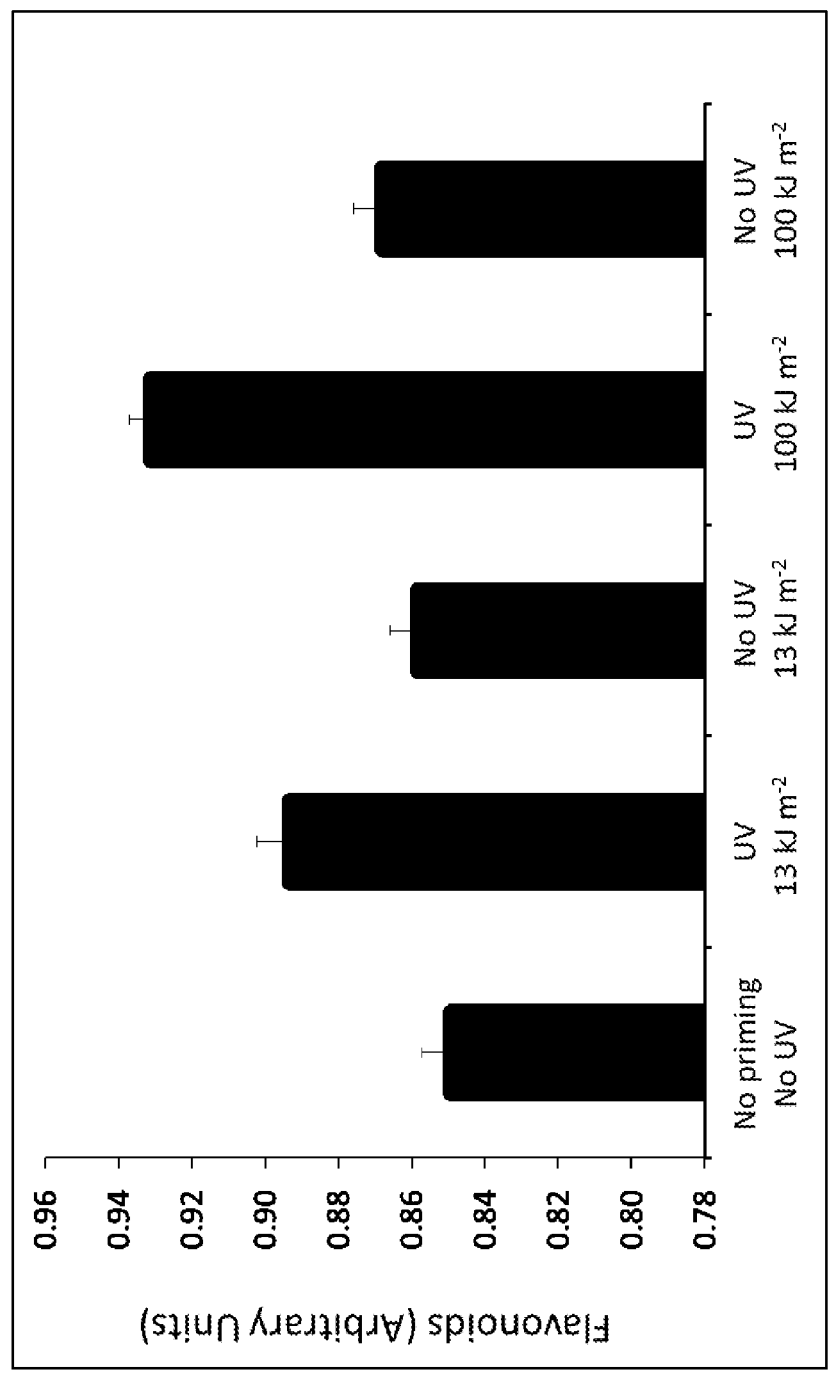
Figure 5C:
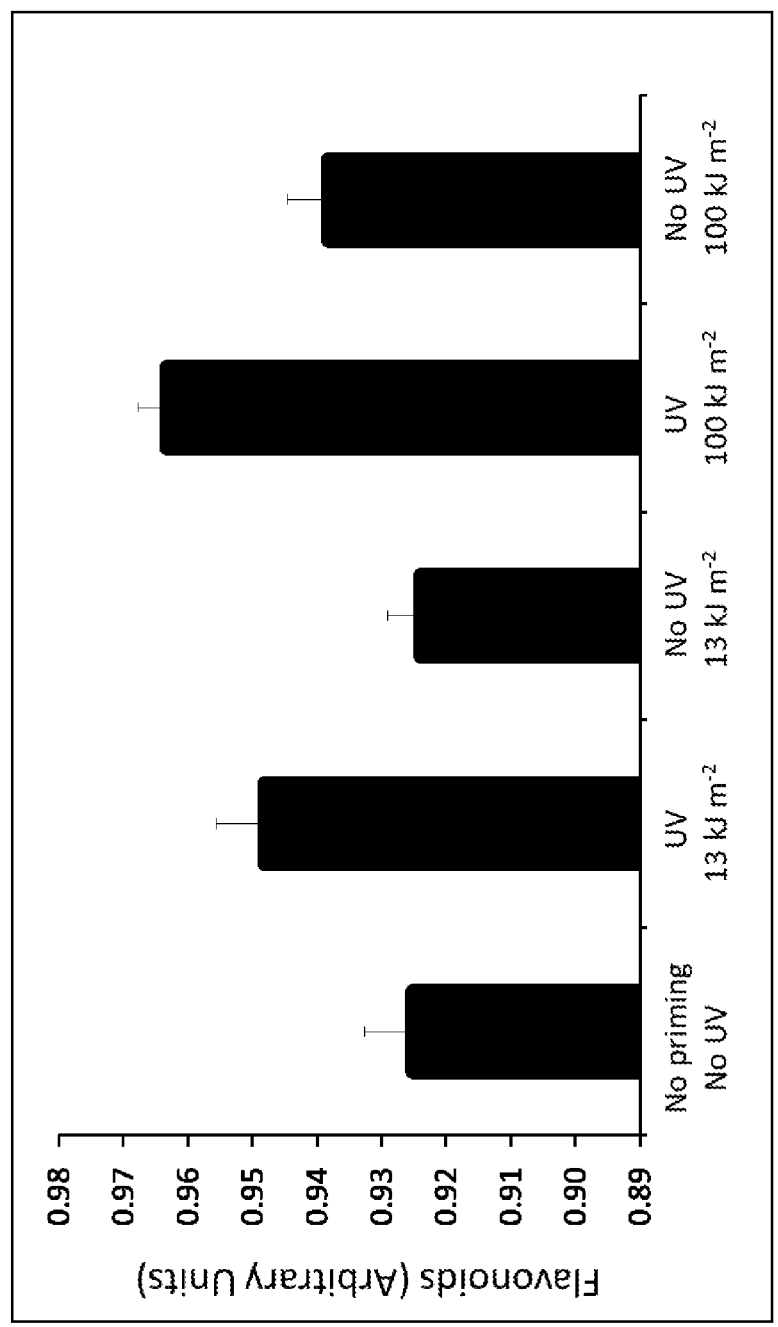
Figure 5D:
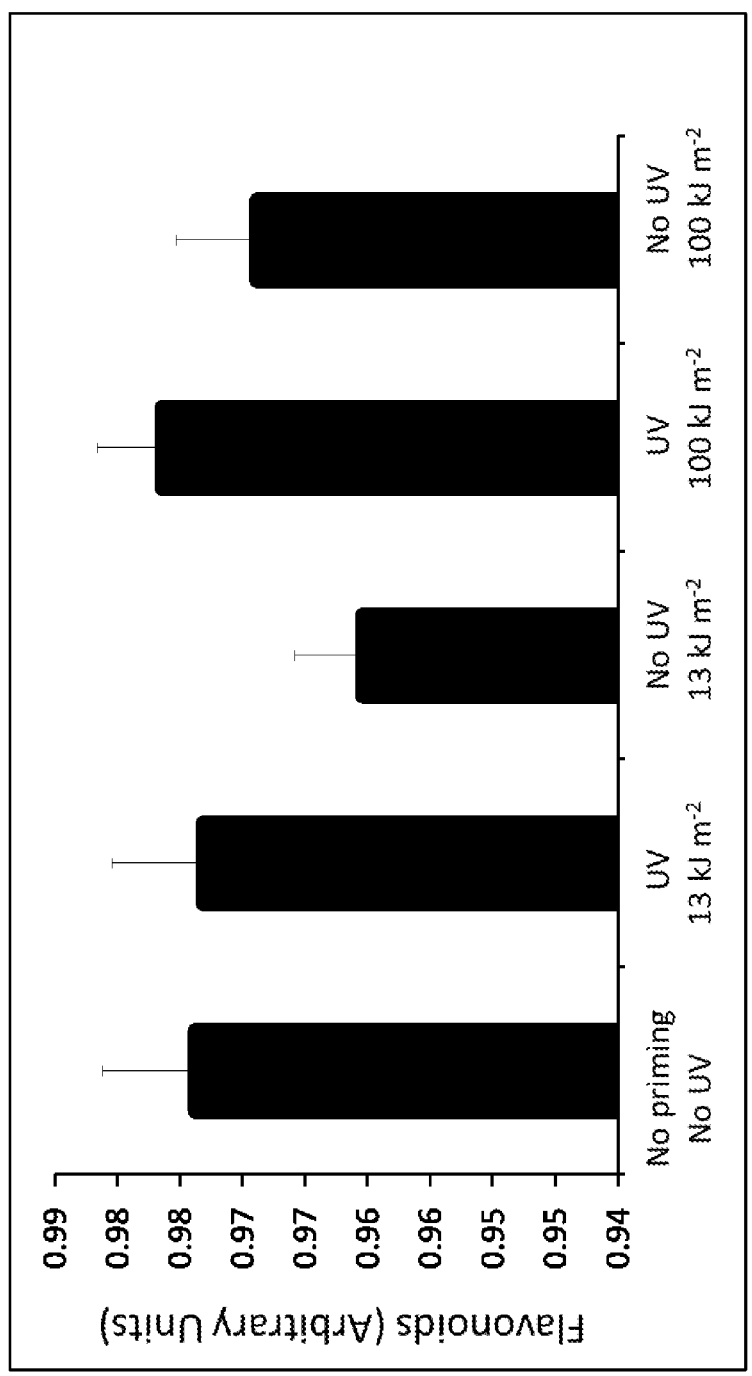
Figure 5E:
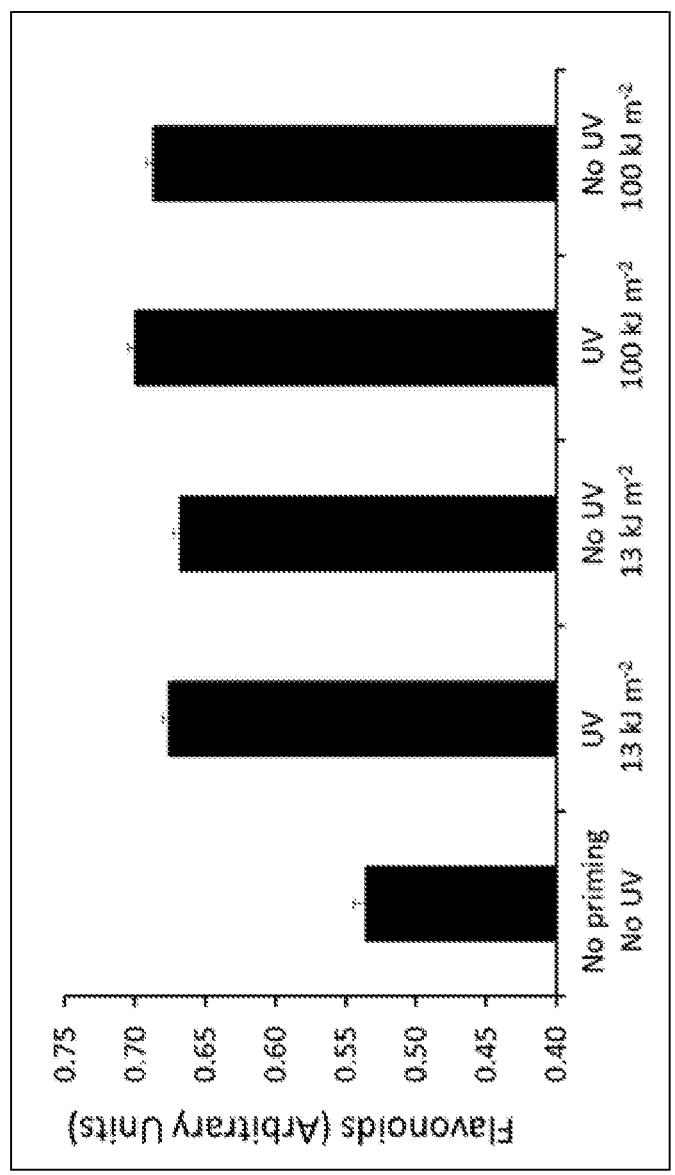
Figure 5F:
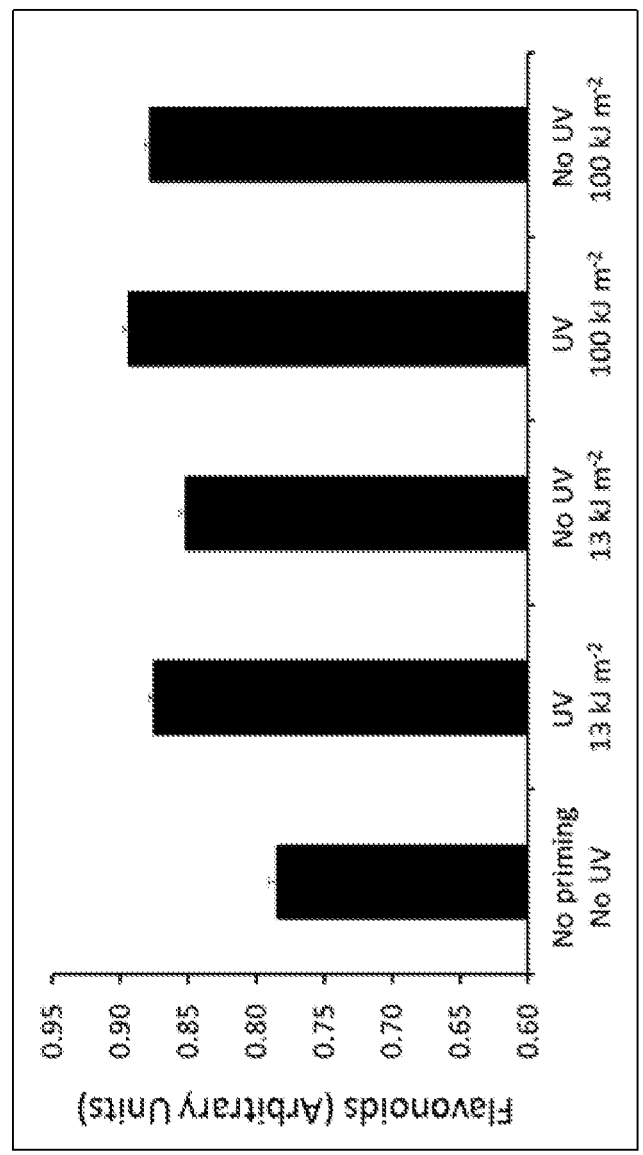
Figure 5G:
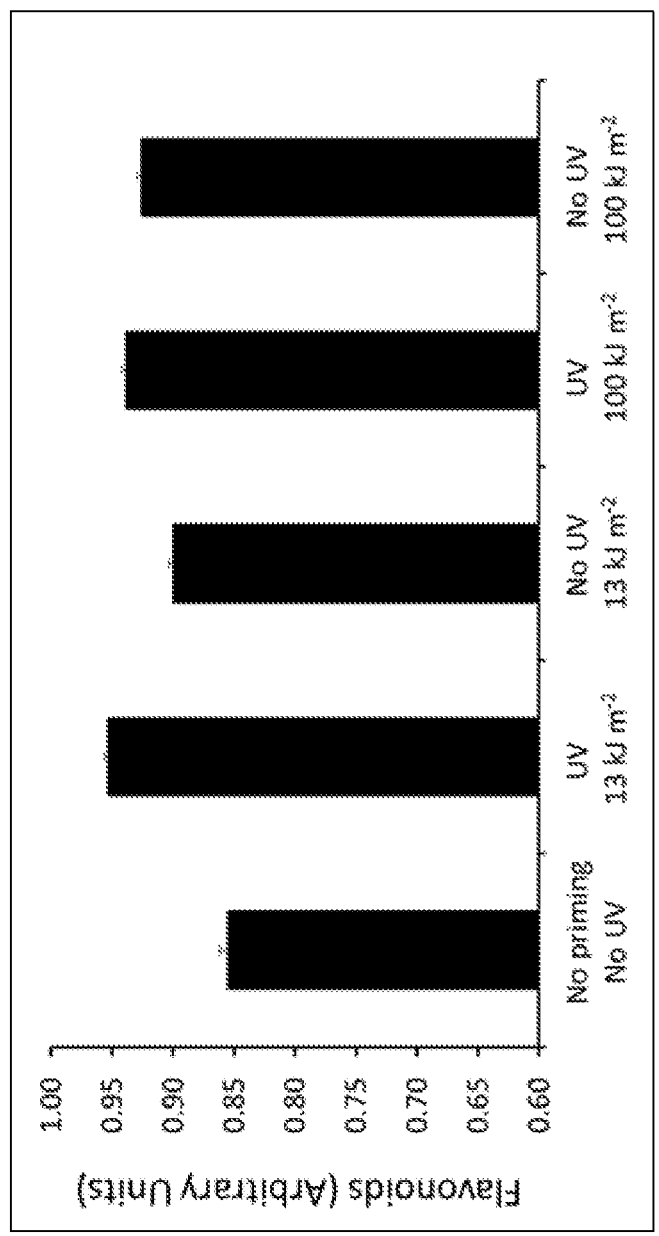
Figure 5H:
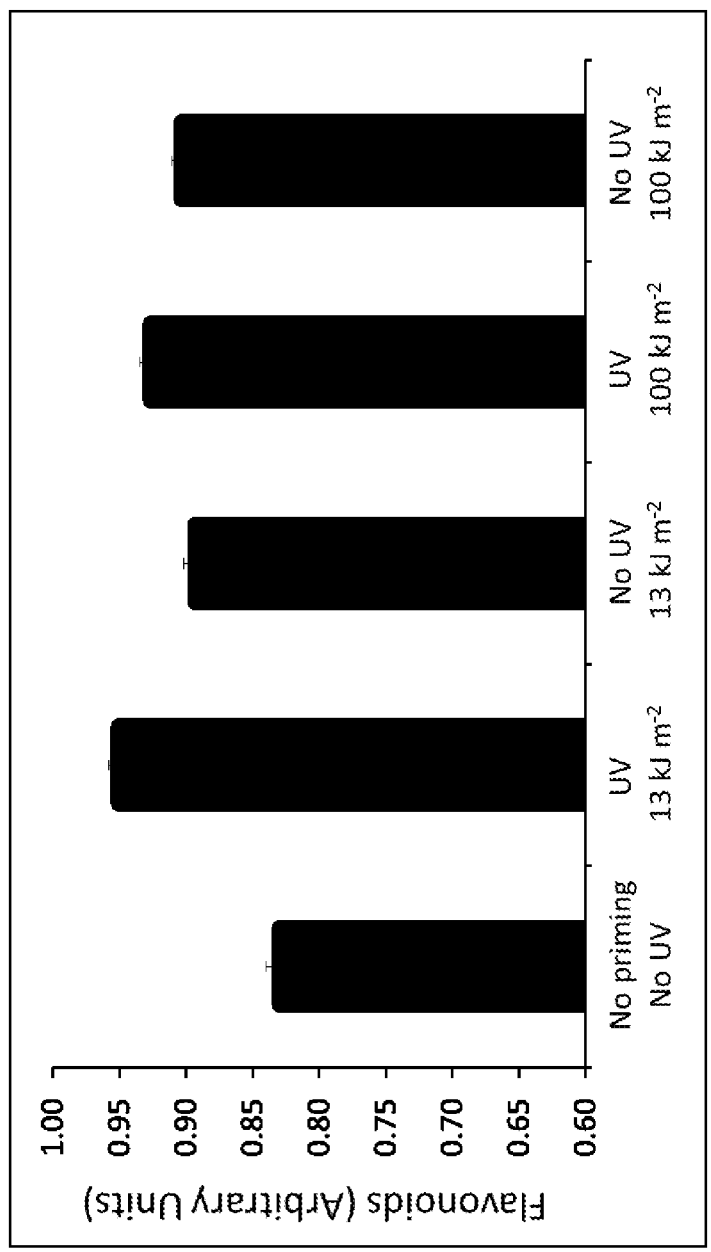
Figure 13:
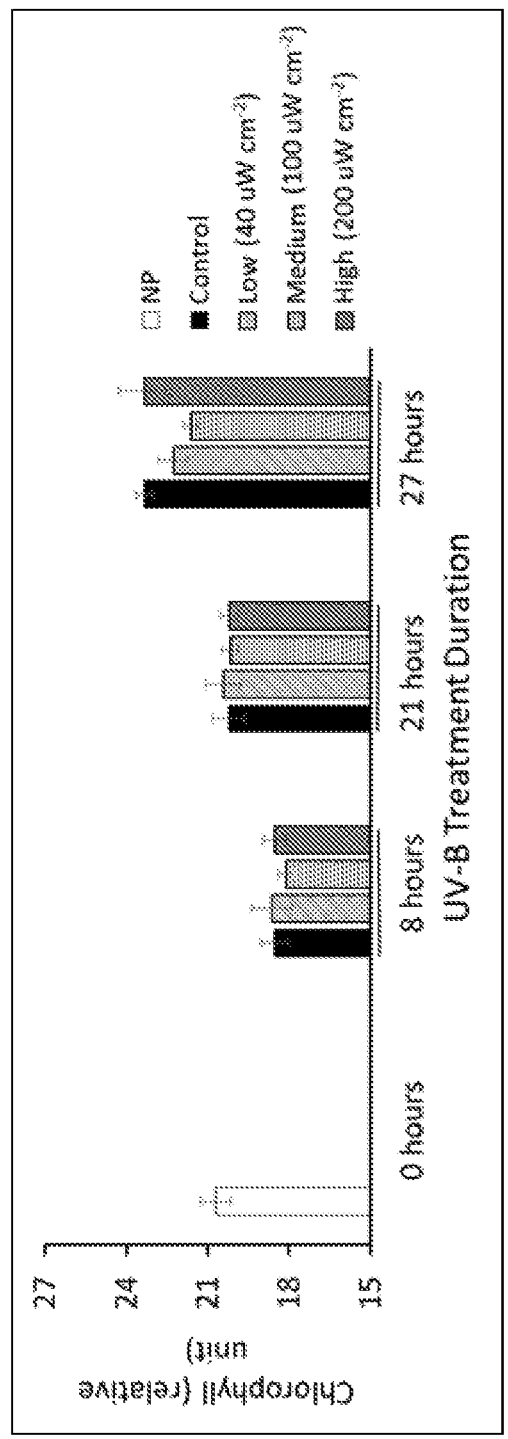
FIG. 13 depicts a graph of chlorophyll levels (relative unit) of lettuce seeds administered control, low (40 uW $cm^{-2}$), medium (100 uW $cm^{-2}$), and high (200 uW $cm^{-2}$) UV-B irradiance. Treatment duration of UV-B includes 0 hours, 8 hours, 21 hours, and 27 hours. "NP" refers to non-primed seeds.

FIGS. 5A-5H depict effects of UV-B dosage on flavonoid levels. Seeds are primed in water for 16 hours followed by administration of visible light with UV-B ("UV") or visible light without UV-B ("No UV"). Dosages of 13 kJ m$^{-2}$ or 100 kJ m$^{-2}$ irradiance are used. UV-B light is supplied by a LED source, the transmittance of which peaks at 280 nm. The x-axis of FIGS. 5A-5H shows the following seed treatment conditions: control samples that are not exposed to UV and not immersed in water ("No priming, No UV"), visible light with UV-B at a dosage of 13 kJ m$^{-2}$ ("UV 13 kJ m$^{-2}$"), visible light without UV-B ("No UV 13 kJ m$^{-2}$"), visible light with UV-B at a dosage of 100 kJ m$^{-2}$ ("UV 100 kJ m$^{-2}$"), and visible light without UV-B at a dosage of 100 kJ m$^{-2}$ ("No UV 100 kJ m$^{-2}$"). The y-axis of FIG. 5A shows flavonoids (arbitrary units) and has a scale of 0.80 to 0.96. Referring to FIG. 5A, 13 kJ m$^{-2}$ and 100 kJ m$^{-2}$ UV-B dosage significantly increase flavonoid levels as compared to the No UV 13 kJ m$^{-2}$ seeds or the No UV 100 kJ m$^{-2}$ seeds, respectively. The y-axis of FIG. 5B shows flavonoids (arbitrary units) and has a scale of 0.78 to 0.96. Referring to FIG. 5B, 13 kJ m$^{-2}$ and 100 kJ m$^{-2}$ UV-B dosage significantly increase flavonoid levels as compared to the No UV 13 kJ m$^{-2}$ seeds or the No UV 100 kJ m$^{-2}$ seeds, respectively. The y-axis of FIG. 5C shows flavonoids (arbitrary units) and has a scale of 0.89 to 0.98. Referring to FIG. 5C, 13 kJ m$^{-2}$ and 100 kJ m$^{-2}$ UV-B dosage significantly increase flavonoid levels as compared to the No UV 13 kJ m$^{-2}$ seeds or the No UV 100 kJ m$^{-2}$ seeds, respectively. The y-axis of FIG. 5D shows flavonoids (arbitrary units) and has a scale of 0.94 to 0.99. Referring to FIG. 5D, 13 kJ m$^{-2}$ and 100 kJ m$^{-2}$ UV-B dosage increase flavonoid levels as compared to the No UV 13 kJ m$^{-2}$ seeds or the No UV 100 kJ m$^{-2}$ seeds, respectively. The y-axis of FIG. 5E shows flavonoids (arbitrary units) and has a scale of 0.40 to 0.75. Referring to FIG. 5E, 13 kJ m$^{-2}$ and 100 kJ m$^{-2}$ UV-B dosage increase flavonoid levels as compared to the No UV 13 kJ m$^{-2}$ seeds or the No UV 100 kJ m$^{-2}$ seeds, respectively. The y-axis of FIG. 5F shows flavonoids (arbitrary units) and has a scale of 0.60 to 0.95. Referring to FIG. 5F, 13 kJ m$^{-2}$ and 100 kJ m$^{-2}$ UV-B dosage increase flavonoid levels as compared to the No UV 13 kJ m$^{-2}$ seeds or the No UV 100 kJ m$^{-2}$ seeds, respectively. The y-axis of FIG. 5G shows flavonoids (arbitrary unit) and has a scale of 0.60 to 1.00. Referring to FIG. 5G, 13 kJ m$^{-2}$ and 100 kJ m$^{-2}$ UV-B dosage increase flavonoid levels as compared to the No UV 13 kJ m$^{-2}$ seeds or the No UV 100 kJ m$^{-2}$ seeds, respectively. The y-axis of FIG. 5H shows flavonoids (arbitrary unit) and has a scale of 0.60 to 1.00. Referring to FIG. 5H, 13 kJ m$^{-2}$ and 100 kJ m$^{-2}$ UV-B dosage increase flavonoid levels as compared to the No UV 13 kJ m$^{-2}$ seeds or the No UV 100 kJ m$^{-2}$ seeds, respectively. These figures demonstrate an increase in flavonoid levels following dosage of UV-B administration.

Figure 6A:
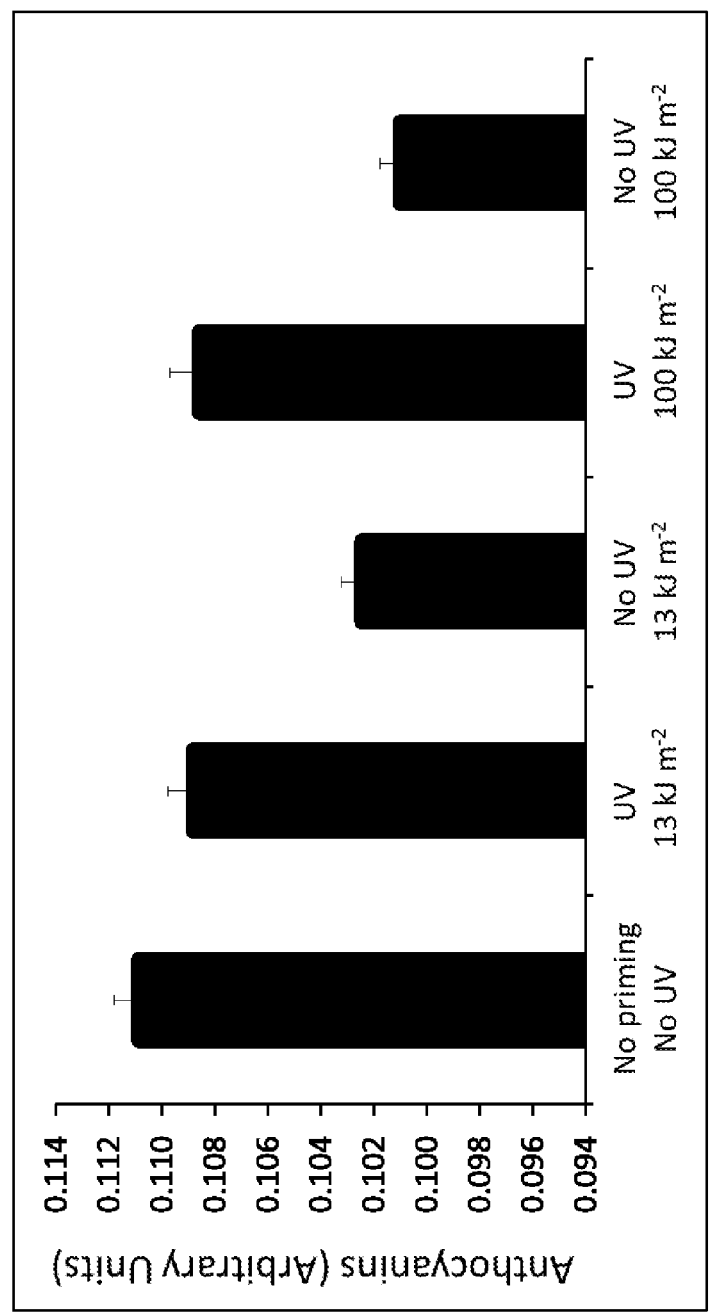
FIGS. 6A-6D illustrate an analysis of anthocyanins in maize seeds after administration of UV-B of 13 kJ $m^{-2}$ dosage and 100 kJ $m^{-2}$ dosage.
Figure 6B:
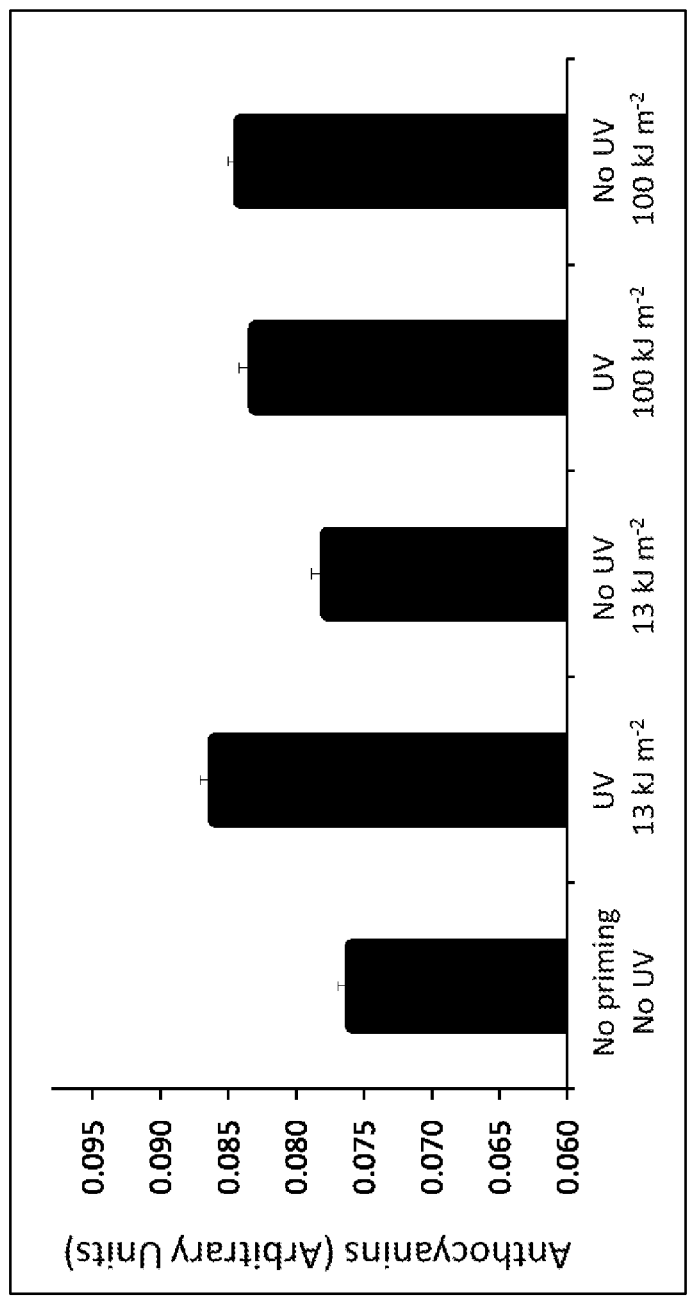
Figure 6C:
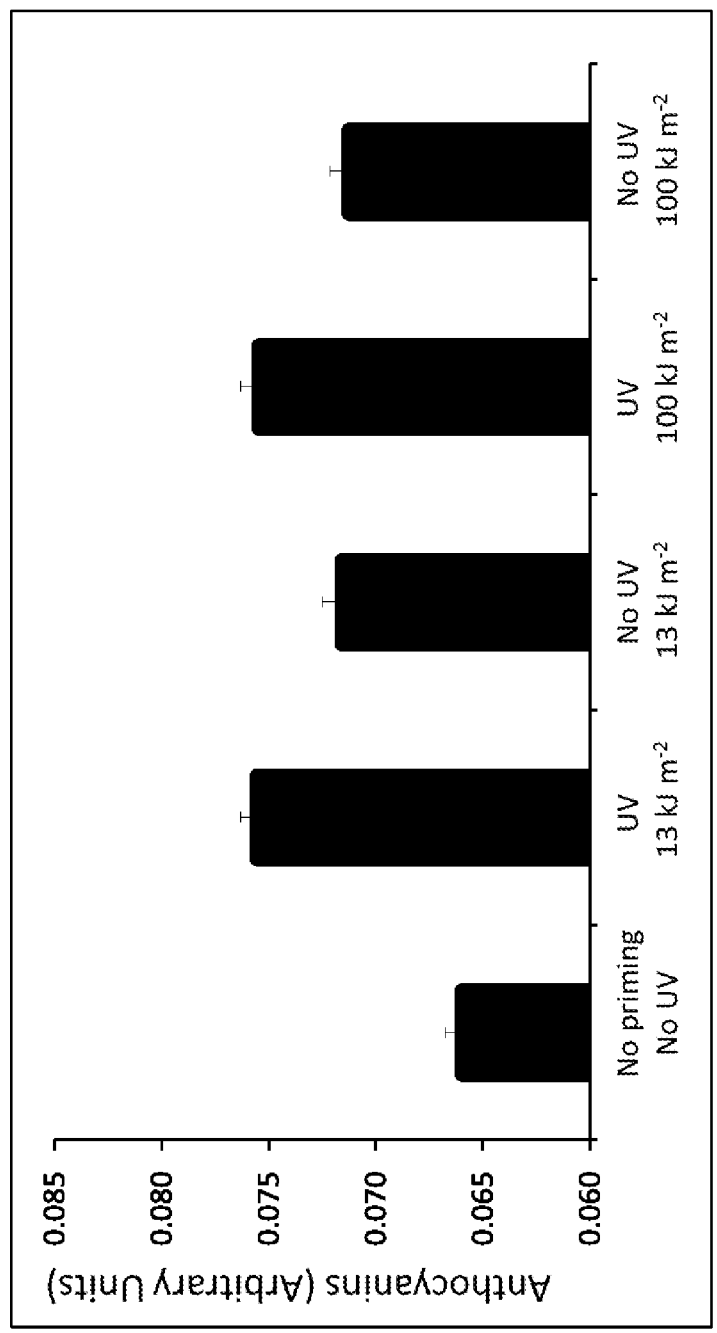
Figure 6D:
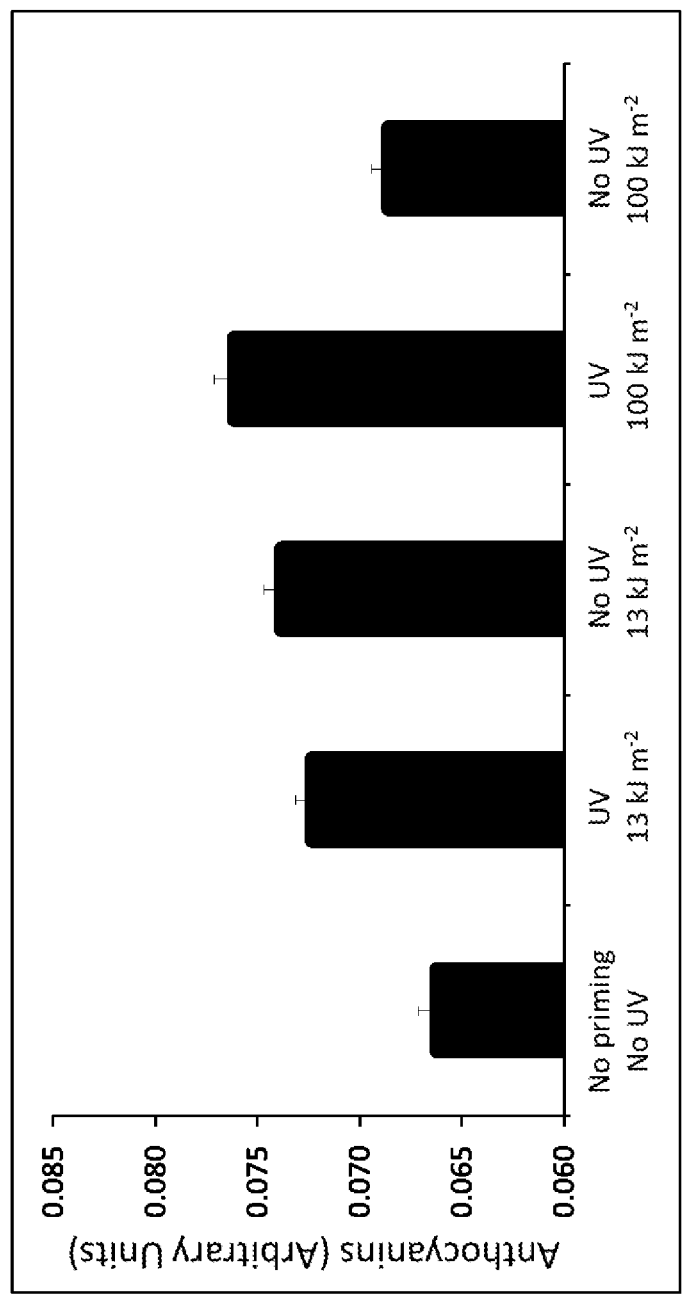

FIGS. 6A-6D show effects of UV-B dosage on anthocyanin levels. Seeds are primed in water for 16 hours followed by administration of visible light with UV-B ("UV") or visible light without UV-B ("No UV"). Dosages of 13 kJ m$^{-2}$ or 100 kJ m$^{-2}$ irradiance are used. Seed treatment duration for a dosage of 13 kJ m$^{-2}$ is 9 hours. Seed treatment duration for a dosage 100 kJ m$^{-2}$ is 21 hours. UV-B light is supplied by a LED source, the transmittance of which peaks at 280 nm. The x-axis of FIGS. 6A-6D shows the different seed treatment conditions: control samples that are not exposed to UV and not immersed in water ("No priming, No UV"), visible light with UV-B at a dosage of 13 kJ m$^{-2}$ ("UV 13 kJ m$^{-2}$"), visible light without UV-B ("No UV 13 kJ m$^{-2}$"), visible light with UV-B at a dosage of 100 kJ m$^{-2}$ ("UV 100 kJ m$^{-2}$"), and visible light without UV-B at a dosage of 100 kJ m$^{-2}$ ("No UV 100 kJ m$^{-2}$"). The y-axis of FIG. 6A shows anthocyanins (arbitrary units) and has a scale of 0.094 to 0.114. Referring to FIG. 6A, 13 kJ m$^{-2}$ and 100 kJ m$^{-2}$ UV-B dosage increase anthocyanin levels as compared to the No UV 13 kJ m$^{-2}$ seeds or the No UV 100 kJ m$^{-2}$ seeds, respectively. The y-axis of FIG. 6B shows anthocyanins (arbitrary units) and has a scale of 0.060 to 0.095. Referring to FIG. 6B, 13 kJ m$^{-2}$ UV-B dosage increase anthocyanin levels as compared to the No UV 13 kJ m$^{-2}$ seeds. The y-axis of FIG. 6C shows anthocyanins (arbitrary units) and has a scale of 0.060 to 0.085. Referring to FIG. 6C, 13 kJ m$^{-2}$ and 100 kJ m$^{-2}$ UV-B dosage increase anthocyanin levels as compared to the No UV 13 kJ m$^{-2}$ seeds or the No UV 100 kJ m$^{-2}$ seeds, respectively. The y-axis of FIG. 6D shows anthocyanins (arbitrary units) and has a scale of 0.060 to 0.085. Referring to FIG. 6D, 100 kJ m$^{-2}$ UV-B dosage increases anthocyanin levels as compared to the No UV 100 kJ m$^{-2}$ seeds. These figures demonstrate an increase in anthocyanin levels following dosage of UV-B administration.

Figure 7:
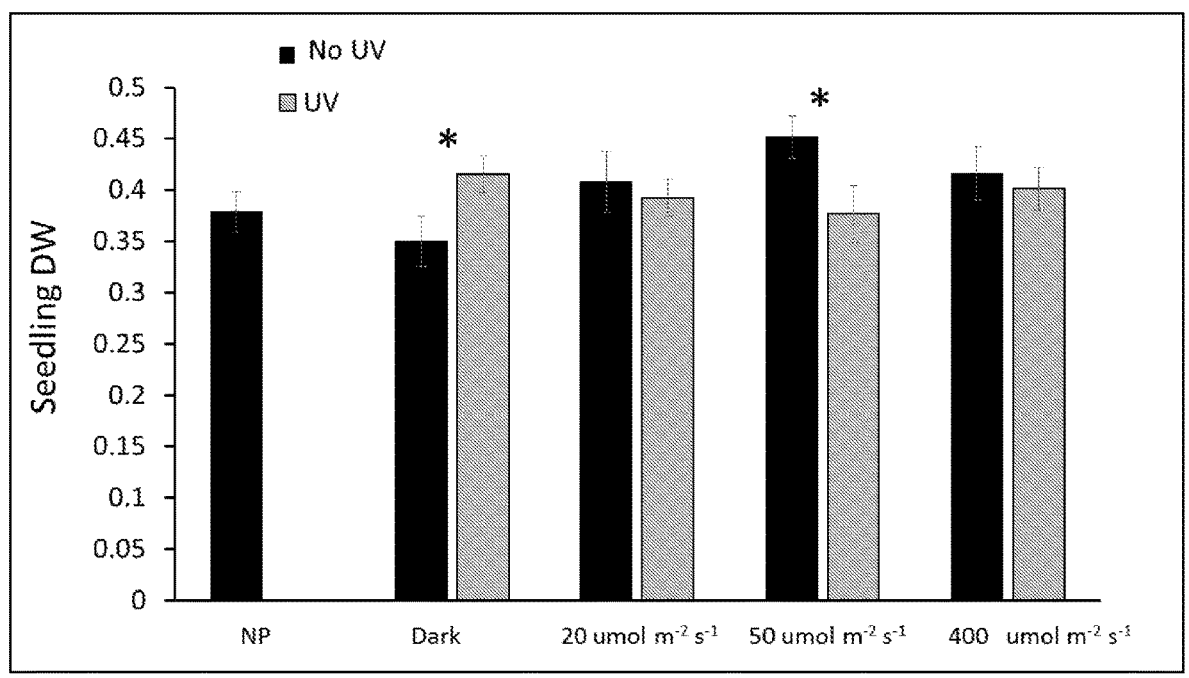
FIG. 7 illustrates an analysis of seedling dry weight (DW) after varying levels of visible light irradiance with or without UV-B (UV) treatment.

FIG. 7 shows effect of light administration on seedling dry weight. Seeds are primed in water for 16 hours followed by treatment without UV-B ("No UV," black bars) or with UV-B ("UV," hashed bars) for 9 hours using a LED source in which the transmittance of which peaked at 280 nm. Various visible light irradiances are used including: 20 umol m$^{-2}$ s$^{-1}$, 50 umol m$^{-2}$ s$^{-1}$, and 400 umol m$^{-2}$ s$^{-1}$. The x-axis shows the following treatment conditions: non-primed seeds in which seeds are not immersed in water but treated with visible light and UV-B ("NP"), seeds maintained under no visible light ("Dark"), visible light irradiance of 20 umol m$^{-2}$ s$^{-1}$ ("20 umol m$^{-2}$ s$^{-1}$"), visible light irradiance of 50 umol m$^{-2}$ s$^{-1}$ ("50 umol m$^{-2}$ s$^{-1}$"), and visible light irradiance of 400 umol m$^{-2}$ s$^{-1}$ ("400 umol m$^{-2}$ s$^{-1}$"). The y-axis shows seedling dry weight (DW) and has a scale of 0 to 0.5. This figure shows co-administration of UV-B with visible light results in an increase in seedling dry weight.

Figure 8A:
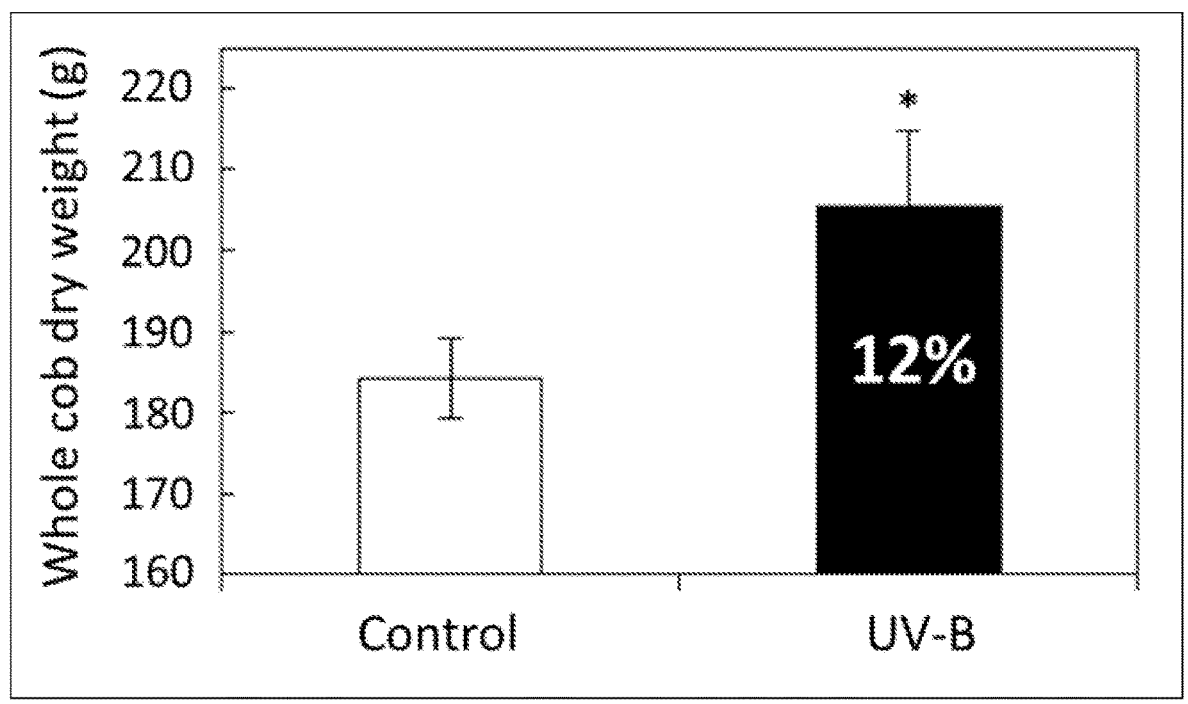
FIGS. 8A-8G depict an analysis of corn-seed productivity after UV-B treatment.
Figure 8B:
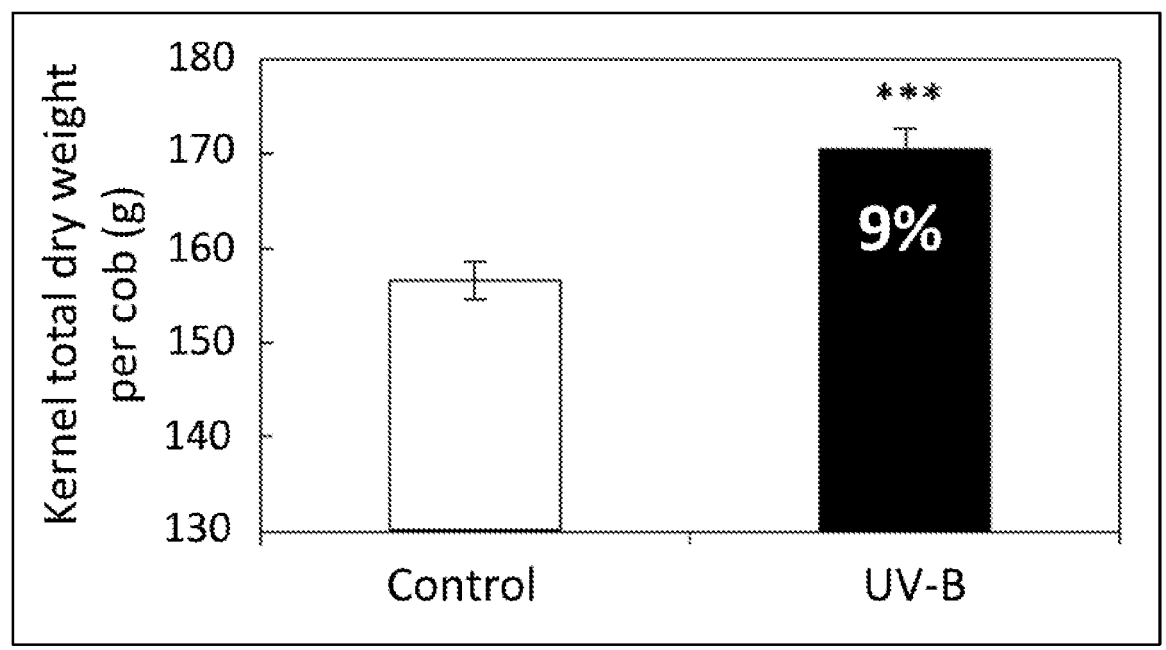
Figure 8C:
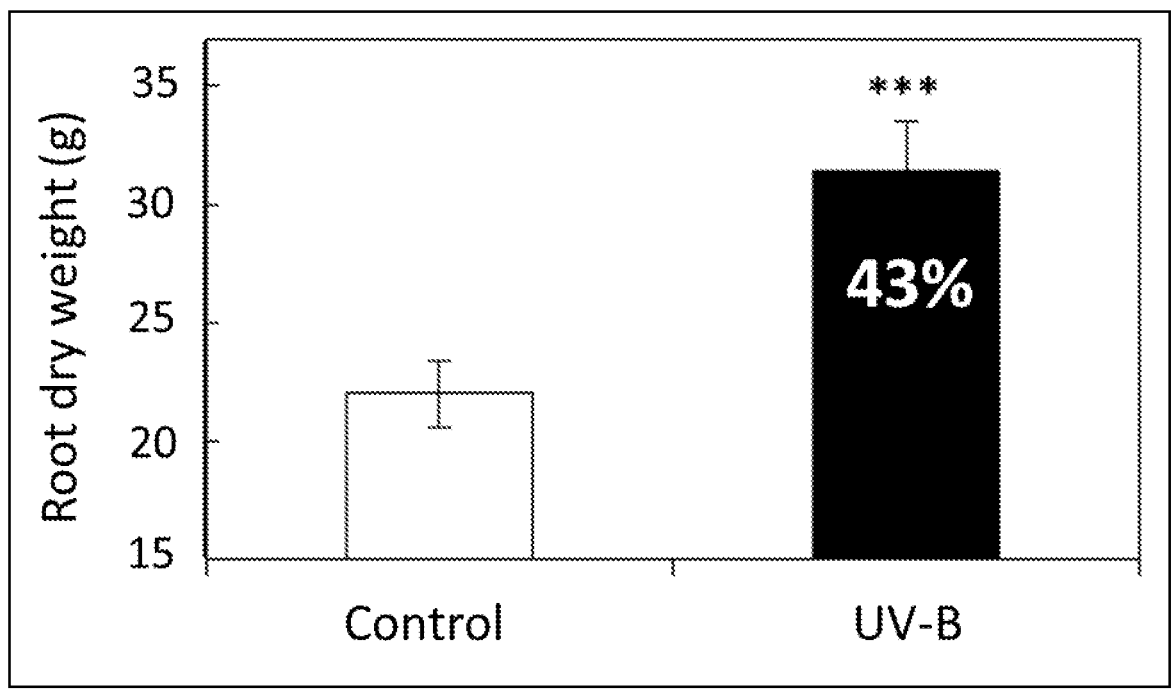
Figure 8D:
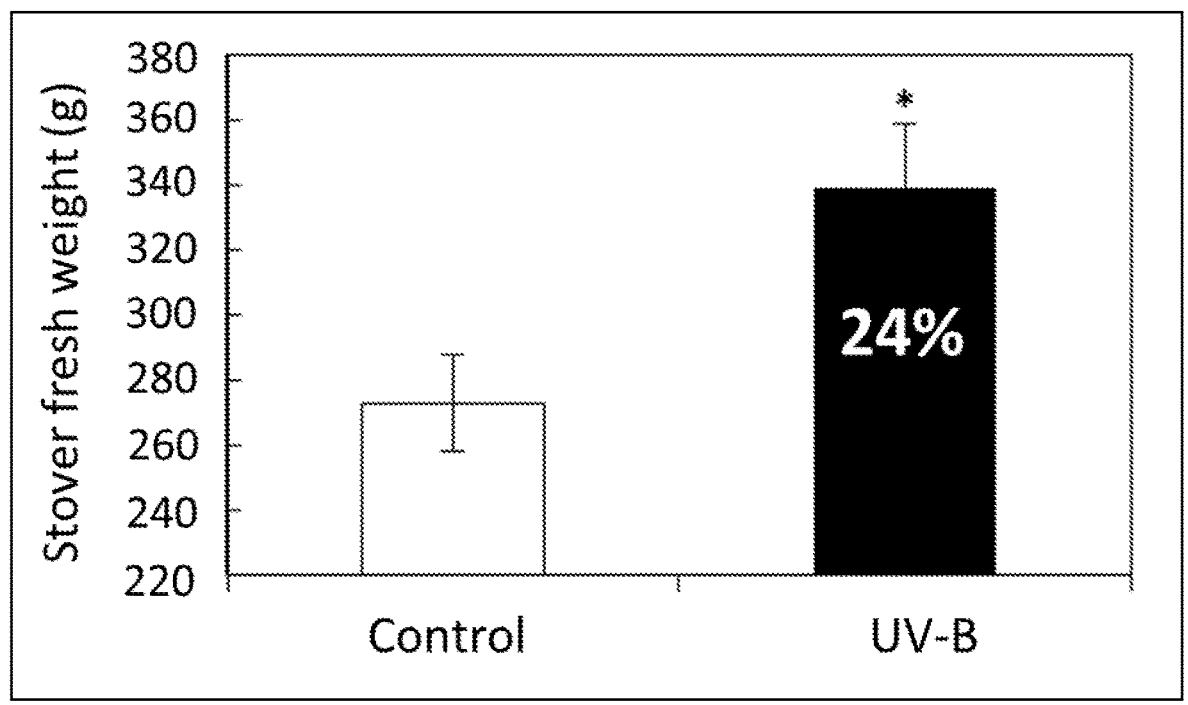
Figure 8E:
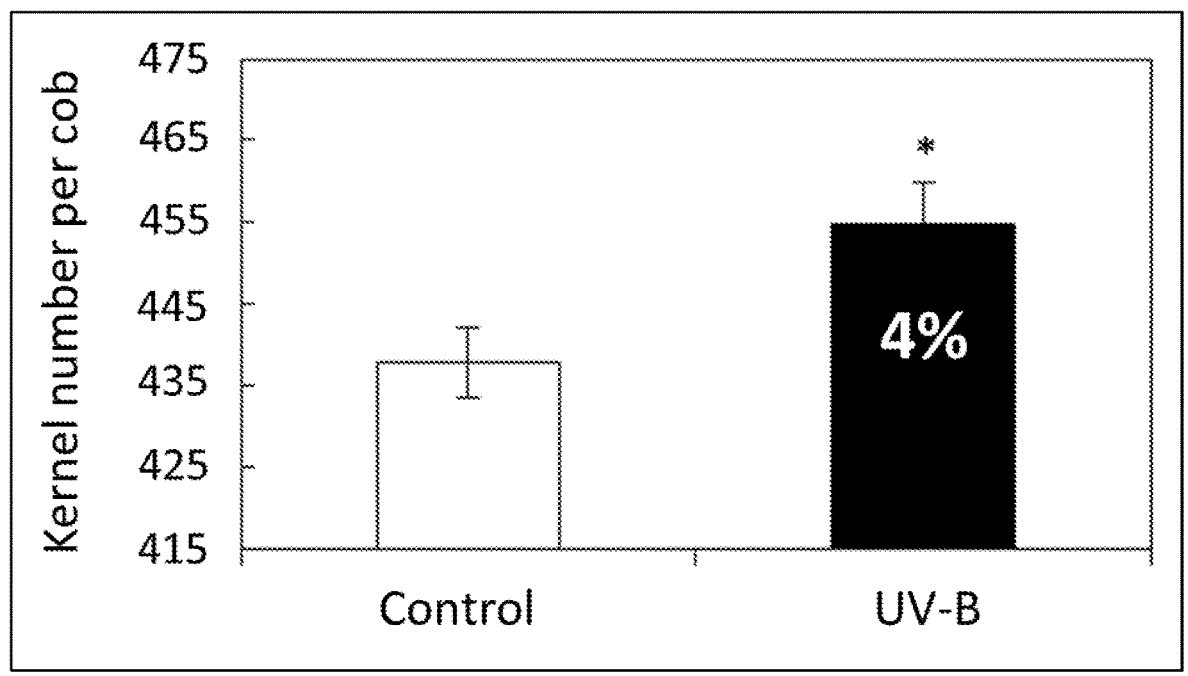
Figure 8F:
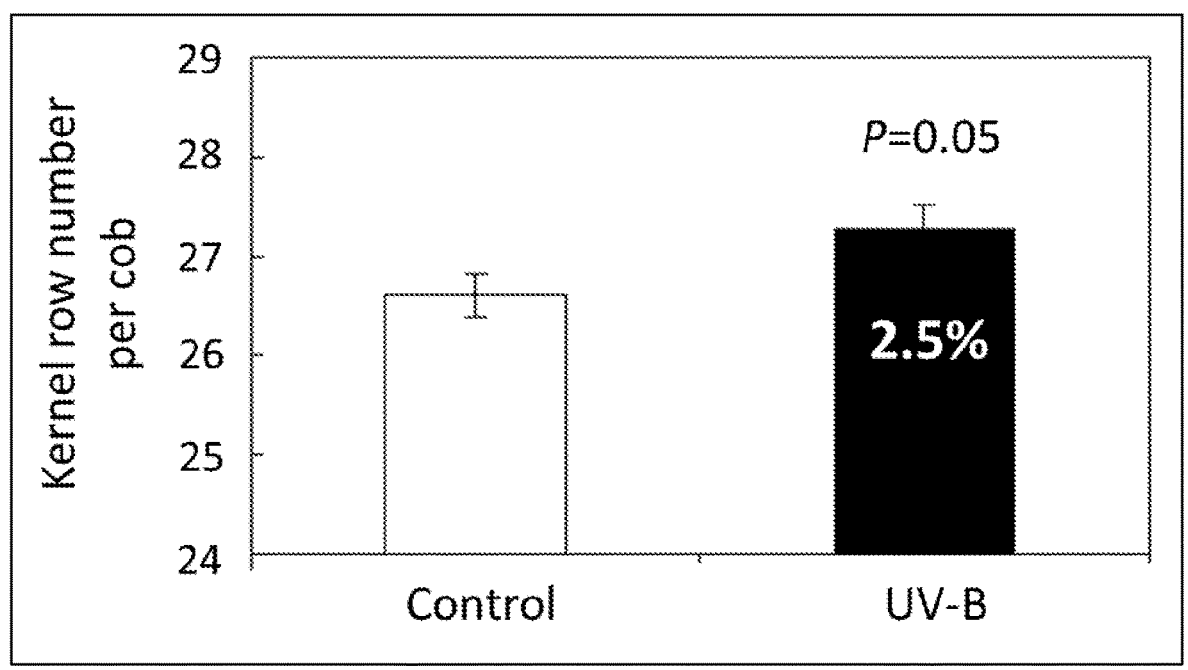
Figure 8G:
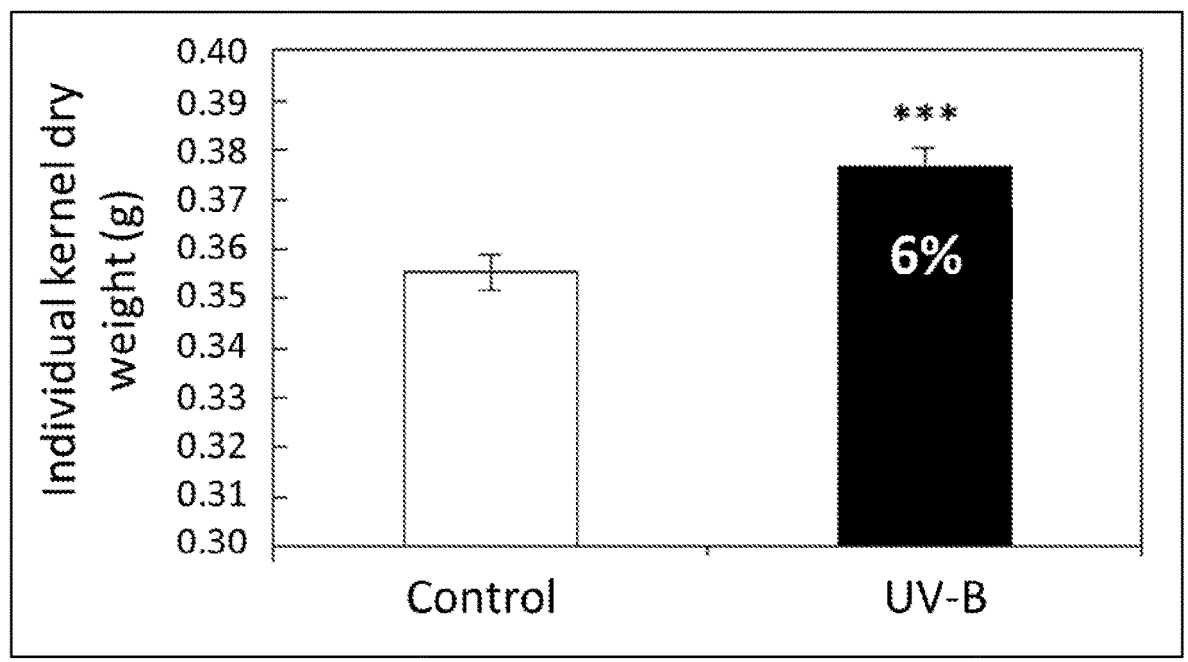

FIGS. 8A-8G show effects on plant performance from maize seeds (Zea mays) following light administration. The x-axis of FIGS. 8A-8G shows the following seed treatments: no UV ("Control") and UV-B administration ("UV-B"). The y-axis of FIG. 8A shows whole cob dry weight in grams (g) and has a scale of 160 to 220. Referring to FIG. 8A, UV-B irradiation significantly increases the whole cob dry weight in grams by 12%. The y-axis of FIG. 8B shows kernel total dry weight per cob in grams (g) and has a scale of 130 to 180. Referring to FIG. 8B, UV-B irradiation significantly increases kernel total dry weight per cob in grams by 9%. The y-axis of FIG. 8C shows root dry weight in grams (g) and has a scale of 15 to 35. Referring to FIG. 8C, UV-B irradiation significantly increases root dry weight by 43%. The y-axis of FIG. 8D shows stover fresh weight in grams (g) and has a scale of 220 to 380. Referring to FIG. 8D, UV-B irradiation significantly increases stover fresh weight by 24%. The y-axis of FIG. 8E shows kernel number per cob and has a scale of 415 to 475. Referring to FIG. 8E, UV-B irradiation significantly increases kernel number per cob by 4%. The y-axis of FIG. 8F shows kernel row number per cob and has a scale of 24 to 29. Referring to FIG. 8F, UV-B irradiation increases kernel row number per cob by 2.5%. The y-axis of FIG. 8G shows individual kernel dry weight in grams (g) and has a scale of 0.30 to 0.40. Referring to FIG. 8G, UV-B irradiation significantly increases individual kernel dry weight by 6%. These figures demonstrate that UV-B administration increases plant productivity.

Figure 9:
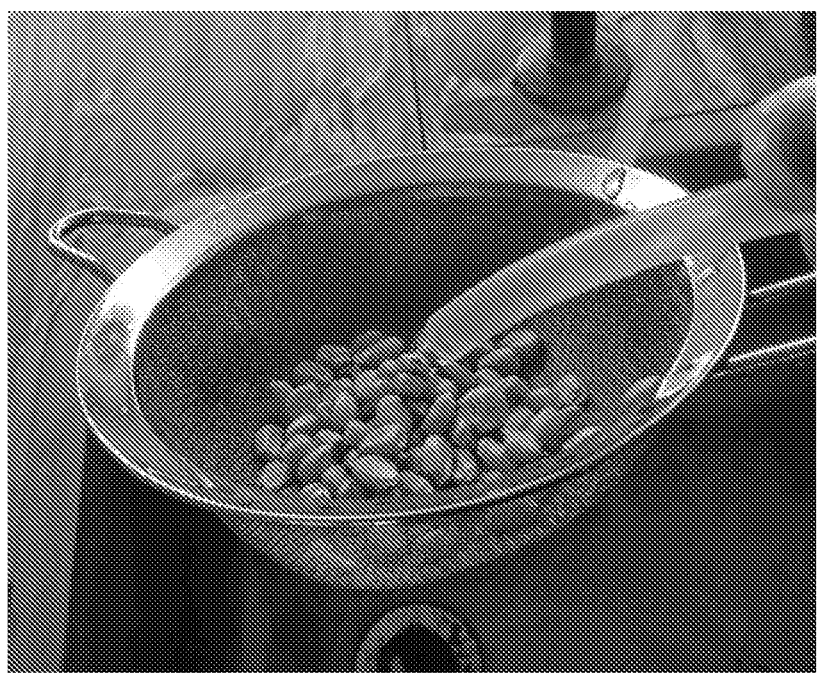
FIG. 9 depicts a method of washing seeds in preparation for priming.

FIG. 9 depicts a method of washing seeds in preparation of light administration.

Figure 10:
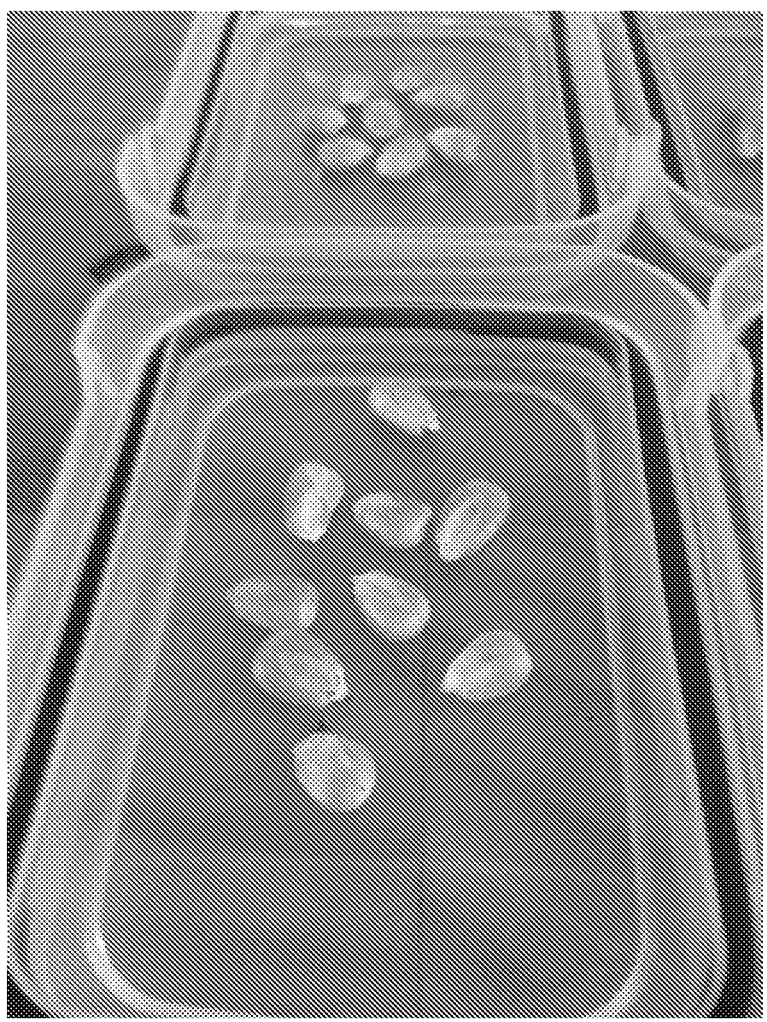
FIG. 10 illustrates an arrangement of seeds on seed trays.

FIG. 10 depicts a positioning of seeds on trays for light administration.

Figure 11:
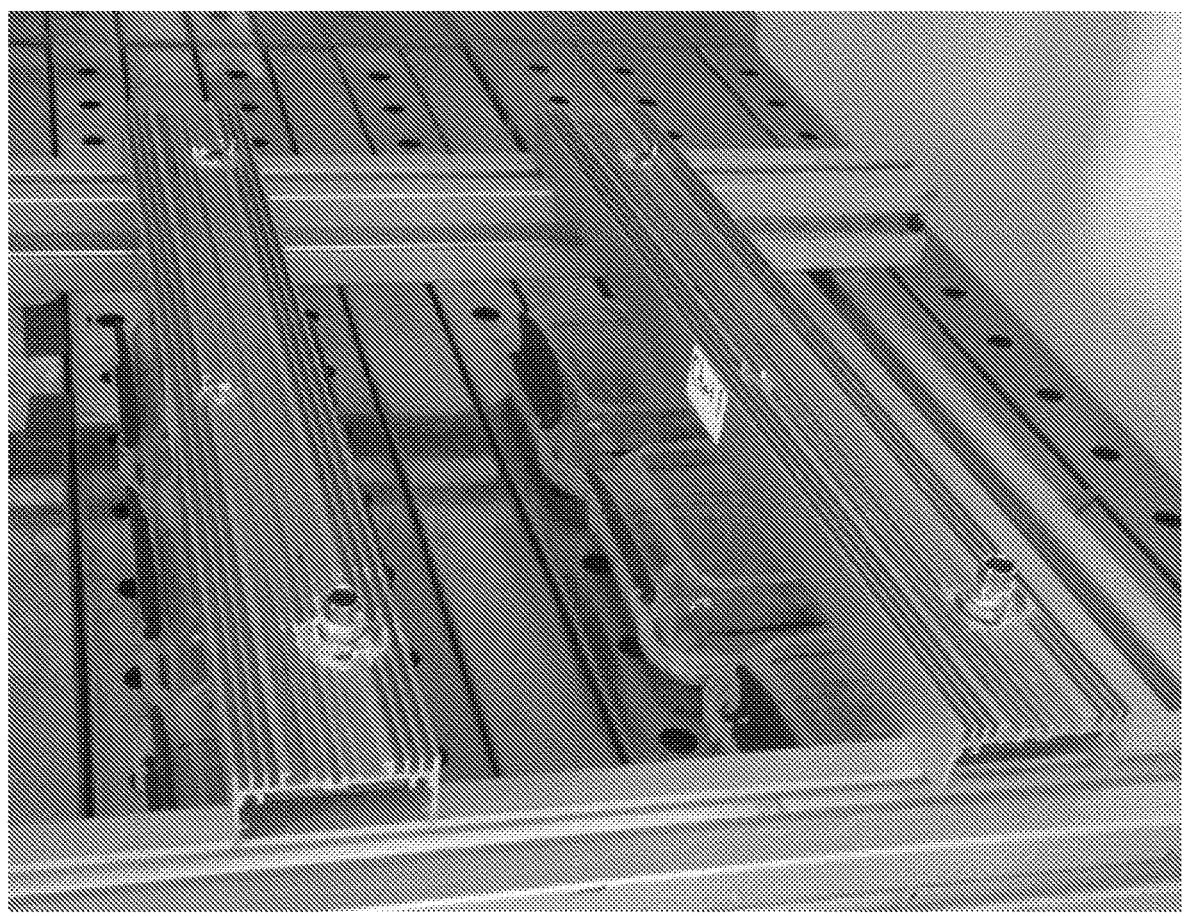
FIG. 11 depicts an arrangement of light emitting diode (LED) panels for placement of seed trays.

FIG. 11 shows an arrangement of light emitting diode (LED) panels for placement of seed trays.

Figure 12:
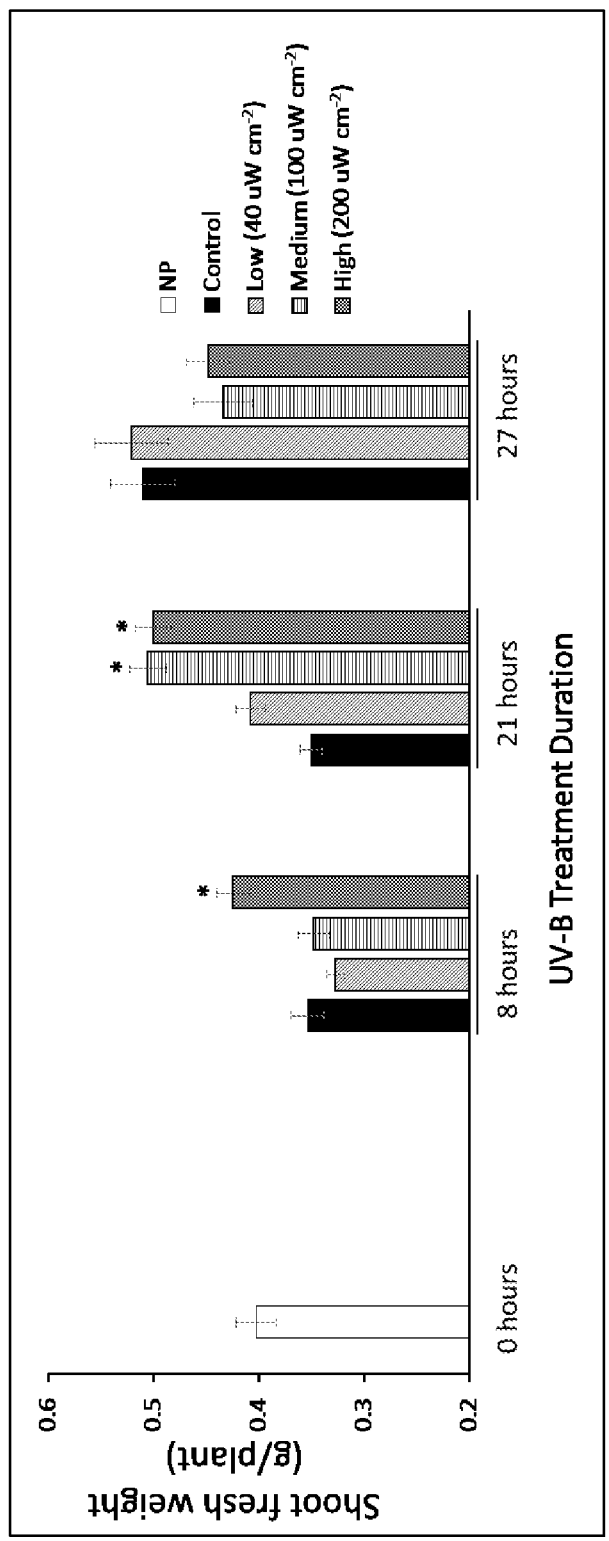
FIG. 12 depicts a graph of shoot fresh weight (g/plant) of lettuce seeds administered control, low (40 uW $cm^{-2}$), medium (100 uW $cm^{-2}$), and high (200 uW $cm^{-2}$) UV-B irradiance. Treatment duration of UV-B includes 0 hours, 8 hours, 21 hours, and 27 hours. "NP" refers to non-primed seeds.

FIG. 12 shows effects of treatment conditions comprising priming, temperature, UV-B dosage, duration of UV-B administration, and seed position on shoot fresh weight in lettuce. Iceberg lettuce seeds are primed in −1.25 bar polyethylene glycol (PEG) dissolved in distilled water. UV-B is administered in a growth cabinet at 10° C. for 0 hours, 8 hours, 21 hours, or 27 hours. UV-B irradiance is administered at 40 uW cm$^{-2}$ ("low," diagonal hashed bars), 100 uW cm$^{-2}$ ("medium," horizontal hashed bars), and 200 uW cm$^{-2}$ ("high," checkered bars). "Control" (black bars) refers to no UV-B. "NP" refers to non-primed seeds in which seeds are not immersed in PEG nor receive an UV treatment. The seeds are positioned on top of a moist filter paper during UV-B administration. The x-axis shows UV-B treatment duration: 0 hours, 8 hours, 21 hours, and 27 hours. The y-axis shows shoot fresh weight (g/plant) and has a scale of 0.2 to 0.6. High UV-B irradiance administration for 8 hours results in a significant increase of about 19% in shoot fresh weight as compared to Control. Medium UV-B irradiance administration for 21 hours results in a significant increase of about 42% in shoot fresh weight as compared to Control. High UV-B irradiance administration for 21 hours results in a significant increase of about 38% in shoot fresh weight as compared to Control. This figure demonstrates treatment conditions comprising priming and administration of UV-B of various irradiance and duration improves plant performance such as shoot fresh weight.

FIG. 13 shows effects of treatment conditions comprising priming, temperature, UV-B dosage, duration of UV-B administration, and seed position on chlorophyll levels in lettuce. Iceberg lettuce seeds are primed in −1.25 bar polyethylene glycol (PEG) dissolved in distilled water. UV-B is administered in a growth cabinet at 10° C. for 0 hours, 8 hours, 21 hours, or 27 hours. UV-B irradiance is administered at 40 uW cm$^{-2}$ ("low," diagonal hashed bars), 100 uW cm$^{-2}$ ("medium," horizontal hashed bars), and 200 uW cm$^{-2}$ ("high," checkered bars). "Control" (black bars) refers to no UV-B treatment in which seeds are immersed in priming medium but did not receive UV. "NP" refers to non-primed seeds in which seeds are not immersed in PEG nor receive an UV treatment. The seeds are positioned on top of a moist filter paper during UV-B administration. The x-axis shows UV-B treatment duration: 0 hours, 8 hours, 21 hours, and 27 hours. The y-axis shows chlorophyll (relative unit) and has a scale of 15 to 27. This figure demonstrates treatment conditions comprising priming and administration of UV-B of various irradiance and duration can improve plant performance such as chlorophyll levels.

Figure 14:
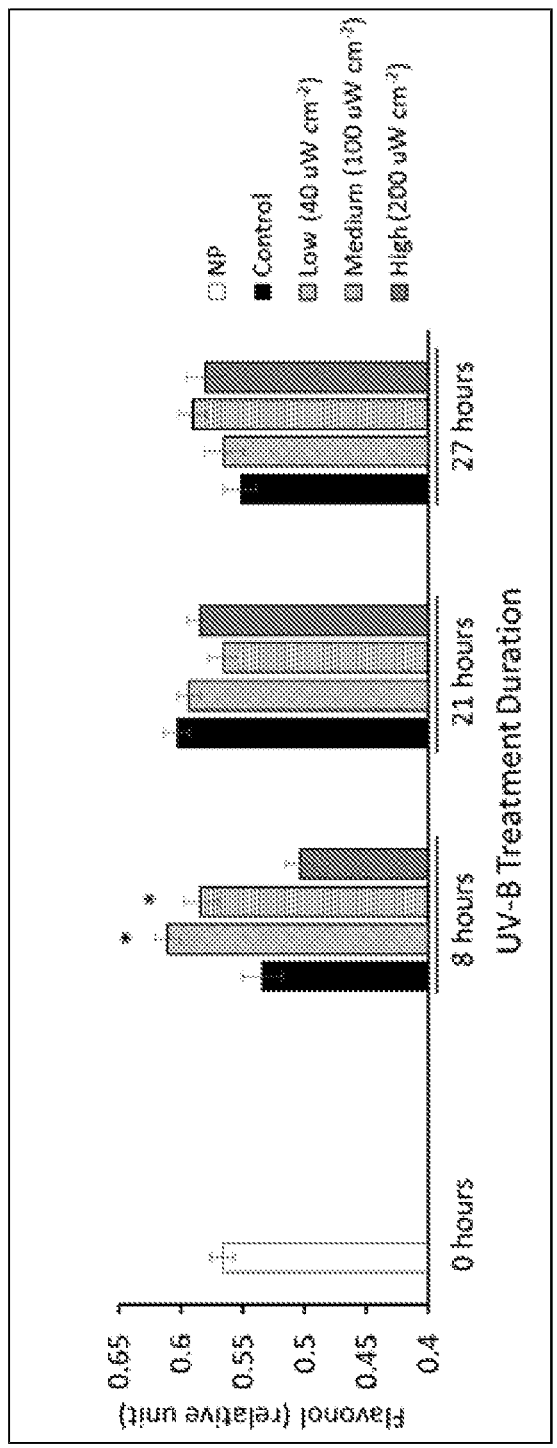
FIG. 14 depicts a graph of flavonoid levels (relative unit) of lettuce seeds administered control, low (40 uW $cm^{-2}$), medium (100 uW $cm^{-2}$), and high (200 uW $cm^{-2}$) UV-B irradiance. Treatment duration of UV-B includes 0 hours, 8 hours, 21 hours, and 27 hours. "NP" refers to non-primed seeds.

FIG. 14 shows effects of treatment conditions comprising priming, temperature, UV-B dosage, duration of UV-B administration, and seed position on flavonoid levels in lettuce. Iceberg lettuce seeds are primed in −1.25 bar polyethylene glycol (PEG) dissolved in distilled water. UV-B is administered in a growth cabinet at 10° C. for 0 hours, 8 hours, 21 hours, or 27 hours. UV-B irradiance is administered at 40 uW cm$^{-2}$ ("low," diagonal hashed bars), 100 uW cm$^{-2}$ ("medium," horizontal hashed bars), and 200 uW cm$^{-2}$ ("high," checkered bars). "Control" (black bars) refers to no UV-B treatment in which seeds are immersed in priming medium but did not receive UV. "NP" refers to non-primed seeds in which seeds are not immersed in PEG nor receive an UV treatment. The seeds are positioned on top of a moist filter paper during UV-B administration. The x-axis shows UV-B treatment duration: 0 hours, 8 hours, 21 hours, and 27 hours. The y-axis shows flavonoid (relative unit) and has a scale of 0.4 to 0.65. Low UV-B irradiance for 8 hours results in a significant increase of about 14% in flavonoid levels as compared to Control. This figure demonstrates treatment conditions comprising priming and administration of UV-B of various irradiance and duration can improve plant performance such as flavonoid levels.

Figure 15:
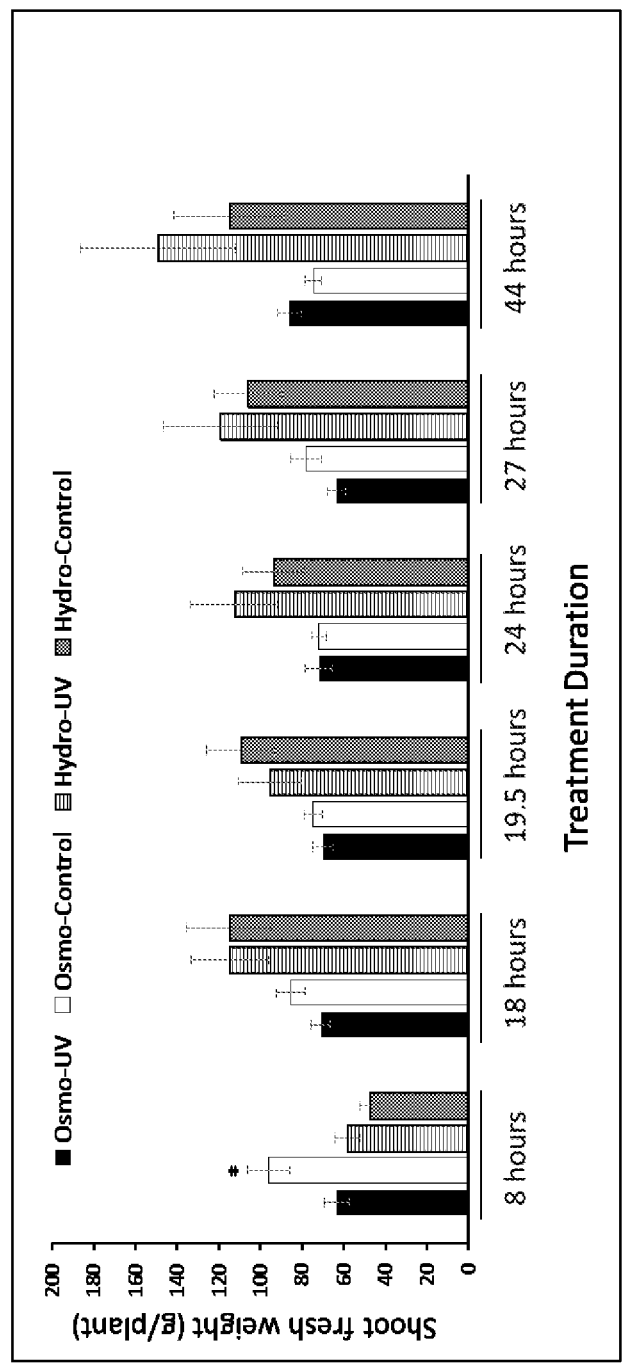
FIG. 15 depicts a graph of shoot fresh weight (g/plant) of broccoli seeds primed in distilled water ("Hydro") or −1.25 bar polyethylene glycol ("Osmo") dissolved in water followed by administration of no UV-B ("Control") or UV-B ("UV"). Duration of imbibing includes 8 hours, 18 hours, 19.5 hours, 24 hours, 27 hours, and 44 hours.

FIG. 15 depicts effects of treatment conditions comprising priming, temperature, UV-B dosage, duration of UV-B administration, and seed position on shoot fresh weight in broccoli. A first set of broccoli seeds are primed in distilled water ("Hydro"). A second set of broccoli seeds are primed in −1.25 bar polyethylene glycol (PEG) dissolved in distilled water ("Osmo"). Both sets of broccoli seeds are primed for 8 hours, 18 hours, 19.5 hours, 24 hours, 27 hours, or 44 hours. Both sets of broccoli seeds are administered 100 uW cm$^{-2}$ UV-B irradiance in a growth cabinet at 22° C. The seeds are submerged in the priming medium during UV-B administration. The x-axis shows imbibing or priming duration: 8 hours, 18 hours, 19.5 hours, 24 hours, 27 hours, and 44 hours. Treatment conditions include the following: seeds prime in PEG and no UV-B ("Osmo-Control," white bars), seeds prime in PEG and UV-B administration ("Osmo-UV," black bars), seeds prime in distilled water and no UV-B ("Hydro-Control," checkered bars), and seeds prime in distilled water and UV-B administration ("Hydro-UV," horizontal hashed bars). The y-axis shows shoot fresh weight (g/plant) and has a scale of 0 to 200. Osmo-UV seeds prime for 8 hours exhibit a significant difference of about 34% decrease in shoot fresh weight as compared to Osmo-Control. There is a significant difference between Osmo-Control and Hydro-Control. This figure demonstrates treatment conditions comprising various priming conditions and administration of UV-B affects plant performance such as shoot fresh weight.

Figure 16:
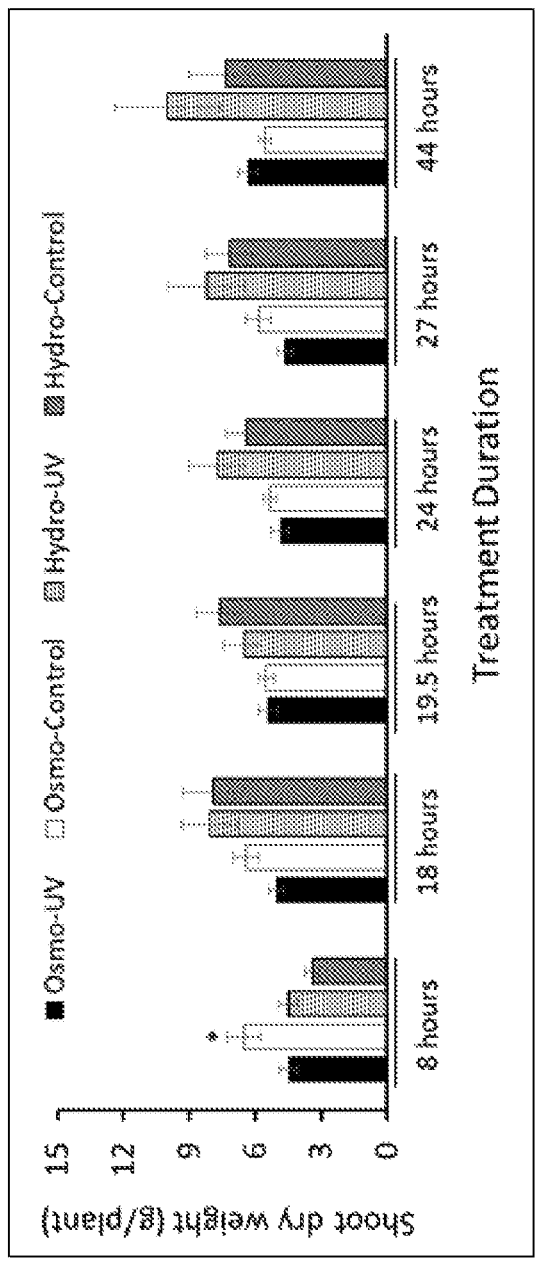
FIG. 16 depicts a graph of shoot dry weight (g/plant) of broccoli seeds primed in distilled water ("Hydro") or −1.25 bar polyethylene glycol ("Osmo") dissolved in water followed by administration of no UV-B ("Control") or UV-B ("UV"). Duration of imbibing includes 8 hours, 18 hours, 19.5 hours, 24 hours, 27 hours, and 44 hours.

FIG. 16 depicts effects of treatment conditions comprising priming, temperature, UV-B dosage, duration of UV-B administration, and seed position on shoot dry weight in broccoli. A first set of broccoli seeds are primed in distilled water ("Hydro"). A second set of broccoli seeds are primed in −1.25 bar polyethylene glycol (PEG) dissolved in distilled water ("Osmo"). Both sets of broccoli seeds are primed for 8 hours, 18 hours, 19.5 hours, 24 hours, 27 hours, or 44 hours. Both sets of broccoli seeds are administered 100 uW cm$^{-2}$ UV-B irradiance in a growth cabinet at 22° C. The seeds are submerged in the priming medium during UV-B administration. The x-axis shows imbibing duration: 8 hours, 18 hours, 19.5 hours, 24 hours, 27 hours, and 44 hours. Treatment conditions include the following: seeds prime in PEG and no UV-B ("Osmo-Control," white bars), seeds prime in PEG and UV-B administration ("Osmo-UV," black bars), seeds prime in distilled water and no UV-B ("Hydro-Control," checkered bars), and seeds prime in distilled water and UV-B administration ("Hydro-UV," horizontal hashed bars). The y-axis shows shoot dry weight (g/plant) and has a scale of 0 to 15. Osmo-UV seeds prime for 8 hours exhibit a difference in shoot dry weight of about 31% decrease as compared to Osmo-Control. There is a significant difference between Osmo-Control and Hydro-Control. This figure demonstrates treatment conditions comprising various priming conditions and administration of UV-B affects plant performance such as shoot dry weight.

Figure 17:
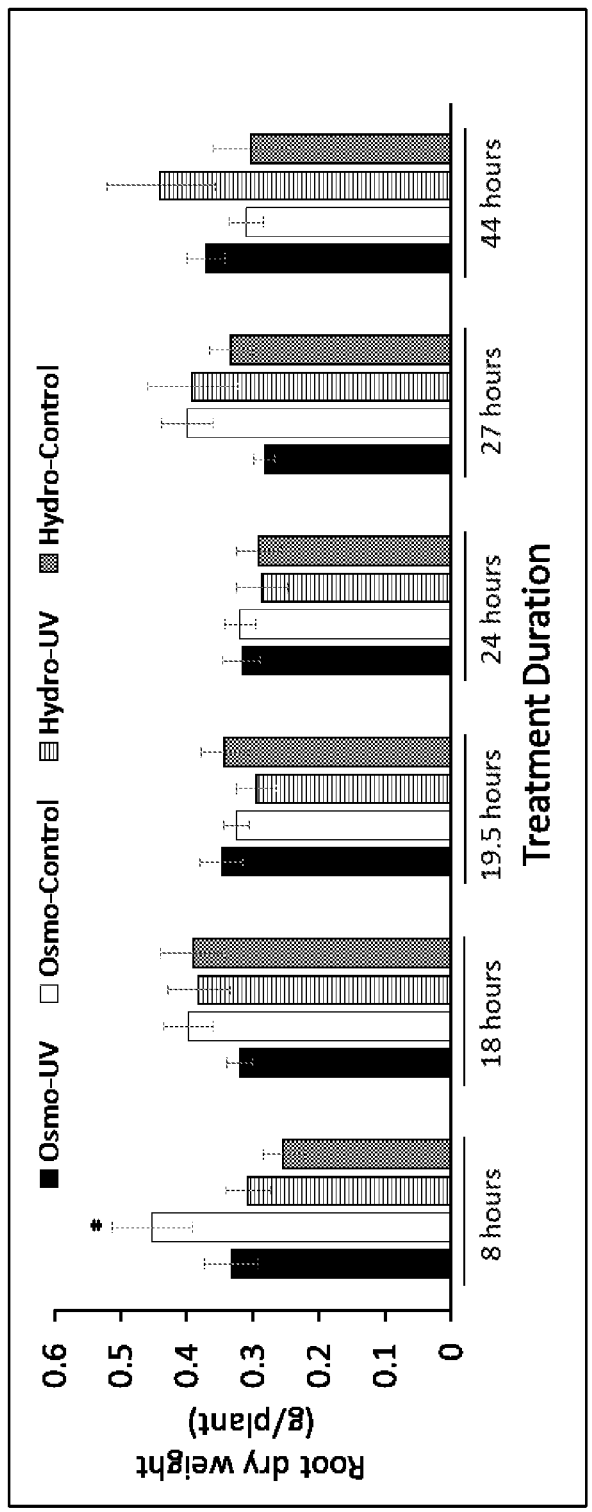
FIG. 17 depicts a graph of root dry weight (g/plant) of broccoli seeds primed in distilled water ("Hydro") or −1.25 bar polyethylene glycol ("Osmo") dissolved in water followed by administration of no UV-B ("Control") or UV-B ("UV"). Duration of imbibing includes 8 hours, 18 hours, 19.5 hours, 24 hours, 27 hours, and 44 hours.

FIG. 17 depicts effects of treatment conditions comprising priming, temperature, UV-B dosage, duration of UV-B administration, and seed position on root dry weight in broccoli. A first set of broccoli seeds are primed in distilled water ("Hydro"). A second set of broccoli seeds are primed in −1.25 bar polyethylene glycol (PEG) dissolved in distilled water ("Osmo"). Both sets of broccoli seeds are primed for 8 hours, 18 hours, 19.5 hours, 24 hours, 27 hours, or 44 hours. Both sets of broccoli seeds are administered 100 uW cm$^{-2}$ UV-B irradiance in a growth cabinet at 22° C. The seeds are submerged in the priming medium during UV-B administration. The x-axis shows imbibing duration: 8 hours, 18 hours, 19.5 hours, 24 hours, 27 hours, and 44 hours. Treatment conditions include the following: seeds prime in PEG and no UV-B ("Osmo-Control," white bars), seeds prime in PEG and UV-B administration ("Osmo-UV," black bars), seeds prime in distilled water and no UV-B ("Hydro-Control," checkered bars), and seeds prime in distilled water and UV-B administration ("Hydro-UV," horizontal hashed bars). The y-axis shows root dry weight (g/plant) and has a scale of 0 to 0.6. Osmo-UV seeds prime for 8 hours exhibit a difference of about 27% decrease in root dry weight as compared to Osmo-Control. There is also a significant difference between Osmo-Control and Hydro-Control. This figure demonstrates treatment conditions comprising various priming conditions and administration of UV-B affects plant performance such as root dry weight.

Figure 18:
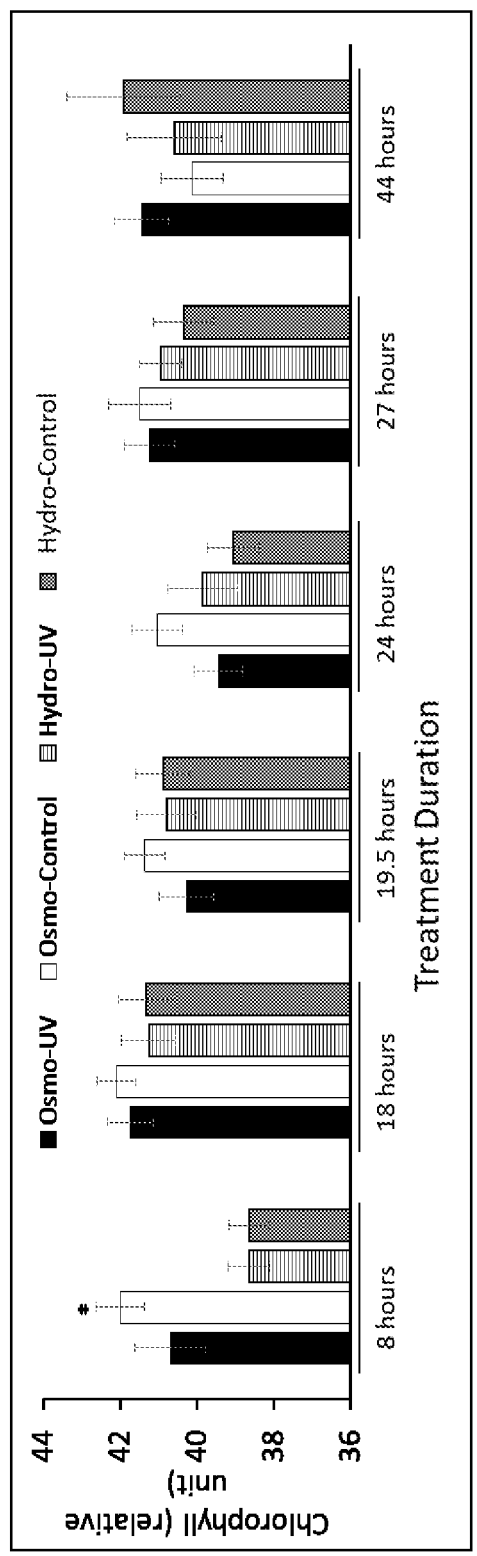
FIG. 18 depicts a graph of chlorophyll levels (relative unit) of broccoli seeds primed in distilled water ("Hydro") or −1.25 bar polyethylene glycol ("Osmo") dissolved in water followed by administration of no UV-B ("Control") or UV-B ("UV"). Duration of imbibing includes 8 hours, 18 hours, 19.5 hours, 24 hours, 27 hours, and 44 hours.

FIG. 18 depicts effects of treatment conditions comprising priming, temperature, UV-B dosage, duration of UV-B administration, and seed position on chlorophyll levels in broccoli. A first set of broccoli seeds are primed in distilled water ("Hydro"). A second set of broccoli seeds are primed in −1.25 bar polyethylene glycol (PEG) dissolved in distilled water ("Osmo"). Both sets of broccoli seeds are primed for 8 hours, 18 hours, 19.5 hours, 24 hours, 27 hours, or 44 hours. Both sets of broccoli seeds are administered 100 uW cm$^{-2}$ UV-B irradiance in a growth cabinet at 22° C. The seeds are submerged in the priming medium during UV-B administration. The x-axis shows imbibing duration: 8 hours, 18 hours, 19.5 hours, 24 hours, 27 hours, and 44 hours. Treatment conditions include the following: seeds prime in PEG and no UV-B ("Osmo-Control," white bars), seeds prime in PEG and UV-B administration ("Osmo-UV," black bars), seeds prime in distilled water and no UV-B ("Hydro-Control," checkered bars), and seeds prime in distilled water and UV-B administration ("Hydro-UV," horizontal hashed bars). The y-axis shows chlorophyll (relative unit) and has a scale of 36 to 44. At 8 hours, the Osmo-Control has significantly higher chlorophyll levels than Hydro-Control or Hydro-UV. This figure demonstrates treatment conditions comprising various priming conditions and administration of UV-B affects plant performance such as chlorophyll levels.

Figure 19:
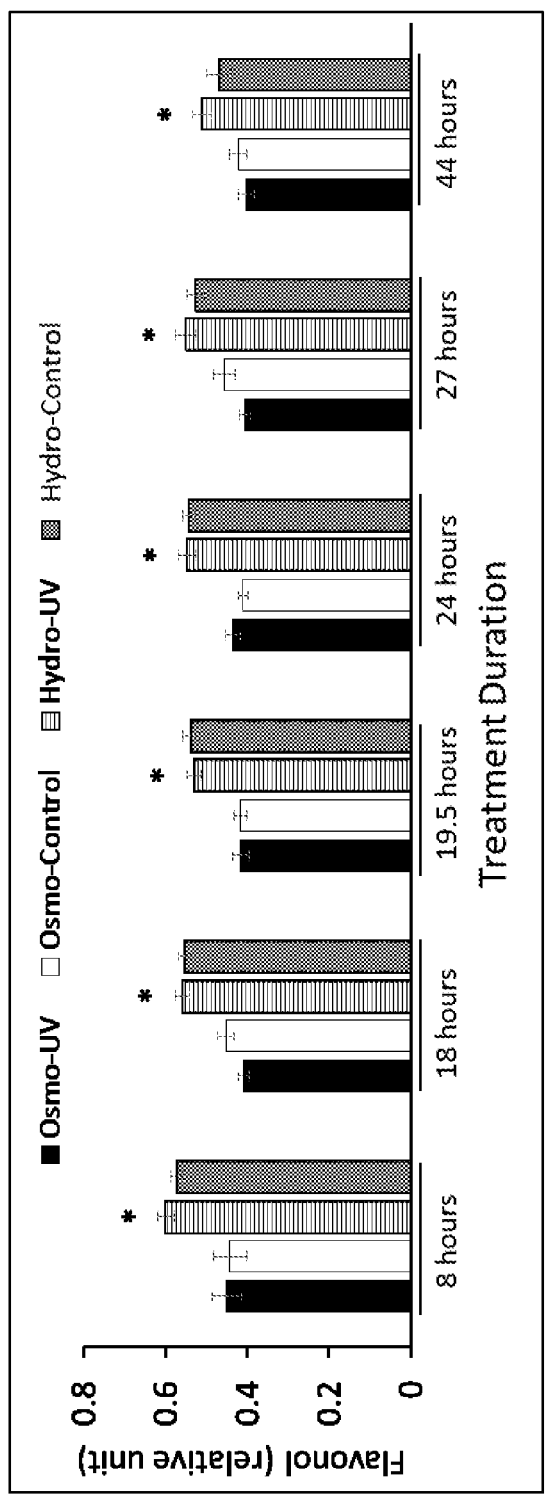
FIG. 19 depicts a graph of flavonoid levels (relative unit) of broccoli seeds primed in distilled water ("Hydro") or −1.25 bar polyethylene glycol ("Osmo") dissolved in water followed by administration of no UV-B ("Control") or UV-B ("UV"). Duration of imbibing includes 8 hours, 18 hours, 19.5 hours, 24 hours, 27 hours, and 44 hours.

FIG. 19 depicts effects of treatment conditions comprising priming, temperature, UV-B dosage, duration of UV-B administration, and seed position on flavonoid levels in broccoli. A first set of broccoli seeds are primed in distilled water ("Hydro"). A second set of broccoli seeds are primed in −1.25 bar polyethylene glycol (PEG) dissolved in distilled water ("Osmo"). Both sets of broccoli seeds are primed for 8 hours, 18 hours, 19.5 hours, 24 hours, 27 hours, or 44 hours. Both sets of broccoli seeds are administered 100 uW cm$^{-2}$ UV-B irradiance in a growth cabinet at 22° C. The seeds are submerged in the priming medium during UV-B administration. The x-axis shows imbibing duration: 8 hours, 18 hours, 19.5 hours, 24 hours, 27 hours, and 44 hours. Treatment conditions include the following: seeds prime in PEG and no UV-B ("Osmo-Control," white bars), seeds prime in PEG and UV-B administration ("Osmo-UV," black bars), seeds prime in distilled water and no UV-B ("Hydro-Control," checkered bars), and seeds prime in distilled water and UV-B administration ("Hydro-UV," horizontal hashed bars). The y-axis shows flavonoid (relative unit) and has a scale of 0 to 0.8. There is a significant difference in flavonoid levels between Hydro priming as compared to Osmo priming. This figure demonstrates treatment conditions comprising various priming conditions and administration of UV-B improves plant performance such as flavonoid levels.

Figure 20:
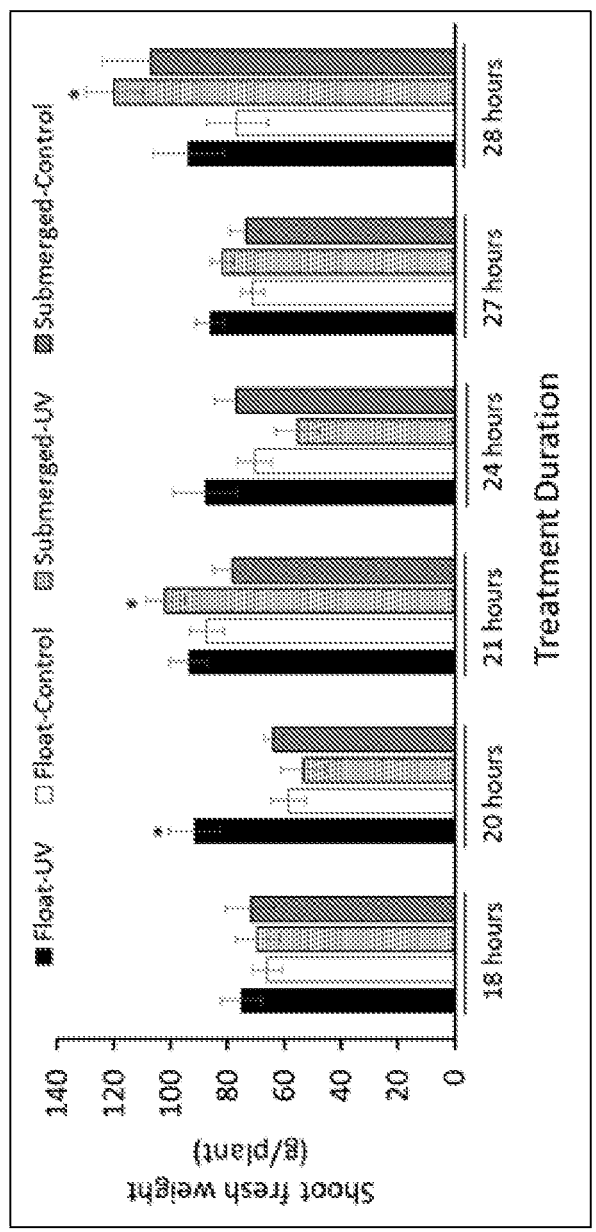
FIG. 20 depicts a graph of shoot fresh weight (g/plant) of broccoli seeds placed on top of a moist filter paper ("Float") or submerged ("Submerged") in priming medium during no UV-B ("Control") or UV-B ("UV") administration. Treatment duration of UV-B includes 18 hours, 20 hours, 21 hours, 24 hours, 27 hours, and 28 hours.

FIG. 20 depicts effects of treatment conditions comprising priming, temperature, UV-B dosage, duration of UV-B administration, and seed position on shoot fresh weight in broccoli. Broccoli seeds are primed in distilled water followed by administration of UV-B in a growth cabinet at 10° C. for 18 hours, 20 hours, 21 hours, 24 hours, 27 hours, or 28 hours. A first set of seeds is placed on top of a most filter paper ("Float") during UV-B administration. A second set of seeds is completely submerged in the priming medium ("Submerged") during UV-B administration. UV-B is administered at 100 uW cm$^{-2}$ UV-B irradiance. The x-axis shows various UV-B treatment durations: 18 hours, 20 hours, 21 hours, 24 hours, 27 hours, or 28 hours. Treatment conditions include the following: seeds place on top of a moist filter paper followed by no UV-B ("Float-Control,"

white bars), seeds place on top of a moist filter paper followed by UV-B administration ("Float-UV," black bars), seeds submerge in priming medium followed by no UV-B ("Submerged-Control," checkered bars), and seeds prime in distilled water followed by UV-B administration ("Submerged-UV," horizontal hashed bars). The y-axis shows shoot fresh weight (g/plant) and has a scale of 0 to 140. Float-UV seeds that are administered UV-B for 20 hours exhibit a significant increase of about 56% in shoot fresh weight as compared to Float-Control seeds. Submerged-UV seeds that are administered UV-B for 21 hours exhibit a significant increase of about 30% in shoot fresh weight as compared to Submerged-Control seeds. At 28 hours, there is a difference between Float-Control and Submerged-UV. This figure shows treatment conditions comprising various seed positioning and administration of UV-B improves plant performance such as shoot fresh weight.

Figure 21:
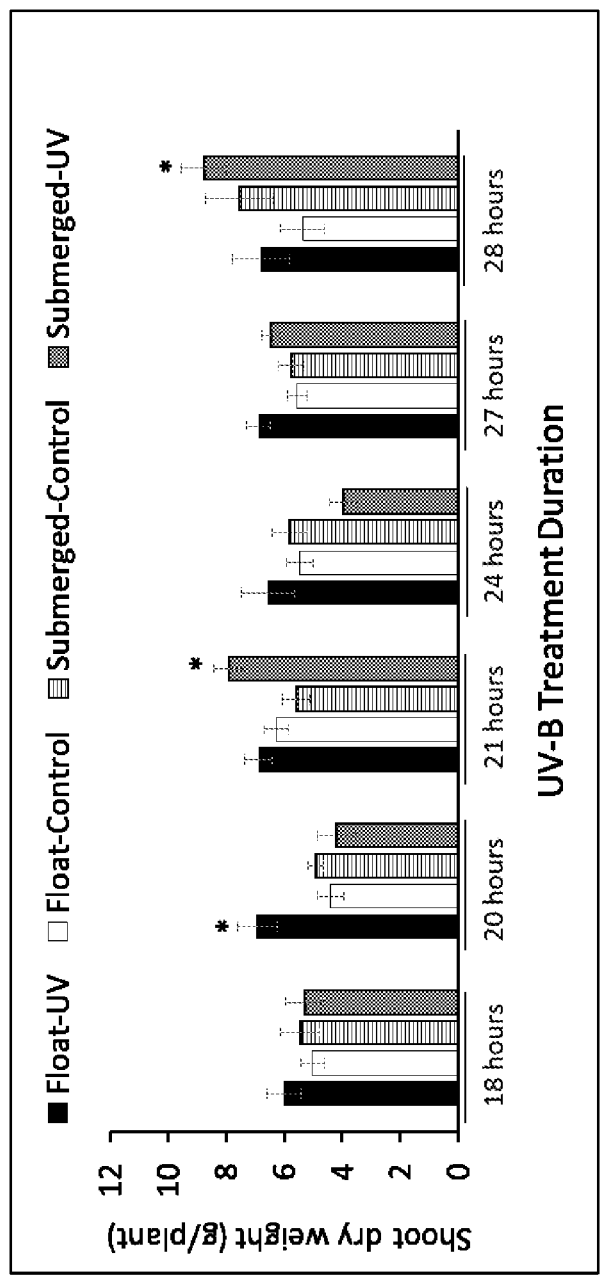
FIG. 21 depicts a graph of shoot dry weight (g/plant) of broccoli seeds placed on top of a moist filter paper ("Float") or submerged ("Submerged") in priming medium during no UV-B ("Control") or UV-B ("UV") administration. Treatment duration of UV-B includes 18 hours, 20 hours, 21 hours, 24 hours, 27 hours, and 28 hours.

FIG. 21 depicts effects of treatment conditions comprising priming, temperature, UV-B dosage, duration of UV-B administration, and seed position on shoot dry weight in broccoli. Broccoli seeds are primed in distilled water followed by administration of UV-B in a growth cabinet at 10° C. for 18 hours, 20 hours, 21 hours, 24 hours, 27 hours, or 28 hours. A first set of seeds is placed on top of a most filter paper ("Float") during UV-B administration. A second set of seeds is completely submerged in the priming medium ("Submerged") during UV-B administration. UV-B is administered at 100 uW cm$^{-2}$ UV-B irradiance. The x-axis shows various UV-B treatment durations: 18 hours, 20 hours, 21 hours, 24 hours, 27 hours, or 28 hours. Treatment conditions include the following: seeds place on top of a moist filter paper followed by no UV-B ("Float-Control," white bars), seeds place on top of a moist filter paper followed by UV-B administration ("Float-UV," black bars), seeds submerge in priming medium followed by no UV-B ("Submerged-Control," horizontal hashed bars), and seeds prime in distilled water followed by UV-B administration ("Submerged-UV," checkered bars). The y-axis shows shoot dry weight (g/plant) and has a scale of 0 to 12. Float-UV seeds that are administered UV-B for 20 hours exhibit a significant increase of about 56% in shoot dry weight as compared to Float-Control seeds. Submerged-UV seeds that are administered UV-B for 21 hours exhibit a significant increase of about 41% in shoot dry weight as compared to Submerged-Control seeds. There is a significant difference at 28 hours between Submerged-UV and Float-Control. This figure shows treatment conditions comprising various seed positioning and administration of UV-B improves plant performance such as shoot dry weight.

Figure 22:
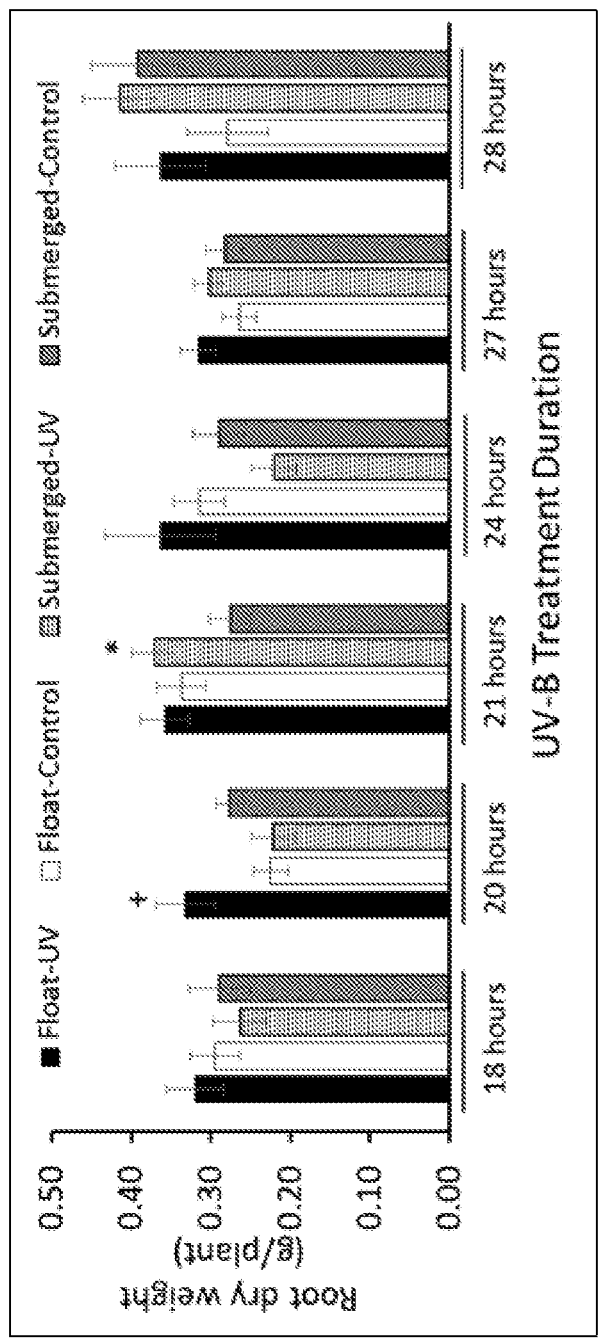
FIG. 22 depicts a graph of root dry weight (g/plant) of broccoli seeds placed on top of a moist filter paper ("Float") or submerged ("Submerged") in priming medium during no UV-B ("Control") or UV-B ("UV") administration. Treatment duration of UV-B includes 18 hours, 20 hours, 21 hours, 24 hours, 27 hours, and 28 hours.

FIG. 22 depicts effects of treatment conditions comprising priming, temperature, UV-B dosage, duration of UV-B administration, and seed position on root dry weight in broccoli. Broccoli seeds are primed in distilled water followed by administration of UV-B in a growth cabinet at 10° C. for 18 hours, 20 hours, 21 hours, 24 hours, 27 hours, or 28 hours. A first set of seeds is placed on top of a most filter paper ("Float") during UV-B administration. A second set of seeds is completely submerged in the priming medium ("Submerged") during UV-B administration. UV-B is administered at 100 uW cm$^{-2}$ UV-B irradiance. The x-axis shows various UV-B treatment durations: 18 hours, 20 hours, 21 hours, 24 hours, 27 hours, or 28 hours. Treatment conditions include the following: seeds place on top of a moist filter paper and administer no UV-B ("Float-Control," white bars), seeds place on top of a moist filter paper and administer UV-B ("Float-UV," black bars), seeds submerge in priming medium and administer no UV-B ("Submerged-Control," checkered bars), and seeds prime in distilled water and administer UV-B ("Submerged-UV," horizontal hashed bars). The y-axis shows root dry weight (g/plant) and has a scale of 0.00 to 0.50. Float-UV seeds that are administered UV-B for 20 hours exhibit an increase of about 50% in root dry weight as compared to Float-Control. Submerged-UV seeds that are administered UV-B for 21 hours exhibit a significant increase of about 32% in root dry weight as compared to Submerged-Control. This figure shows treatment conditions comprising various seed positioning and administration of UV-B improves plant performance such as root dry weight.

Figure 23:
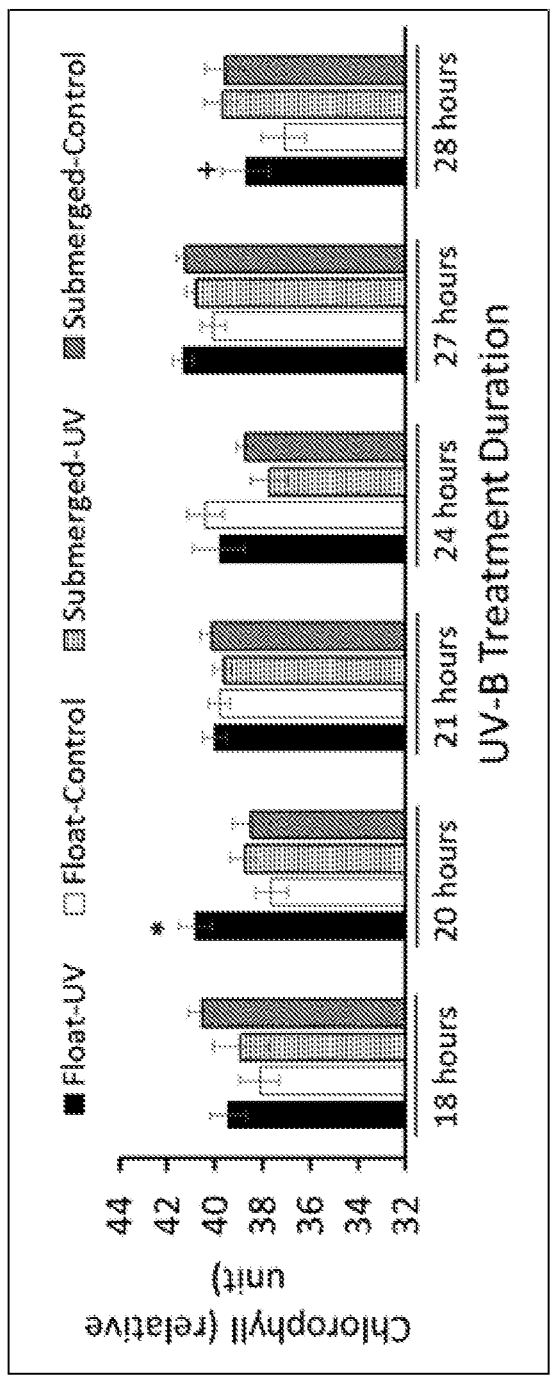
FIG. 23 depicts a graph of chlorophyll levels (relative unit) of broccoli seeds placed on top of a moist filter paper ("Float") or submerged ("Submerged") in priming medium during no UV-B ("Control") or UV-B ("UV") administration. Treatment duration of UV-B includes 18 hours, 20 hours, 21 hours, 24 hours, 27 hours, and 28 hours.

FIG. 23 depicts effects of treatment conditions comprising priming, temperature, UV-B dosage, duration of UV-B administration, and seed position on chlorophyll levels in broccoli. Broccoli seeds are primed in distilled water followed by administration of UV-B in a growth cabinet at 10° C. for 18 hours, 20 hours, 21 hours, 24 hours, 27 hours, or 28 hours. A first set of seeds is placed on top of a most filter paper ("Float") during UV-B administration. A second set of seeds is completely submerged in the priming medium ("Submerged") during UV-B administration. UV-B is administered at 100 uW cm$^{-2}$ UV-B irradiance. The x-axis shows various UV-B treatment durations: 18 hours, 20 hours, 21 hours, 24 hours, 27 hours, or 28 hours. Treatment conditions include the following: seeds place on top of a moist filter paper and administer no UV-B ("Float-Control," white bars), seeds place on top of a moist filter paper and administer UV-B ("Float-UV," black bars), seeds submerge in priming medium and administer no UV-B ("Submerged-Control," checkered bars), and seeds prime in distilled water and administer UV-B ("Submerged-UV," horizontal hashed bars). The y-axis shows chlorophyll (relative unit) and has a scale of 32 to 44. Float-UV seeds that are administered UV-B for 20 hours exhibit a significant increase of about 8% in chlorophyll levels as compared to Float-Control. There is also significance between Submerged-UV and Float-Control. This figure shows treatment conditions comprising various seed positioning and administration of UV-B improves plant performance such as chlorophyll levels.

Figure 24:
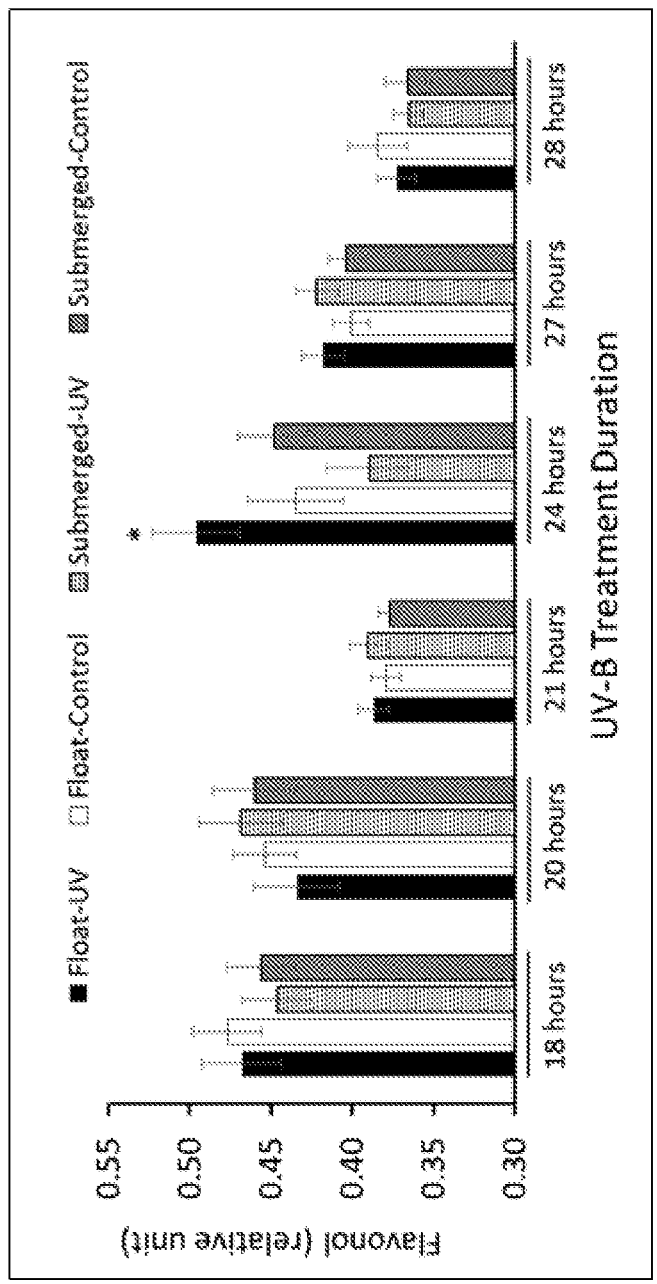
FIG. 24 depicts a graph of flavonoid levels (relative unit) of broccoli seeds placed on top of a moist filter paper ("Float") or submerged ("Submerged") in priming medium during no UV-B ("Control") or UV-B ("UV") administration. Treatment duration of UV-B includes 18 hours, 20 hours, 21 hours, 24 hours, 27 hours, and 28 hours.

FIG. 24 depicts effects of treatment conditions comprising priming, temperature, UV-B dosage, duration of UV-B administration, and seed position on flavonoid levels in broccoli. Broccoli seeds are primed in distilled water followed by administration of UV-B in a growth cabinet at 10° C. for 18 hours, 20 hours, 21 hours, 24 hours, 27 hours, or 28 hours. A first set of seeds is placed on top of a most filter paper ("Float") during UV-B administration. A second set of seeds is completely submerged in the priming medium ("Submerged") during UV-B administration. UV-B is administered at 100 uW cm$^{-2}$ UV-B irradiance. The x-axis shows various UV-B treatment durations: 18 hours, 20 hours, 21 hours, 24 hours, 27 hours, or 28 hours. Treatment conditions include the following: seeds place on top of a moist filter paper and administer no UV-B ("Float-Control," white bars), seeds place on top of a moist filter paper and administer UV-B ("Float-UV," black bars), seeds submerge in priming medium and administer no UV-B ("Submerged-Control," checkered bars), and seeds prime in distilled water and administer UV-B ("Submerged-UV," horizontal hashed bars). The y-axis shows flavonoid (relative unit) and has a scale of 0.30 to 0.55. Float-UV seeds that are administered UV-B for 24 hours exhibit an increase of about 14% in flavonoid levels as compared to Float-Control. This figure shows treatment conditions comprising various seed positioning and administration of UV-B improves plant performance such as flavonoid levels.

Figure 25:
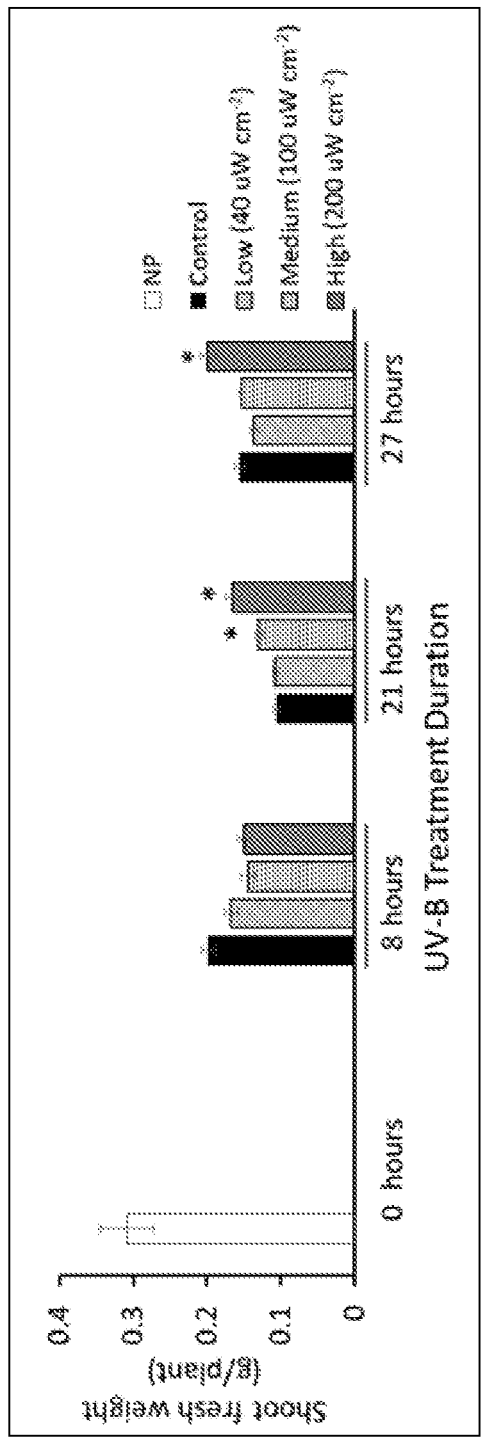
FIG. 25 depicts a graph of shoot fresh weight (g/plant) of broccoli seeds administered control, low (40 uW cm$^{-2}$), medium (100 uW cm$^{-2}$), and high (200 uW cm$^{-2}$) UV-B irradiance. Treatment duration of UV-B includes 0 hours, 8 hours, 21 hours, and 27 hours. "NP" refers to non-primed seeds.

FIG. 25 depicts effects of treatment conditions comprising priming, temperature, UV-B dosage, duration of UV-B administration, and seed position on shoot fresh weight of broccoli. Broccoli seeds are primed in −1.25 bar polyethylene glycol (PEG) dissolved in distilled water. Seeds are administered UV-B in a growth cabinet at 10° C. for 0 hours, 8 hours, 21 hours, or 27 hours. UV-B irradiance is administered at 40 uW cm$^{-2}$ ("low," diagonal hashed bars), 100 uW cm$^{-2}$ ("medium," horizontal hashed bars), and 200 uW cm$^{-2}$ ("high," checkered bars). "Control" (black bars) refers to no UV-B treatment in which seeds are immersed in priming medium but did not receive UV. "NP" refers to non-primed seeds in which seeds are not immersed in PEG nor receive an UV treatment. The seeds are placed on a moist filter paper during UV-B administration. The x-axis shows UV-B treatment duration: 0 hours, 8 hours, 21 hours, and 27 hours. The y-axis shows shoot fresh weight (g/plant) and has a scale of 0.0 to 0.4. Medium UV-B irradiance administration for 21 hours results in a significant increase of about 22% in shoot fresh weight as compared to Control. High UV-B irradiance administration for 21 hours results in a significant increase of about 56% in shoot fresh weight as compared to Control. High UV-B irradiance administration for 27 hours results in a significant increase of about 27% in shoot fresh weight as compared to Control. This figure illustrates plant performance such as shoot fresh weight is improved from seeds primed and administered UV-B irradiation.

Figure 26:
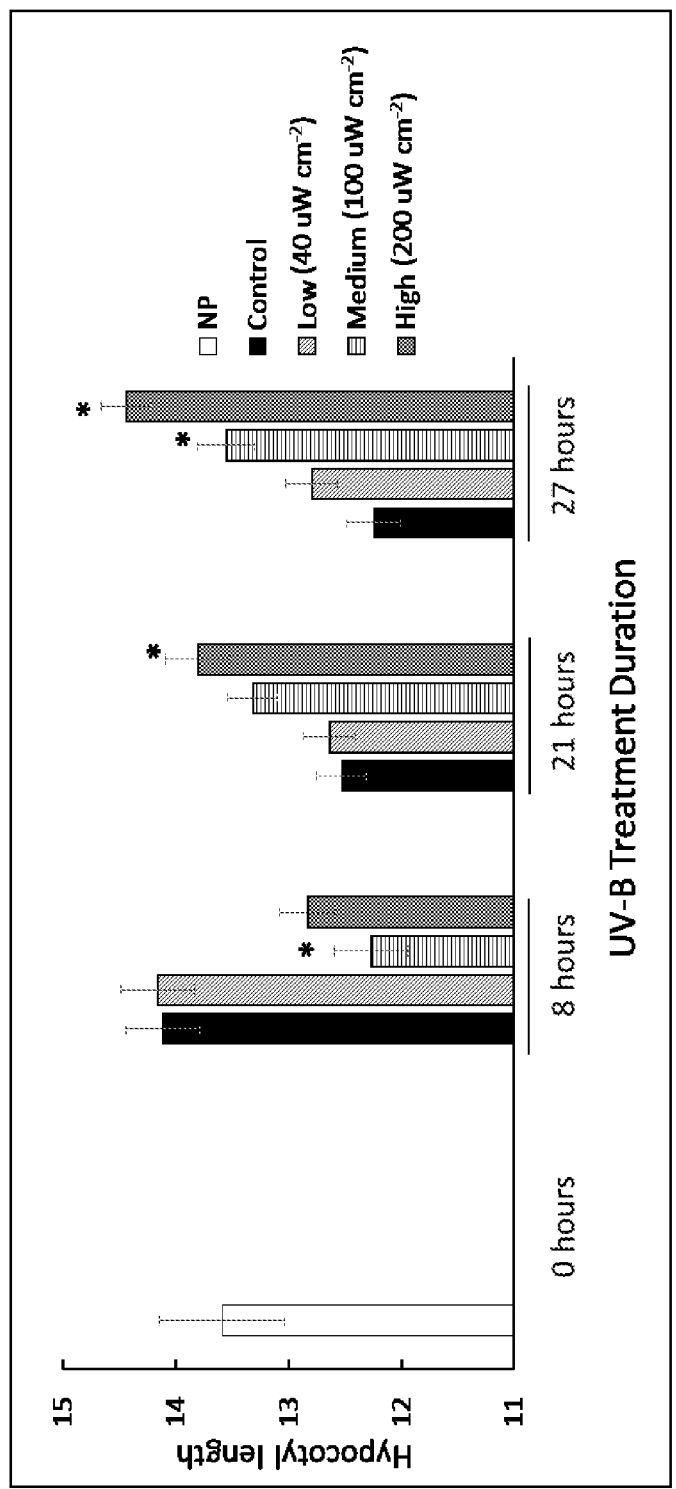
FIG. 26 depicts a graph of hypocotyl length of broccoli seeds administered control, low (40 uW cm$^{-2}$), medium (100 uW cm$^{-2}$), and high (200 uW cm$^{-2}$) UV-B irradiance. Treatment duration of UV-B includes 0 hours, 8 hours, 21 hours, and 27 hours. "NP" refers to non-primed seeds.

FIG. 26 depicts effects of treatment conditions comprising priming, temperature, UV-B dosage, duration of UV-B administration, and seed position on hypocotyl length (mm/plant) of broccoli. Broccoli seeds are primed in −1.25 bar polyethylene glycol (PEG) dissolved in distilled water. Seeds are administered UV-B in a growth cabinet at 10° C. for 0 hours, 8 hours, 21 hours, or 27 hours. UV-B irradiance is administered at 40 uW cm$^{-2}$ ("low," diagonal hashed bars), 100 uW cm$^{-2}$ ("medium," horizontal hashed bars), and 200 uW cm$^{-2}$ ("high," checkered bars). "Control" (black bars) refers to no UV-B treatment in which seeds are immersed in priming medium but did not receive UV. "NP" refers to non-primed seeds in which seeds are not immersed in PEG nor receive an UV treatment. The seeds are placed on a moist filter paper during UV-B administration. The x-axis shows UV-B treatment duration: 0 hours, 8 hours, 21 hours, and 27 hours. The y-axis shows hypocotyl length and has a scale of 11 to 15. Medium UV-B irradiance administration for 8 hours results in a significant difference of about 13% decrease in hypocotyl length as compared to Control. High UV-B irradiance administration for 21 hours results in a significant increase of about 10% in hypocotyl length as compared to Control. Medium UV-B irradiance administration for 27 hours results in a significant increase of about 6% in hypocotyl length as compared to Control. High UV-B irradiance administration for 27 hours results in a significant increase of about 17% in hypocotyl length as compared to Control. This figure illustrates plant performance such as hypocotyl length is improved from seeds primed and administered UV-B irradiation.

Figure 27:
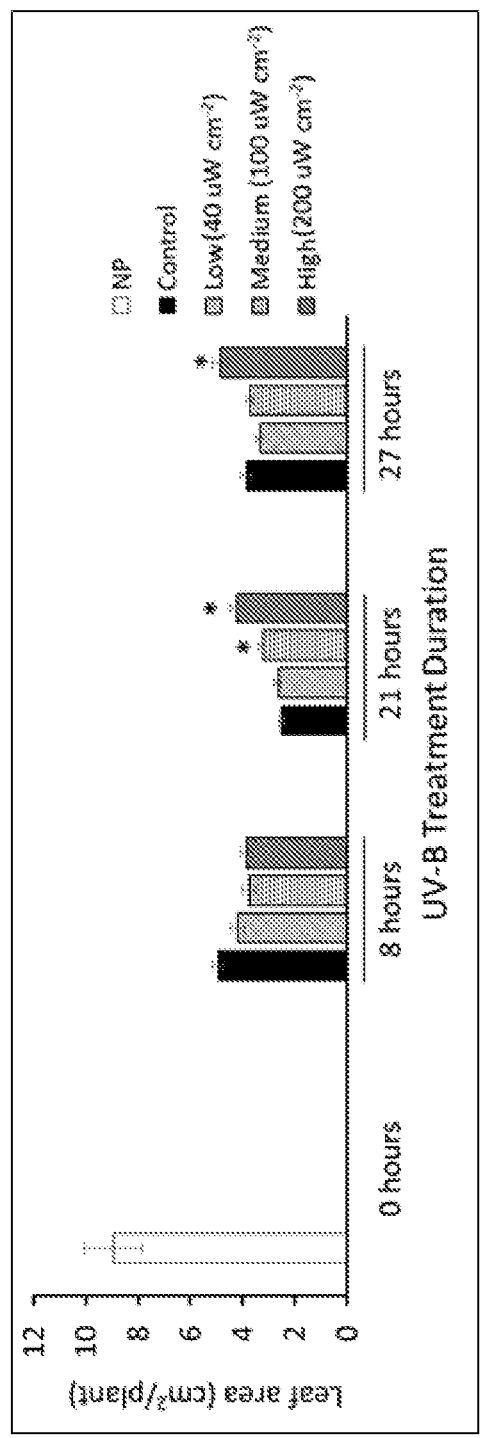
FIG. 27 depicts a graph of leaf area (cm$^2$/plant) of broccoli seeds administered control, low (40 uW cm$^{-2}$), medium (100 uW cm$^{-2}$), and high (200 uW cm$^{-2}$) UV-B irradiance. Treatment duration of UV-B includes 0 hours, 8 hours, 21 hours, and 27 hours. "NP" refers to non-primed seeds.

FIG. 27 depicts effects of treatment conditions comprising priming, temperature, UV-B dosage, duration of UV-B administration, and seed position on leaf area (cm$^2$/plant) of broccoli. Broccoli seeds are primed in −1.25 bar polyethylene glycol (PEG) dissolved in distilled water. Seeds are administered UV-B in a growth cabinet at 10° C. for 0 hours, 8 hours, 21 hours, or 27 hours. UV-B irradiance is administered at 40 uW cm$^{-2}$ ("low," diagonal hashed bars), 100 uW cm$^{-2}$ ("medium," horizontal hashed bars), and 200 uW cm$^{-2}$ ("high," checkered bars). "Control" (black bars) refers to no UV-B treatment in which seeds are immersed in priming medium but did not receive UV. "NP" refers to non-primed seeds in which seeds are not immersed in PEG nor receive an UV treatment. The seeds are placed on a moist filter paper during UV-B administration. The x-axis shows UV-B treatment duration: 0 hours, 8 hours, 21 hours, and 27 hours. The y-axis shows leaf area (cm$^2$/plant) and has a scale of 0 to 12. Medium UV-B irradiance administration for 21 hours resulted in a significant increase of about 27% in leaf area as compared to Control. High UV-B irradiance administration for 21 hours results in a significant increase of about 67% in leaf area as compared to Control. High UV-B irradiance administration for 27 hours results in a significant increase of about 26% in leaf area as compared to Control. This figure illustrates plant performance such as leaf area is improved from seeds primed and administered UV-B irradiation.

Figure 28:
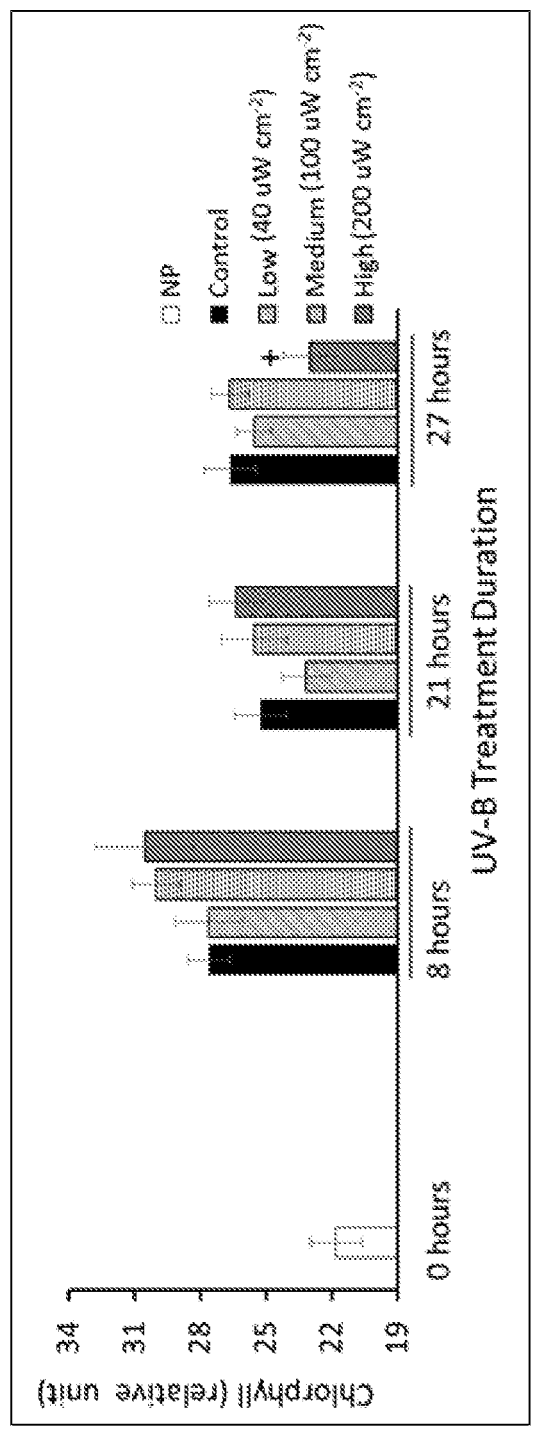
FIG. 28 depicts a graph of chlorophyll levels (relative unit) of broccoli seeds administered control, low (40 uW cm$^{-2}$), medium (100 uW cm$^{-2}$), and high (200 uW cm$^{-2}$) UV-B irradiance. Treatment duration of UV-B includes 0 hours, 8 hours, 21 hours, and 27 hours. "NP" refers to non-primed seeds.

FIG. 28 depicts effects of treatment conditions comprising priming, temperature, UV-B dosage, duration of UV-B administration, and seed position on chlorophyll levels of broccoli. Broccoli seeds are primed in −1.25 bar polyethylene glycol (PEG) in distilled water. Seeds are administered UV-B in a growth cabinet at 10° C. for 0 hours, 8 hours, 21 hours, or 27 hours. UV-B irradiance is administered at 40 uW cm$^{-2}$ ("low," diagonal hashed bars), 100 uW cm$^{-2}$ ("medium," horizontal hashed bars), and 200 uW cm$^{-2}$ ("high," checkered bars). "Control" (black bars) refers to no UV-B treatment in which seeds are immersed in priming medium but did not receive UV. "NP" refers to non-primed seeds in which seeds are not immersed in PEG nor receive an UV treatment. The seeds are placed on a moist filter paper during UV-B administration. The x-axis shows UV-B treatment duration: 0 hours, 8 hours, 21 hours, and 27 hours. The y-axis shows chlorophyll (relative unit) and has a scale of 19 to 34. High UV-B irradiance administration for 27 hours results in a 13% decrease in chlorophyll as compared to Control. This figure illustrates plant performance such as chlorophyll is improved from seeds primed and administered UV-B irradiation.

Figure 29:
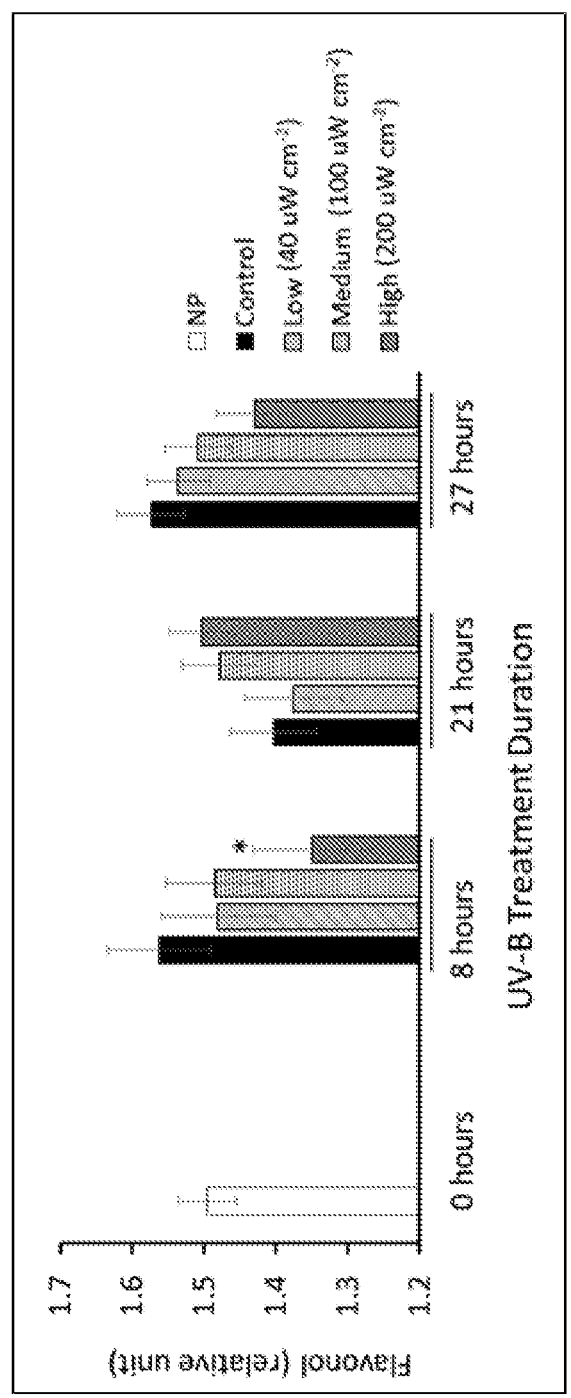
FIG. 29 depicts a graph of flavonoid levels (relative unit) of broccoli seeds administered control, low (40 uW cm$^{-2}$), medium (100 uW cm$^{-2}$), and high (200 uW cm$^{-2}$) UV-B irradiance. Treatment duration of UV-B includes 0 hours, 8 hours, 21 hours, and 27 hours. "NP" refers to non-primed seeds.

FIG. 29 depicts effects of treatment conditions comprising priming, temperature, UV-B dosage, duration of UV-B administration, and seed position on flavonoid levels of broccoli. Broccoli seeds are primed in −1.25 bar polyethylene glycol (PEG) dissolved in distilled water. Seeds are administered UV-B in a growth cabinet at 10° C. for 0 hours, 8 hours, 21 hours, or 27 hours. UV-B irradiance is administered at 40 uW cm$^{-2}$ ("low," diagonal hashed bars), 100 uW cm$^{-2}$ ("medium," horizontal hashed bars), and 200 uW cm$^{-2}$ ("high," checkered bars). "Control" (black bars) refers to no UV-B treatment in which seeds are immersed in priming medium but did not receive UV. "NP" refers to non-primed seeds in which seeds are not immersed in PEG nor receive an UV treatment. The seeds are placed on a moist filter paper during UV-B administration. The x-axis shows UV-B treatment duration: 0 hours, 8 hours, 21 hours, and 27 hours. The y-axis shows flavonoid (relative unit) and has a scale of 1.2 to 1.7. High UV-B irradiance administration for 8 hours results in a significant difference of about a 15% decrease in flavonoid as compared to Control. This figure illustrates plant performance such as flavonoid levels is improved from seeds primed and administered UV-B irradiation.

Figure 30:
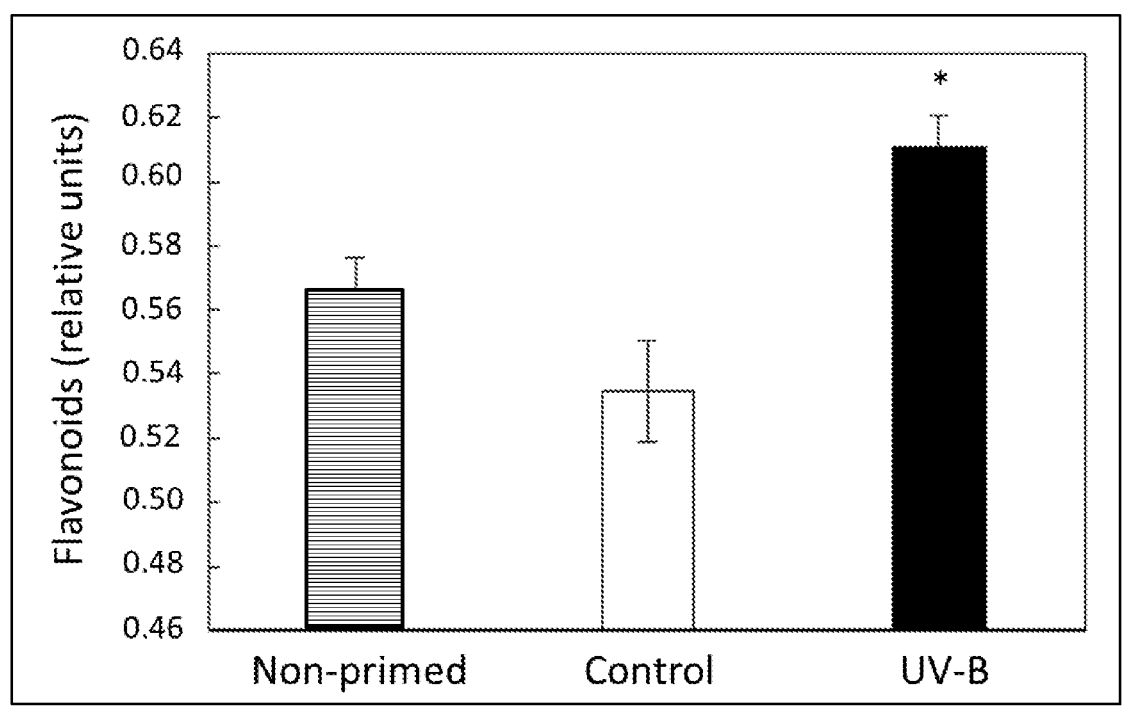
FIG. 30 depicts a graph of flavonoid levels in lettuce leaves from non-primed seeds, control seeds, and UV-B administered seeds.

FIG. 30 depicts effects of UV-B administration on levels of secondary metabolites in lettuce leaves. Lettuce seeds are primed and administered UV-B ("UV-B," black bar). Control seeds are seeds that are primed but not administered UV-B ("Control," white bar). Non-primed seeds are seeds grown from identical seed lot but not primed and not administered UV-B ("Non-primed," horizontal hashed bars). Leaves at 2-3 true leaf stage are sampled for foliar flavonoid levels 45 days from sowing using Dualex optical sensor (relative units). The y-axis of FIG. 30 depicts flavonoids (relative units) and has a scale of 0.46 to 0.64. Referring to FIG. 30, plants from UV-B administered seeds ("UV-B," black bar) exhibit a significant increase in flavonoids as compared to plants from non-UV-B treated seeds ("Control," white bar) and plants from non-UV-B and non-primed seeds ("Non-primed," horizontal hashed bars). This figure shows UV-B administration of seeds results in increase in protective secondary metabolites in resultant plants.

Figure 31:
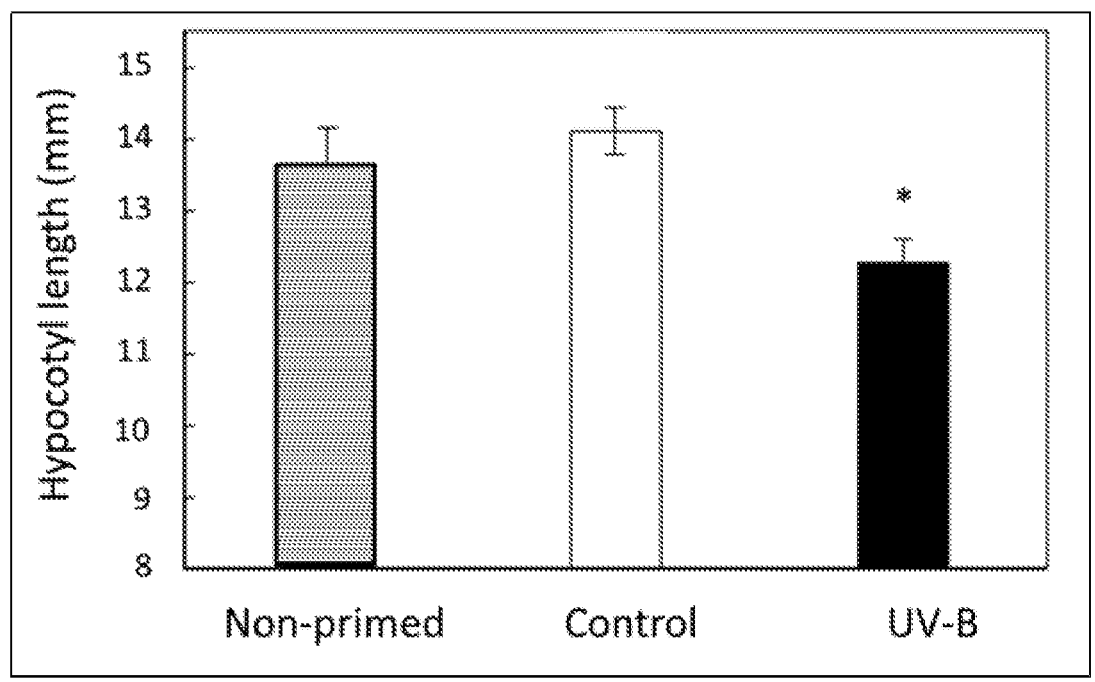
FIG. 31 depicts a graph of hypocotyl length in broccoli plants from non-primed seeds, control seeds, and UV-B administered seeds.

FIG. 31 depicts effects of UV-B administration on broccoli stem elongation. Broccoli seeds are primed and administered UV-B ("UV-B," black bar). Control seeds are seeds that are primed but not administered UV-B ("Control," white bar). Non-primed seeds are seeds grown from identical seed lot but not primed and not administered UV-B ("Non-primed," horizontal hashed bars). Plant hypocotyls are assessed at 45 days from sowing. The y-axis of FIG. 31 shows hypocotyl length (mm/plant) and has a scale of 8 to 15. Referring to FIG. 31, broccoli plants from UV-B administered seeds ("UV-B," black bar) exhibited a significant reduction in hypocotyl length (as compared to plants from non-UV-B treated seeds ("Control," white bar) and plants from non-UV-B and non-primed seeds ("Non-primed," horizontal hashed bars). This figure shows UV-B administration of seeds results affects hypocotyl elongation.

Figure 32:
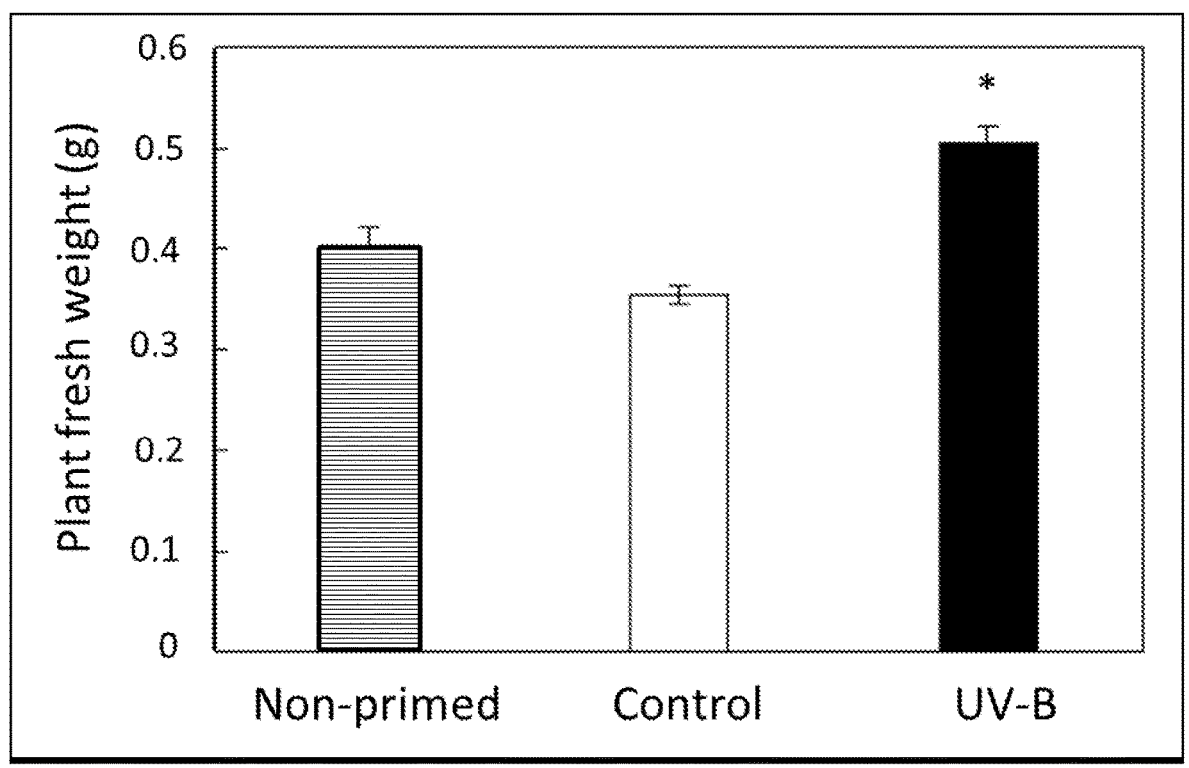
FIG. 32 depicts a graph of lettuce plant biomass from non-primed seeds, control seeds, and UV-B administered seeds.

FIG. 32 shows lettuce plant biomass following UV-B administration. Lettuce seeds are primed and administered UV-B ("UV-B," black bar). Control seeds are seeds that were primed but not administered UV-B ("Control," white bar). Non-primed seeds are seeds grown from identical seed lot but not primed and not administered UV-B ("Non-primed, horizontal hashed bars"). Plants are harvested for shoot fresh weight 45 days after sowing. The y-axis of FIG. 32 shows plant fresh weight (g) and has a scale of 0 to 0.6. Referring to FIG. 32, plant fresh weight of lettuce plants grown from UV-B administered seeds ("UV-B," black bar) is significantly increased as compared to plants from non-UV-B treated seeds ("Control," white bar) and plants from non-UV-B and non-primed seeds ("Non-primed," horizontal hashed bars). This figure shows UV-B administration of seeds results in an increase in plant biomass in resultant plants.

Figure 33A:
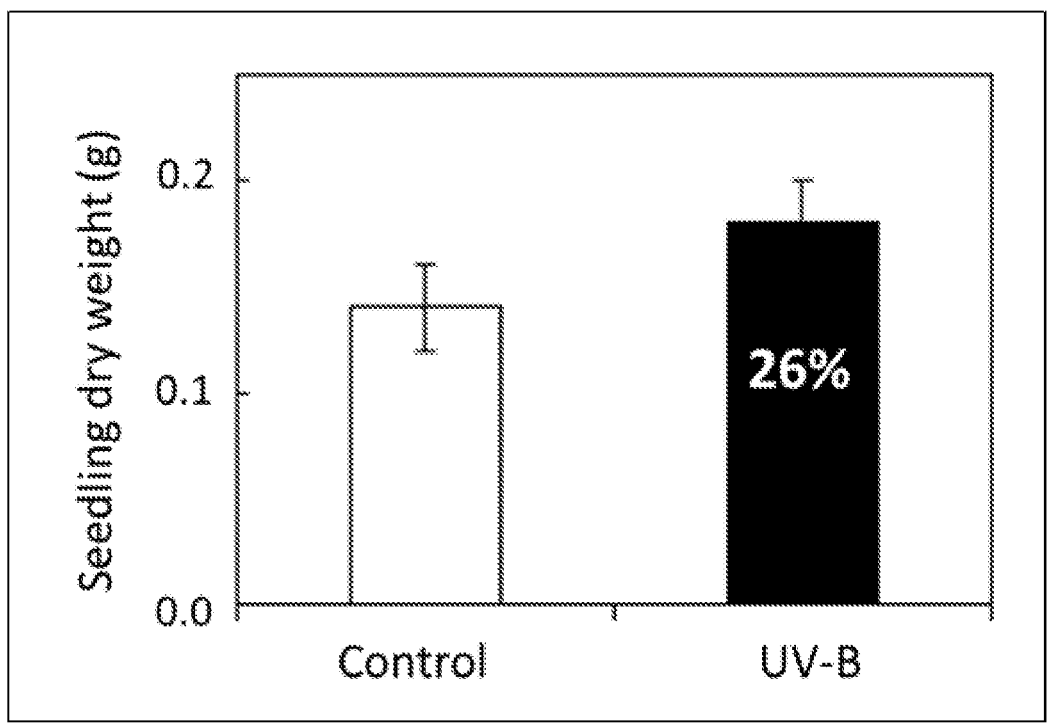
FIGS. 33A-33B depict graphs of growth in corn seedlings from control seeds and UV-B administered seeds.
Figure 33B:
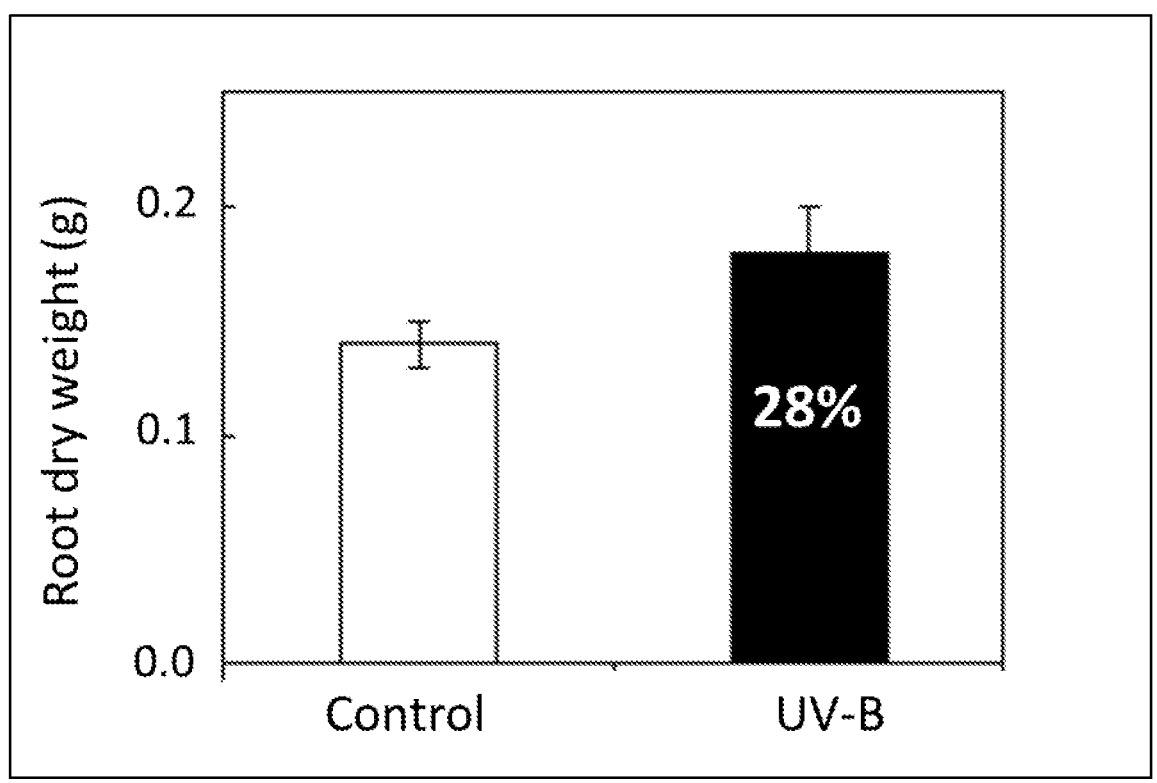

FIGS. 33A-33B depict effects of UV-B administration on corn seedling growth. Maize seeds (*Zea mays*) are primed and administered UV-B ("UV-B," black bar). Control seeds are seeds that were primed but not administered UV-B ("Control," white bar). Seedlings are harvested at 4 weeks old. The y-axis of FIG. 33A depicts seedling dry weight (g) and has a scale of 0.0 to 0.2. Referring to FIG. 33A, seedling dry weight from UV-B administered maize seeds ("UV-B," black bar) is increased 26% as compared to plants from non-UV-B treated seeds ("Control," white bar). The y-axis of FIG. 33B depicts root dry weight (g) and has a scale of 0.0 to 0.2. Referring to FIG. 33B, root dry weight (grams, y-axis) from UV-B administered maize seeds ("UV-B," black bar) is increased 28% as compared to plants from non-UV-B treated seeds ("Control," white bar). This figure shows UV-B administration of seeds results in an increase in growth in resultant seedlings.

Figure 34:
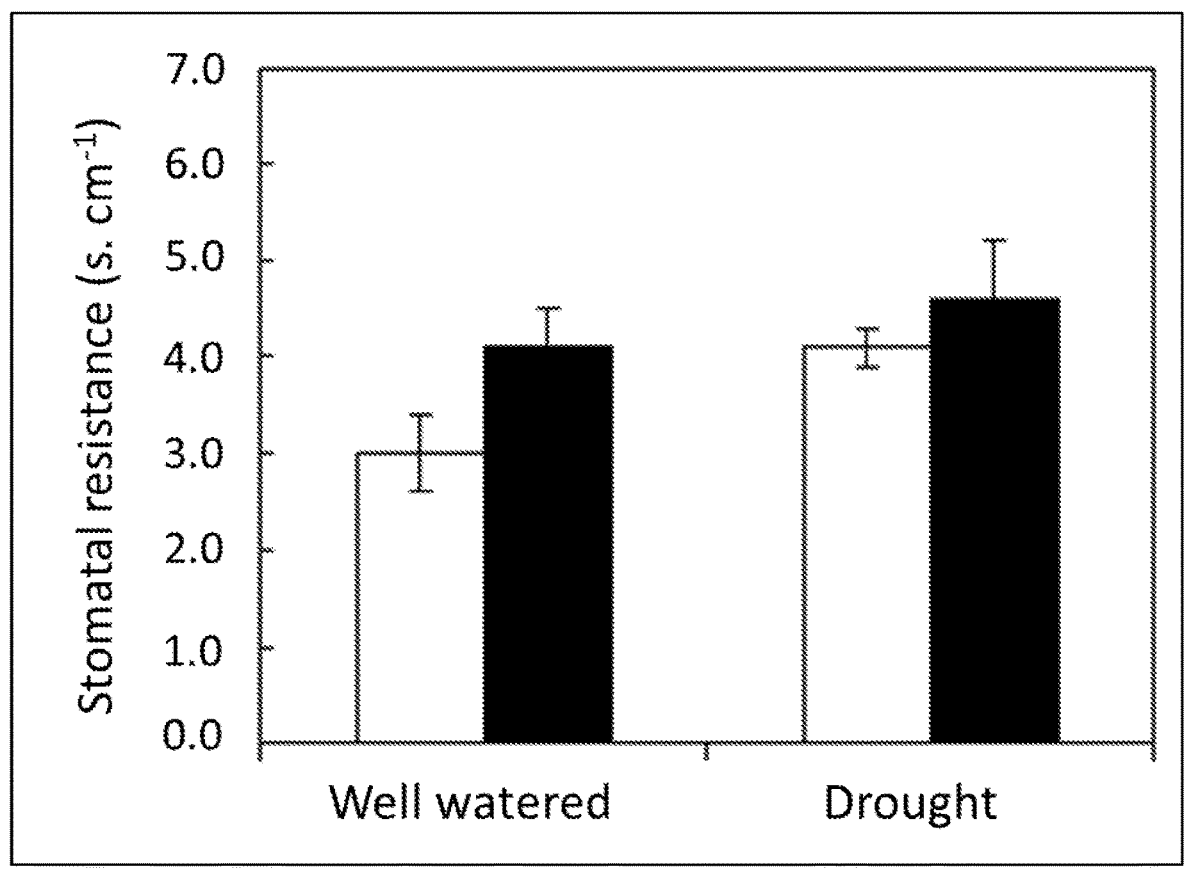
FIG. 34 depicts a graph of stomatal resistance in lettuce seedlings from control seeds and UV-B administered seeds subject to well-watered or drought conditions.

FIG. 34 depicts UV-B administration on stomatal resistance in lettuce seedlings. Lettuce seeds are primed and administered UV-B ("UV-B," black bar). Control seeds are seeds that are primed but not administered UV-B ("Control," white bar). At 4 weeks, seedlings from UV-B administered seeds and control seeds are subject to 11 days of well-watered or drought conditions. The y-axis of FIG. 34 shows stomatal resistance (s·cm-1) and has a scale of 0.0 to 7.0. Referring to FIG. 34, seedlings from UV-B administered seeds ("UV-B," black bar) exhibit increased stomatal resistance under well-watered conditions. This figure shows UV-B administration results in improved water use efficiency.

FIG. 35 depicts an exemplary device for administering UV-B.

FIG. 36 depicts a computer system.

Definitions

Unless defined otherwise, all technical and scientific terms used herein have the same meaning as is commonly understood by one of skill in the art to which this disclosure belongs. All patents and publications referred to herein are incorporated by reference.

As used in the specification and claims, the singular form "a", "an" and "the" includes plural references unless the context clearly dictates otherwise.

The term "including" is used to mean "including but not limited to." "Including" and "including but not limited to" are used interchangeably.

The term comprising as used herein is intended to refer to an open-ended set, such that a claim or list 'comprising' an element is not precluded from also reciting additional elements not listed.

The term "seed for sowing" as used herein refers to any embryonic plant prior to, and/or intended to be used for, planting to grow any form of plant life or crop for subsequent use (typically, but not solely, for human and animal consumption). Substantially any type of seed may be used according to the present disclosure, of which there are currently about 35,000 types currently known worldwide, as noted in U.S. Pat. No. 8,001,722. Results indicated that UV-B treatment of seeds improved plant performance that is extendable to any plant species.

Some non-limiting examples of seeds for are seeds of agricultural or ornamental plants, such as lettuce, beans, broccoli, cabbage, carrot, cauliflower, cucumber, melon, onion, peas, peppers, pumpkin, spinach, squash, sweetcorn, tomato, watermelon, alfalfa, canola, corn, cotton, sorghum, soybeans, sugarbeets, wheat, mint, sunflowers, or other agriculturally or ornamentally relevant plant species.

The term "plant material" refers a seed, seedling, whole plant, fruit, leaves, roots, cuttings, runners, or any other plant material and progeny thereof.

The term "seed" refers to an embryonic plant enclosed in a protective outer covering. The formation of the seed is part of the process of reproduction in seed plants, the spermatophytes, including gymnosperm and angiosperm plants. Seeds are the product of the ripened ovule, after fertilization by pollen and some growth within the mother plant. The embryo is developed from the zygote and the seed coat from the integuments of the ovule.

The term "seed germination" refers to a process by which a seed embryo develops into a seedling. It involves the activation of the metabolic pathways that lead to growth, and the emergence of the radicle or seed root and plumule or shoot. In general, seed germination is initiated through stratification, which varies among plant species according to their original ecological setting. Often though not uniformly, seed germination is triggered through a three-phase process involving water imbibition, lag phase, and radicle emergence. Seed germination may be affected by environmental conditions including, but not limited to, water, oxygen, temperature, and light.

The term "plant performance" as used herein refers to improving at least one of resilience and growth. Resilience, as used herein refers to biotic or abiotic environmental stress, which can impact the seed, the seedling, the resulting plant, the resultant crop before or after harvesting. "Growth" generally refers to performance in the absence of an abiotic or biotic stress, such as performance under healthy or 'best case scenario' growth conditions. One observes that, depending upon growth conditions, both increase resilience and improvements in growth can result in increases in yield, depending upon growth conditions. One observes that improving both growth and resilience has the effect of improving yield of harvestable crop material relative plants resulting from untreated seeds independent of growth conditions. Plant performance also refers in some cases to improving quality of harvestable crop material, such that plant value is increased per unit yield even if yield, more coarsely defined, is unaffected. Some non-limiting examples of improved stress resilience are improved drought resistance, salinity stress, transplantation shock, long-term hardiness, high visible light stress, insect pest stress, fungal or bacterial stress, or other disease-related stress. The term "crop productivity" may in some cases be used interchangeably with "plant performance."

The term "long-term hardiness" as used herein refers to the ability of a plant to withstand one or more stresses during crop production and to allow desirable yield and/or quality of the plant at harvesting. Some non-limiting examples of how improved yield is measured include weight of harvestable crop material, such as lettuce leaves, soybeans, tomato fruit, in comparison to harvestable crop material where the seeds for sowing were not treated with UV-B. Other examples of how improved yield are measured include fresh shoot weight or whole plant dry weight, improved germination of seeds resulting from the treatment method, and improved water use efficiency of the resulting plant. In some cases, improved quality is assessed as a quantitative or qualitative assessment of at least one of a lack of blemishes on the crop (either internal or on the surface, typically from insects), improved shelf life, improved resistance to bruising or other post-harvest handling, lack of deformities, lack of irregular shapes, lack of irregular sizes, improved taste, size, shape, color, and texture. An advantage of the present disclosure is that both stress resilience and plant yield were observed (often these traits can work in an inverse relationship, where resilience is achieved at the cost of yield as seen with UV-C treatment).

The term "ultraviolet (UV) irradiation" as used herein refers to electromagnetic radiation with a wavelength shorter than visible light, but longer than X-rays, and is in between the range of 10 nm to 400 nm (corresponding to 3 eV to 124 eV). The UV radiation spectrum is considered to be invisible to humans, and therefore differentiated from visible light in the spectrum of about 400 nm to 700 nm.

The term "UV-B radiation" as used herein refers to radiation specifically within the waveband of 320 nm to 280 nm (herein described as the UV-B range). This is distinguishable from the UV-C waveband (280 to 100 nm) and UV-A waveband (400-320 nm). It should also be distinguishable from natural sunlight which although provides UV-B radiation, also includes other UV radiation. In some cases, the UV-B radiation is administered via LED lights.

The term "harvestable crop material" as used herein refers to any material from the plant which may be harvested to be used for subsequent purposes or human or animal consumption. Often the crop material is harvested seeds to be consumed as food or used for subsequent planting or breeding purposes. The harvested material includes but is not limited to a fruit, a vegetable, a tree, a shrub, a grass, a herb, and an extract or component of any one of the above crop materials. In some cases, the present disclosure includes the material that is actually harvested or the material used to build plant performance without any harvesting. A non-limiting example of material not intended to be farmed is forest regeneration. Some non-limiting examples of harvestable crop material are lettuce, beans, broccoli, cabbage, carrot, cauliflower, cucumber, melon, onion, peas, peppers, pumpkin, spinach, squash, sweetcorn, tomato, watermelon, alfalfa, canola, corn, cotton, sorghum, soybeans, sugarbeets, wheat and combinations thereof.

A "fruit" refers to any seed-containing organ of a plant.

The term "flavonoid" as used herein refers to a class of plant secondary metabolites which have the general structure of a 15-carbon skeleton, consisting of two phenyl rings and heterocyclic ring (C6-C3-C6). Flavonoids are associated in some cases with stress resistance, such that an increase in their accumulation levels corresponds to an increase in plant stress resistance.

The terms "stratify", "imbibe", "imbibition", "prime", "priming" or grammatical equivalents are used interchangeably herein. These terms refer to taking steps to initiate germination on dormant seeds, for example by immersing seed in water in order for the embryo to imbibe or soak up water, which causes the embryo to well thereby splitting the seed coat. The nature of the seed coat may determine how rapidly water can penetrate and subsequently initiate germination. The rate of imbibition can be dependent on the permeability of the seed coat, amount of water in the environment and the area of contact the seed has to the source of water.

The terms "improved crop yield", "improved growth", or "improved plant performance" are used interchangeably herein. They refer to a plant which may have either larger fruit, larger stems, larger leafs, larger flowers or any combination of the above. The tissue of the enlarged plant is at least 1%, 2%, 3%, 4%, 5%, 6%, 7%, 8%, 9%, 10%, 15%, 20% 30, 40%, 50%, 60%, 70%, 80%, 90%, 99% or larger than that of a wild type plant.

The term "light intensity" refers herein to measurement of light described herein including but not limited to radiant intensity, luminous intensity, irradiance, radiance, intensity, brightness, luminance, photometry, and radiometry.

The term "irradiance" refers to a radiometric quantity, measured in watts per meter squared ($W/m^2$) or microwatts per centimeter squared ($uW/cm^2$).

The term "radiance" refers to intensity ($W \cdot sr^{-1} \cdot m^{-2}$).

The term "standard regimen" refers to the industry standard.

The term "about" as used herein means a range spanning from 10% below the number to 10% above the number.

The term "about" as used herein in reference to a range refers to 10% below the lowest value of the listed range up to 10% above the highest value of the listed range.

The term "about" as used herein in reference to wavelength refers to 1% below the number to 1% above the number.

Numbered Embodiments

Numbered embodiment 1 comprises a method for improving at least one of plant performance and hardiness, comprising: (a) priming a seed using a priming medium; and (b) concurrently administering light enriched for UV-B. Numbered embodiment 2 comprises the method of numbered embodiment 1, wherein the priming medium is water. Numbered embodiment 3 comprises the method of numbered embodiments 1-2, wherein the priming medium is polyethylene glycol. Numbered embodiment 4 comprises the method of numbered embodiments 1-3, wherein the seed is submerged in the priming medium. Numbered embodiment 5 comprises the method of numbered embodiments 1-4, wherein administering light occurs in a growth chamber. Numbered embodiment 6 comprises the method of numbered embodiments 1-5, wherein the growth chamber is maintained up to 40° C. Numbered embodiment 7 comprises the method of numbered embodiments 1-6, wherein the growth chamber is maintained at about 22° C. Numbered embodiment 8 comprises the method of numbered embodiments 1-7, wherein the growth chamber is maintained at about 10° C. Numbered embodiment 9 comprises the method of numbered embodiments 1-8, wherein an irradiance of UV-B is up to 300 uW cm$^{-2}$. Numbered embodiment 10 comprises the method of numbered embodiments 1-9, wherein an irradiance of UV-B is in a range of about 40 uW cm$^{-2}$ to about 200 uW cm$^{-2}$. Numbered embodiment 11 comprises the method of numbered embodiments 1-10, wherein an irradiance of UV-B is about 40 uW cm$^{-2}$. Numbered embodiment 12 comprises the method of numbered embodiments 1-11, wherein an irradiance of UV-B is about 100 uW cm$^{-2}$. Numbered embodiment 13 comprises the method of numbered embodiments 1-12, wherein an irradiance of UV-B is about 200 uW cm$^{-2}$. Numbered embodiment 14 comprises the method of numbered embodiments 1-13, wherein a duration of priming the seed and concurrently administering UV-B is in a range of about 1 hour to about 30 hours, about 2 hours to about 27 hours, about 3 hours to about 25 hours, about 4 hours to about 24 hours, about 5 hours to about 22 hours, or about 6 hours to about 21 hours. Numbered embodiment 15 comprises the method of numbered embodiments 1-14, wherein a duration of priming the seed and concurrently administering UV-B is about 20 hours. Numbered embodiment 16 comprises the method of numbered embodiments 1-15, wherein a duration of priming the seed and concurrently administering UV-B is about 24 hours. Numbered embodiment 17 comprises the method of numbered embodiments 1-16, wherein a duration of priming the seed and concurrently administering UV-B is about 27 hours. Numbered embodiment 18 comprises the method of numbered embodiments 1-17, wherein a wavelength of the UV-B is in a range of about 280 nm to about 290 nm. Numbered embodiment 19 comprises the method of numbered embodiments 1-18, wherein a wavelength of the UV-B is 280 nm. Numbered embodiment 20 comprises the method of numbered embodiments 1-19, wherein a wavelength of the UV-B is 290 nm. Numbered embodiment 21 comprises the method of numbered embodiments 1-20, wherein the light enriched for UV-B comprises at least 50% UV-B. Numbered embodiment 22 comprises the method of numbered embodiments 1-21, wherein the light enriched for UV-B comprises at least 50% more UV-B than any other wavelength. Numbered embodiment 23 comprises the method of numbered embodiments 1-22, wherein the light comprises blue light. Numbered embodiment 24 comprises the method of numbered embodiments 1-23, wherein the light comprises red light. Numbered embodiment 25 comprises the method of numbered embodiments 1-24, wherein the light comprises visible light. Numbered embodiment 26 comprises the method of numbered embodiments 1-25, wherein the visible light is administered no more than 400 umol m$^{-2}$ s$^{-1}$. Numbered embodiment 27 comprises the method of numbered embodiments 1-26, wherein the visible light is administered in a range from at least one of 0.1 m$^{-2}$ s$^{-1}$-20 umol m$^{-2}$ s$^{-1}$, 20 m$^{-2}$ s$^{-1}$-50 umol m$^{-2}$ s$^{-1}$, and 50 m$^{-2}$ s$^{-1}$-400 umol m$^{-2}$ s$^{-1}$. Numbered embodiment 28 comprises the method of numbered embodiments 1-27, wherein the visible light is administered at about 400 umol m$^{-2}$ s$^{-1}$. Numbered embodiment 29 comprises the method of numbered embodiments 1-28, wherein the visible light is administered at about 50 umol m$^{-2}$ s$^{-1}$. Numbered embodiment 30 comprises the method of numbered embodiments 1-29, wherein the visible light is administered at about 20 umol m$^{-2}$ s$^{-1}$. Numbered embodiment 31 comprises the method of numbered embodiments 1-30, wherein the UV-B is administered at no more than 100 kJ m$^{-2}$. Numbered embodiment 32 comprises the method of numbered embodiments 1-31, wherein the UV-B is administered in a range from at least one of 0.1-13 kJ m$^{-2}$, 13-50 kJ m$^{-2}$, and 50-100 kJ m$^{-2}$. Numbered embodiment 33 comprises the method of numbered embodiments 1-32, wherein the UV-B is administered at about 100 kJ m$^{-2}$. Numbered embodiment 34 comprises the method of numbered embodiments 1-33, wherein the UV-B is administered at about 13 kJ m$^{-2}$. Numbered embodiment 35 comprises the method of numbered embodiments 1-34, wherein an UV-B irradiance is administered no more than $1.3\times10^{-4}$ W cm$^{-2}$ s$^{-1}$. Numbered embodiment 36 comprises the method of numbered embodiments 1-35, wherein an UV-B irradiance is in the range of about $4\times10^{-5}$ W cm$^{-2}$ s$^{-1}$ to $1.3\times10^{-4}$ W cm$^{-2}$ s$^{-1}$. Numbered embodiment 37 comprises the method of numbered embodiments 1-36, wherein an UV-B irradiance is about $4\times10^{-5}$ W cm$^{-2}$ s$^{-1}$. Numbered embodiment 38 comprises the method of numbered embodiments 1-37, wherein an UV-B irradiance is about $1.3\times10^{-4}$ W cm$^{-2}$ s$^{-1}$. Numbered embodiment 39 comprises the method of numbered embodiments 1-38, wherein the UV-B is administered by a LED light. Numbered embodiment 40 comprises the method of numbered embodiments 1-39, wherein one or more panels of the LED light is at a height of about 80 mm above the seed. Numbered embodiment 41 comprises the method of numbered embodiments 1-40, wherein the seed is placed in a tray directly below the one or more panels in order to position the seed to receive irradiation. Numbered embodiment 42 comprises the method of numbered embodiments 1-41, wherein positioning the seed in a tray below the panel increases efficacy of UV-B irradiation. Numbered embodiment 43 comprises the method of numbered embodiments 1-42, wherein positioning the seed in the tray below the panel maximizes UV-B irradiation. Numbered embodiment 44 comprises the method of numbered embodiments 1-43, wherein the light comprises UV-A light. Numbered embodiment 45 comprises the method of numbered embodiments 1-44, wherein the seed comprises a crop species of a vegetable, a fruit, and a flower. Numbered embodiment 46 comprises the method of numbered embodiments 1-45, wherein the crop is selected from a group consisting of at least one of lettuce, beans, broccoli, cabbage, carrot, cauliflower, cucumber, melon, onions, peas, peppers, pumpkin, spinach, squash, sweetcorn, tomato, watermelon, alfalfa, canola, corn, cotton, sorghum, soybeans, sugarbeets, and wheat. Numbered embodiment 47 comprises the method of numbered embodiments 1-46, wherein the crop is a commercially grown crop. Numbered embodiment 48 comprises the method of numbered embodiments 1-47, wherein the improvements in the plant performance is selected from a group comprising fruit fresh weight, number of fruit harvested, Brix content, fruit width, fruit length, leaf size, leaf surface area, dry weight, nitrogen content, shoot dry weight, shoot fresh weight, root dry weight, vegetable development, yield of fruiting parts, increased weight of fruiting parts, hardiness, and seed germination rate. Numbered embodiment 49 comprises the method of numbered embodiments 1-48, wherein the hardiness is selected from a group consisting of an improved resistance to stress caused by weather damage, an improved resistance to stress caused by sun exposure, an improved resistance to stress caused by disease, and an improved resistance to stress caused by insects. Numbered embodiment 50 comprises the method of numbered embodiments 1-49, wherein the at least one of plant performance and hardiness is improved by at least about 8%. Numbered embodiment 51 comprises the method of numbered embodiments 1-50, wherein the at least one of plant performance and hardiness is improved by at least about 10%. Numbered embodiment 52 comprises the method of numbered embodiments 1-51, wherein the at least one of plant performance and hardiness is improved by at least about 12%. Numbered embodiment 53 comprises the method of numbered embodiments 1-52, wherein the at least one of plant performance and hardiness is improved by at least about 15%. Numbered embodiment 54 comprises the method of numbered embodiments 1-53, wherein the at least one of plant performance and hardiness is improved by at least about 18%. Numbered embodiment 55 comprises the method of numbered embodiments 1-54, wherein the at least one of plant performance and hardiness is improved by at least about 20%. Numbered embodiment 56 comprises a method for improving at least one of plant performance and hardiness, comprising: (a) priming a seed using a priming medium; (b) concurrently inducing metabolic activation in the seed; and (c) subsequently reducing internal moisture of the seed. Numbered embodiment 57 comprises the method of numbered embodiments 1-56, wherein the priming medium is water. Numbered embodiment 58 comprises the method of numbered embodiments 1-57, wherein the priming medium is polyethylene glycol. Numbered embodiment 59 comprises the method of numbered embodiments 1-58, wherein the seed is submerged in the priming medium. Numbered embodiment 60 comprises the method of numbered embodiments 1-59, wherein reducing the internal moisture comprises using air, reducing humidity, adjusting a temperature, or using a desiccant. Numbered embodiment 61 comprises the method of numbered embodiments 1-60, wherein inducing metabolic activation comprises administering light, hormones, chemicals, steroids, or vitamins. Numbered embodiment 62 comprises the method of numbered embodiments 1-61, wherein the light is enriched for UV-B. Numbered embodiment 63 comprises the method of numbered embodiments 1-62, wherein a wavelength of the UV-B is in a range of about 280 nm to about 290 nm. Numbered embodiment 64 comprises the method of numbered embodiments 1-63, wherein a wavelength of the UV-B is 280 nm. Numbered embodiment 65 comprises the method of numbered embodiments 1-64, wherein a wavelength of the UV-B is 290 nm. Numbered embodiment 66 comprises the method of numbered embodiments 1-65, wherein an irradiance of UV-B is up to 300 uW cm$^{-2}$. Numbered embodiment 67 comprises the method of numbered embodiments 1-66, wherein an UV-B irradiance is administered no more than $1.3 \times 10^{-4}$ W cm$^{-2}$ s$^{-1}$. Numbered embodiment 68 comprises the method of numbered embodiments 1-67, wherein the light enriched for UV-B comprises at least 50% UV-B. Numbered embodiment 69 comprises the method of numbered embodiments 1-68, wherein the light enriched for UV-B comprises at least 50% more UV-B than any other wavelength. Numbered embodiment 70 comprises the method of numbered embodiments 1-69, wherein the light comprises blue light. Numbered embodiment 71 comprises the method of numbered embodiments 1-70, wherein the light comprises red light. Numbered embodiment 72 comprises the method of numbered embodiments 1-71, wherein the light comprises visible light. Numbered embodiment 73 comprises the method of numbered embodiments 1-72, wherein the visible light is administered no more than 400 umol m$^{-2}$ s$^{-1}$. Numbered embodiment 74 comprises the method of numbered embodiments 1-73, wherein the UV-B is administered at no more than 100 kJ m$^{-2}$. Numbered embodiment 75 comprises the method of numbered embodiments 1-74, wherein a duration of priming the seed and concurrently administering UV-B is in a range of about 1 hour to about 30 hours, about 2 hours to about 27 hours, about 3 hours to about 25 hours, about 4 hours to about 24 hours, about 5 hours to about 22 hours, or about 6 hours to about 21 hours. Numbered embodiment 76 comprises the method of numbered embodiments 1-75, wherein the at least one of plant performance and hardiness is improved by at least about 10%. Numbered embodiment 77 comprises a method for improving at least one of plant performance and hardiness, comprising: (a) priming a seed; and (b) administering light enriched for UV-B of a wavelength about 280 nm to about 290 nm for at least 8 hours and using an irradiance of at least 40 uW cm$^{-2}$. Numbered embodiment 78 comprises the method of numbered embodiments 1-77, wherein administering light is for about 8 hours. Numbered embodiment 79 comprises the method of numbered embodiments 1-78, wherein administering light is for at least 19 hours. Numbered embodiment 80 comprises the method of numbered embodiments 1-79, wherein administering light is for 21 hours. Numbered embodiment 81 comprises the method of numbered embodiments 1-80, wherein administering light is for at least 27 hours. Numbered embodiment 82 comprises the method of numbered embodiments 1-81, wherein administering light is for 27 hours. Numbered embodiment 83 comprises the method of numbered embodiments 1-82, wherein the irradiance is about 40 uW cm$^{-2}$. Numbered embodiment 84 comprises the method of numbered embodiments 1-83, wherein the irradiance is at least 100 uW cm$^{-2}$. Numbered embodiment 85 comprises the method of numbered embodiments 1-84, wherein step (a) and step (b) occur concurrently. Numbered embodiment 86 comprises the method of numbered embodiments 1-85, wherein priming comprises using a priming medium. Numbered embodiment 87 comprises the method of numbered embodiments 1-86, wherein the priming medium is water. Numbered embodiment 88 comprises the method of numbered embodiments 1-87, wherein the priming medium is polyethylene glycol. Numbered embodiment 89 comprises the method of numbered embodiments 1-88, wherein the seed is submerged in the priming medium. Numbered embodiment 90 comprises the method of numbered embodiments 1-89, wherein administering light occurs in a growth chamber. Numbered embodiment 91 comprises the method of numbered embodiments 1-90, wherein the growth chamber is maintained up to 40° C. Numbered embodiment 92 comprises the method of numbered embodiments 1-91, wherein the growth chamber is maintained at about 22° C. Numbered embodiment 93 comprises the method of numbered embodiments 1-92, wherein the growth chamber is maintained at about 10° C. Numbered embodiment 94 comprises the method of numbered embodiments 1-93, wherein a duration of priming the seed is in a range of about 1 hour to about 30 hours, about 2 hours to about 27 hours, about 3 hours to about 25 hours, about 4 hours to about 24 hours, about 5 hours to about 22 hours, or about 6 hours to about 21 hours. Numbered embodiment 95 comprises the method of numbered embodiments 1-94, wherein a duration of priming is about 20 hours. Numbered embodiment 96 comprises the method of numbered embodiments 1-95, wherein a duration of priming is about 24 hours. Numbered embodiment 97 comprises the method of numbered embodiments 1-96, wherein a duration of priming is about 27 hours. Numbered embodiment 98 comprises the method of numbered embodiments 1-97, wherein the wavelength of UV-B is 280 nm. Numbered embodiment 99 comprises the method of numbered embodiments 1-98, wherein the wavelength of UV-B is 290 nm. Numbered embodiment 100 comprises the method of numbered embodiments 1-99, wherein the light enriched for UV-B comprises at least 50% UV-B. Numbered embodiment 101 comprises the method of numbered embodiments 1-100, wherein the light enriched for UV-B comprises at least 50% more UV-B than any other wavelength. Numbered embodiment 102 comprises the method of numbered embodiments 1-101, wherein the light comprises blue light. Numbered embodiment 103 comprises the method of numbered embodiments 1-102, wherein the light comprises red light. Numbered embodiment 104 comprises the method of numbered embodiments 1-103, wherein the improvements in the plant performance is selected from a group comprising fruit fresh weight, number of fruit harvested, Brix content, fruit width, fruit length, leaf size, leaf surface area, dry weight, nitrogen content, shoot dry weight, shoot fresh weight, root dry weight, vegetable development, yield of fruiting parts, increased weight of fruiting parts, hardiness, and seed germination rate. Numbered embodiment 105 comprises the method of numbered embodiments 1-104, wherein the hardiness is selected from a group consisting of an improved resistance to stress caused by weather damage, an improved resistance to stress caused by sun exposure, an improved resistance to stress caused by disease, and an improved resistance to stress caused by insects. Numbered embodiment 106 comprises the method of numbered embodiments 1-105, wherein the at least one of plant performance and hardiness is improved by at least about 8%. Numbered embodiment 107 comprises the method of numbered embodiments 1-106, wherein the at least one of plant performance and hardiness is improved by at least about 10%. Numbered embodiment 108 comprises the method of numbered embodiments 1-107, wherein the at least one of plant performance and hardiness is improved by at least about 12%. Numbered embodiment 109 comprises the method of numbered embodiments 1-108, wherein the at least one of plant performance and hardiness is improved by at least about 15%. Numbered embodiment 110 comprises the method of numbered embodiments 1-109, wherein the at least one of plant performance and hardiness is improved by at least about 18%. Numbered embodiment 111 comprises the method of numbered embodiments 1-110, wherein the at least one of plant performance and hardiness is improved by at least about 20%. Numbered embodiment 112 comprises a method for improving at least one of plant performance and hardiness, comprising: (a) priming a seed; and (b) administering light enriched for UV-B of a wavelength about 280 nm to about 290 nm for at least 19 hours and using an irradiance of at least 100 uW cm$^{-2}$. Numbered embodiment 113 comprises the method of numbered embodiments 1-112, wherein administering light is for 21 hours. Numbered embodiment 114 comprises the method of numbered embodiments 1-113, wherein administering light is for 27 hours. Numbered embodiment 115 comprises the method of numbered embodiments 1-114, wherein the irradiance is about 100 uW cm$^{-2}$. Numbered embodiment 116 comprises the method of numbered embodiments 1-115, wherein the irradiance is at least 200 uW cm$^{-2}$. Numbered embodiment 117 comprises the method of numbered embodiments 1-116, wherein the irradiance is about 200 uW cm$^{-2}$. Numbered embodiment 118 comprises the method of numbered embodiments 1-117, wherein step (a) and step (b) occur concurrently. Numbered embodiment 119 comprises the method of numbered embodiments 1-118, wherein priming comprises using a priming medium. Numbered embodiment 120 comprises the method of numbered embodiments 1-119, wherein the priming medium is water. Numbered embodiment 121 comprises the method of numbered embodiments 1-120, wherein the priming medium is polyethylene glycol. Numbered embodiment 122 comprises the method of numbered embodiments 1-121, wherein the seed is submerged in the priming medium. Numbered embodiment 123 comprises the method of numbered embodiments 1-122, wherein administering light occurs in a growth chamber. Numbered embodiment 124 comprises the method of numbered embodiments 1-122, wherein the growth chamber is maintained up to 40° C. Numbered embodiment 125 comprises the method of numbered embodiments 1-124, wherein the growth chamber is maintained at about 22° C. Numbered embodiment 126 comprises the method of numbered embodiments 1-125, wherein the growth chamber is maintained at about 10° C. Numbered embodiment 127 comprises the method of numbered embodiments 1-126, wherein a duration of priming the seed is in a range of about 1 hour to about 30 hours, about 2 hours to about 27 hours, about 3 hours to about 25 hours, about 4 hours to about 24 hours, about 5 hours to about 22 hours, or about 6 hours to about 21 hours. Numbered embodiment 128 comprises the method of numbered embodiments 1-127, wherein a duration of priming is about 20 hours. Numbered embodiment 129 comprises the method of numbered embodiments 1-128, wherein a duration of priming is about 24 hours. Numbered embodiment 130 comprises the method of numbered embodiments 1-129, wherein a duration of priming is about 27 hours. Numbered embodiment 131 comprises the method of numbered embodiments 1-130, wherein the wavelength of UV-B is 280 nm. Numbered embodiment 132 comprises the method of numbered embodiments 1-131, wherein the wavelength of UV-B is 290 nm. Numbered embodiment 133 comprises the method of numbered embodiments 1-132, wherein the light enriched for UV-B comprises at least 50% UV-B. Numbered embodiment 134 comprises the method of numbered embodiments 1-133, wherein the light enriched for UV-B comprises at least 50% more UV-B than any other wavelength. Numbered embodiment 135 comprises the method of numbered embodiments 1-134, wherein the light comprises blue light. Numbered embodiment 136 comprises the method of numbered embodiments 1-135, wherein the light comprises red light. Numbered embodiment 137 comprises the method of numbered embodiments 1-136, wherein the improvements in the plant performance is selected from a group comprising fruit fresh weight, number of fruit harvested, Brix content, fruit width, fruit length, leaf size, leaf surface area, dry weight, nitrogen content, shoot dry weight, shoot fresh weight, root dry weight, vegetable development, yield of fruiting parts, increased weight of fruiting parts, hardiness, and seed germination rate. Numbered embodiment 138 comprises the method of numbered embodiments 1-137, wherein the hardiness is selected from a group consisting of an improved resistance to stress caused by weather damage, an improved resistance to stress caused by sun exposure, an improved resistance to stress caused by disease, and an improved resistance to stress caused by insects. Numbered embodiment 139 comprises the method of numbered embodiments 1-138, wherein the at least one of plant performance and hardiness is improved by at least about 8%. Numbered embodiment 140 comprises the method of numbered embodiments 1-139, wherein the at least one of plant performance and hardiness is improved by at least about 10%. Numbered embodiment 141 comprises the method of numbered embodiments 1-140, wherein the at least one of plant performance and hardiness is improved by at least about 12%. Numbered embodiment 142 comprises the method of numbered embodiments 1-141, wherein the at least one of plant performance and hardiness is improved by at least about 15%. Numbered embodiment 143 comprises the method of numbered embodiments 1-142, wherein the at least one of plant performance and hardiness is improved by at least about 18%. Numbered embodiment 144 comprises the method of numbered embodiments 1-143, wherein the at least one of plant performance and hardiness is improved by at least about 20%. Numbered embodiment 145 comprises a method for improving at least one of plant performance and hardiness, comprising: (a) priming a seed using a priming medium for a duration of no more than about 50 hours; and (b) administering light enriched for UV-B of a wavelength about 280 nm to about 290 nm in a growth chamber of at least about 10° C., wherein the UV-B is administered for no more than about 30 hours using a dose of no more than about 270 kJ $m^{-2}$ and an irradiance of no more than about 200 uW $cm^{-2}$. Numbered embodiment 146 comprises the method of numbered embodiments 1-145, wherein the priming medium is water. Numbered embodiment 147 comprises the method of numbered embodiments 1-146, wherein the priming medium is polyethylene glycol. Numbered embodiment 148 comprises the method of numbered embodiments 1-147, wherein step (a) and step (b) occur concurrently. Numbered embodiment 149 comprises the method of numbered embodiments 1-148, wherein the growth chamber is maintained at about 10° C. Numbered embodiment 150 comprises the method of numbered embodiments 1-149, wherein the growth chamber is maintained at about 20° C. Numbered embodiment 151 comprises the method of numbered embodiments 1-150, wherein the UV-B is administered at about 100 kJ $m^{-2}$. Numbered embodiment 152 comprises the method of numbered embodiments 1-151, wherein the UV-B is administered at about 13 kJ $m^{-2}$. Numbered embodiment 153 comprises the method of numbered embodiments 1-152, wherein the irradiance of UV-B is about 40 uW $cm^{-2}$. Numbered embodiment 154 comprises the method of numbered embodiments 1-153, wherein the irradiance of UV-B is about 100 uW $cm^{-2}$. Numbered embodiment 155 comprises the method of numbered embodiments 1-154, wherein the UV-B is administered for about 20 hours. Numbered embodiment 156 comprises the method of numbered embodiments 1-155, wherein the UV-B is administered for about 24 hours. Numbered embodiment 157 comprises the method of numbered embodiments 1-156, wherein the UV-B is administered for about 27 hours. Numbered embodiment 158 comprises the method of numbered embodiments 1-157, wherein the duration of priming is about 44 hours. Numbered embodiment 159 comprises the method of numbered embodiments 1-158, wherein the duration of priming is about 27 hours. Numbered embodiment 160 comprises the method of numbered embodiments 1-159, wherein the duration of priming is about 24 hours. Numbered embodiment 161 comprises the method of numbered embodiments 1-160, wherein the duration of priming is about 20 hours. Numbered embodiment 162 comprises the method of numbered embodiments 1-161, wherein the duration of priming is about 8 hours. Numbered embodiment 163 comprises the method of numbered embodiments 1-162, further comprising placing the seed on a moist surface prior to step (b). Numbered embodiment 164 comprises the method of numbered embodiments 1-163, wherein the moist surface comprises a moist filter paper. Numbered embodiment 165 comprises the method of numbered embodiments 1-164, further comprising submerging the seed prior to step (b). Numbered embodiment 166 comprises the method of numbered embodiments 1-165, wherein the wavelength of UV-B is 280 nm. Numbered embodiment 167 comprises the method of numbered embodiments 1-166, wherein the wavelength of UV-B is 290 nm. Numbered embodiment 168 comprises the method of numbered embodiments 1-167, wherein the light enriched for UV-B comprises at least 50% UV-B. Numbered embodiment 169 comprises the method of numbered embodiments 1-168, wherein the light enriched for UV-B comprises at least 50% more UV-B than any other wavelength. Numbered embodiment 170 comprises the method of numbered embodiments 1-169, wherein the UV-B is co-administered using a visible light. Numbered embodiment 171 comprises the method of numbered embodiments 1-170, wherein the visible light is at least one of a blue and a red light. Numbered embodiment 172 comprises the method of numbered embodiments 1-171, wherein the visible light is administered no more than 400 umol $m^{-2}$ $s^{-1}$. Numbered embodiment 173 comprises the method of numbered embodiments 1-172, wherein the visible light is administered within a range of at least one of 0 $m^{-2}$ $s^{-1}$-20 umol $m^{-2}$ $s^{-1}$, 20 $m^{-2}$ $s^{-1}$-50 umol $m^{-2}$ $s^{-1}$, and 50 $m^{-2}$ $s^{-1}$-400 umol $m^{-2}$ $s^{-1}$. Numbered embodiment 174 comprises the method of numbered embodiments 1-173, wherein the visible light is administered at about 400 umol $m^{-2}$ $s^{-1}$. Numbered embodiment 175 comprises the method of numbered embodiments 1-174, wherein the visible light is administered at about 50 umol $m^{-2}$ $s^{-1}$. Numbered embodiment 176 comprises the method of numbered embodiments 1-175, wherein the visible light is administered at about 20 umol $m^{-2}$ $s^{-1}$. Numbered embodiment 177 comprises the method of numbered embodiments 1-176, wherein the visible light comprises blue light. Numbered embodiment 178 comprises the method of numbered embodiments 1-177, wherein the visible light comprises red light. Numbered embodiment 179 comprises the method of numbered embodiments 1-178, wherein improvements in the plant performance is selected from a group consisting of fruit fresh weight, number of fruit harvested, Brix content, fruit width, fruit length, leaf size, leaf surface area, dry weight, nitrogen content, shoot dry weight, shoot fresh weight, root dry weight, vegetable development, yield of fruiting parts, increased weight of fruiting parts, hardiness, and seed germination rate. Numbered embodiment 180 comprises the method of numbered embodiments 1-179, wherein the hardiness is selected from a group consisting of an improved resistance to stress caused by weather damage, an improved resistance to stress caused by sun exposure, an improved resistance to stress caused by disease, and an improved resistance to stress caused by insects. Numbered embodiment 181 comprises the method of numbered embodiments 1-180, wherein the plant performance is improved by at least about 8%. Numbered embodiment 182 comprises the method of numbered embodiments 1-181, wherein the at least one of plant performance and hardiness is improved by at least about 10%. Numbered embodiment 183 comprises the method of numbered embodiments 1-182, wherein the at least one of plant performance and hardiness is improved by at least about 12%. Numbered embodiment 184 comprises the method of numbered embodiments 1-183, wherein the at least one of plant performance and hardiness is improved by at least about 15%. Numbered embodiment 185 comprises the method of numbered embodiments 1-184, wherein the at least one of plant performance and hardiness is improved by at least about 18%. Numbered embodiment 186 comprises the method of numbered embodiments 1-185, wherein the at least one of plant performance and hardiness is improved by at least about 20%. Numbered embodiment 187 comprises a method for improving at least one of plant performance and hardiness, comprising: (a) priming a seed; (b) administering light enriched for UV-B of a wavelength of about 280 nm to about 290 nm to the seed; and (c) measuring improvements in plant performance, wherein plant performance is improved by at least 5%. Numbered embodiment 188 comprises the method of numbered embodiments 1-187, wherein priming the seed comprises using a priming medium. Numbered embodiment 189 comprises the method of numbered embodiments 1-188, wherein the priming medium is water. Numbered embodiment 190 comprises the method of numbered embodiments 1-189, wherein the priming medium is polyethylene glycol. Numbered embodiment 191 comprises the method of numbered embodiments 1-190, further comprising placing the seed on a moist surface prior to step (b). Numbered embodiment 192 comprises the method of numbered embodiments 1-191, wherein the moist surface comprises a moist filter paper. Numbered embodiment 193 comprises the method of numbered embodiments 1-192, further comprising submerging the seed in a priming medium prior to step (b). Numbered embodiment 194 comprises the method of numbered embodiments 1-193, wherein the priming medium is water. Numbered embodiment 195 comprises the method of numbered embodiments 1-194, wherein the priming medium is polyethylene glycol. Numbered embodiment 196 comprises the method of numbered embodiments 1-195, wherein step (a) and step (b) occur concurrently. Numbered embodiment 197 comprises the method of numbered embodiments 1-196, wherein administering light occurs in a growth chamber. Numbered embodiment 198 comprises the method of numbered embodiments 1-197, wherein the growth chamber is maintained up to 40° C. Numbered embodiment 199 comprises the method of numbered embodiments 1-198, wherein the growth chamber is maintained at about 22° C. Numbered embodiment 200 comprises the method of numbered embodiments 1-199, wherein the growth chamber is maintained at about 10° C. Numbered embodiment 201 comprises the method of numbered embodiments 1-200, wherein an irradiance of UV-B is up to 300 uW cm$^{-2}$. Numbered embodiment 202 comprises the method of numbered embodiments 1-201, wherein an irradiance of UV-B is in a range of about 40 uW cm$^{-2}$ to about 200 uW cm$^{-2}$. Numbered embodiment 203 comprises the method of numbered embodiments 1-202, wherein an irradiance of UV-B is about 40 uW cm$^{-2}$. Numbered embodiment 204 comprises the method of numbered embodiments 1-203, wherein an irradiance of UV-B is about 100 uW cm$^{-2}$. Numbered embodiment 205 comprises the method of numbered embodiments 1-204, wherein an irradiance of UV-B is about 200 uW cm$^{-2}$. Numbered embodiment 206 comprises the method of numbered embodiments 1-205, wherein a duration of administering UV-B is in a range of about 1 hour to about 30 hours, about 2 hours to about 27 hours, about 3 hours to about 25 hours, about 4 hours to about 24 hours, about 5 hours to about 22 hours, or about 6 hours to about 21 hours. Numbered embodiment 207 comprises the method of numbered embodiments 1-206, wherein a duration of administering UV-B is about 20 hours. Numbered embodiment 208 comprises the method of numbered embodiments 1-207, wherein a duration of administering UV-B is about 24 hours. Numbered embodiment 209 comprises the method of numbered embodiments 1-208, wherein a duration of administering UV-B is about 27 hours. Numbered embodiment 210 comprises the method of numbered embodiments 1-209, wherein a duration of priming is up to 50 hours. Numbered embodiment 211 comprises the method of numbered embodiments 1-210, wherein a duration of priming is in a range of about 1 hour to about 50 hours, about 2 hours to about 48 hours, about 3 hours to about 44 hours, about 4 hours to about 40 hours, about 5 hours to about 35 hours, about 6 hours to about 32 hours, about 7 hours to about 30 hours, or about 8 hours to about 27 hours. Numbered embodiment 212 comprises the method of numbered embodiments 1-211, wherein a duration of priming is about 44 hours. Numbered embodiment 213 comprises the method of numbered embodiments 1-212, wherein a duration of priming is about 27 hours. Numbered embodiment 214 comprises the method of numbered embodiments 1-213, wherein a duration of priming is about 24 hours. Numbered embodiment 215 comprises the method of numbered embodiments 1-214, wherein a duration of priming is about 20 hours. Numbered embodiment 216 comprises the method of numbered embodiments 1-215, wherein a duration of priming is about 8 hours. Numbered embodiment 217 comprises the method of numbered embodiments 1-216, wherein the wavelength of UV-B is 280 nm. Numbered embodiment 218 comprises the method of numbered embodiments 1-217, wherein the wavelength of UV-B is 290 nm. Numbered embodiment 219 comprises the method of numbered embodiments 1-218, wherein the light enriched for UV-B comprises at least 50% UV-B. Numbered embodiment 220 comprises the method of numbered embodiments 1-219, wherein the light enriched for UV-B comprises at least 50% more UV-B than any other wavelength. Numbered embodiment 221 comprises the method of numbered embodiments 1-220, wherein the light comprises blue light. Numbered embodiment 222 comprises the method of numbered embodiments 1-221, wherein the light comprises red light. Numbered embodiment 223 comprises the method of numbered embodiments 1-222, wherein the improvements in the plant performance is selected from a group comprising fruit fresh weight, number of fruit harvested, Brix content, fruit width, fruit length, leaf size, leaf surface area, dry weight, nitrogen content, shoot dry weight, shoot fresh weight, root dry weight, vegetable development, yield of fruiting parts, increased weight of fruiting parts, hardiness, and seed germination rate. Numbered embodiment 224 comprises the method of numbered embodiments 1-223, wherein the hardiness is selected from a group consisting of an improved resistance to stress caused by weather damage, an improved resistance to stress caused by sun exposure, an improved resistance to stress caused by disease, and an improved resistance to stress caused by insects. Numbered embodiment 225 comprises the method of numbered embodiments 1-224, wherein the at least one of plant performance and hardiness is improved by at least about 8%. Numbered embodiment 226 comprises the method of numbered embodiments 1-225, wherein the at least one of plant performance and hardiness is improved by at least about 10%. Numbered embodiment 227 comprises the method of numbered embodiments 1-226, wherein the at least one of plant performance and hardiness is improved by at least about 12%. Numbered embodiment 228 comprises the method of numbered embodiments 1-227, wherein the at least one of plant performance and hardiness is improved by at least about 15%. Numbered embodiment 229 comprises the method of numbered embodiments 1-228, wherein the at least one of plant performance and hardiness is improved by at least about 18%. Numbered embodiment 230 comprises the method of numbered embodiments 1-229, wherein the at least one of plant performance and hardiness is improved by at least about 20%. Numbered embodiment 231 comprises a method for treating a seed for sowing to improve plant performance, the method comprising: (a) priming the seed; (b) positioning the seed such that an embryo of said seed is not blocked from receiving irradiation; and (c) treating the seed using light enriched for UV-B. Numbered embodiment 232 comprises the method of numbered embodiments 1-231, wherein positioning the seed such that the embryo of said seed is positioned to receive irradiation increases efficacy of UV-B irradiation. Numbered embodiment 233 comprises the method of numbered embodiments 1-232, wherein positioning of said seed maximizes UV-B irradiation. Numbered embodiment 234 comprises a method of reducing environmental impact of growing a crop, comprising the steps of: (a) priming a seed; (b) treating the seed using light enriched for UV-B; (c) sowing the seed; (d) providing no more than at least one of a standard fertilizer regimen, a standard pesticide regimen, a standard herbicide regimen, and a standard insecticide regimen; and € harvesting the crop from said seed, wherein a crop yield of the crop from said seed is at least 5% greater than a standard yield. Numbered embodiment 235 comprises a method of reducing fertilizer use without reduction to a crop yield compared to standard fertilizer use comprising the steps of: (a) priming a seed; (b) treating the seed using light enriched for UV-B; (c) sowing the seed; (d) providing no more than 95% of the standard fertilizer regimen; and (e) harvesting a crop from said seed, wherein the crop requires less fertilizer than a crop from non-UV-B irradiated seed. Numbered embodiment 236 comprises the method of numbered embodiments 1-235, wherein the crop yield is increased. Numbered embodiment 237 comprises the method of numbered embodiments 1-236, wherein the crop is harvested sooner compared to the crop from the non-UV-B irradiated seed. Numbered embodiment 238 comprises a method of growing a crop by reducing pesticide use without impacting loss due to pest damage comprising the steps of: (a) priming a seed; (b) treating the seed using light enriched for UV-B; (c) sowing the seed; (d) providing no more than 95% of the standard pesticide regimen; and (e) harvesting the crop from said seed, wherein the crop requires less pesticide than a crop from a non-UV-B irradiated seed. Numbered embodiment 239 comprises the method of numbered embodiments 1-238, wherein the crop yield is increased. Numbered embodiment 240 comprises the method of numbered embodiments 1-239, wherein the crop is harvested sooner compared to the crop from the non-UV-B irradiated seed. Numbered embodiment 241 comprises the method of numbered embodiments 1-240, wherein the organic crop is fed to an animal. Numbered embodiment 242 comprises a method of increasing disease resistance in a crop comprising the steps of: (a) priming a seed; (b) treating the seed using light enriched for UV-B; (c) sowing the seed; and (d) harvesting the crop, wherein the crop has increased disease resistance than a crop from a non-UV-B irradiated seed. Numbered embodiment 243 comprises the method of numbered embodiments 1-242, wherein the disease is caused by at least one of a fungal pathogen, a bacterium, a oomycete, a virus, a viroid, a virus-like organism, a phytoplasma, a protozoa, a nematode, and a parasitic plant. Numbered embodiment 244 comprises the method of numbered embodiments 1-243, wherein a crop yield is increased. Numbered embodiment 245 comprises the method of numbered embodiments 1-244, wherein the crop is harvested sooner compared to the crop from the non-UV-B irradiated seed. Numbered embodiment 246 comprises a method of increasing damage resistance in a crop comprising the steps of: (a) priming a seed; (b) treating the seed using light enriched for UV-B; (c) sowing the seed; and (d) harvesting the crop from said seed, wherein the crop has increased damage resistance than a crop from a non-UV-B irradiated seed. Numbered embodiment 247 comprises the method of numbered embodiments 1-246, wherein the damage comprises at least one of heat, flood, drought, frost, unusual climate events, salinity stress, and high visible light stress. Numbered embodiment 248 comprises the method of numbered embodiments 1-247, wherein a crop yield is increased. Numbered embodiment 249 comprises the method of numbered embodiments 1-248, wherein the crop is harvested sooner compared to the crop from the non-UV-B irradiated seed. Numbered embodiment 250 comprises a method of growing a crop by reducing insecticide use without impacting loss due to pest damage comprising the steps of: (a) priming a seed; (b) treating the seed using light enriched for UV-B; (c) sowing the seed; (d) providing no more than 95% of the standard insecticide regimen; and (e) harvesting the crop from said seed, wherein the crop requires less insecticide than a crop from a non-UV-B irradiated seed. Numbered embodiment 251 comprises the method of numbered embodiments 1-250, wherein a crop yield is increased. Numbered embodiment 252 comprises the method of numbered embodiments 1-251, wherein the crop is harvested sooner compared to the crop from the non-UV-B irradiated seed. Numbered embodiment 253 a method of growing an improved quality crop compared to a crop from non-UV-B irradiated seed comprising the steps of: (a) priming a seed; (b) treating the seed using light enriched for UV-B; (c) sowing the seed; and (d) harvesting the crop from said seed, wherein the quality of the crop is improved compared to the crop from a non-UV-B irradiated seed. Numbered embodiment 254 comprises the method of numbered embodiments 1-253, wherein the improved quality comprises at least one of a longer shelf-life, a resistance to bruising or post-harvesting handling, an increased nutrient value, and an improved taste, shape, color, size, and texture. Numbered embodiment 255 comprises the method of numbered embodiments 1-254, wherein a crop yield is increased. Numbered embodiment 256 comprises the method of numbered embodiments 1-255, wherein the crop is harvested sooner compared to the crop from the non-UV-B irradiated seed. Numbered embodiment 257 comprises a seed characterized by the method of numbered embodiments 1-256. Numbered embodiment 258 comprises a seed characterized by the method of numbered embodiments 1-257, wherein the seed has at least one of an increased flavonoid level and an increased anthocyanin level compared to a non-irradiated seed. Numbered embodiment 259 comprises a seed characterized by the method of numbered embodiments 1-258, wherein a plurality of said seeds have an improved germination. Numbered embodiment 260 comprises a crop derived from a method according to any one of numbered embodiments 1-256. Numbered embodiment 261 comprises a crop derived from a method according to any one of numbered embodiments 1-256, wherein the crop has at least one of an increased flavonoid level and increased anthocyanin level compared to non-UV-B irradiated seed. Numbered embodiment 262 comprises a crop derived from a method according to any one of numbered embodiments 1-256, wherein the crop has an improved yield. Numbered embodiment 263 comprises a crop derived from a method according to any one of numbered embodiments 1-256, wherein improvements in plant performance is selected from a group comprising fruit fresh weight, number of fruit harvested, Brix content, fruit width, fruit length, leaf size, leaf surface area, dry weight, nitrogen content, shoot dry weight, shoot fresh weight, root dry weight, vegetable development, yield of fruiting parts, increased weight of fruiting parts, hardiness, and seed germination rate. Numbered embodiment 264 comprises a crop derived from a method according to any one of numbered embodiments 1-256, wherein the crop is a commercially grown crop. Numbered embodiment 265 comprises a crop derived from a method according to any one of numbered embodiments 1-256, wherein the improved yield is an improved water use. Numbered embodiment 266 comprises a crop grown from a seed administered light enriched for UV-B irradiation in a wavelength of about 280 nm to about 290 nm. Numbered embodiment 267 comprises a tray characterized by a method according to any one of embodiments 1-266, wherein the tray is used to position a seed to increase UV-B irradiation efficacy. Numbered embodiment 268 comprises a system for priming and concurrently administering UV-B to a seed, comprising: (a) a computer having a readable input file to generate instructions for administering light enriched for UV-B; (b) a lighting controller for receiving the instructions for administering light enriched for UV-B; and (c) a surface for priming and concurrently administering light enriched for UV-B. Numbered embodiment 269 comprises a system according to any numbered embodiments 1-268, wherein the instructions relate to a dose, an irradiance, or a duration for priming and concurrently administering light enriched for UV-B. Numbered embodiment 270 comprises a system according to any numbered embodiments 1-269, wherein the irradiance of UV-B is in a range of about 40 uW $cm^{-2}$ to about 200 uW $cm^{-2}$. Numbered embodiment 271 comprises a system according to any numbered embodiments 1-270, wherein the irradiance of UV-B is about 40 uW $cm^{-2}$. Numbered embodiment 272 comprises a system according to any numbered embodiments 1-271, wherein the irradiance of UV-B is about 100 uW $cm^{-2}$. Numbered embodiment 273 comprises a system according to any numbered embodiments 1-272, wherein the irradiance of UV-B is about 200 uW $cm^{-2}$. Numbered embodiment 274 comprises a system according to any numbered embodiments 1-273, wherein the duration for priming and concurrently administering light enriched for UV-B is in a range of about 1 hour to about 30 hours, about 2 hours to about 27 hours, about 3 hours to about 25 hours, about 4 hours to about 24 hours, about 5 hours to about 22 hours, or about 6 hours to about 21 hours. Numbered embodiment 275 comprises a system according to any numbered embodiments 1-274, wherein the duration for priming and concurrently administering light enriched for UV-B is about 20 hours. Numbered embodiment 276 comprises a system according to any numbered embodiments 1-275, wherein the duration for priming and concurrently administering light enriched for UV-B is about 24 hours. Numbered embodiment 277 comprises a system according to any numbered embodiments 1-276, wherein the duration for priming and concurrently administering light enriched for UV-B is about 27 hours. Numbered embodiment 278 comprises a system according to any numbered embodiments 1-277, wherein a wavelength of the UV-B is in a range of about 280 nm to about 290 nm. Numbered embodiment 279 comprises a system according to any numbered embodiments 1-278, wherein a wavelength of the UV-B is 280 nm. Numbered embodiment 280 comprises a system according to any numbered embodiments 1-279, wherein a wavelength of the UV-B is 290 nm. Numbered embodiment 281 comprises a system according to any numbered embodiments 1-280, wherein the light enriched for UV-B comprises at least 50% UV-B. Numbered embodiment 282 comprises a system according to any numbered embodiments 1-281, wherein the light enriched for UV-B comprises at least 50% more UV-B than any other wavelength. Numbered embodiment 283 comprises a system according to any numbered embodiments 1-282, wherein the surface comprises a priming medium. Numbered embodiment 284 comprises a system according to any numbered embodiments 1-283, wherein the priming medium is water. Numbered embodiment 285 comprises a system according to any numbered embodiments 1-284, wherein the priming medium is polyethylene glycol. Numbered embodiment 286 comprises a system according to any numbered embodiments 1-285, wherein the light comprises blue light. Numbered embodiment 287 comprises a system according to any numbered embodiments 1-286, wherein the light comprises red light. Numbered embodiment 288 comprises a system according to any numbered embodiments 1-287, wherein the light comprises visible light. Numbered embodiment 289 comprises a system according to any numbered embodiments 1-288, wherein the visible light is administered no more than 400 umol $m^{-2}$ $s^{-1}$. Numbered embodiment 290 comprises a system according to any numbered embodiments 1-289, wherein the visible light is administered in a range from at least one of 0.1 $m^{-2}$ $s^{-1}$-20 umol $m^{-2}$ $s^{-1}$-20 $m^{-2}$ $s^{-1}$-50 umol $m^{-2}$ $s^{-1}$ and 50 $m^{-2}$ $s^{-1}$-400 umol $m^{-2}$ $s^{-1}$. Numbered embodiment 290 comprises a system according to any numbered embodiments 1-290, wherein the visible light is administered at about 400 umol $m^{-2}$ $s^{-1}$. Numbered embodiment 292 comprises a system according to any numbered embodiments 1-291, wherein the visible light is administered at about 50 umol $m^{-2}$ $s^{-1}$. Numbered embodiment 293 comprises a system according to any numbered embodiments 1-292, wherein the visible light is administered at about 20 umol $m^{-2}$ $s^{-1}$. Numbered embodiment 294 comprises a system according to any numbered embodiments 1-293, wherein the dose of UV-B administered is no more than 100 kJ $m^{-2}$. Numbered embodiment 295 comprises a system according to any numbered embodiments 1-294, wherein the dose of UV-B administered is in a range from at least one of 0.1-13 kJ $m^{-2}$, 13-50 kJ $m^{-2}$, and 50-100 kJ $m^{-2}$. Numbered embodiment 296 comprises a system according to any numbered embodiments 1-295, wherein the dose of UV-B administered is about 100 kJ $m^{-2}$. Numbered embodiment 297 comprises a system according to any numbered embodiments 1-296, wherein the dose of UV-B administered is about 13 kJ $m^{-2}$. Numbered embodiment 298 comprises a system according to any numbered embodiments 1-297, wherein the UV-B irradiance is administered no more than $1.3 \times 10^{-4}$ W $cm^{-2}$ $s^{-1}$. Numbered embodiment 299 comprises a system according to any numbered embodiments 1-298, wherein the UV-B irradiance is in the range of about $4 \times 10^{-5}$ W $cm^{-2}$ $s^{-1}$ to $1.3 \times 10^{-4}$ W $cm^{-2}$ $s^{-1}$. Numbered embodiment 300 comprises a system according to any numbered embodiments 1-299, wherein the UV-B irradiance is about $4 \times 10^{-5}$ W $cm^{-2}$ $s^{-1}$. Numbered embodiment 301 comprises a system according to any numbered embodiments 1-300, wherein the UV-B irradiance is about $1.3 \times 10$ W $cm^{-2}$ $s^{-1}$. Numbered embodiment 302 comprises a device for administering light enriched for UV-B to a seed comprising: (a) at least one light source for administering light enriched for UV-B; (b) a lighting controller; and (c) a platform for concurrently priming and administering the light enriched for UV-B. Numbered embodiment 303 comprises a device according to any numbered embodiments 1-302, wherein the at least one light source is stationary. Numbered embodiment 304 comprises a device according to any numbered embodiments 1-303, wherein the at least one light source adjusts position during UV-B administration. Numbered embodiment 305 comprises a device according to any numbered embodiments 1-304, further comprising a computer processor. Numbered embodiment 306 comprises a method for improving at least one of plant performance and hardiness, comprising: (a) priming a seed using a priming medium; (b) concurrently inducing metabolic activation in the seed; and (c) subsequently reducing internal moisture of the seed. Numbered embodiment 307 comprises a method according to any numbered embodiments 1-306, further comprising storing the seed. Numbered embodiment 308 comprises a method according to any numbered embodiments 1-307, further comprising bagging the seed for sale. Numbered embodiment 309 comprises a method according to any numbered embodiments 1-308, wherein the priming medium is water. Numbered embodiment 310 comprises a method according to any numbered embodiments 1-309, wherein the priming medium is polyethylene glycol. Numbered embodiment 311 comprises a method according to any numbered embodiments 1-310, wherein reducing the internal moisture comprises using air, reducing humidity, adjusting a temperature, or using a desiccant. Numbered embodiment 312 comprises a method according to any numbered embodiments 1-311, wherein inducing metabolic activation comprises administering light, hormones, chemicals, steroids, or vitamins. Numbered embodiment 313 comprises a method according to any numbered embodiments 1-312, wherein the light is enriched for UV-B. Numbered embodiment 314 comprises a method according to any numbered embodiments 1-313, wherein a wavelength of the UV-B is in a range of about 280 nm to about 290 nm. Numbered embodiment 315 comprises a method according to any numbered embodiments 1-314, wherein an irradiance of the UV-B is up to 300 uW $cm^{-2}$. Numbered embodiment 316 comprises a method according to any numbered embodiments 1-315, wherein an irradiance of the UV-B is no more than $1.3 \times 10-4$ W $cm^{-2}$ $s^{-1}$. Numbered embodiment 317 comprises a method according to any numbered embodiments 1-316, wherein the light enriched for UV-B comprises at least 50% UV-B. Numbered embodiment 318 comprises a method according to any numbered embodiments 1-317, wherein the light enriched for UV-B comprises at least 50% more UV-B than any other wavelength. Numbered embodiment 319 comprises a method according to any numbered embodiments 1-318, wherein the light comprises visible light. Numbered embodiment 320 comprises a method according to any numbered embodiments 1-319, wherein the visible light is administered no more than 400 umol $m^{-2}$ $s^{-1}$. Numbered embodiment 321 comprises a method according to any numbered embodiments 1-320, wherein the UV-B is administered at no more than 100 kJ $m^{-2}$. Numbered embodiment 322 comprises a method according to any numbered embodiments 1-321, wherein a duration of priming the seed and concurrently inducing metabolic activation is in a range of about 1 hour to about 30 hours, about 2 hours to about 27 hours, about 3 hours to about 25 hours, about 4 hours to about 24 hours, about 5 hours to about 22 hours, or about 6 hours to about 21 hours.

Numbered embodiment 323 comprises a method according to any numbered embodiments 1-322, wherein the at least one of plant performance and hardiness is improved by at least about 8%. Numbered embodiment 324 comprises a method for improving at least one of plant performance and hardiness, comprising: (a) priming a seed using a priming medium; and (b) concurrently administering light enriched for UV-B. Numbered embodiment 325 comprises a method according to any numbered embodiments 1-324, further comprising storing the seed. Numbered embodiment 326 comprises a method according to any numbered embodiments 1-325, further comprising bagging the seed for sale. Numbered embodiment 327 comprises a method according to any numbered embodiments 1-326, wherein the priming medium is water. Numbered embodiment 328 comprises a method according to any numbered embodiments 1-327, wherein the priming medium is polyethylene glycol. Numbered embodiment 329 comprises a method according to any numbered embodiments 1-328, wherein the seed is submerged in the priming medium. Numbered embodiment 330 comprises a method according to any numbered embodiments 1-329, wherein an irradiance of UV-B is up to 300 uW $cm^{-2}$. Numbered embodiment 331 comprises a method according to any numbered embodiments 1-330, wherein a duration of priming the seed and concurrently administering UV-B is in a range of about 1 hour to about 30 hours, about 2 hours to about 27 hours, about 3 hours to about 25 hours, about 4 hours to about 24 hours, about 5 hours to about 22 hours, or about 6 hours to about 21 hours. Numbered embodiment 332 comprises a method according to any numbered embodiments 1-331, wherein a duration of priming the seed and concurrently administering UV-B is about 20 hours. Numbered embodiment 333 comprises a method according to any numbered embodiments 1-332, wherein a wavelength of the UV-B is in a range of about 280 nm to about 290 nm. Numbered embodiment 334 comprises a method according to any numbered embodiments 1-333, wherein the light enriched for UV-B comprises at least 50% UV-B. Numbered embodiment 335 comprises a method according to any numbered embodiments 1-334, wherein the light enriched for UV-B comprises at least 50% more UV-B than any other wavelength. Numbered embodiment 336 comprises a method according to any numbered embodiments 1-335, wherein the light comprises visible light. Numbered embodiment 337 comprises a method according to any numbered embodiments 1-336, wherein the visible light is administered no more than 400 umol $m^{-2}$ $s^{-1}$. Numbered embodiment 338 comprises a method according to any numbered embodiments 1-337, wherein the UV-B is administered at no more than 100 kJ $m^{-2}$. Numbered embodiment 339 comprises a method according to any numbered embodiments 1-338, wherein an UV-B irradiance is administered no more than $1.3 \times 10-4$ W $cm^{-2}$ $s^{-1}$. Numbered embodiment 340 comprises a method according to any numbered embodiments 1-339, wherein the improvements in the plant performance is selected from a group comprising fruit fresh weight, number of fruit harvested, Brix content, fruit width, fruit length, leaf size, leaf surface area, dry weight, nitrogen content, shoot dry weight, shoot fresh weight, root dry weight, vegetable development, yield of fruiting parts, increased weight of fruiting parts, hardiness, and seed germination rate. Numbered embodiment 341 comprises a method according to any numbered embodiments 1-340, wherein the hardiness is selected from a group consisting of an improved resistance to stress caused by weather damage, an improved resistance to stress caused by sun exposure, an improved resistance to stress caused by disease, and an improved resistance to stress caused by insects. Numbered embodiment 342 comprises a method according to any numbered embodiments 1-341, wherein the at least one of plant performance and hardiness is improved by at least about 8%. Numbered embodiment 343 comprises a method of reducing environmental impact of growing a crop, comprising the steps of: (a) priming a seed; (b) treating the seed using light enriched for UV-B; (c) sowing the seed; (d) providing no more than at least one of a standard fertilizer regimen, a standard pesticide regimen, a standard herbicide regimen, and a standard insecticide regimen; and (e) harvesting the crop from said seed, wherein a crop yield of the crop from said seed is at least 5% greater than a standard yield. Numbered embodiment 344 comprises a method of reducing fertilizer use without reduction to a crop yield compared to standard fertilizer use comprising the steps of: (a) priming a seed; (b) treating the seed using light enriched for UV-B; (c) sowing the seed; (d) providing no more than 95% of the standard fertilizer regimen; and (e) harvesting a crop from said seed, wherein the crop requires less fertilizer than a crop from non-UV-B irradiated seed. Numbered embodiment 345 comprises a method for improving a crop yield, comprising: (a) priming a seed; (b) administering light enriched for UV-B of a wavelength of about 280 nm to about 290 nm to the seed; and (c) measuring improvements in plant performance, wherein the plant performance is improved by at least 5% as compared to a comparable crop. Numbered embodiment 346 comprises a method according to any numbered embodiments 1-345, wherein step (a) and step (b) occur concurrently. Numbered embodiment 347 comprises a method according to any numbered embodiments 1-346, further comprising storing the seed following step (b). Numbered embodiment 348 comprises a method according to any numbered embodiments 1-347, further comprising bagging the seed for sale following step (b). Numbered embodiment 349 comprises a method for improving at least one of plant performance and hardiness, comprising: (a) priming a seed; (b) administering light enriched for UV-B of a wavelength of about 280 nm to about 290 nm to the seed; and (c) measuring improvements in plant performance, wherein plant performance is improved by at least 5%. Numbered embodiment 350 comprises a system for priming and concurrently administering UV-B to a seed, comprising: (a) a computer having a readable input file to generate instructions for administering light enriched for UV-B; (b) a lighting controller for receiving the instructions for administering light enriched for UV-B; and (c) a surface for priming and concurrently administering light enriched for UV-B. Numbered embodiment 351 comprises a method according to any numbered embodiments 1-350, wherein the instructions relate to a dose, an irradiance, or a duration for priming and concurrently administering light enriched for UV-B. Numbered embodiment 352 comprises a device for administering light enriched for UV-B to a seed comprising: (a) at least one light source for administering light enriched for UV-B; (b) a lighting controller; and (c) a platform for concurrently priming and administering the light enriched for UV-B. Numbered embodiment 353 comprises a method according to any numbered embodiments 1-352, wherein the at least one light source is stationary. Numbered embodiment 354 comprises a method according to any numbered embodiments 1-353, wherein the at least one light source adjusts position during UV-B administration.

EXAMPLES

Example 1—Analysis of Flavonoid Levels in Seeds Following UV-B Treatment

In this example, seeds were exposed to a UV-B treatment, and were then frozen for analysis of UV-B absorbing secondary metabolites in the seed themselves.

Seeds of the variety Legacy (Egmont Seeds, New Zealand) were spread on water soaked filter paper. Seed were then exposed to a narrow-band UV-B dosage peaking at 286 nm ("UV") using an LED (Light Emitting Diode) array for 40 minutes. As a control, seeds were exposed to a visible light dosage only ("Vis") composed of blue and red light LEDs for 40 min. Seeds were exposed to light dosages at different time-points following initial water imbibing of seeds for 0 hours ("T0") or 24 hours ("T24"). The seeds were kept at 16° C. between treatments, and until the end of the trial at 48 hours, when seed were frozen in liquid nitrogen for UV-B absorbing compound analysis. Analysis of UV-B absorbing compounds (presumptive flavonoids, y-axis) was carried out by homogenization of seed in acidified methanol, centrifugation, and measurement of supernatant absorbance by spectrophotometer at 300 nm.

The results are shown in FIG. 2. FIG. 2 shows presumptive flavonoids for each treatment comprising three replicate lots per treatment and each lot comprising 80 individual seeds. It can be seen that an increase in presumptive flavonoids (detected at 300 nm) was seen after 24 hours after treatment in both UV-B treated and visible light treated samples. The level of flavonoids was substantially increased in the UV-B treated sample compared to the visible light treated sample at the same 24 hour time point. Flavonoids were 18% higher in seeds treated with UV-B treated 24 hours following water imbibing ("UV T24") compared to seeds treated with visible light 24 hours following water imbibing ("Vis T24"). Flavonoids were 60% higher in UV T24 compared to seeds treated with visible light 0 hours following water imbibing ("Vis T0").

Example 2—Analysis of Flavonoid Levels in Ezmina Lettuce Plant Leafs 20 Days after UV-B Seed Treatment In this example, seeds were exposed to a UV-B treatment and then germinated, transplanted onto soil, and grown to a certain age, prior to assessments of leaf polyphenols being made.

Lettuce seeds of the variety Ezmina (Enza Zaden, Netherlands) were spread on water soaked filter paper. Plants were then exposed to a narrow-band UV-B dosage peaking at 286 nm ("UV") using an LED (Light Emitting Diode) array for 40 minutes. As one control, seeds were exposed to a visible light dosage ("Vis") only, composed of blue and red light LEDs for 40 minutes. Seed were exposed to light dosages at different time-points following initial water imbibing of seed for 0 hours ("T0") or 24 hours ("T24"). A second form of control consisted of seeds being wrapped in aluminum foil and not exposed to any light ("Control").

Germinating seeds were then transferred onto soil, and following seedling propagation, plants were maintained in outside ambient conditions for 10 days. Following this time period, non-invasive measurements of leaf flavonoid levels were made with a Dualex Scientific polyphenol meter (Force-A, Paris).

The results are shown in FIG. 3A, which measure flavonoid levels 20 days after seed treatments. Values presented are means of 11-14 plants according to individual treatments, ±standard error (S.E). The UV-B treated sample showed significantly higher flavonoid levels at 20 days compared to the visible light sample at 20 days, either if treated at 24 hours and 0 hours after water imbibing. Interestingly, the flavonoid level at 20 days in the sample treated with visible light 24 hours following water imbibing actually was lower compared to the levels when treated at the zero time point.

This study illustrates a relationship between the UV-B induced flavonoid concentration seen in seeds and the resulting plant material.

Example 3—Analysis in Plant Productivity (Measured by Fresh Shoot Weight) Following UV-B Treatment In this example, seeds were exposed to a UV-B treatment, and were then germinated, transplanted onto soil, and grown to a certain age, prior to assessments of plant shoot fresh weight being made, as an indication of plant yield following seed treatment.

Seeds of the variety Legacy (Egmont Seeds, New Zealand) were spread on water soaked filter paper. Seed were then exposed to a narrow-band UV-B dosage peaking at 286 nm using an LED (Light Emitting Diode) array for 40 minutes. As a control, seeds were exposed to a visible light dosage only, composed of blue and red light LEDs for 40 min. Seed were exposed to light dosages at different timepoints following initial water imbibing of seeds (0 hours, 24 hours). Following treatment, seed were transferred onto soil, and grown for 30 days. Shoot fresh weight of plants (i.e. above ground biomass) was then assessed as an indication of plant yield.

The results are shown in FIG. 3B. As observed that in the UV-B treated samples ("UV T24"), average fresh weight in plants was increased by 17% compared to control plants ("Vis T0"). This result illustrates the advantage of increased plant performance and in particular crop yield.

Example 4—Analysis of Leaf Flavonoids in Kale (Brassica Forage Crop)

In this example, kale seedlings were treated with UV-B prior to sowing, and another set of seedlings grown from seed were not treated with UV-B.

Kale (*Brassica oleracea* var. Regal) seeds were first primed by being immersed in a PEG8000 solution (−1.25 mPA) and kept in the dark at 16° C. After 20 hours, seeds were irradiated with 500 umol m$^{-2}$ s$^{-1}$ of continuous red/blue light. 50% of these seeds were additionally treated with $3.19 \times 10^{-5}$ W cm$^{-2}$ s$^{-1}$ UV-B light supplied by a UV-LED source, the transmittance of which peaked at 286 nm. After 28 hours of continued treatment (total priming duration 48 hours), seeds were removed and air dried for 72 hours at 16° C. Seeds were then sown and grown in PEG8000 (−1.25 mPA, 400 ml) to induce drought stress. After 3 weeks of continued drought stress, leaf flavonoid concentrations were determined using a Dualex Scientific+chlorophyll and polyphenol meter (Force-A, Orsay, France).

The results are shown in Table 1 below. "S.E." represents standard error. There was a 12% increase in leaf flavonoids in kale seedlings where seeds were treated with UV prior to sowing, compared to seedlings grown from seed which were not treated with UV prior to sowing.

This supports that the resultant plant following UV-B seed treatment has increased levels of flavonoids compared to an untreated seed.

TABLE 1

|  | Control | S.E. | UV-treated | S.E. | Increase in UV-treated compared to control (%) |
|---|---|---|---|---|---|
| Flavonoid Index | 0.61 | 0.03 | 0.7 | 0.02 | 12* |

*statistically significant increase at P < 0.05

Example 5—Analysis of Drought Stress

In this example, a drought stress was applied to kale plants from the point of seed germination. One group of seeds was UV-B treated, and another group was not treated with UV-B.

Kale (*Brassica oleracea* var. Regal) seeds were immersed in water and kept in the dark at 16° C. After 4 hours, seeds were irradiated with 500 umol m$^{-2}$ s$^{-1}$ of continuous red/blue light. 50% of these seeds were additionally treated with $1.42 \times 10^{-4}$ W cm$^{-2}$ UV-B light supplied by a UV-LED source, the transmittance of which peaked at 286 nm. After 30 hours of treatment, seeds were air dried for 72 hours at 16° C.

Seeds were then subjected to a drought stress during germination. UV-primed and control seeds were germinated in either water or one of 2 concentrations of PEG8000 (−1 mPA "Drought", −1.5 mPA "Severe drought"). After 72 hours, seedling weight and radicle length were quantified.

The results are shown in Table 2 below. "S.E." represents standard error. After drought stress, emerging kale seedlings from seeds that had been UV-B treated ("UV-treated"), accumulated more biomass and displayed longer radicle lengths 72 hours after sowing, compared to seedlings sown from seed that were not treated with UV ("Control") prior to sowing. See FIGS. 4A-4B.

This trial supports that UV-B seed treatment provides protection against yield-limiting stresses encountered in the growing environment, such as drought or salinity stress.

TABLE 2

|  | Medium | UV-treated | S.E. | Control | S.E. | Increase in UV-treated compared to control (%) |
|---|---|---|---|---|---|---|
| Radicle length (mm) | Well-watered | 9.1 | 0.6 | 7.4 | 0.9 | 24 |
|  | Drought | 8.3 | 0.6 | 6.9 | 0.7 | 20 |
|  | Severe drought | 6.8 | 0.8 | 5.7 | 0.6 | 20 |
| Biomass (mg) | Well-watered | 18.3 | 0.8 | 14.1 | 0.7 | 30** |
|  | Drought | 14.8 | 0.6 | 12.9 | 1.0 | 15 |
|  | Severe drought | 13.1 | 0.5 | 11.7 | 0.7 | 13 |

**statistically significant increase at P < 0.001

Example 6—Analysis of Seedling Size, Leaf Chlorophyll Level and Nitrogen Index In this example, kale seeds were subject to UV-B treatment and then seedling size, leaf chlorophyll level and relative nitrogen index were all assessed in growing plants, all of which are key indicators of good plant performance.

Kale (*Brassica oleracea* var. Regal) seeds were immersed in water and kept in the dark at 16° C. After 4 hours, seeds were irradiated with 500 umol $m^{-2}$ $s^{-1}$ of continuous red/blue light. 50% of these seeds were additionally treated with $1.01 \times 10^{-4}$ W $cm^{-2}$ $s^{-1}$ with UV-B light supplied by a UV-LED source, the transmittance of which peaked at 286 nm. After 6 hours of treatment, seeds were air dried for 72 hours at 16° C. and then sown. At 10 days old, plants were assessed for cotyledon leaf size, and at 21 days old, plants were assessed for relative leaf chlorophyll index and nitrogen index, which were determined using a Dualex Scientific+meter (Force-A, Orsay, France).

The results are shown in Table 3 below. "S.E." represents standard error. There are clear increases in kale seedling growth and plant performance where seeds were treated with UV-B ("UV-treated") prior to sowing, compared to seedlings grown from seed that were not treated with UV-B ("Control") prior to sowing.

TABLE 3

| | Control | S.E. | UV-treated | S.E. | Increase in UV-treated compared to control (%) |
|---|---|---|---|---|---|
| Cotyledon leaf size ($mm^2$) | 113.3 | 5.2 | 120.6 | 5.4 | 6 |
| Chlorophyll index | 18.9 | 0.3 | 19.6 | 0.4 | 4 |
| Nitrogen index | 45.9 | 2.3 | 50.3 | 3.0 | 9 |

Example 7—Analysis of Seedling Weight

Following example 6, the kale seedling weight of seeds treated with UV-B were measured compared to non-treated kale seedlings.

Seed were treated and plants grown exactly as per the methods described for Example 6 above. At 8 weeks old, plants were harvested and leaf area and fresh weights were quantified.

As shown in Table 4, kale plants grown from seeds that were UV-B treated ("UV-treated") showed a 5% increase in plant weight compared to those grown from non-UV-B treated ("Control") seeds. Furthermore, the variability of fresh weights within the population was reduced by 36% in UV seed-treated plants, as demonstrated by the reduced standard error (S.E.) values in UV treated resultant plants. This further supports treating a seed for sowing with UV-B radiation improved subsequent plant performance.

TABLE 4

| | Control | S.E. | UV-treated | S.E. | Increase in UV-treated compared to control (%) |
|---|---|---|---|---|---|
| Shoot fresh weight (g) | 3.75 | 0.14 | 3.94 | 0.09 | 5% |

Example 8—Size Analysis of First Fully Expanded Leaf

In this example, the $4^{th}$ fully expanded leaf area in lettuce seedlings in UV-B treated and untreated samples was assessed. True leaf growth compaction in young seedlings can be a good indicator of hardiness against future stresses in the growing environment.

Lettuce (*Lactuca sativa* var. Legacy) seeds were immersed in water and kept in the dark at 16° C. After 6 hours, seeds were irradiated with 500 umol $m^{-2}$ $s^{-1}$ of continuous red/blue light. 50% of these seeds were additionally treated with $3.19 \times 10^{-5}$ W $cm^{-2}$ $s^{-1}$ UV-B light supplied by a UV-LED source, the transmittance of which peaked at 286 nm. After 1 hour, 3 hours, 6 hours of treatment (Seed treatments 1, 2, and 3 respectively; Table 5), seeds were removed and air dried for 72 hours at 16° C. and then sown. At 33 days old, the $4^{th}$ fully expanded leaf area was assessed.

The results are shown in Table 5. A maximum 31% average reduction in size of the $4^{th}$ fully expanded leaf in lettuce seedlings was observed in seeds treated with UV-B ("UV-treated) prior to sowing compared to seedlings grown from seeds which were not treated with UV ("Control") prior to sowing. "S.E." represents standard error.

This initial growth compaction supports the induction of hardiness against future stresses encountered in the growing environment in transplant lettuce seedlings and other crops.

TABLE 5

| Leaf area ($mm^2$) | Control | S.E. | UV-treated | S.E. | Decrease in UV-treated compared to control (%) |
|---|---|---|---|---|---|
| Seed treatment 1 | 15.6 | 0.9 | 13.8 | 1.0 | 11 |
| Seed treatment 2 | 14.2 | 0.9 | 9.8 | 0.7 | 31** |
| Seed treatment 3 | 16.2 | 1.6 | 15.5 | 1.9 | 4 |

**statistically significant increase at $P < 0.001$

Example 9—Analysis of Dry Weight of Maize Plants

In this example, maize seeds were treated with UV-B radiation, and a range of performance parameters of the resulting plants were compared to plants that did not have UV-B treatment of the seeds prior to sowing.

Maize (*Zea mays* var. NZ yellow F1 Hybrid) seeds were immersed in water and kept in the dark at 16° C. After 16 hours, seeds were irradiated with 500 umol $m^{-2}$ $s^4$ of continuous red/blue light. 50% of these seeds were additionally treated with $3.19 \times 10^{-5}$ W $cm^{-2}$ $s^{-1}$ UV-B light supplied by a UV-LED source, the transmittance of which peaked at 286 nm. After 9 hours of treatment, seeds were air dried for 72 hours at 16° C. and then sown. Seedlings were harvested at 4 weeks old, and fresh and dry weights of shoots and roots were quantified. Indices for leaf chlorophyll, flavonoid and nitrogen index were assessed using a Dualex Scientific+chlorophyll and polyphenol meter (Force-A, Orsay, France).

The results are shown in Table 6. Increases in whole plant dry weight of maize plants were observed in seeds were treated with UV-B ("UV-treated") prior to sowing compared to seedlings grown from seeds that were not treated with UV-B ("Control") prior to sowing. Increases in leaf flavonoid levels and leaf nitrogen index were observed in UV-treated seeds as Control. "S.E." represents standard error.

This further supports that treating seeds for sowing with UV-B radiation improves subsequent plant performance.

TABLE 6

| | UV-treated | S.E. | Control | S.E. | Increase in UV-treated compared to control (%) |
|---|---|---|---|---|---|
| Shoot FW (g) | 1.8 | 0.2 | 1.6 | 0.2 | 17% |
| Shoot DW (g) | 0.18 | 0.02 | 0.14 | 0.02 | 26% |
| Root DW (g) | 0.18 | 0.02 | 0.14 | 0.01 | 28% |
| Whole plant DW (g) | 0.36 | 0.04 | 0.28 | 0.03 | 28% |
| Flavonoid index | 0.8 | 0.07 | 0.7 | 0.03 | 4% |
| Leaf nitrogen index | 40 | 7 | 38 | 2 | 6% |

Example 10—Drought Tolerance and Water Use Efficiency of Lettuce Plants

In a similar study to that seen in Example 5, an increase in physiological tolerance to drought stress imposed on lettuce plants for 11 days following UV-B treatment of the seeds prior to sowing was assessed.

Lettuce (*Lactuca sativa* var. Legacy) seeds were immersed in water and kept in the dark at 16° C. After 4 hours, seeds were irradiated with 500 umol m$^{-2}$ s$^{-1}$ of continuous red/blue light. 50% of these seeds were additionally treated with 1.42×10$^{-4}$ W cm$^{-2}$ s$^{-1}$ UV-B light supplied by a UV-LED source, the transmittance of which peaked at 286 nm. After 10 hours of treatment, seeds were air dried for 72 hours at 16° C. and then sown. After 4 weeks, seedlings were transplanted into individual planting cells, each containing 250 mL of potting mix, the maximum water-holding capacity of which was 130 mL. For half of the UV-treated seedlings and half of the control seedlings, the water content of each cell of potting mix was maintained at 130 mL. The remaining plants were subjected to a drought stress, achieved by maintaining the water content of each cell of potting mix at 40 mL. After 11 days of drought stress, stomatal resistance was assessed using a Delta-T porometer (Delta-T Devices, Cambridge, UK), and indices for leaf chlorophyll, flavonoid and nitrogen content were calculated using a Dualex Scientific+meter (Force-A, Orsay, France).

The results are shown in Table 7. Increased physiological tolerance to drought stress (signified by an increase in stomatal resistance) was observed in the lettuce plants originating from seeds that had been treated with UV-B ("UV-treated") prior to sowing as compared to seeds that had not been treated with UV-B ("Control"). An increase in stomatal resistance was also observed in well-watered plants in UV-treated as compared to Control, indicating the potential for plants raised from UV treated seed to exhibit increased Water Use Efficiency (WUE), regardless of the presence of a drought stress. "S.E." represents standard error.

This further supports that UV-B seed treatment provides protection against yield-limiting stresses encountered in the growing environment, such as drought or salinity stress. These data also support that UV-B seed treatment may provide increased water use efficiency capability in plants raised from UV treated seed.

TABLE 7

| Stomatal resistance (s · cm$^{-1}$) | Control | S.E. | UV-treated | S.E. | Increase in UV-treated compared to control (%) |
|---|---|---|---|---|---|
| Well-watered | 3.0 | 0.4 | 4.2 | 0.4 | 36 |
| Drought stressed | 4.1 | 0.2 | 4.6 | 0.6 | 11 |

Example 11—Salinity Stress on Kale and Lettuce Plants

In another test, kale plants (both from seeds UV-B treated and non-treated seeds) were subjected to salinity stress.

Lettuce (*Lactuca sativa* var. Legacy) and kale (*Brassica oleracea* var. Regal) seeds were immersed in water and kept in the dark at 16° C. After 4 hours, seeds were irradiated with 500 umol m$^{-2}$ s$^{-1}$ of continuous red/blue light. 50% of these seeds were additionally treated with 1.42×10$^{-2}$ W cm$^{-2}$ s$^{-1}$ UV-B light supplied by a UV-LED source, the transmittance of which peaked at 286 nm. After 8 hours and 72 hours for lettuce and kale respectively, the treatment stopped, seeds were air dried for 72 hours at 16° C. and then sown. After 4 weeks, seedlings were transplanted into 250 mL of potting mix, the maximum water holding capacity of which was 130 mL. Half the UV-primed seedlings and half the control seedlings were then subjected to a salt stress (150 mM NaCl; 100 mL administered every 7 days; topped up with water every 3 days) and the remaining seedlings were watered with H$_2$O. After 25 days of salinity stress, plants were harvested and shoot weight was assessed.

The results are shown in Table 8. There was a 13% reduced sensitivity to salinity stress (in terms of salinity-induced reductions in plant fresh weight) in both kale and lettuce plant in seeds treated with UV-B ("UV-treated") prior to sowing compared to plants grown from seeds which were not treated with UV-B ("Control") prior to sowing.

This further shows that UV-B seed treatment provides protection against yield-limiting stresses encountered in the growing environment, such as drought or salinity stress.

TABLE 8

| % decrease in growth [in whole shoot fresh weight] under salt stress | Control | UV-treated | Difference between control & UV-treated [%] |
|---|---|---|---|
| Kale | 22 | 9 | 13 |
| Lettuce | 47 | 34 | 13 |

Example 12—Analysis of Crop Quality Measured by Leaf Based Pigments of Lettuce

To assess crop quality (e.g. color, taste, shelf life), leaf-based pigments in a red cultivar of lettuce were assessed following UV-B treatment of seed prior to sowing. Increases in such red pigments as anthocyanins are associated with increased crop quality, taste and shelf-life. Zhang et al. Anthocyanins Double the Shelf Life of Tomatoes by Delaying Overripening and Reducing Susceptibility to Gray Mold. Current Biology. 23(12): 1094-1100 (2013).

Lettuce (*Lactuca sativa* var. Red Oak) seeds were immersed in water and kept in the dark at 16° C. After 3 hours, seed were subjected to 500 umol m$^{-2}$ s$^{-1}$ of continuous red/blue light with 50% of those seeds additionally receiving 1.42×10$^{-4}$ W cm$^{-2}$ s$^{-1}$ UV-B light, supplied by a UV-LED source, the transmittance of which peaked at 286 nm. 12 hours after the initial imbibition process, seeds were removed from water and UV-B treatment. Seeds were air-dried for 72 hours at 16° C. then sown. After 35 days, indices for anthocyanins (red leaf pigments) were assessed in seedlings using a Dualex Scientific+chlorophyll and polyphenol meter (Force-A, Orsay, France). Seedlings were then dried to a constant mass in order to represent anthocyanins per unit (g) plant dry weight.

The results are shown in Table 9 below. Increases in leaf-based pigments in a red cultivar of lettuce were observed from seeds treated with UV-B ("UV-treated") prior to sowing, compared to plants grown from seed which were not treated with UV ("Control) prior to sowing. "S.E." represents standard error.

These data support that UV seed treatment can increase crop quality characteristics such as color, taste, shelf-life in plants grown from treated seed.

TABLE 9

| Treatment | Anthocyanin index g · DW$^{-1}$ | S.E. | % induction of anthocyanins in plants from UV treated seed compared to control |
|---|---|---|---|
| Control | 0.3196 | 0.01 | — |
| UV-treated | 0.3422 | 0.02 | 7.0 |

Example 13—Increased Seed Germination in Treated Seed

In this example, maize seeds were treated with UV-B or not treated with UV-B, with seed germination subsequently assessed.

Maize (*Zea mays* var. NZ yellow F1 Hybrid) seeds were immersed in water and kept in the dark at 16° C. After 20 hours, seeds were irradiated with 500 umol m$^{-2}$ s$^{-1}$ of continuous red/blue light. 50% of these seeds were additionally treated with $3.19 \times 10^{-5}$ W cm$^{-2}$ s$^{-1}$ UV-B light supplied by a UV-LED source, the transmittance of which peaked at 286 nm. After 8 hours, 24 hours, 32 hours of treatment (Seed treatments 1, 2, and 3 respectively; Table 10), seeds were air dried for 72 hours at 16° C. and then sown, with germination success subsequently assessed.

The results are in Table 10. It can be seen that germination of seed was improved where seeds were treated with UV-B ("UV-treated") prior to wetting for germination compared to seed that were not treated with UV-B ("Control") prior to sowing.

This supports the use of UV-B treatment of seed to improve germination ability of seed.

TABLE 10

| % germination | Control | UV-treated | % improvement in UV-treated seed germination |
|---|---|---|---|
| Seed treatment 1 | 45.45 | 72.73 | 27.28 |
| Seed treatment 2 | 27.27 | 63.64 | 36.37 |
| Seed treatment 3 | 45.45 | 54.55 | 9.1 |
| Average of all treatments | 39.39 | 63.64 | 24.25 |

Example 14—Use of Another UV-B Peak Wavelength to Improve Seedling Germination Under Drought Stress In a similar study to that seen in Example 5, an increased physiological tolerance to drought stress imposed during the germination of seed following UV-B treatment of those seed prior to sowing was assessed. In this example, a different peak wavelength was used within the UV-B waveband.

Kale (*Brassica oleracea* var. Regal) seeds were immersed in water and kept in the dark at 16° C. After 4 hours, seeds were irradiated with 500 umol m$^{-2}$ s$^{-1}$ of continuous red/ blue light. 50% of these seeds were exclusively treated with red/blue light as described before, while the remaining 50% were additionally treated with $1.64 \times 10^{-5}$ W cm$^{-2}$ s$^{-1}$ UV-B light supplied by a UV-LED source, the transmittance of which peaked at 317 nm. After 30 hours of treatment, seeds were air dried for 72 hours at 16° C.

Seeds were then subjected to a drought stress during germination. UV-primed and control seeds were germinated in either water or one of two concentrations of PEG8000 (−1, −1.5 mPA). After 72 hours, seedling weight and radicle length were quantified.

The results are shown in Table 11 below. After drought stress, emerging kale seedlings from seeds which had been UV-B treated ("UV-treated"), accumulated more biomass and displayed longer radicle lengths 72 hours after sowing compared to seedlings sown from seed which were not treated with UV ("Control") prior to sowing. "S.E." represents standard error.

This example supports that UV seed treatment provides protection against yield-limiting stresses encountered in the growing environment, such as drought or salinity stress, and that the advantages of the present disclosure can be achieved by using a treatment at different wavelengths within the UV-B waveband.

TABLE 11

| | Medium | UV-treated | S.E. | Control | S.E. | Increase in UV-treated compared to control (%) |
|---|---|---|---|---|---|---|
| Radicle length (mm) | Well-watered | 6.4 | 0.9 | 7.7 | 0.9 | −17 |
| | Drought | 11.2 | 1.0 | 5.6 | 0.5 | 99 |
| | Severe drought | 7.1 | 0.6 | 7.2 | 0.5 | −2 |
| Biomass (mg) | Well-watered | 13.6 | 0.7 | 13.8 | 0.7 | −1 |
| | Drought | 16.3 | 0.8 | 12.2 | 0.6 | 33 |
| | Severe drought | 14.9 | 1.0 | 13.5 | 0.9 | 11 |

Example 15—Increased Flavonoid Levels in Seeds with Varying Dosage of UV-B Irradiation for Different Amount of Time The effects of the dosage and length of time of UV-B irradiation on flavonoid levels were assessed.

Seeds that were stored at 4° C. were washed under cold water to remove the red fungicide coating. Seeds were primed in a plant growth chamber followed by water immersion for 16 hours. The seeds were then treated with visible light with ("UV") or without UV-B ("No UV"). 13 kJ m$^{-2}$ or 100 kJ m$^{-2}$ irradiance dosages were used. UV-B light was supplied by a LED source, the transmittance of which peaked at 280 nm. "No priming, No UV" were control samples that were not exposed to UV and not immersed in water.

As seen in FIG. 5A, both 13 kJ m$^{-2}$ and 100 kJ m$^{-2}$ of UV-B dosage significantly increased flavonoid levels as compared to the No UV 13 kJ m$^{-2}$ seeds or the No UV 100 kJ m$^{-2}$ seeds, respectively. In FIG. 5B, both 13 kJ m$^{-2}$ and 100 kJ m$^{-2}$ of UV-B irradiance dosages significantly increased flavonoid levels, particularly the 100 kJ m$^{-2}$ irradiance dosage as compared to the No UV 13 kJ m$^{-2}$ seeds or the No UV 100 kJ m$^{-2}$ seeds, respectively. Seeds treated with UV-B at 13 kJ m$^{-2}$ and 100 kJ m$^{-2}$ dosages also exhibited increased flavonoid levels compared to the No UV 13 kJ m$^{-2}$ seeds or the No UV 100 kJ m$^{-2}$ seeds, respectively as seen in FIG. 5C. FIG. 5D demonstrated an increase in flavonoid levels. FIG. 5E demonstrated an increase in flavonoid levels after 13 kJ m$^{-2}$ or 100 kJ m$^{-2}$ UV-B irradiation. As seen in FIG. 5F, UV-B irradiation increased flavonoid levels. Dosage of 13 kJ m$^{-2}$ or 100 kJ m$^{-2}$ UV-B irradiation increased flavonoid levels as seen in FIG. 5G. FIG. 5H depicts increased flavonoid levels in response to 13 kJ m$^{-2}$ or 100 kJ m$^{-2}$ of UV-B treatment. Often UV-supplement was demonstrated to increase flavonoid levels as compared to samples not treated with UV-B, particularly as seen in FIGS. 5A-5C. FIGS. 5A-5C illustrate particularly effective dosage parameters where seeds were treated with UV-B irradiation at 13 kJ m$^{-2}$ or 100 kJ m$^{-2}$.

Example 16—Increased Anthocyanin Levels in Seeds with Varying Dosage of UV-B Irradiation for Different Amounts of Time The effects of the dosage and length of UV-B irradiation on anthocyanin levels were determined in seeds.

Seeds that were stored at 4° C. were washed under cold water to remove the red fungicide coating. Seeds were primed in a plant growth chamber followed by water immersion for 16 hours. The seeds were then treated with visible light with (UV) or without UV-B (No UV). 13 kJ m$^{-2}$ or 100 kJ m$^{-2}$ irradiance dosages were used. UV-B light was supplied by a LED source, the transmittance of which peaked at 280 nm. The light treatments were for 9 hours for the 13 kJ m$^{-2}$ and 21 hours for the 100 kJ m$^{-2}$. "No priming, No UV" samples were control samples that were not exposed to UV and not immersed in water.

As seen in FIG. 6A, 13 kJ m$^{-2}$ and 100 kJ m$^{-2}$ UV-B irradiation dosage increased anthocyanin levels. Referring to FIG. 6B, 13 kJ m$^{-2}$ increased anthocyanin levels. Referring to FIG. 6C, 13 kJ m$^{-2}$ and 100 kJ m$^{-2}$ UV-B irradiation dosage increased anthocyanin levels. Referring to FIG. 6D, seeds treated with 100 kJ m$^{-2}$ of UV-B irradiation exhibited increased anthocyanin levels. UV-B treatment, as seen in FIGS. 6A-6D, at 13 kJ m$^{-2}$ or 100 kJ m$^{-2}$ dosages increased anthocyanin levels.

Example 17—the Effect of UV-B Co-Administered with Visible Light on Seedling Weight The effects of the combination of visible light with UV-B treatment on seedling weight were measured.

Seeds that were stored at 4° C. were washed under cold water to remove the red fungicide coating. Seeds were primed in a plant growth chamber followed by water immersion for 16 hours. The seeds were then treated with visible light and UV-B ("UV") or visible light without UV-B ("No UV") for 9 hours. UV-B light was supplied by a LED source, the transmittance of which peaked at 280 nm. "NP" refers to non-primed seeds in which seeds were not immersed in water but treated with visible light and UV-B. Dark refers to seeds conducted with no visible light. The visible light irradiance used were 20 umol m$^{-2}$ s$^{-1}$, 50 umol m$^{-2}$ s$^{-1}$, and 400 umol m$^{-2}$ s$^{-1}$.

As seen in FIG. 7, visible light irradiance of 20 umol m$^{-2}$ s$^{-1}$, 50 umol m$^{-2}$ s$^{-1}$, and 400 umol m$^{-2}$ s$^{-1}$ on seedling dry weight were assessed in No UV seeds (black bars, on the left of a given column pair) or UV-B treated seeds (hashed bars, on the right for a given column pair). Co-administration of UV-B with visible light resulted in an increase in seedling dry weight compared to the non-primed cells and the dark control.

This example shows an increase in seedling dry weight following co-administration of UV-B and visible light.

Example 18—UV-B Irradiation on Corn-Seed Productivity

The long-term effects of UV-B irradiation were measured.

Maize seed (Zea mays) that were stored at 4° C. were washed under cold water to remove the red fungicide coating. Seeds were treated similarly to previous examples. Seed treatments included no UV ("Control") and UV-B administration ("UV-B").

Two field sites were used for sowing the treated seed. One site consisted of a silt loam soil type. The other site consisted of a sandy loam soil type. Both trial sites were four rows wide, each row was spaced 30 inches apart, seeds were sown 5.1 inches apart, and rows were situated within a large-scale commercial maize population. This sowing density provided an equivalent density of 40,000 seed/acre. The trial area at one site was 50 feet in length and the other site's trial area was 150 feet in length. Results from both trial sites were analyzed together.

FIGS. 8A-8G depict exemplary effects of UV-B irradiation on corn-seed productivity using the methods described herein. As seen in FIG. 8A, UV-B irradiation significantly increased the whole cob dry weight in grams by 12%. Kernel total dry weight per cob in grams was significantly increased by 9% after UV-B irradiation treatment as seen in FIG. 8B. Root dry weight as seen in FIG. 8C was increased by 43% with UV-B irradiation. As seen in FIG. 8D, stover fresh weight was significantly increased by 24%. The kernel number per cob as in FIG. 8E increased by 4%, and kernel row number per cob as seen in FIG. 8F significantly improved with UV-B irradiation treatment by 2.5%. UV-B irradiation significantly increased the individual kernel dry weight by 6% as seen in FIG. 8G.

FIGS. 8A-8G demonstrate that application of UV-B irradiation increased several parameters of corn-seed productivity.

Example 19—Preparation of Seeds for Priming

To prepare the seeds for priming, maize seeds (Zea mays) that were stored at 4° C. were washed under cold water. After seeds were washed to remove the red fungicide coating, the seeds were dried. Seeds were then arranged embryo-side up on seed dishes. Often, the seeds were split between many dishes to reduce pseudo-replication. Seeds were then left at 4° C. overnight.

The seeds were then primed in a plant growth chamber at 25° C. and relative 95% humidity in the dark. The LED panels were assembled where the height was 80 mm, the distance between UV panels was 10 mm, and the minimum distance between the UV and control panels was 400 mm. Seed trays were filled with 50 mL of water for imbibing the seeds so that the water level was 1-2 mm about fully submerged seeds. Any floating seeds were tapped down until fully submerged.

The seed trays were arranged directly below the panels. The arrays were placed at a height of 8 cm and spaced 20 cm between each treatment in order to prevent direct irradiance from adjacent treatments. A cover was placed over the panels in order to avoid evaporation but removed at the start of the treatment. The water levels were monitored, and evaporated water was replaced.

Seeds were imbibed in water for 16 hours and followed by light treatments. The UV is set to have irradiance in a range between $4\times10^{-5}$ to $1.3\times10^{-4}$ W cm$^{-2}$ s$^{-1}$. The UV-B wavelength about $280\pm5$ nm. The UV-B can be at a dose in a range of about 0 kJ m$^{-2}$ and 100 kJ m$^{-2}$. The UV-B dose is often at 13 kJ m$^{-2}$ or 100 kJ m$^{-2}$.

After 9 hours of treatment, the light treatment and growth chambers were turned off. Seeds were then air dried for 72 hours.

Seeds were then sown and analyzed for different performance parameters.

Once the cotyledons were large enough, which was typically Day 5, seedlings were harvested. Using a Dualex Scientific+meter (Force-A, Orsay, France), indices for leaf chlorophyll, flavonoid and nitrogen content were calculated.

Seeds were also harvested when the seedlings were 21 days old, at stage V2. Shoot fresh weights, leaf area, and shoot and dry weights were collected.

Example 20—UV Administration in Lettuce

Iceberg lettuce seeds were treated with a combination of conditions followed by analysis of shoot fresh weight, leaf chlorophyll levels, and flavonoid levels.

Lettuce seeds were primed in −1.25 bar polyethylene glycol (PEG) dissolved in distilled water. Seeds were administered UV-B in a growth cabinet at 10° C. for 0 hours, 8 hours, 21 hours, or 27 hours. The dose of UV-B irradiance administered was 40 uW cm$^{-2}$ ("low," diagonal hashed bars), 100 uW cm$^{-2}$ ("medium," horizontal hashed bars), and 200 uW cm$^{-2}$ ("high," checkered bars). The seeds were positioned on top of a moist filter paper during UV-B administration. "Control" refers to no UV-B treatment in which seeds were immersed in priming medium but did not receive UV. "NP" refers to non-primed seeds in which seeds were not immersed in PEG nor received an UV treatment.

Seeds were then sown and analyzed for different performance parameters. Seedlings were harvested and shoot fresh weight (FIG. 12), chlorophyll levels (FIG. 13), and flavonoid levels (FIG. 14) were assessed.

Referring to FIG. 12, high UV-B irradiance administration for 8 hours resulted in a significant increase in shoot fresh weight (g/plant, y-axis) as compared to Control (black bar). Medium UV-B irradiance administration for 21 hours resulted in a significant increase of about 42% in shoot fresh weight as compared to control (black bar). High UV-B irradiance administration for 21 hours resulted in a significant increase of about 38% in shoot fresh weight as compared to Control (black bar).

Referring to FIG. 14, low UV-B irradiance for 8 hours resulted in a significant increase of about 14% in flavonoid levels as compared to Control (black bar).

This example shows treatment conditions comprising priming and administration of UV-B of various irradiance and duration increases plant performance.

Example 21—Priming and UV-B Administration in Broccoli

Broccoli seeds were treated with various priming conditions followed by analysis of shoot fresh weight, shoot dry weight, root dry weight, leaf chlorophyll levels, and flavonoid levels.

Different priming methods were tested. A first set of broccoli seeds were primed in distilled water ("Hydro"). A second set of broccoli seeds were primed in −1.25 bar polyethylene glycol (PEG) dissolved in distilled water ("Osmo"). Both sets of broccoli seeds were primed for 8, 18, 19.5, 24, 27, or 44 hours. Both sets of broccoli seeds were administered 100 uW cm$^{-2}$ UV-B irradiance in a growth cabinet at 22° C. The seeds were submerged in the priming medium during UV-B administration.

Seeds were then sown and analyzed for different performance parameters. Seedlings were harvested and shoot fresh weight (FIG. 15), shoot dry weight (FIG. 16), root dry weight (FIG. 17), chlorophyll levels (FIG. 18), and flavonoid levels (FIG. 19) were assessed. "*" indicates significant difference, p<0.05.

Referring to FIG. 15, shoot fresh weight (g/plant, y-axis) was measured in seeds primed in PEG followed by no UV-B ("Osmo-Control," white bars) and in seeds primed in PEG followed UV-B administration ("Osmo-UV," black bars). Shoot fresh weight was also measured in seeds primed in distilled water followed by no UV-B ("Hydro-Control," checkered bars), and seeds primed in distilled water followed by UV-B administration ("Hydro-UV," horizontal hashed bars). Osmo-UV seeds primed for 8 hours exhibited a difference of about 34% decrease in shoot fresh weight as compared to Osmo-Control. There was also a significant difference between Osmo-Control and Hydro-Control.

Referring to FIG. 16, shoot dry weight (g/plant, y-axis) was measured in seeds primed in PEG followed by no UV-B ("Osmo-Control," white bars) and in seeds primed in PEG followed by UV-B administration ("Osmo-UV," black bars). Shoot dry weight was also measured in seeds primed in distilled water followed by no UV-B ("Hydro-Control," checkered bars), and seeds primed in distilled water followed by UV-B administration ("Hydro-UV," horizontal hashed bars). Osmo-UV seeds primed for 8 hours exhibited a difference of about 31% decrease in shoot dry weight as compared to Osmo-Control. There was also a significant difference between Osmo-Control and Hydro-Control.

Referring to FIG. 17, root dry weight (g/plant, y-axis) was measured in seeds primed in PEG followed by no UV-B ("Osmo-Control," white bars) and in seeds primed in PEG followed by UV-B administration ("Osmo-UV," black bars). Root dry weight was also measured in seeds primed in distilled water followed by no UV-B ("Hydro-Control," checkered bars), and seeds primed in distilled water followed by UV-B administration ("Hydro-UV," horizontal hashed bars). Osmo-UV seeds primed for 8 hours exhibited a difference of about 27% decrease in root dry weight as compared to Osmo-Control. There was also a significant difference between Osmo-Control and Hydro-Control.

Referring to FIG. 18, chlorophyll levels (relative unit, y-axis) were measured in seeds primed in PEG followed by no UV-B ("Osmo-Control," white bars) and in seeds primed in PEG followed by UV-B administration ("Osmo-UV," black bars). Chlorophyll levels were also measured in seeds primed in distilled water followed by no UV-B ("Hydro-Control," checkered bars), and seeds primed in distilled water followed by UV-B administration ("Hydro-UV," horizontal hashed bars). At 8 hours, the Osmo-Control had significantly higher chlorophyll levels than Hydro-Control or Hydro-UV.

Referring to FIG. 19, flavonoid levels (relative unit, y-axis) were measured in seeds primed in PEG followed by no UV-B ("Osmo-Control," white bars) and in seeds primed in PEG followed by UV-B administration ("Osmo-UV," black bars). Flavonoid levels were also measured in seeds primed in distilled water followed by no UV-B ("Hydro-Control," checkered bars), and seeds primed in distilled water followed by UV-B administration ("Hydro-UV," horizontal hashed bars). There was a significant difference in flavonoid levels between Hydro priming as compared to Osmo priming.

This example shows improvements in plant performance using various conditions priming methods and UV-B administration.

Example 22—Seed Position and UV-B Administration in Broccoli

Effect of seed positions during UV-B administration was assessed in broccoli seeds. Shoot fresh weight, shoot dry weight, root dry weight, leaf chlorophyll levels, and flavonoid levels were assessed.

Broccoli seeds were primed in distilled water. Seeds were then administered UV-B in a growth cabinet at 10° C. for 18 hours, 20 hours, 21 hours, 24 hours, 27 hours, or 28 hours. A first set of seeds was placed on top of a most filter paper ("Float") during UV-B administration. A second set of seeds was completely submerged in the priming medium ("Submerged") during UV-B administration. UV-B was administered at 100 uW cm$^{-2}$ UV-B irradiance.

Seeds were then sown and analyzed for different performance parameters. Seedlings were harvested and shoot fresh weight (FIG. 20), shoot dry weight (FIG. 21), root dry weight (FIG. 22), chlorophyll levels (FIG. 23), and flavonoid levels (FIG. 24) were assessed. "*" indicates significant difference, p<0.05. "+" indicates p=0.06.

Referring to FIG. 20, shoot fresh weight (g/plant, y-axis) was measured in seeds placed on top of a most filter paper that were administered no UV-B ("Float-Control," white bars) or UV-B ("Float-UV," black bars). Shoot fresh weight was also measured in seeds completely submerged in the priming medium that were administered no UV-B ("Submerged-Control," checkered bars) or UV-B ("Submerged-UV," horizontal hashed bars). Float-UV seeds that were administered UV-B for 20 hours exhibited a significant increase of about 56% in shoot fresh weight as compared to Float-Control seeds. Submerged-UV seeds that were administered UV-B for 21 hours exhibited a significant increase of about 30% in shoot fresh weight as compared to Submerged-Control seeds. At 28 hours, there was a difference between Float-Control and Submerged-UV.

Referring to FIG. 21, shoot dry weight (g/plant, y-axis) was measured in seeds placed on top of a most filter paper that were administered no UV-B ("Float-Control," white bars) or UV-B ("Float-UV," black bars). Shoot dry weight was also measured in seeds completely submerged in the priming medium that were administered no UV-B ("Submerged-Control," horizontal hashed bars) or UV-B ("Submerged-UV," checkered bars). Float-UV seeds administered UV-B for 20 hours exhibited a significant increase of about 56% in shoot dry weight as compared to Float-Control seeds. Submerged-UV seeds administered UV-B for 21 hours exhibited a significant increase of about 41% in shoot dry weight as compared to Submerged-Control seeds. There was also a significant difference at 28 hours between Submerged-UV and Float-Control.

Referring to FIG. 22, root dry weight (g/plant, y-axis) was measured in seeds placed on top of a most filter paper that were administered no UV-B ("Float-Control," white bars) or UV-B ("Float-UV," black bars). Root dry weight was also measured in seeds completely submerged in the priming medium that were administered no UV-B ("Submerged-Control," checkered bars) or UV-B ("Submerged-UV," horizontal hashed bars). Float-UV seeds administered UV-B for 20 hours exhibited an increase of about 50% in root dry weight as compared to Float-Control. Submerged-UV seeds administered UV-B for 21 hours exhibited an increase of about 32% in root dry weight as compared to Submerged-Control.

Referring to FIG. 23, chlorophyll levels (relative unit, y-axis) were measured in seeds placed on top of a most filter paper that were administered no UV-B ("Float-Control," white bars) or UV-B ("Float-UV," black bars). Chlorophyll levels were also measured in seeds completely submerged in the priming medium that were administered no UV-B ("Submerged-Control," checkered bars) or UV-B ("Submerged-UV," horizontal hashed bars). Float-UV seeds administered UV-B for 20 hours exhibited a significant increase of about 8% as compared to Float-Control. There was also significance between Submerged-UV and Float-Control.

Referring to FIG. 24, flavonoid levels (relative unit, y-axis) were measured in seeds placed on top of a most filter paper that were administered no UV-B ("Float-Control," white bars) or UV-B ("Float-UV," black bars). Flavonoid levels were also measured in seeds completely submerged in the priming medium that were administered no UV-B ("Submerged-Control," checkered bars) or UV-B ("Submerged-UV," horizontal hashed bars). Float-UV seeds administered UV-B for 24 hours exhibited a 14% increase in flavonoid levels as compared to Float-Control.

This example shows improvement in plant performance as a result of seed positioning followed by UV-B administration.

Example 23—UV-B Irradiance in Broccoli

Broccoli seeds were treated with a combination of conditions followed by analysis of shoot fresh weight, hypocotyl length, leaf area, leaf chlorophyll levels, and flavonoid levels.

Broccoli seeds were primed in −1.25 bar polyethylene glycol (PEG) dissolved in distilled water. Seeds were administered UV-B in a growth cabinet at 10° C. for 0, 8, 21, or 27 hours. The dose of UV-B irradiance administered was 40 uW cm$^{-2}$ ("low," diagonal hashed bars), 100 uW cm$^{-2}$ ("medium," horizontal hashed bars), and 200 uW cm$^{-2}$ ("high," checkered bars). "Control" (black bars) refers to no UV-B treatment in which seeds were immersed in priming medium but did not receive UV. "NP" refers to non-primed seeds in which seeds were not immersed in PEG nor received an UV treatment. The seeds were positioned on top of a moist filter paper during UV-B administration.

Seeds were then sown and analyzed for different performance parameters. Seedlings were harvested, and shoot fresh weight (FIG. 25), hypocotyl length (FIG. 26), leaf area (FIG. 27), chlorophyll levels (FIG. 28), and flavonoid levels (FIG. 29) were assessed.

Referring to FIG. 25, medium UV-B irradiance administration for 21 hours resulted in a significant increase of about 22% in shoot fresh weight (g/plant, y-axis) as compared to control (black bar). High UV-B irradiance administration for 21 hours resulted in a significant increase of about 56% in shoot fresh weight (g/plant, y-axis) as compared to control (black bar). High UV-B irradiance administration for 27 hours resulted in a significant increase of about 27% in shoot fresh weight (g/plant, y-axis) as compared to Control (black bar).

Referring to FIG. 26, medium UV-B irradiance administration for 8 hours resulted in a significant difference of about 13% decrease in hypocotyl length as compared to Control. High UV-B irradiance administration for 21 hours resulted in a significant increase of about 10% in hypocotyl length as compared to Control (black bar). Medium UV-B irradiance administration for 27 hours resulted in a significant increase of about 6% in hypocotyl length as compared to Control (black bar). High UV-B irradiance administration for 27 hours resulted in a significant increase of about 17% in hypocotyl length as compared to Control (black bar).

Referring to FIG. 27, medium UV-B irradiance administration for 21 hours resulted in a significant increase of about 27% in leaf area ($cm^2$/plant) as compared to Control (black bar). High UV-B irradiance administration for 21 hours resulted in a significant increase of about 67% in leaf area ($cm^2$/plant) as compared to Control (black bar). High UV-B irradiance administration for 27 hours resulted in a significant increase of about 26% in leaf area ($cm^2$/plant) as compared to Control (black bar).

Referring to FIG. 28, high UV-B irradiance administration for 27 hours resulted in about a 13% decrease in chlorophyll (relative unit) as compared to Control (black bar).

Referring to FIG. 29, high UV-B irradiance administration for 8 hours resulted in a significant difference of about a 15% decrease in flavonoid (relative unit) as compared to Control (black bar).

This example illustrates treatment conditions comprising priming methods and various UV-B irradiance and duration affect plant performance.

Example 24—UV-B Administration on Protective Secondary Metabolites in Lettuce Leaves Effects of UV-B administration on flavonoid levels in lettuce leaves were determined.

Lettuce seeds were primed and administered UV-B. Control seeds were seeds that were primed but not administered UV-B. Non-primed seeds were seeds grown from identical seed lot but not primed and not administered UV-B. Leaves at 2-3 true leaf stage were sampled for foliar flavonoid levels 45 days from sowing using Dualex optical sensor (relative units). Two independent experiments were performed. A total of 34 plants from UV-B administered seeds, 35 plants from non-UV-B treated seeds, and 64 plants from non-UV-B and non-primed seeds were analyzed.

Referring to FIG. 30, plants from UV-B administered seeds ("UV-B," black bar) exhibited a significant increase in flavonoids in relative units (y-axis) as compared to plants from non-UV-B treated seeds ("Control," white bar) and plants from non-UV-B and non-primed seeds ("Non-primed," horizontal hashed bars).

This figure shows UV-B administration of seeds results in increase in protective secondary metabolites in resultant plants.

Example 25—UV-B Administration on Broccoli Stem Elongation

Effects of UV-B administration on broccoli stem elongation were determined.

Broccoli seeds were primed and administered UV-B. Control seeds were seeds that were primed but not administered UV-B. Non-primed seeds were seeds grown from identical seed lot but not primed and not administered UV-B. Plant hypocotyls were assessed at 45 days from sowing. Three independent experiments were performed. A total of 27 plants from UV-B administered seeds, 35 plants from non-UV-B treated seeds, and 39 plants from non-UV-B and non-primed seeds were analyzed.

Referring to FIG. 31, broccoli plants from UV-B administered seeds ("UV-B," black bar) exhibited a significant reduction in hypocotyl length (mm, y-axis) as compared to plants from non-UV-B treated seeds ("Control," white bar) and plants from non-UV-B and non-primed seeds ("Non-primed," horizontal hashed bars).

This figure shows UV-B administration of seeds results affects hypocotyl elongation.

Example 26—UV-B Administration on Lettuce Plant Biomass

Lettuce plant biomass was determined following UV-B administration.

Lettuce seeds were primed and administered UV-B. Control seeds were seeds that were primed but not administered UV-B. Non-primed seeds were seeds grown from identical seed lot but not primed and not administered UV-B. Plants were harvested for shoot fresh weight 45 days after sowing. A total of 66 plants from UV-B administered seeds, 60 plants from non-UV-B treated seeds, and 64 plants from non-UV-B and non-primed seeds were analyzed.

Referring to FIG. 32, plant fresh weight (grams, y-axis) of lettuce plants grown from UV-B administered seeds ("UV-B," black bars) was significantly increased as compared to plants from non-UV-B treated seeds ("Control," white bar) and plants from non-UV-B and non-primed seeds ("Non-primed," horizontal hashed bars).

This figure shows UV-B administration of seeds results in an increase in plant biomass in resultant plants.

Example 27—UV-B Administration on Corn Seedling Growth

Effects of UV-B administration on corn seedling growth were determined.

Maize seeds (*Zea mays*) were primed and administered UV-B. Control seeds were seeds that were primed but not administered UV-B. Seedlings were harvested at 4 weeks old.

Referring to FIG. 33A, seedling dry weight (grams, y-axis) from UV-B administered maize seeds ("UV-B," black bar) was increased 26% as compared to plants from non-UV-B treated seeds ("Control," white bar).

Referring to FIG. 33B, root dry weight (grams, y-axis) from UV-B administered maize seeds ("UV-B," black bar) was increased 28% as compared to plants from non-UV-B treated seeds ("Control," white bar).

This figure shows UV-B administration of seeds results in an increase in growth in resultant seedlings.

Example 28—Stomatal Resistance in Lettuce Seedlings Following UV-B Administration Stomatal resistance was determined in lettuce seedlings.

Lettuce seeds were primed and administered UV-B. Control seeds were seeds that were primed but not administered UV-B. At 4 weeks, seedlings from UV-B administered seeds and control seeds were then subject to 11 days of well-watered or drought conditions.

Referring to FIG. 34, seedlings from UV-B administered seeds ("UV-B," black bar) exhibited increased stomatal resistance under well-watered conditions.

This figure shows UV-B administration results in improved water use efficiency.

Example 29—Improved Flavonoid and Anthocyanin Levels in Seeds with a Different Dose of UV-B The levels of flavonoid and anthocyanin are measured in seeds following irradiation with 280 nm of UV-B.

Seeds that are stored at 4° C. are washed under cold water to remove the red fungicide coating. Seeds are primed in a plant growth chamber followed by water immersion for 16 hours. The seeds are then treated with visible light with (UV) or without UV-B (No UV) for 9 hours. UV-B light is supplied by a LED source, the transmittance of which peaked at 280 nm. The UV is set to have irradiance in a range between $4\times10^{-5}$ to $1.3\times10^{-4}$ W cm$^{-2}$ s$^{-1}$. The UV-B can be at a dose in a range of about 0 kJ m$^{-2}$ and 100 kJ m$^{-2}$. The UV-B dose is often at about 13 kJ m$^{-2}$ or about 100 kJ m$^{-2}$.

After 9 hours of treatment, the light treatment and growth chambers are turned off. Seeds are then air dried for 72 hours.

Analysis of UV-B absorbing compounds such as flavonoids are carried out by homogenization of seed in acidified methanol, centrifugation, and measurement of supernatant absorbance by spectrophotometer at 300 nm. Anthocyanins are assessed in seeds using a Dualex Scientific+chlorophyll and polyphenol meter (Force-A, Orsay, France).

This example illustrates the effect of a different dose of UV-B on flavonoid and anthocyanin levels in seeds.

Example 30—Improved Plant Performance with a Different Dose of UV-B

The effects of the 280 nm dose of UV-B on plant performance is assessed.

Seeds that are stored at 4° C. are washed under cold water to remove the red fungicide coating. Seeds are primed in a plant growth chamber followed by water immersion for 16 hours. The seeds are then treated with visible light with (UV) or without UV-B (No UV) for 9 hours. UV-B light is supplied by a LED source, the transmittance of which peaked at 280 nm. The UV is set to have irradiance in a range between $4\times10^{-5}$ to $1.3\times10^{-4}$ W cm$^{-2}$ s$^{-1}$. The UV-B can be at a dose in a range of about 0 kJ m$^{-2}$ and 100 kJ m$^{-2}$. The UV-B dose is often at about 13 kJ m$^{-2}$ or about 100 kJ m$^{-2}$. After 9 hours of treatment, the light treatment and growth chambers are turned off. Seeds are then air dried for 72 hours.

Seedlings are harvested at 4 weeks old. Using a Dualex Scientific+meter (Force-A, Orsay, France), indices for leaf chlorophyll, flavonoid and nitrogen content are calculated. Size, dry weight, nitrogen index, shoot dry weight, shoot fresh weight, shoot length, radical length, pigment production, leaf size, and root dry weight are also measured.

There is an increase in at least one of flavonoid levels, anthocyanin levels, size, dry weight, nitrogen index, shoot dry weight, shoot fresh weight, shoot length, radical length, pigment production, leaf size, and root dry weight in seeds that are treated with UV-B prior to sowing than seeds that are not treated with UV-B.

This example illustrates improved plant performance in seedlings that are planted from seeds irradiated with the 280 nm dose of UV-B.

Example 31—Improved Plant Performance with a Different Dose of UV-B in Response to Stress The effect of the 280 nm UV-B dose on plant performance in seeds irradiated with UV-B in response to stress is assessed.

Seeds that are stored at 4° C. are washed under cold water to remove the red fungicide coating. Seeds are primed in a plant growth chamber followed by water immersion for 16 hours. The seeds are then treated with visible light with (UV) or without UV-B (No UV) for 9 hours. UV-B light is supplied by a LED source, the transmittance of which peaked at 280 nm. The UV is set to have irradiance in a range between $4\times10^{-5}$ to $1.3\times10^{-4}$ W cm$^{-2}$ s$^{-1}$. The UV-B can be at a dose in a range of about 0 kJ m$^{-2}$ and 100 kJ m$^{-2}$. The UV-B dose is often at about 13 kJ m$^{-2}$ or about 100 kJ m$^{-2}$. After 9 hours of treatment, the light treatment and growth chambers are turned off. Seeds are then air dried for 72 hours.

After 4 weeks, seedlings are transplanted to individual planting cells. For half of the UV-B treated cells and for half of the non-UV-B treated cells, the cells are subjected to one of heat, flood, frost, or high visible light stress. Cells exposed to heat are maintained at 37° C. Cells exposed to frost are maintained at 4° C. Cells exposed to flood stress are submerged in water. Other cells are exposed to high visible light stress of 400-500 nm.

After 11 days of either heat, flood, frost, or high visible light stress, indices for leaf chlorophyll, flavonoid, and nitrogen content are calculated using a Dualex Scientific+ meter (Force-A, Orsay, France). Size, dry weight, nitrogen index, shoot dry weight, shoot fresh weight, shoot length, radical length, pigment production, leaf size, and root dry weight are also measured.

There is an increase in at least one of flavonoid levels, anthocyanin levels, size, dry weight, nitrogen index, shoot dry weight, shoot fresh weight, shoot length, radical length, pigment production, leaf size, and root dry weight in seeds that are treated with UV-B prior to sowing than seeds that are not treated with UV-B. In addition, plants from seeds irradiated with UV-B show improved plant performance in response to stress compared to plants from non-UV-B irradiated seeds.

This example illustrates improvement in plant performance in seedlings that are planted from seeds irradiated with UV-B in response to stress.

Example 32—Improved Plant Performance with a Different Dose of UV-B in Response to Disease The effect of the 280 nm UV-B dose on plant performance from seeds irradiated with UV-B following disease stress is tested.

Seeds that are stored at 4° C. are washed under cold water to remove the red fungicide coating. Seeds are primed in a plant growth chamber followed by water immersion for 16 hours. The seeds are then treated with visible light with (UV) or without UV-B (No UV) for 9 hours. UV-B light is supplied by a LED source, the transmittance of which peaked at 280 nm. The UV is set to have irradiance in a range between $4\times10^{-5}$ to $1.3\times10^{-4}$ W cm$^{-2}$ s$^{-1}$. The UV-B can be at a dose in a range of about 0 kJ m$^{-2}$ and 100 kJ m$^{-2}$. The UV-B dose is often at about 13 kJ m$^{-2}$ or about 100 kJ m$^{-2}$. After 9 hours of treatment, the light treatment and growth chambers are turned off. Seeds are then air dried for 72 hours.

After 4 weeks, seedlings are transplanted to individual planting cells. For half of the UV-B treated cells and for half of the non-UV-B treated cells, the cells are inoculated with a disease of either a fungal pathogen, a bacterium, a oomycete, a virus, a viroid, a virus-like organism, a phytoplasma, a protozoa, a nematode, or a parasite.

After 4 days, indices for leaf chlorophyll, flavonoid, and nitrogen content are calculated using a Dualex Scientific+ meter (Force-A, Orsay, France). Size, dry weight, nitrogen index, shoot dry weight, shoot fresh weight, shoot length, radical length, pigment production, leaf size, and root dry weight are also measured.

There is an increase in at least one of flavonoid levels, anthocyanin levels, size, dry weight, nitrogen index, shoot dry weight, shoot fresh weight, shoot length, radical length, pigment production, leaf size, and root dry weight in seeds that are treated with UV-B prior to sowing than seeds that are not treated with UV-B. Furthermore, following disease inoculation, plants from UV-B irradiated seeds show improved plant performance compared to plants from non-UV-B irradiated plants.

This example illustrates improved plant performance in seedlings planted from seeds irradiated with UV-B in response to disease.

Example 33—Reduction of Environmental Impact of Plants from Seeds Irradiated with UV-B Seeds that are stored at 4° C. are washed under cold water to remove the red fungicide coating. Seeds are primed in a plant growth chamber followed by water immersion for 16 hours. The seeds are then treated with visible light with (UV) or without UV-B (No UV) for 9 hours. UV-B light is supplied by a LED source, the transmittance of which peaked at 280 nm. The UV is set to have irradiance in a range between $4 \times 10^{-5}$ to $1.3 \times 10^{-4}$ W cm$^{-2}$ s$^{-1}$. The UV-B can be at a dose in a range of about 0 kJ m$^{-2}$ and 100 kJ m$^{-2}$. The UV-B dose is often at about 13 kJ m$^{-2}$ or about 100 kJ m$^{-2}$. After 9 hours of treatment, the light treatment and growth chambers are turned off. Seeds are then air dried for 72 hours.

After 4 weeks, seedlings are transplanted to individual planting cells. For half of the UV-B treated cells and for half of the non-UV-B treated cells, the cells contain soil with 20% reduction of fertilizer compared to the standard regimen. In another set, half of the UV-B treated cells and for half of the non-UV-B treated cells, either one of an insecticide, herbicide, or pesticide is applied at a 20% reduction to control plants that is administered once a week.

After an additional four weeks, indices for leaf chlorophyll, flavonoid, and nitrogen content are calculated using a Dualex Scientific+meter (Force-A, Orsay, France). Size, dry weight, nitrogen index, shoot dry weight, shoot fresh weight, shoot length, radical length, pigment production, leaf size, and root dry weight are also measured.

There is an increase in at least one of flavonoid levels, anthocyanin levels, size, dry weight, nitrogen index, shoot dry weight, shoot fresh weight, shoot length, radical length, pigment production, leaf size, and root dry weight in seeds that are treated with UV-B prior to sowing than seeds that are not treated with UV-B. Furthermore, plants from UV-B treated seeds exhibit equal or even improved plant performance compared to those plants from non-UV-B treated seeds grown with fertilizer or exposed to an insecticide, herbicide, or pesticide. The data indicate that plants UV-B irradiated seeds require less fertilizer, insecticide, herbicide, or pesticide compared to control plants.

This example illustrates the environmental impact of growing plants from UV-B irradiated seeds as measured as a reduction in fertilizer, herbicide, insecticide, or pesticide use.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the appended claims define the scope of the disclosure and that methods and structures within the scope of these claims and their equivalents be covered thereby.

What we claim is:

1. A method for improving at least one of plant performance and hardiness, comprising:
   administering light enriched for UV-B to a seed, wherein at least 50% of the wavelengths of the administered light comprise UV-B, wherein the seed is treated at a temperature range of about 15° C. to 40° C.; and
   bagging the seed for sale.

2. The method of claim 1, further comprising storing the seed.

3. The method of claim 1, wherein a wavelength of the UV-B is in a range of about 280 nm to about 290 nm.

4. The method of claim 3, wherein an irradiance of the UV-B is up to 300 uW cm$^{-2}$.

5. The method of claim 3, wherein an irradiance of the UV-B is more than 300 uW cm$^{-2}$.

6. The method of claim 3, wherein the UV-B is administered at no more than 100 kJ m$^{-2}$.

7. The method of claim 1, wherein a duration of administering the light is in a range of about 1 hour to about 30 hours.

8. The method of claim 1, wherein the seed is treated at a relative humidity in a range of about 30% to about 100%.

9. The method of claim 1, wherein a duration of light administration is for less than or at least 60 minutes.

10. The method of claim 1, wherein a peak wavelength comprises 282 nm.

11. The method of claim 1, wherein a wavelength of the UV-B is in a range of about 280 nm to about 290 nm, the irradiance is no more than $1.3 \times 10^{-4}$ W cm$^{-2}$s$^{-1}$, the UV-B is administered at no more than 100 kJ m$^{-2}$, and a duration of light administration is for less than or at least 60 minutes.

12. A method for improving at least one of plant performance and hardiness, comprising: administering light enriched for UV-B to a seed wherein at least 50% of the wavelengths of the administered light comprises UV-B, wherein the seed is treated at a temperature range of about 14° C. to 40° C., wherein a wavelength of the UV-B is in a range of about 280 nm to about 290 nm, and wherein an irradiance of the UV-B is more than 300 uW cm$^{-2}$.

13. The method of claim 12, wherein the UV-B is administered at no more than 100 kJ m$^{-2}$.

14. The method of claim 12, wherein the seed is treated at a relative humidity in a range of about 30% to about 100%.

15. The method of claim 12, wherein a duration of light administration is for less than or at least 60 minutes.

16. A method for improving at least one of plant performance and hardiness, comprising: administering light enriched for UV-B to a seed wherein at least 50% of the wavelengths of the administered light comprises UV-B, wherein the seed is treated at a temperature range of about 14° C. to 40° C., and wherein the seed is treated at a relative humidity in a range of about 30% to about 100%.

17. The method of claim 16, wherein an irradiance of the UV-B is up to 300 uW cm$^{-2}$.

18. The method of claim 16, wherein an irradiance of the UV-B is more than 300 uW cm$^{-2}$.

19. The method of claim 16, wherein a duration of light administration is for less than or at least 60 minutes.

* * * * *